US012478669B1

(12) United States Patent
Song et al.

(10) Patent No.: US 12,478,669 B1
(45) Date of Patent: Nov. 25, 2025

(54) HERPES ZOSTER mRNA VACCINE, PREPARATION METHOD THEREFOR, AND USE THEREOF

(71) Applicant: Hangzhou Tianlong Pharmaceutical Co., Ltd., Zhejiang (CN)

(72) Inventors: Gengshen Song, Zhejiang (CN); Kai Dong, Zhejiang (CN); Zhongbin Chen, Zhejiang (CN); Yanfen Li, Zhejiang (CN); Yuting Zhou, Zhejiang (CN); Jing Li, Zhejiang (CN); Xin Chai, Zhejiang (CN); Zhongcai Gao, Zhejiang (CN); Jinyu Zhang, Zhejiang (CN); Huanyu Wang, Zhejiang (CN)

(73) Assignee: Hangzhou Tianlong Pharmaceutical Co., Ltd., Hangzhou (CN)

( * ) Notice: Subject to any disclaimer, the term of this patent is extended or adjusted under 35 U.S.C. 154(b) by 0 days.

(21) Appl. No.: 19/031,360

(22) Filed: Jan. 18, 2025

(30) Foreign Application Priority Data

May 27, 2024 (CN) ......................... 202410659996.0

(51) Int. Cl.

| | |
|---|---|
| ***A61K 39/25*** | (2006.01) |
| ***A61K 9/51*** | (2006.01) |
| ***A61K 31/7105*** | (2006.01) |
| ***A61K 39/00*** | (2006.01) |
| ***A61P 37/04*** | (2006.01) |
| ***C12N 15/86*** | (2006.01) |

(52) U.S. Cl.
CPC .............. *A61K 39/25* (2013.01); *A61P 37/04* (2018.01); *A61K 2039/53* (2013.01); *A61K 2039/54* (2013.01); *A61K 2039/6018* (2013.01)

(58) Field of Classification Search
CPC ................ A61K 39/25; A61K 2039/53; A61K 2039/6018; A61K 39/12; A61P 31/22
See application file for complete search history.

(56) References Cited

U.S. PATENT DOCUMENTS

| | | | |
|---|---|---|---|
| 8,278,063 | B2 | 10/2012 | Pandey et al. |
| 9,012,219 | B2 | 4/2015 | Kariko et al. |
| 11,643,441 | B1 | 5/2023 | Ciaramella et al. |
| 11,918,644 | B2 | 3/2024 | Ciaramella |
| 2011/0086907 | A1 | 4/2011 | Zouboulis |
| 2012/0195936 | A1 | 8/2012 | Rudolph et al. |
| 2023/0233671 | A1 | 7/2023 | Bennett et al. |

FOREIGN PATENT DOCUMENTS

| | | | |
|---|---|---|---|
| CN | 102625696 | A | 8/2012 |
| CN | 107090463 | A | 8/2017 |
| CN | 108472309 | A | 8/2018 |
| CN | 110520409 | A | 11/2019 |
| CN | 108368028 | B | 9/2021 |
| CN | 114081943 | A | 2/2022 |
| CN | 114044741 | B | 4/2022 |
| CN | 115677518 | B | 4/2023 |
| CN | 115745820 | B | 4/2023 |
| CN | 114957027 | B | 5/2023 |
| CN | 115784921 | B | 5/2023 |
| CN | 116082275 | A | 5/2023 |
| CN | 116178193 | B | 7/2023 |
| CN | 116375592 | A | 7/2023 |
| CN | 116396178 | A | 7/2023 |
| CN | 116785265 | A | 9/2023 |
| CN | 116789764 | A | 9/2023 |
| CN | 116535381 | B | 10/2023 |
| CN | 116854754 | A | 10/2023 |
| TW | 202340136 | A | 10/2023 |
| WO | 2013052523 | A1 | 4/2013 |
| WO | 2014071963 | A1 | 5/2014 |
| WO | 2014093924 | A1 | 6/2014 |
| WO | 2015051169 | A2 | 4/2015 |
| WO | 2015051173 | A2 | 4/2015 |
| WO | 2015089511 | A2 | 6/2015 |
| WO | 2015196118 | A1 | 12/2015 |
| WO | 2015196128 | A2 | 12/2015 |
| WO | 2015196130 | A2 | 12/2015 |
| WO | 2017153936 | A1 | 9/2017 |
| WO | 2023031394 | A1 | 3/2023 |

OTHER PUBLICATIONS

Jun. 21, 2024 First Chinese Search Report issued in Chinese Patent Application No. 202410659996.0.
Jun. 26, 2024 1st Office Action issued in Chinese Patent Application No. 202410659996.0.
Jul. 20, 2024 2nd Office Action issued in Chinese Patent Application No. 202410659996.0.
Aug. 8, 2024 3rd Office Action issued in Chinese Patent Application No. 202410659996.0.
Nov. 13, 2024 Notice of Allowance and Supplementary Search Report issued in Chinese Patent Application No. 202410659996.0.
Stephen F. Altschul et al., Gapped BLAST and PSI-BLAST: a new generation of protein database search programs, Nucleic Acids Research, vol. 25, No. 17, Sep. 1, 1997, pp. 3389-3402.
M. A. Monslow et al., Immunogenicity generated by mRNA vaccine encoding VZV gE antigen is comparable to adjuvanted subunit vaccine and better than live attenuated vaccine in nonhuman primates, Vaccine, Aug. 10, 2020, 38 (36): 5793-5802.
Aug. 28, 2025 1st Office Action issued in Eurasian Patent Application No. 202591320/28.
Sep. 12, 2025 1st Office Action issued in Korean Patent Application No. 10-2025-0069264.

*Primary Examiner* — Barry A Chestnut

(57) ABSTRACT

The present disclosure belongs to the technical field of mRNA vaccines, and specifically relates to a herpes zoster mRNA vaccine, a preparation method therefor, and a use thereof. The herpes zoster mRNA vaccine provided by the present disclosure comprises an RNA encoding a varicella-zoster virus gE glycoprotein or a variant thereof. The vaccine can prevent herpes zoster infection and its complications.

49 Claims, 4 Drawing Sheets

Specification includes a Sequence Listing.

HERPES ZOSTER mRNA VACCINE, PREPARATION METHOD THEREFOR, AND USE THEREOF

CROSS-REFERENCE TO RELATED APPLICATION

The present application claims priority from Chinese Patent Application No. 202410659996.0 filed on May 27, 2024, the contents of which are incorporated herein by reference in their entirety.

REFERENCE TO SEQUENCE LISTING

This application includes a Sequence Listing filed electronically as an XML file named "P24435598US_SEQ.xml", created on Jan. 17, 2025, with a size of 448,212 bytes. The Sequence Listing is incorporated herein by reference.

TECHNICAL FIELD

The present disclosure belongs to the technical field of mRNA vaccines, and specifically relates to a herpes zoster mRNA vaccine, a preparation method therefor, and a use thereof.

BACKGROUND

Herpes zoster is an infectious skin disease caused by the reactivation of varicella-zoster virus (VZV), which has been latent in the dorsal root ganglia or cranial ganglia for an extended period. Herpes zoster is a common disease in dermatology that is often accompanied by neuropathic pain in addition to skin damage. The disease mainly occurs in elderly people, immunosuppressed or immunodeficient groups, and is more common in spring and autumn. The incidence shows a significant increase with age.

VZV is not completely eliminated from the human body following recovering from varicella infection, but remains latent in the cranial ganglia, dorsal root ganglia, and autonomic ganglia throughout the neuraxis, and persists throughout life. After infection with VZV that results in varicella, the body produces specific antibodies against VZV and T cell-mediated cellular immunity (e.g., $CD4^+$/$CD8^+$/memory T cells, etc.). These two immune functions play an important role in the maintenance of latent VZV infection and the prevention of herpes zoster. VZV can spontaneously reactivate with age or when some external or internal factors that cause the immunity of the body to be suppressed occur, leading to herpes zoster (HZ).

Common activating factors for herpes zoster include age factors (e.g., old age), cellular immunodeficiency, genetic susceptibility, trauma, systemic diseases (e.g., diabetes, kidney disease, etc.), stress, fatigue, etc. In contrast to varicella infection in children, herpes zoster in adults (elderly) can easily lead to complications, with postherpetic neuralgia (PHN) being the most common complication, which can cause pain lasting 3 to 12 months after healing of herpes zoster.

Both herpes zoster and postherpetic neuralgia are common and prevalent diseases. Chronic pain (postherpetic neuralgia) and other complications caused by herpes zoster, commonly known as "shingles", seriously affect the quality of life of patients, particularly affecting the elderly and those with weak immune systems. Due to the unknown mechanism of pain, postherpetic neuralgia remains one of the intractable pains.

Herpes zoster has two notable features: a high infection rate; and significant suffering for the patients. Survey data from Europe and the United States show that the annual incidence of herpes zoster is generally 2 to 6‰. The incidence tends to increase with age. Statistics indicate that the incidence among individuals aged 10 to 49 is approximately 4‰, while the incidence among those over 75 years old is as high as 14‰. Additionally, women are slightly more likely to develop herpes zoster than men. The global incidence of herpes zoster is on the rise. Survey data from 1994 to 2018 show that the annual incidence of herpes zoster increases by 3.1% per year, with a more pronounced increase in the incidence especially among individuals aged 20 to 49.

Herpes zoster has not been included in the category of Class A and B notifiable infectious diseases in China, and there have been relatively few relevant population-wide epidemiological studies. According to statistics, in China, approximately 99.5% of adults aged 50 or older carry latent VZV, with around 1.56 million new cases reported each year. In China, the average annual incidence of herpes zoster among individuals aged 50 to 60 is 2.666‰, while the average annual incidence among those aged 80 or older is as high as 8.55‰. The incidence of postherpetic neuralgia (PHN) also increases with age, with studies showing that in China, the incidence of PHN among elderly patients with herpes zoster is 18.8%, and the incidence of PHN among those over 75 years old is 31.7%.

Vaccines are the most effective way to prevent herpes zoster. The main technology routes involved in the development of herpes zoster vaccines include live attenuated vaccines, recombinant protein vaccines, adenovirus vector vaccines, and mRNA vaccines.

There are only four vaccines available worldwide for preventing herpes zoster: Zostavax® (discontinued), a live attenuated vaccine from Merck; Shingrix®, a recombinant protein vaccine from GlaxoSmithKline (GSK); SkyZoster® (only sold in South Korea) from SK Chemicals; and a recently launched live attenuated vaccine from BCHT Biotechnology in China. The live attenuated vaccine Zostavax® from Merck was the first herpes zoster vaccine approved for marketing in the world, which was launched in the United States and Europe respectively in 2006. However, due to its low protective efficacy (with a protective efficiency of approximately 70% effective in reducing the development of herpes) and unsuitability for individuals with immunosuppression or immune system disorders, its scope of application was greatly limited, and the vaccine was discontinued in 2018. The recombinant protein vaccine Shingrix® from GSK was launched in the United States in 2017, then launched in Europe in 2018, and applied for approval in China in 2019. With its global sales reaching US$2.4 billion in 2021 and US$3.2 billion in 2022, the vaccine has been among the top ten best-selling vaccines in the world for several consecutive years. However, the vaccine is a protein subunit vaccine, which is expensive and has difficulty in scaling up production capacity due to the use of a special adjuvant from GSK. More importantly, the vaccine has severe side effects, in which the incidence of adverse reactions is significantly higher than that of live attenuated vaccines.

mRNA vaccines represent the third generation of vaccine technology following traditional vaccines and protein subunit vaccines. The mRNA vaccine enters human cells through a specific delivery system and uses the body's own cells to translate mRNA into protein. The expressed protein becomes a certain antigenic protein possessed by the virus and is recognized as a foreign antigen by antigen-presenting cells (APCs), which drives the maturation of dendritic cells (DCs) and subsequently activates B cells and T cells to generate a robust immune response, triggering both humoral and cellular immune responses. The mRNA vaccine breaks through the immune activation pattern of traditional vaccines by innovatively using the body's own cells to produce antigens, thereby activating dual-specific immunity, establishing immune memory, and providing longer-lasting specific immunity. The greatest advantage of mRNA vaccines lies in their ability to quickly develop mRNA vaccines once the antigenic gene sequences of the pathogen are known. The rapid design and construction, high adaptability to viral mutations, efficient and universal platform for fully synthetic production process, ease of standardized production, and other technical advantages of mRNA vaccines result in short production chains and development cycles, relatively simple processes, and rapid large-scale production capabilities.

The herpes zoster mRNA vaccine has the following advantages over traditional vaccines: 1) it is a non-infectious and non-integrating agent with no risk of infection or insertion of mutations; 2) the mRNA vaccine activates specific immunity in humans through in vivo expression of antigens, allowing for more durable and effective specific immunity; 3) the mRNA vaccine enables stable delivery into cells for efficient in vivo expression; 4) the production of mRNA vaccines can undergo rigorous quality control.

gE, a major target protein for the development of herpes zoster vaccines, is one of the most abundant glycoproteins in VZV, and plays a key role in viral replication and viral transmission between ganglion cells. As a highly glycosylated type I membrane protein, gE can be transported between the endoplasmic reticulum (ER), trans Golgi network (TGN), and endosomes.

Based on the above problems, in order to further reduce the risk of herpes zoster in individuals with low immunity, there is an urgent need to provide a novel mRNA vaccine to prevent VZV, which can significantly enhance the effect of humoral and cellular immunity after vaccination.

SUMMARY

The present disclosure provides a herpes zoster mRNA vaccine that can safely direct the body's cellular mechanism to produce virtually any protein of interest, ranging from natural proteins to antibodies and other completely novel proteins that can have preventive activity inside and outside cells. The herpes zoster mRNA vaccine of the present disclosure can be used to elicit a balanced immune response against VZV, including both cellular and humoral immune responses, without many of the risks associated with attenuated virus vaccination.

RNA (e.g., mRNA) vaccines can be used in a variety of settings depending on the prevalence of infection or the degree or level of unmet medical need. RNA (e.g., mRNA) vaccines can be used to prevent VZV in a variety of genotypes, strains, and isolates. RNA (e.g., mRNA) vaccines are superior because they generate much greater antibody potency and earlier responses than commercially available antiviral therapeutic treatments. Although not wishing to be bound by theory, it is believed that, like mRNA polynucleotides, RNA vaccines are better designed to produce an appropriate protein conformation through translation when the RNA vaccine assigns a natural cellular mechanism. Unlike traditional vaccines, which are manufactured ex vivo and can trigger adverse cellular responses, RNA (e.g., mRNA) vaccines are delivered to cellular systems in a more natural manner.

The present disclosure innovatively designs a series of mRNA vaccine candidate antigens based on the important structure and biological function of the VZV gE protein, compares their immunogenicity with that of mRNA vaccines in the prior art (e.g., antigen YK-VZV-007, see CN108472309A; and the marketed recombinant subunit vaccine Shingrix®), and successfully screens a number of herpes zoster mRNA vaccine candidates with novel antigenic structures and superior immunogenicity, which provides the basis for successful development of herpes zoster mRNA vaccines.

Based on the wild-type VZV gE glycoprotein, the present disclosure obtains a variety of ribonucleic acids encoding VZV gE glycoprotein variants through a specific combination (including sequence truncation, site mutation, and/or sequence deletion), and accordingly provides a novel mRNA vaccine for the prevention of VZV Experiments have demonstrated that the vaccine can significantly enhance the effect of humoral and cellular immunity after vaccination, which includes: improving the content of IgG antibody against VZV gE protein, increasing the number of immune cells (including $CD4^+$ and $CD8^+$ that secrete IFN-$\gamma^+$ and/or IL-$2^+$), and promoting the secretion of cytokines (including IFN-$7^+$ and IL-$2^+$) by immune cells in the herpes zoster mRNA vaccine.

The mRNA vaccine as provided herein may comprise an RNA polynucleotide of at least one VZV glycoprotein provided in the accompanying Sequence Listing, or a fragment, homologue (e.g., having at least 80%, 81%, 82%, 83%, 84%, 85%, 86%, 87%, 88%, 89%, 90%, 91%, 92%, 93%, 94%, 95%, 96%, 97%, 98%, 99%, or 100% identity), variant, or derivative thereof.

In some embodiments, the antigen encodes a VZV gE polypeptide.

In some embodiments, the VZV gE polypeptide (full length) comprises amino acids 1 to 623 (e.g., SEQ ID NO: 3, 51, 55, 171, 135, 139, 143, 147, 19, 23, 151, 27, 31, 35, 39, 43, 47, 163, 167).

In some embodiments, the VZV gE polypeptide is a variant. In some embodiments, the VZV gE variant is a truncated VZV gE polypeptide lacking an anchor domain (ER retention domain).

In some embodiments, the truncated VZV gE polypeptide comprises amino acids 1 to 539 (e.g., SEQ ID NO: 7).

In some embodiments, the truncated VZV gE polypeptide comprises amino acids 1 to 573 (e.g., SEQ ID NO: 15, 59, 63, 67, 71, 75, 79, 83, 87, 91).

In some embodiments, the truncated VZV gE polypeptide comprises amino acids 1 to 568 (e.g., SEQ ID NO: 11).

In some embodiments, the truncated VZV gE polypeptide comprises amino acids 1 to 587 (e.g., SEQ ID NO: 95, 99, 103, 107, 111, 115, 119, 123, 127, 131).

In some embodiments, the truncated VZV gE polypeptide comprises amino acids 1 to 601 (e.g., SEQ ID NO: 155, 159).

In some embodiments, the VZV gE variant is a full-length or truncated polypeptide. Herein, the VZV gE variant further comprises a mutation in one or more motifs associated with targeting Golgi or trans Golgi network (TGN), which results in decreased targeting or localization of the VZV gE polypeptide to Golgi or TGN. In particular, the present inventors unexpectedly found that the motifs associated with targeting gE proteins to Golgi or trans Golgi network comprise an "$A_{568}Y_{569}R570V_{571}$" motif (with a specific mutant antigen sequence such as YK-VZV-011 (SEQ ID NO: 35)), especially having an A568D mutation and/or a Y569K mutation.

Additionally, in some embodiments, the VZV gE variant may have a Y582A/G mutation, or a Y569K/A mutation, or a combination of Y582G and Y569A mutations. Other mutation types also include a site mutation in a phosphorylated acidic motif such as $S_{593}EST_{596}DT_{598}$ (SEQ ID NO: 182).

In some embodiments, the variant VZV gE polypeptide is a full-length or truncated polypeptide. Herein, the variant VZV gE polypeptide further comprises a mutation in one or more motifs $Y_{582}AGL_{585}$ (SEQ ID NO: 185) associated with VZV gE internalization or endocytosis, which results in reduced endocytosis of the VZV gE polypeptide.

In some embodiments, the VZV gE variant is a full-length polypeptide having a Y569K mutation (SEQ ID NO: 27, 31, 35, 39, 43, 47, 143, 147).

In some embodiments, the VZV gE variant is a full-length polypeptide having a Y582A mutation (SEQ ID NO: 23, 27, 31, 43, 47, 135, 139, 171).

In some embodiments, the VZV gE variant is a full-length polypeptide having a Y582A mutation and a Y569K mutation (SEQ ID NO: 27, 31, 43, 47).

In some embodiments, the VZV gE variant is a full-length polypeptide having an $A_{593}EA_{595}A_{596}DA_{598}$ sequence (SEQ ID NO: 183).

In some embodiments, the VZV gE variant is a full-length or truncated polypeptide having an $A_{593}EA_{595}A_{596}DA_{598}$ sequence (SEQ ID NO: 183) and having a Y582G mutation, or a Y569K mutation, or a combination of Y582G and Y569K mutations.

In some embodiments, the VZV gE variant comprises any one or more site mutations selected from the group consisting of: A568D, Y569K, Y569A, R570E, V571K, Y582A, S593A, S595A, T596A, T598A; preferably A568D, Y569K, R570E, V571K.

In some embodiments, the site mutation is any one of the following combinations:

1) A568D; Y569K; R570E; V571K; (YK-VZV-023, YK-VZV-011)
2) A568D; Y569A; R570E; V571K; (YK-VZV-024)
3) Y569K; R570E; V571K; (YK-VZV-025)
4) A568D; Y569K; R570E; V571K; Y582A; (YK-VZV-030, YK-VZV-013)
5) A568D; Y569K; R570E; V571K; Y582G; (YK-VZV-031, YK-VZV-038)
6) A568D; Y582A; (YK-VZV-032)
7) Y569K; Y582A; (YK-VZV-033, YK-VZV-009)
8) R570E; Y582A; (YK-VZV-034)
9) V571K; Y582A; (YK-VZV-035)
10) S593A; S595A; T596A; T598A; (YK-VZV-016, YK-VZV-044)
11) Y582A; S593A; S595A; T596A; T598A; (YK-VZV-037)
12) A568D; Y569K; R570E; V571K; Y582G; S593A; S595A; T596A; T598A; (YK-VZV-039)
13) A568D; Y569K; R570E; V571K; Y582A; S593A; S595A; T596A; T598A; (YK-VZV-014)
14) Y582G; S593A; S595A; T596A; T598A; (YK-VZV-040)
15) Y569K; Y582A; S593A; S595A; T596A; T598A; (YK-VZV-010)
16) A568D; Y569K; R570E; V571K; S593A; S595A; T596A; T598A; (YK-VZV-012)
17) Y582G; (YK-VZV-029)
18) A568D; (YK-VZV-018)
19) Y569K; (YK-VZV-020)
20) R570E; (YK-VZV-021)
21) V571K; (YK-VZV-022)
22) Y582A; (YK-VZV-028, YK-VZV-036)

In some embodiments, the VZV gE variant further comprises a sequence deletion, wherein the sequence deletion is selected from any one or more of the group consisting of:

1) $A_{568}$,
2) $Y_{569}RVDKSPYNQS_{579}$ (SEQ ID NO: 186),
3) $Y_{569}RVDKSPYNQSMYYAGLPV_{587}$(SEQ ID NO: 187).

The VZV gE antigen of the present disclosure has various combinations of mutations, comprising amino acid truncations at the C-terminus of gE antigen, and deletions or substitutions at key amino acid sites, as further described below by way of specific examples.

The present disclosure also provides a preparation method for the composition, comprising:

providing a template that can transcribe the RNA of VZV;
transcribing the RNA using the template under conditions suitable for transcription.

In some embodiments, the preparation method comprises the following steps:

synthesizing a DNA sequence of the VZV gE antigen and then recombining it into the PVAX1 vector by homologous recombination;
obtaining a plasmid after transformation and culture of *E. coli;*
obtaining a linearized plasmid after digestion of the plasmid;
using T7 RNA polymerase with the linearized plasmid as a template, adding NTP starting materials, followed by co-transcriptional capping, and then purifying to obtain RNA, preferably mRNA.

In some preferred embodiments, the purification method comprises one or a combination of the following: lithium chloride precipitation, affinity chromatography, ultrafiltration exchange, and cellulose chromatography.

In some embodiments, the preparation method for the composition comprises synthesizing a DNA sequence according to an antigen gene and inserting it into a plasmid DNA construct. The plasmid DNA is cleaved using DNA restriction endonuclease to obtain a linearized template. Under the catalysis of T7 RNA polymerase, with the linearized plasmid as a template, key starting materials such as NTP and cap analogs are added for transcription and synthesis of mRNA, followed by RNA modification, where a cap is added at the 5' end. The modified mRNA is then purified by methods such as lithium chloride precipitation and affinity chromatography to remove contaminants, enzymes, free nucleotides, and other impurities.

In a third aspect, the composition of the present disclosure is in the form of a vaccine, i.e., a herpes zoster vaccine, which comprises a pharmaceutically acceptable carrier in addition to the composition.

In some preferred embodiments, the pharmaceutically acceptable carrier comprises a lipid mixture, preferably a lipid nanoparticle (LNP).

In some preferred embodiments, the lipid nanoparticle comprises, for example, a cationic lipid, a neutral lipid, a structural lipid, and a polymer-conjugated lipid.

In a fourth aspect, the present disclosure also provides a method for preparing the vaccine composition, comprising mixing the RNA of the VZV with the pharmaceutically acceptable carrier, for example to encapsulate at least a portion of the RNA in lipid nanoparticles. In some embodiments, the preparation method comprises the following steps: mixing RNA, preferably mRNA, with lipid nanoparticles to encapsulate it in lipid nanoparticles, followed by purification to remove an unencapsulated component.

In some more specific embodiments, the preparation method comprises the following specific steps: formulating the mRNA in the lipid nanoparticles (LNPs), i.e., mixing the purified mRNA with a lipid mixture in a microfluidic chip, allowing for self-assembly of lipid nanoparticles, with the mRNA encapsulated in the liposomes; the lipid nanoparticle solution is subjected to dialysis or filtration to remove the unencapsulated mRNA, non-aqueous solvent, and bacteria; the filtered lipid nanoparticle solution is packaged into sterile vials for storage to complete the preparation and production of an mRNA vaccine.

The present disclosure first discovered:

Based on the wild-type VZV gE glycoprotein, the present disclosure obtains a number of ribonucleic acids encoding VZV gE glycoprotein variants through a specific combination (including sequence truncation, site mutation, and/or sequence deletion), and provides a novel mRNA vaccine for the prevention of VZV. Experiments have demonstrated that the vaccine can significantly enhance the effect of humoral and cellular immunity after vaccination, which includes: improving the content of IgG antibody against VZV gE protein, increasing the number of immune cells (including $CD4^+$ and $CD8^+$ that secrete IFN-$\gamma^+$ and/or IL-$2^+$), and promoting the secretion of cytokines (including IFN-$\gamma^+$ and IL-$2^+$) by immune cells in the herpes zoster mRNA vaccine. Specifically, the present disclosure includes the following findings and results:

1. The results of Western Blot detection of 43 designed VZV gE antigen variants showed that 39 antigen sequences exhibited significant protein expression, including YK-VZV-001, YK-VZV-003, YK-VZV-009, YK-VZV-010, YK-VZV-011, YK-VZV-012, YK-VZV-013, YK-VZV-014, YK-VZV-015, YK-VZV-016, YK-VZV-017, YK-VZV-018, YK-VZV-019, YK-VZV-020, YK-VZV-021, YK-VZV-022, YK-VZV-023, YK-VZV-024, YK-VZV-025, YK-VZV-026, YK-VZV-027, YK-VZV-028, YK-VZV-029, YK-VZV-030, YK-VZV-031, YK-VZV-032, YK-VZV-033, YK-VZV-034, YK-VZV-035, YK-VZV-036, YK-VZV-037, YK-VZV-038, YK-VZV-039, YK-VZV-040, YK-VZV-044, as well as YK-VZV-004 (Comparative Example 1), YK-VZV-006 (Comparative Example 2), YK-VZV-045 (Comparative Example 3), and YK-VZV-007 (Comparative Example 4), which can serve as effective candidate antigens for subsequent immunogenicity screening and evaluation.

2. Based on the above 39 sequences and the gE-specific antibody IgG titer results on day 42, a total of 14 variants were extracted, including YK-VZV-009, YK-VZV-011, YK-VZV-013, YK-VZV-014, YK-VZV-010, YK-VZV-012, YK-VZV-018, YK-VZV-020, YK-VZV-030, YK-VZV-031, YK-VZV-038, YK-VZV-021, YK-VZV-024, YK-VZV-028, as well as 4 control sequences including YK-VZV-004 (Comparative Example 1), YK-VZV-006 (Comparative Example 2), YK-VZV-045 (Comparative Example 3), and YK-VZV-007 (Comparative Example 4).

The effect of these sequences was 3.3 to 5.3 times that of the Shingrix® positive control and 1.8 to 2.8 times that of the YK-VZV-007 (Comparative Example 4) sequence. The effect of these sequences was superior to Shingrix®, YK-VZV-007 (Comparative Example 4), YK-VZV-004 (Comparative Example 1), YK-VZV-006 (Comparative Example 2), and YK-VZV-045 (Comparative Example 3).

3. As shown by the measurement results of the percentage of $CD4^+$ T and $CD8^+$ T cells secreting IFN-γ and IL-2 in the spleens of mice, (i) a total of 9 sequences were screened out based on the percentage of $CD4^+$ T cells, including YK-VZV-010, YK-VZV-013, YK-VZV-011, YK-VZV-020, YK-VZV-012, YK-VZV-018, YK-VZV-028, YK-VZV-038, and YK-VZV-031;

the total percentage of IFN-$\gamma^+$ $CD4^+$ T cells and IL-$2^+$ $CD4^+$ T cells was 2 times or more and up to 7 times that of the Shingrix® positive control, and approximately 1.8 to 5.3 times that of YK-VZV-007 (Comparative Example 4);

the percentage of IFN-$\gamma^+$ $CD4^+$ T cells was 1.00 to 2.00%, which was 3 times or more and up to 6.7 times that of the Shingrix® positive control vaccine, and approximately 2.2 to 4.4 times that of YK-VZV-007 (Comparative Example 4);

the percentage of IL-$2^+$ $CD4^+$ T cells was more than 1%, which was 3.7 times or more that of the Shingrix® positive control vaccine and 2.2 times or more that of YK-VZV-007;

(ii) a total of 5 sequences were further screened out based on the percentage of $CD8^+$ T cells, including YK-VZV-010, YK-VZV-013, YK-VZV-020, YK-VZV-018, and YK-VZV-011;

the total percentage of IFN-$\gamma^+$ $CD8^+$ T cells and IL-$2^+$ $CD8^+$ T cells was 4 to 7 times or more that of the Shingrix® vaccine and approximately 3 to 5 times that of YK-VZV-007 (Comparative Example 4);

the percentage of IFN-$\gamma^+$ $CD8^+$ T cells was optimal at 5.0% or more, which was 4.5 to 7 times or more that of the Shingrix® positive control vaccine and approximately 2.5 to 4.5 times that of YK-VZV-007;

the percentage of IL-$2^+$ $CD8^+$ T cells was optimal at 0.3 to 0.5%, which was 2.5 to 4 times or more that of the Shingrix® positive control vaccine and approximately 1.5 to 3 times that of YK-VZV-007;

the results were significantly higher than those of the comparative examples (YK-VZV-004, YK-VZV-006, YK-VZV-045, and YK-VZV-007).

4. To validate the above results, the VZV binding-gE antibody IgG titer in the serum of immunized mice on day 56 was further measured for validation based on the test results on day 42.

The results showed that on day 56 after the mice were immunized with mRNA vaccines including YK-VZV-009, YK-VZV-010, YK-VZV-011, YK-VZV-013, YK-VZV-020, YK-VZV-014, YK-VZV-012, YK-VZV-018, YK-VZV-021, YK-VZV-024, YK-VZV-028, YK-VZV-030, YK-VZV-031, and YK-VZV-038, the gE-specific antibody IgG titers of these vaccines were superior to the Shingrix® positive control, being approximately 1.8 to 5.0 times that of the Shingrix® vaccine;

specifically, the antibody GMT of YK-VZV-011, YK-VZV-013, YK-VZV-020, YK-VZV-018, and YK-VZV-010 could reach $650\times10^4$ or more, being 4.0 to 5.0 times or more that of the Shingrix® vaccine and 2 times or more that of YK-VZV-007 (Comparative Example 4); moreover, the results were significantly better than those of YK-VZV-004 (Comparative Example 1) and YK-VZV-045 (Comparative Example 3).

5. Through the comprehensive analysis of IgG and multiparameter flow cytometry results, a total of 5 optimal antigen sequences (including YK-VZV-010, YK-VZV-013, YK-VZV-011, YK-VZV-020, and YK-VZV-018) were screened out and further validated by ELISPOT, and the results are as follows:

(i) The amount of cytokine IFN-γ secreted by T cells stimulated by the mRNA vaccine was 500 SFU or more, with a maximum close to 600 SFU, which was approximately 16 to 19 times that of the Shingrix® positive control and 2.5 to 3.0 times that of Comparative Example 4 (YK-VZV-007); and which was significantly better than that of the cytokine secreted and stimulated by the mRNA vaccine corresponding to Comparative Example 1 (YK-VZV-004), Comparative Example 2 (YK-VZV-006), or Comparative Example 3 (YK-VZV-045).

Specifically, the mRNA vaccine prepared from the YK-VZV-010 sequence reached a maximum of 598.8 SFU, which was 18.7 times that of the Shingrix® positive control and nearly 3 times that of the YK-VZV-007 control.

The IFN-γ secretion levels from high to low were YK-VZV-010, YK-VZV-011, YK-VZV-018, YK-VZV-020, and YK-VZV-013, with no significant difference between the groups, indicating a good and significant immune effect.

(ii) The amount of cytokine IL-2 secreted by T cells stimulated by the mRNA vaccine was 400 to 600 SFU or more, which was 10 to 16 times that of the Shingrix® positive control and 2.0 to 3.0 times that of the YK-VZV-007 control; and which was significantly better than that of the cytokine secreted and stimulated by the mRNA vaccine corresponding to Comparative Example 1 (YK-VZV-004), Comparative Example 2 (YK-VZV-006), or Comparative Example 3 (YK-VZV-045).

Specifically, the mRNA vaccine prepared from the YK-VZV-010 sequence reached a maximum of 614.5 SFU, which was 16.0 times that of the Shingrix® positive control and 3 times or more that of the YK-VZV-007 control.

The IL-2 secretion levels from high to low were YK-VZV-010, YK-VZV-011, YK-VZV-018, YK-VZV-013, and YK-VZV-020, with no significant difference between the groups, indicating a good and significant immune effect.

6. In addition, the antigen localization results of the above five sequences indicated their localization in the Golgi apparatus, cell membrane, or cytoplasm.

DETAILED DESCRIPTION OF THE PREFERRED EMBODIMENT

Figure 1:
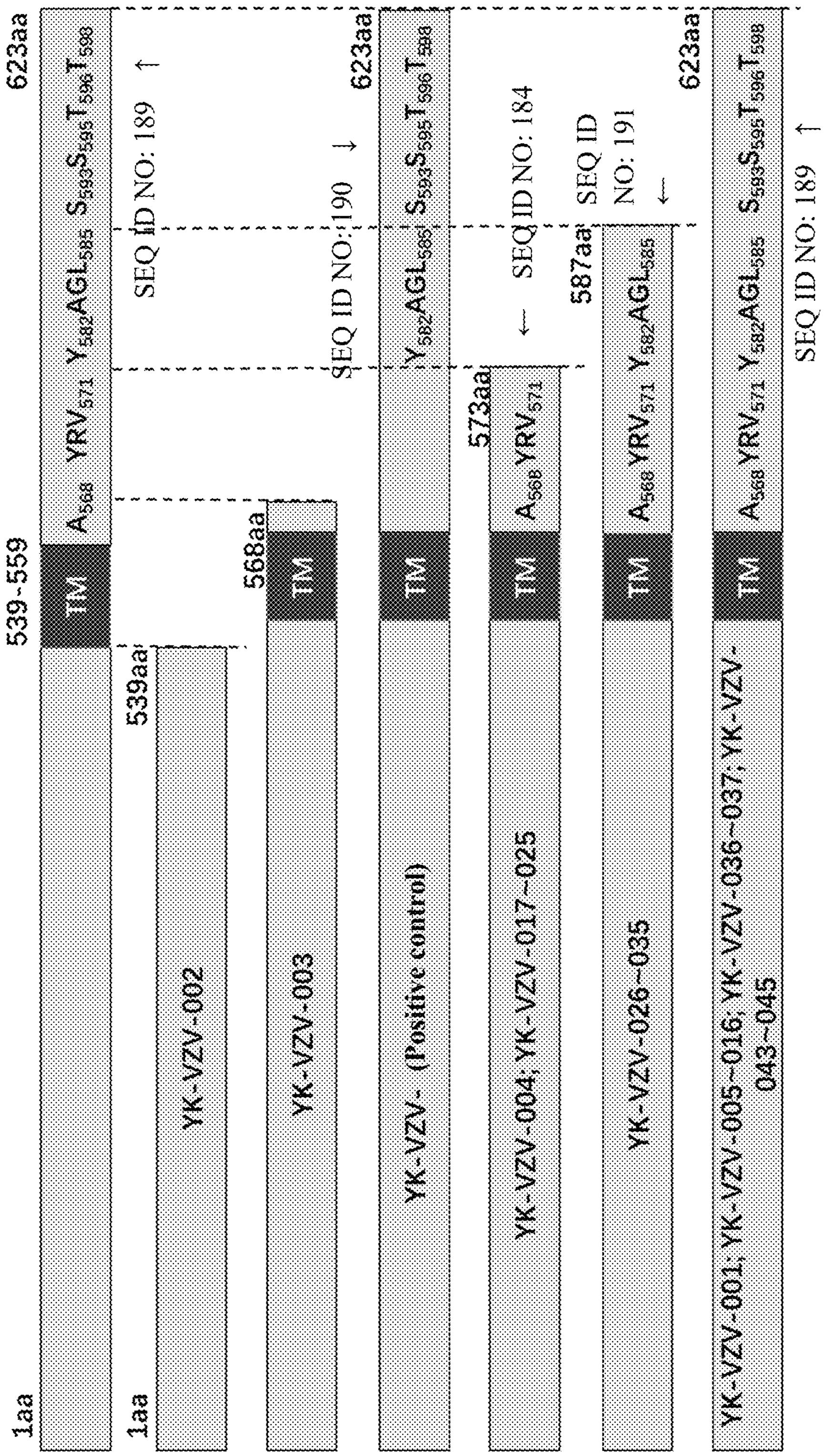
FIG. 1 shows the main functional domains of VZV gE protein and a series of deletion mutants.

The present disclosure is further described below by way of examples. It should be understood that the examples of the present disclosure are given only for illustrating the present disclosure and are not intended to limit the present disclosure, and any simple improvements to the present disclosure under the premise of the technical solution of the present disclosure are within the scope of protection of the present disclosure.

As used herein, the term "selected from" means selecting any one or any combination of two or three or more of the listed objects or elements.

It should be understood that the term "a compound" as used herein may include the compound, an N-oxide thereof, a solvate thereof, a pharmaceutically acceptable salt thereof, a stereoisomer thereof, and a mixture thereof.

Antigen sequence design: Antigens are proteins capable of inducing an immune response (e.g., causing an immune system to produce antibodies against the antigens). As used herein, the term "antigen" is used to encompass immunogenic proteins and immunogenic fragments (an immunogenic fragment that induces or is capable of inducing an immune response) to a varicella-zoster virus (e.g., VZV), unless otherwise stated. It should be understood that the term "protein" encompasses peptides and the term "antigen" encompasses antigenic fragments. Exemplary sequences of the VZV antigens and the RNA encoding the VZV antigens of the composition of the present disclosure are provided in Table 1.

Nucleic acids: Nucleic acids comprise a polymer of nucleotides (nucleotide monomers). The composition of the present disclosure comprises an RNA having an open reading frame (ORF) encoding a VZV antigen. In some embodiments, the RNA is a messenger RNA (mRNA). In some embodiments, the RNA (e.g., mRNA) further comprises a 5' UTR, a 3' UTR, a poly(A) tail, and/or a 5' cap analog.

Messenger RNA (mRNA) is any RNA that encodes (at least one) protein (a naturally occurring, non-naturally occurring, or modified polymer of amino acids) and can be translated to produce the encoded protein in vitro, in vivo, in situ, or ex vivo. Those skilled will appreciate that, unless otherwise stated, the nucleic acid sequences set forth in the present disclosure may recite a "T" in a representative DNA sequence but where the sequence represents RNA (e.g., mRNA), the "T" will be substituted for a "U". Accordingly, any DNA disclosed and identified herein by a particular sequence identification number also disclose a corresponding RNA (e.g., mRNA) sequence that is complementary to the DNA, in which each "T" of the DNA sequence is substituted by a "U".

An open reading frame (ORF) is a continuous stretch of DNA or RNA beginning with a start codon (e.g., methionine (ATG)) and ending with a stop codon (e.g., TAA, TAG, or TGA, or UAA or UAG). An ORF typically encodes a protein. It should be understood that the sequences disclosed herein may further comprise additional elements, such as 5' and 3' UTRs.

Variant RNA: Antigen variants or other polypeptide variants refers to molecules that differ in their amino acid sequence from a wild-type, native, or reference sequence. The antigen/polypeptide variants may have substitutions, deletions, and/or insertions at certain positions within the amino acid sequence, as compared to a native or reference sequence. Typically, the variants have at least 50% identity with a wild-type, native, or reference sequence. In some embodiments, the variants share at least 80% or at least 90% identity with a wild-type, native, or reference sequence.

In some embodiments, a composition comprises an RNA or an RNA ORF comprising a nucleotide sequence of any one of the sequences provided herein (see, e.g., Sequence Listing and Table 1), or comprising a nucleotide sequence that has at least 80%, at least 85%, at least 90%, at least 95%, at least 96%, at least 97%, at least 98%, or at least 99% identity with a nucleotide sequence of any one of the sequences provided herein.

The term "identity" refers to a relationship between the sequences of two or more polypeptides (e.g., antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithm"). The identity of related antigens or nucleic acids can be readily calculated by known methods. "Percent identity (%)", when applied to a polypeptide or polynucleotide sequence, is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps (if necessary), to achieve the maximum percent identity. Methods and computer programs for alignment are well known in the art. It should be understood that identity depends on a calculation of percent identity but may differ in value due to gaps and penalties introduced in the calculation. Generally, variants of a particular polynucleotide or polypeptide (e.g., antigen) have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity with the particular reference polynucleotide or polypeptide as determined by sequence alignment programs and parameters described herein and known to those skilled in the art. Such tools for alignment include those of the BLAST suite (Stephen F. Altsch, et al. (1997), "Gapped BLAST and PSI-BLAST: a new generation of protein database search programs", Nucleic Acids Res. 25: 3389-3402).

As such, polynucleotides encoding peptides or polypeptides containing substitutions, insertions and/or additions, and deletions with respect to reference sequences, particularly the antigen sequences disclosed herein, are included within the scope of the present disclosure. Amino acid residues located in the carboxy- and amino-terminal regions of the amino acid sequence of a peptide or protein may optionally be deleted to provide a truncated sequence. According to the structure and use of the sequence, gE proteins have a number of important domains related to their primary functions (see FIG. 1). gE proteins have a number of important domains related to their primary functions (see FIG. 3). (1) TM transmembrane domain, which consists of amino acids 539 to 559; (2) $A_{568}YRV_{571}$, which mediates gE transport between the endoplasmic reticulum (ER), trans Golgi network (TGN), and endosomes; (3) $Y_{582}AGL_{585}$, which mediates gE transport between the endoplasmic reticulum (ER), trans Golgi network (TGN), and endosomes; (4) $S_{593}ES_{595}T_{596}DT_{598}$, which is an important glycosylation site and mediates gE transport between the endoplasmic reticulum (ER), trans Golgi network (TGN), and endosomes. In some embodiments, important structural sites can be removed and replaced with appropriate residues, thereby altering the transport and expression of the antigen to enhance the immunogenicity of the antigen. Such sequences can be readily identified by those skilled in the art. It should also be understood that some of the sequences provided herein contain sequence tags or terminal peptide sequences (e.g., at the N-terminus or C-terminus) that can be deleted, for example, prior to use in the preparation of an RNA (e.g., mRNA) vaccine.

As recognized by those skilled in the art, protein fragments, functional protein domains, and homologous proteins are also considered to be within the scope of varicella-zoster virus antigens of interest. For example, provided herein is any protein fragment of a reference protein (meaning a polypeptide sequence that is at least one amino acid residue shorter than a reference antigen sequence but otherwise identical), provided that the fragment is immunogenic and confers a protective immune response against the varicella-zoster virus. In addition to variants that are identical to a reference protein but are truncated, in some embodiments, the antigen comprises 2, 3, 4, 5, 6, 7, 8, 9, 10, or more site mutations, as shown in any one of the sequences provided or referenced herein. Antigens/antigenic polypeptides may range in length from approximately 4, 6, or 8 amino acids to full-length proteins.

VZV antigen variants: The present disclosure includes a variant VZV antigenic polypeptide. In some embodiments, the variant VZV antigenic polypeptide is a variant VZV gE polypeptide. The variant VZV gE polypeptide is designed to avoid ER/Golgi retention of the polypeptide, leading to increased surface expression of the antigen. In some embodiments, the variant gE polypeptide is truncated to remove an ER retention portion or a cytoplasmic tail portion of the polypeptide. In some embodiments, the variant VZV gE polypeptide is mutated to reduce the localization of the VZV polypeptide to the ER/Golgi/TGN. Such modifications inhibit ER trapping and therefore accelerate transport to the cell membrane. Thus, in some embodiments, the VZV glycoprotein is a variant gE polypeptide. VZV gE has a targeting sequence for the TGN at its C-terminus and is transported from the ER to the TGN in infected and gE-transfected cells. Most gE in the TGN appears to be retrieved from the plasma membrane by endocytosis and delivered from endosomes to the TGN, followed by recycling to the plasma membrane. gE is accumulated in the TGN, along with other VZV proteins (e.g., tegument proteins) associated with the production of fully enveloped VZV virions. Thus, mutations to reduce TGN localization and endocytosis contribute to the transport of gE to the cell membrane. The variant VZV gE polypeptide may be any truncated polypeptide lacking an anchor domain (ER retention domain). For example, the variant VZV gE polypeptide may be a truncated VZV gE polypeptide comprising at least amino acids 1 to 124, such as amino acids 1 to 124, 1 to 140, 1 to 160, 1 to 200, 1 to 250, 1 to 300, 1 to 350, 1 to 360, 1 to 400, 1 to 450, 1 to 500, 1 to 511, 1 to 550, and 1 to 561, as well as a polypeptide fragment having fragment sizes within the recited size ranges. In some embodiments, the variant VZV gE polypeptide is a truncated polypeptide lacking a carboxy-terminal tail domain. Thus, in some embodiments, the truncated VZV gE polypeptide comprises amino acids 1 to 573 of SEQ ID NO: 59. In some embodiments, the variant VZV gE polypeptide has at least one mutation in one or more motifs associated with ER retention, wherein the mutation in one or more motifs results in decreased retention of the VZV gE polypeptide in the ER and/or Golgi. In some embodiments, the variant VZV gE polypeptide has at least one mutation in one or more phosphorylated acidic motifs. For example, the variant VZV gE polypeptide may be a full-length VZV gE polypeptide having a Y582G mutation, a Y569K mutation, or both a Y582G mutation and a Y569K mutation. Alternatively, the variant VZV gE polypeptide may be an antigenic fragment comprising, for example, amino acids 1 to 573 of VZV gE and having a Y569K mutation. Alternatively, the variant VZV gE polypeptide may be an antigenic fragment having a mutation in a phosphorylated acidic motif (e.g., SSTT motif, SEQ ID NO: 188). For example, the variant VZV gE polypeptide may be an antigenic fragment having an AEAADA sequence (SEQ ID NO: 183).

Naturally occurring eukaryotic mRNA molecules may contain stabilizing elements, including, but not limited to, an untranslated region (UTR) at their 5' end (5' UTR) and/or at their 3' end (3' UTR), in addition to other structural features, such as a 5'-cap structure or a 3'-poly(A) tail. Both the 5' UTR and the 3' UTR are typically transcribed from genomic DNA and are elements of premature mRNA. Characteristic structural features of mature mRNA (e.g., the 5'-cap and the 3'-poly(A) tail) are typically added to the transcribed (premature) mRNA during mRNA processing.

In some embodiments, the composition comprises an RNA polynucleotide having an open reading frame encoding at least one antigenic polypeptide having at least one modification, and at least one 5' terminal cap, and is formulated within a lipid nanoparticle. 5'-capping of polynucleotides can be accomplished simultaneously during an in vitro transcription reaction using a chemical RNA cap analog to generate a 5'-guanosine cap structure according to manufacturer's protocols. In some instances, 5'-capping of modified RNA can also be accomplished post-transcriptionally using a vaccinia virus capping enzyme to generate a "cap" structure. Cap 1 structure can be generated using a vaccinia virus capping enzyme and a 2'-O methyl-transferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-O methyl-transferase. Enzymes can be derived from recombinant sources. The 3'-poly(A) tail is typically a stretch of adenine nucleotides added to the 3' end of the transcribed mRNA. In some instances, it may comprise up to approximately 400 adenine nucleotides. In some embodiments, the length of the 3'-poly(A) tail may be an essential element with respect to the stability of the individual mRNA.

Chemical modification: In some embodiments, the composition of the present disclosure comprises an RNA having an open reading frame encoding a VZV antigen, wherein the nucleic acid comprises nucleotides and/or nucleosides that may be standard (unmodified) or modified as known in the art. In some embodiments, the nucleotides and nucleosides of the present disclosure comprise modified nucleotides or nucleosides. Such modified nucleotides and nucleosides may be naturally occurring modified nucleotides and nucleosides or non-naturally occurring modified nucleotides and nucleosides. Such modifications may include those at the sugar, backbone, or nucleobase portions of the nucleotides and/or nucleosides as recognized in the art.

In some embodiments, the naturally occurring modified nucleotides or nucleosides of the present disclosure are nucleotides or nucleosides as generally known or recognized in the art. Non-limiting examples of such naturally occurring modified nucleotides and nucleosides can be found particularly in the widely recognized MODOMICS database.

In some embodiments, the non-naturally occurring modified nucleotides or nucleosides of the present disclosure are nucleotides or nucleosides as generally known or recognized in the art. Non-limiting examples of such non-naturally occurring modified nucleotides and nucleosides can be found particularly in published U.S. Application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367, all of which are incorporated herein by reference.

Thus, the nucleic acids of the disclosure (e.g., DNA nucleic acids and RNA nucleic acids, such as mRNA nucleic acids) may comprise standard nucleotides and nucleosides, naturally occurring nucleotides and nucleosides, non-naturally occurring nucleotides and nucleosides, or any combination thereof.

In some embodiments, the nucleic acids of the disclosure (e.g., DNA nucleic acids and RNA nucleic acids, such as mRNA nucleic acids) comprise a plurality (more than one) of different types of standard and/or modified nucleotides and nucleosides. In some embodiments, a particular region of the nucleic acid contains one, two, or more (optionally different) types of standard and/or modified nucleotides and nucleosides.

In some embodiments, a modified RNA nucleic acid (e.g., a modified mRNA nucleic acid), introduced into a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively, relative to an unmodified nucleic acid comprising standard nucleotides and nucleosides.

In some embodiments, the nucleic acids (e.g., RNA nucleic acids, such as mRNA nucleic acids) comprise non-naturally modified nucleotides that are introduced during synthesis or post-synthesis of the nucleic acids to achieve desired functions or properties. The modification may be present on internucleotide linkages, purine or pyrimidine bases, or sugars. The modification can be chemically synthesized or introduced by a polymerase at the terminal of a chain or anywhere else in the chain. Any region of a nucleic acid can be chemically modified.

The present disclosure provides modified nucleosides and nucleotides of a nucleic acid (e.g., RNA nucleic acids, such as mRNA nucleic acids). A "nucleoside" refers to a compound containing a sugar molecule (e.g., pentose or ribose) or a derivative thereof in combination with an organic base (e.g., purine or pyrimidine) or a derivative thereof (also referred to herein as "nucleobase"). A "nucleotide" refers to a nucleoside that includes a phosphate group. Modified nucleotides can by synthesized by any useful method, such as chemical, enzymatic, or recombinant methods, to include one or more modified or non-natural nucleosides. The nucleic acid may comprise one or more regions of linked nucleosides. Such regions may have variable backbone linkages. The linkage may be a standard phosphodiester linkage, in which case the nucleic acid would comprise a region of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, for example, in those nucleic acids having at least one chemical modification. One example of such non-standard base pairing is the base pairing between the modified nucleotide inosine and adenine, cytosine, or uracil. Any combination of base/sugar or linker can be incorporated into the nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, polyribonucleotides comprise a combination of at least two (e.g., 2, 3, 4, or more) of any of the aforementioned modified nucleobases, including, but not limited to, chemical modifications.

In some embodiments, the mRNA of the present disclosure comprises a 1-methyl-pseudouridine (m1ψ) substitution at one or more or all uridine positions of the nucleic acid.

In some embodiments, the mRNA of the present disclosure comprises a 1-methyl-pseudouridine (m1ψ) substitution at one or more or all uridine positions of the nucleic acid and a 5-methyl cytidine substitution at one or more or all cytidine positions of the nucleic acid.

In some embodiments, the mRNA of the present disclosure comprises a pseudouridine (ψ) substitution at one or more or all uridine positions of the nucleic acid.

In some embodiments, the mRNA is uniformly modified (e.g., fully modified, modified throughout the sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue, such as those set forth above.

The nucleic acid may contain from approximately 1% to approximately 100% modified nucleotides (relative to overall nucleotide content, or relative to one or more types of nucleotides, i.e., any one or more of A, G, U, or C) or any intervening percentage (e.g., 1% to 20%, 1% to 25%, 1% to 50%, 1% to 60%, 1% to 70%, 1% to 80%, 1% to 90%, 1% to 95%, 10% to 20%, 10% to 25%, 10% to 50%, 10% to 60%, 10% to 70%, 10% to 80%, 10% to 90%, 10% to 95%, 10% to 100%, 20% to 25%, 20% to 50%, 20% to 60%, 20% to 70%, 20% to 80%, 20% to 90%, 20% to 95%, 20% to 100%, 50% to 60%, 50% to 70%, 50% to 80%, 50% to 90%, 50% to 95%, 50% to 100%, 70% to 80%, 70% to 90%, 70% to 95%, 70% to 100%, 80% to 90%, 80% to 95%, 80% to 100%, 90% to 95%, 90% to 100%, and 95% to 100%). It should be understood that any remaining percentage is accounted for by the presence of unmodified A, G, U, or C.

The mRNA may contain at minimum 1% and at maximum 100% modified nucleotides or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acid may contain a modified pyrimidine, such as a modified uracil or cytosine. In some embodiments, at least 5%, at least 10%, at least 25%, at least 50%, at least 80%, at least 90%, or 100% of the uracil in the nucleic acid is replaced by a modified uracil (e.g., a 5-substituted uracil). The modified uracil can be replaced by a compound having a single unique structure, or can be replaced by a plurality of compounds having different structures (e.g., 2, 3, 4, or more unique structures). In some embodiments, at least 5%, at least 10%, at least 25%, at least 50%, at least 80%, at least 90%, or 100% of the cytosine in the nucleic acid is replaced by a modified cytosine (e.g., a 5-substituted cytosine). The modified cytosine can be replaced by a compound having a single unique structure, or can be replaced by a plurality of compounds having different structures (e.g., 2, 3, 4, or more unique structures).

Untranslated region (UTR): The mRNA of the present disclosure may comprise one or more regions or portions which act or function as an untranslated region. When the mRNA is designed to encode at least one antigen of interest, the nucleic acid may comprise one or more of these untranslated regions (UTRs). A wild-type untranslated region of the nucleic acid is transcribed but not translated. In mRNA, the 5' UTR starts at the transcription start site and continues to but not including the start codon; whereas the 3' UTR starts immediately following the stop codon and continues until the transcription termination signal. There is growing evidence for the regulatory role of the UTR in the stability and translation of nucleic acid molecules. The regulatory features of the UTR can be incorporated into the polynucleotides of the present disclosure to particularly enhance the stability of the molecule. The specific features can also be incorporated to ensure controlled down-regulation of transcripts in case they are misdirected to undesired organ sites. A variety of 5' UTR and 3' UTR sequences are known and available in the art.

In some embodiments of the present disclosure, the 5' UTR is a heterologous UTR, i.e., is a UTR found in nature associated with a different ORF. In another embodiment, the 5' UTR is a synthetic UTR, i.e., does not occur in nature. The synthetic UTR includes UTRs that have been mutated to improve their properties, such as UTRs that increase gene expression as well as fully synthetic UTRs. Exemplary 5' UTRs include *Xenopus* or human α-globin or β-globin (U.S. Pat. Nos. 8,278,063; 9,012,219), human cytochrome b-245a polypeptide, hydroxysteroid (17b) dehydrogenase, and tobacco etch virus (U.S. Pat. Nos. 8,278,063, 9,012,219).

In some embodiments, the 5' UTR of the present disclosure comprises a sequence selected from SEQ ID NO: 173 to 174.

In some preferred embodiments, the 5' UTR of the present disclosure comprises a sequence selected from SEQ ID NO: 174.

The 3' UTR is a region of an mRNA that is directly downstream (3') from the stop codon (the codon of an mRNA transcript that signals a termination of translation). The 3' UTR does not encode a protein (which is non-coding). Native or wild-type 3' UTRs are known to have stretches of adenosine (A) and uridine (U) embedded in them. These AU-rich elements are particularly prevalent in genes with high rates of turnover.

The introduction, removal, or modification of 3' UTR AU-rich elements (AREs) can be used to modulate the stability of the nucleic acids (e.g., RNA) of the present disclosure. When engineering a specific nucleic acid, one or more copies of an ARE can be introduced to make the nucleic acids of the present disclosure less stable, thereby reducing translation and decreasing the production of the resulting protein. Likewise, AREs can be identified and removed or mutated to increase the intracellular stability, thereby increasing translation and production of the resulting protein.

The 3' UTR may be heterologous or synthetic. With respect to 3' UTRs, globin UTRs (including *Xenopus* β-globin UTRs and human β-globin UTRs) are known in the art (U.S. Pat. Nos. 8,278,063, 9,012,219, US20110086907). A nucleic acid (e.g., mRNA) encoding a modified β-globin with enhanced stability in some cell types has been developed by cloning two sequential human 3-globin 3' UTRs head to tail and is well known in the art (US2012/0195936, WO2014/071963).

In some embodiments, the 3' UTR of the present disclosure comprises a sequence selected from SEQ ID NO: 175.

Those of ordinary skill in the art will understand that 5' UTRs that are heterologous or synthetic may be used with any desired 3' UTR sequence. For example, a heterologous 5' UTR may be used with a synthetic 3' UTR or a heterologous 3' UTR.

It should be understood that any UTR from any gene may be incorporated into a region of a nucleic acid. Furthermore, multiple wild-type UTRs of any known gene may be utilized. It is also within the scope of the present disclosure to provide artificial UTRs which are not variants of the wild-type region. These UTRs or portions thereof may be placed in the same orientation as in the transcript from which they are selected, or may be altered in orientation or location. Thus, a 5' or 3' UTR may be inverted, shortened, lengthened, or prepared with one or more other 5' UTRs or 3' UTRs. As used herein, the term “altered” as it relates to a UTR sequence, means that the UTR has been changed in some way relative to a reference sequence. For example, a 3' UTR or 5' UTR may be altered relative to a wild-type or native UTR by the change in orientation or location as taught above, or may be altered by the inclusion of additional nucleotides, deletion of nucleotides, exchange or transposition of nucleotides. Any of these changes producing an “altered” UTR (whether 3' or 5') comprises a variant UTR.

In vitro transcription of RNA: cDNA encoding the polynucleotides described herein may be transcribed using an in vitro transcription (IVT) system. In some embodiments, the RNA transcript is generated in an in vitro transcription reaction using a non-amplified, linearized DNA template to generate the RNA transcript. In some embodiments, the template DNA is isolated DNA. In some embodiments, the template DNA is cDNA. In some embodiments, the cDNA is formed by digestion of circular plasmid DNA. In some embodiments, cells, such as bacterial cells, such as *E. coli* cells, such as DH-1 cells are transfected with a plasmid DNA template. In some embodiments, the transfected cells are cultured to replicate the plasmid DNA, which is then isolated and purified. In some embodiments, the DNA template comprises an RNA polymerase promoter, such as a T7 promoter located 5' to and operably linked to the target gene.

In some embodiments, an in vitro transcription template encodes a 5' untranslated region (UTR), contains an open reading frame, and encodes a 3' UTR and a poly(A) tail. The specific nucleic acid sequence composition and length of the in vitro transcription template will depend on the mRNA encoded by the template.

“5' untranslated region” (UTR) refers to a region of an mRNA that is directly upstream (i.e., 5') from the start codon (i.e., the first codon of an mRNA transcript translated by a ribosome) that does not encode a polypeptide. When generating RNA transcripts, the 5' UTR may comprise a promoter sequence. Such promoter sequences are known in the art. It should be understood that such promoter sequences will not be present in the vaccine of the present disclosure.

“3' untranslated region” (UTR) refers to a region of an mRNA that is directly downstream (i.e., 3') from the stop codon (i.e., the codon of an mRNA transcript that signals a termination of translation) that does not encode a polypeptide.

An “open reading frame” is a continuous stretch of DNA beginning with a start codon (e.g., methionine (ATG)) and ending with a stop codon (e.g., TAA, TAG, or TGA), and encodes a polypeptide.

A “poly(A) tail” is a region of an mRNA that is downstream, such as directly downstream (i.e., 3') from the 3' UTR that contains multiple consecutive adenosine monophosphates. The poly(A) tail may contain 10 to 300 adenosine monophosphates. For example, the poly(A) tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 adenosine monophosphates. In some embodiments, the poly(A) tail contains 50 to 250 adenosine monophosphates. In a relevant biological context (e.g., in cells, in vivo), the poly(A) tail functions to protect an mRNA from enzymatic degradation, e.g., in the cytoplasm, and aids in transcription termination, and/or export of the mRNA from the nucleus and translation.

In some embodiments, the nucleic acid comprises 200 to 3000 nucleotides. For example, the nucleic acid may comprise 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides.

The in vitro transcription system typically comprises a transcription buffer, a nucleotide triphosphate (NTP), an RNase inhibitor, an inorganic pyrophosphate, and a polymerase.

The NTP may be manufactured internally, may be selected from a supplier, or may be synthesized as described herein. The NTP may be selected from, but is not limited to, those described herein including natural and non-natural (modified) NTPs.

Any number of RNA polymerases or variants may be used in the method of the present disclosure. The polymerase may be selected from, but is not limited to, a phage RNA polymerase, such as a T7 RNA polymerase, a T3 RNA polymerase, a SP6 RNA polymerase, and/or a mutant polymerase such as, but not limited to, polymerases capable of incorporating modified nucleic acids and/or modified nucleotides (including chemically modified nucleic acids and/or nucleotides). Some embodiments exclude the use of DNase.

In some embodiments, the RNA transcript can be capped by enzymatic capping or co-transcriptional capping reactions. In some embodiments, the RNA comprises a 5' terminal cap, such as 7mG(5')ppp(5')NlmpNp.

Purification of mRNA: Purification of the nucleic acids described herein may include, but is not limited to, nucleic acid purification, quality assurance, and quality control. Purification may be performed by methods known in the art such as, but not limited to, lithium chloride precipitation, beads (Beckman Coulter Genomics, Danvers, MA), poly-T beads, LNA™ oligo-T capture probes (corporation, Vedbaek, Denmark), or HPLC-based purification methods such as, but not limited to, strong anion-exchange HPLC, weak anion-exchange HPLC, reverse-phase HPLC (RP-HPLC), and hydrophobic interaction HPLC (HIC-HPLC). The term “purified” when used in relation to a nucleic acid such as a “purified nucleic acid” refers to one that is separated from at least one contaminant. A “contaminant” is any substance that makes another substance unfit, impure, or inferior. Thus, the purified nucleic acid (e.g., DNA and RNA) is present in a form or environment different from that in which it is found in nature, or a form or environment different from that in which it was present prior to being subjected to a processing or purification method.

Quality assurance and/or quality control check may be performed using methods such as, but not limited to, gel electrophoresis, UV absorbance, or analytical HPLC.

Quantification: In some embodiments, the nucleic acid may be quantified using methods such as, but not limited to, ultraviolet-visible spectroscopy (UV/Vis). Anon-limiting example of a UV/Vis spectrometer is a spectrometer (Thermo Fisher, Waltham, MA). The quantified nucleic acid may be analyzed in order to determine if the nucleic acid may be of appropriate size and to check that no degradation of the nucleic acid has occurred. Degradation of the nucleic acid may be checked by methods such as, but not limited to, agarose gel electrophoresis; HPLC-based purification methods such as, but not limited to, strong anion-exchange HPLC, weak anion-exchange HPLC, reverse-phase HPLC (RP-HPLC), and hydrophobic interaction HPLC (HIC-HPLC); liquid chromatography-mass spectrometry (LCMS), capillary electrophoresis (CE), and capillary gel electrophoresis (CGE).

Lipid nanoparticle (LNP): In some embodiments, the RNA (e.g., mRNA) of the present disclosure is formulated in a lipid nanoparticle (LNP). The lipid nanoparticle typically comprises an ionizable cationic lipid, a non-cationic lipid, a sterol, a PEG lipid component, and a nucleic acid cargo of interest. The lipid nanoparticles of the present disclosure can be generated using components, compositions, and methods commonly known in the art, see for example CN116535381B, TW202340136A, CN116178193B, CN116178193B, CN115784921B, CN115745820B, CN115677518B, CN114957027B, CN114044741B, CN116854754A, CN116785265A, CN116789764A, CN116396178A, CN116375592A, and CN116082275A, all of which are incorporated herein by reference in their entirety.

As used herein, the term "cationic lipid" refers to a lipid that is positively charged at a selected pH value. Cationic lipids are prone to bind to negatively charged nucleic acids, i.e., to form lipid nanoparticles (LNPs) by interacting with negatively charged phosphate groups present in nucleic acids through electrostatic forces. LNP is currently one of the mainstream delivery carriers.

As used herein, the term "neutral lipid" refers to an auxiliary lipid that is uncharged or exists in a zwitterionic form at a selected pH value. The neutral lipid may regulate the flow of nanoparticles into a lipid bilayer structure and improve efficiency by promoting lipid phase transition, and may also affect target organ specificity.

As used herein, a "structural lipid" refers to a lipid that enhances the stability of nanoparticles by filling the gaps between lipids. The structural lipid may be selected from, but is not limited to, the group consisting of cholesterol, nonsterol, sitosterol, ergosterol, campesterol, stigmasterol, brassinosterol, tomatine, ursolic acid, α-tocopherol, corticosteroid, and mixtures thereof. In some embodiments, the structural lipid is cholesterol. In some embodiments, the structural lipid includes cholesterol, corticosteroid (e.g., prednisolone, dexamethasone, prednisone, and hydrocortisone), or any combination thereof.

In some embodiments, the molar ratio of the cationic lipid to the structural lipid is about 1:1 to 5:1, for example, about 1.0:1, 1.1:1, 1.2:1, 1.3:1, 1.4:1, 1.5:1, 1.6:1, 1.7:1, 1.8:1, 1.9:1, or 2.0:1.

In some embodiments, the molar ratio of the cationic lipid to the neutral lipid is about (1 to 10):1, for example, about 1:1, 2:1, 3:1, 4:1, 5:1, 6:1, 7:1, 8:1, 9:1, or 10:1.

In some embodiments, the molar ratio of the cationic lipid to the structural lipid is about (1 to 5):1, for example, about 1:1, 2:1, 3:1, 4:1, or 5:1.

In some embodiments, the molar ratio of the cationic lipid, the neutral lipid, the structural lipid, and the polymer-conjugated lipid is (25 to 65):(5 to 25):(25 to 45):(0.5 to 5). For example, in some embodiments, by proportion (relative number of moles), the cationic lipid is 25 parts, 30 parts, 35 parts, 40 parts, 45 parts, 50 parts, 55 parts, 60 parts, or 65 parts; the neutral lipid is 5 parts, 10 parts, 15 parts, 20 parts, or 25 parts; the structural lipid is 25 parts, 30 parts, 35 parts, 40 parts, or 45 parts; the polymer-conjugated lipid is 0.5 parts, 1 part, 1.5 parts, 2 parts, 2.5 parts, 3.0 parts, 3.5 parts, 4.0 parts, 4.5 parts, or 5.0 parts.

In some embodiments, the molar ratio of the cationic lipid, the neutral lipid, the structural lipid, and the polymer-conjugated lipid is (49 to 50):10:(38.5 to 39.5):1. For example, in some embodiments, by proportion (relative number of moles), the cationic lipid is 49 parts or 50 parts; the neutral lipid is 10 parts; the structural lipid is 38.5 parts, 39.0 parts, or 39.5 parts; the polymer-conjugated lipid is 1 part; such as 50:10:38.5:1.5 or 49:10:39.5:1.5.

As used herein, the term "polymer-conjugated lipid" refers to a lipid modified with polyethylene glycol (PEG). Hydrophilic PEG stabilizes LNPs, regulates nanoparticle size by limiting lipid fusion, and increases nanoparticle half-life by reducing non-specific interactions with macrophages. In some embodiments, the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, or PEG-modified dialkylglycerol. The molecular weight of PEG for the PEG modification is usually 350 to 5000 Da. For example, the polymer-conjugated lipid is selected from one or more of distearoyl phosphatidylethanolamine polyethylene glycol 2000 (DSPE-PEG2000), dimyristoylglycero-3-methoxypolyethylene glycol 2000 (DMG-PEG2000), or methoxypolyethylene glycol ditetradecylacetamide (ALC-0159).

In one embodiment of the compositions/carriers of the present disclosure, the polymer-conjugated lipid is DMG-PEG2000.

In one embodiment of the compositions/carriers of the present disclosure, the carrier comprises a neutral lipid, a structural lipid, and a polymer-conjugated lipid, wherein the molar ratio of the cationic lipid, the neutral lipid, the structural lipid, and the polymer-conjugated lipid is (25 to 65):(5 to 25):(25 to 45):(0.5 to 5), such as (45 to 55):(9 to 11):(34 to 43):(0.5 to 2.5).

In one embodiment of the compositions/carriers of the present disclosure, the carrier comprises a neutral lipid, a structural lipid, and a polymer-conjugated lipid, wherein the molar ratio of the cationic lipid, the neutral lipid, the structural lipid, and the polymer-conjugated lipid is 50:10:38.5:1.5.

As used herein, the term "alkyl" is meant to include branched and linear saturated aliphatic monovalent hydrocarbon groups having a specified number of carbon atoms. As used herein, the term "alkylene" is meant to include branched and linear saturated aliphatic divalent hydrocarbon groups having a specified number of carbon atoms. $C_{n-m}$ refers to a group having n to m carbon atoms. For example, $C_{2-5}$ alkylene includes $C_2$ alkylene, $C_3$ alkylene, $C_4$ alkylene, and $C_5$ alkylene. $C_{2-8}$ alkylene includes $C_2$ alkylene, $C_3$ alkylene, $C_4$ alkylene, $C_5$ alkylene, $C_6$ alkylene, $C_7$ alkylene, and $C_8$ alkylene. $C_{1-6}$ alkylene includes $C_1$ alkylene, $C_2$ alkylene, $C_3$ alkylene, $C_4$ alkylene, $C_5$ alkylene, and $C_6$ alkylene. $C_{1-3}$ alkylene includes $C_1$ alkylene, $C_2$ alkylene, and $C_3$ alkylene. $C_{6-15}$ linear alkyl includes a linear alkyl group having 6, 7, 8, 9, 10, 11, 12, 13, 14, or 15 carbon atoms. $C_{12-25}$ branched alkyl includes a branched alkyl group having 12, 13, 14, 15, 16, 17, 18, 19, 20, 21, 22, 23, 24, or 25 carbon atoms. An alkyl (or alkylene) group can be unsubstituted, or an alkyl (or alkylene) group can be substituted in which at least one hydrogen is replaced by another chemical group.

As used herein, a "therapeutically effective amount" is an amount of a therapeutic agent that improves a disease or condition when administered to a patient. A "prophylactically effective amount" is an amount of a prophylactic agent that prevents a disease or condition when administered to a subject. The "therapeutically effective amount" for a therapeutic agent or the "prophylactically effective amount" for a prophylactic agent varies with the therapeutic/prophylactic agent, the disease state and its severity, the age and weight of a patient/subject to be treated/prevented, etc. The therapeutically effective amount and the prophylactically effective amount can be routinely determined by those of ordinary skill in the art based on their knowledge and the present disclosure.

As used herein, the composition may be used to induce a protective immune response against VZV in a subject in need thereof, wherein the protective immune response comprises, for example, the production of a neutralizing antibody. In some embodiments, the subject is immunocompromised. In some embodiments, the subject is 10 years of age or older, such as 45, 50, 51, 52, 53, 54, 55, 56, 57, 58, 59, 60, 60, 61, 62, 63, 64, 65, 66, 67, 68, 69, 70, 71, 72, 73, 74, 75, 76, 77, 78, 79, or 80 years of age.

The vaccines of the present disclosure are typically formulated in lipid nanoparticles. In some embodiments, the lipid nanoparticle comprises at least one ionizable cationic lipid, at least one non-cationic lipid, at least one sterol, and/or at least one polyethylene glycol (PEG)-modified lipid.

In some preferred embodiments, the lipid nanoparticle comprises a cationic lipid, a neutral lipid, a structural lipid, and a polymer-conjugated lipid.

In some preferred embodiments, the cationic lipid is a compound with the structure of formula I, or an N-oxide, a solvate, a pharmaceutically acceptable salt, or a stereoisomer thereof, wherein $G_1$ is $C_{1-6}$ alkylene; $G_2$ is $C_{2-8}$ alkylene; $G_3$ is $C_{1-3}$ alkylene; $L_1$ is $C_{6-15}$ linear alkyl; $L_2$ is $C_{12-25}$ branched alkyl. For example, YK-009 with the structure of formula I-I (see patent CN114044741B).

formula I

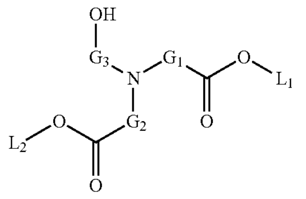

formula I-I

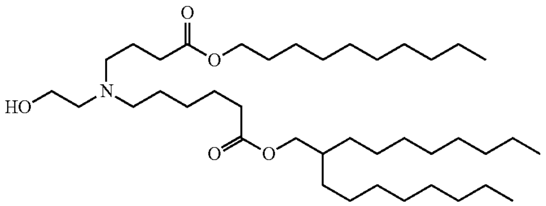

YK-009 .

In some preferred embodiments, the cationic lipid is a compound with the structure of formula II, or an N-oxide, a solvate, a pharmaceutically acceptable salt, or a stereoisomer thereof, wherein $G_1$ is $C_{2-8}$ alkylene; $G_2$ is $C_{2-8}$ alkylene; $L_1$ is —C(O)O— or —OC(O)—; $L_2$ is —C(O)O— or —OC(O)—; $R_1$ is $C_{6-25}$ linear or branched alkyl; $R_2$ is $C_{6-25}$ linear or branched alkyl; $G_3$ is $HO(CH_2)_2$— or $HO(CH_2)_3$—; $G_4$ is $HO(CH_2)_2$— or $HO(CH_2)_3$—; L is $(CH_2)_2$—, —$(CH_2)_3$—, or —$(CH_2)_4$—. For example, YK-401 with the structure of formula II-I or YK-402 with the structure of formula II-II (see patent CN115784921B).

formula II

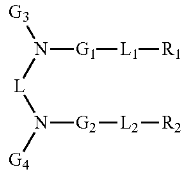

formula II-I

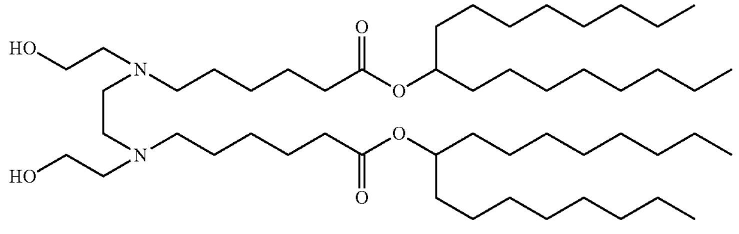

YK-401

-continued formula II-II

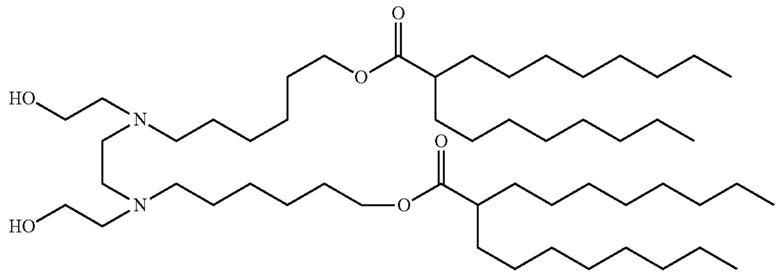

YK-402

In some preferred embodiments, the cationic lipid is a compound with the structure of formula III, or an N-oxide, a solvate, a pharmaceutically acceptable salt, or a stereoisomer thereof, wherein $G_1$ is $C_{1-6}$ alkylene; $G_2$ is $C_{2-8}$ alkylene; $R_1$ is $C_{6-20}$ linear or branched alkyl; $R_2$ is $C_{12-25}$ branched alkyl; $G_3$ is $HO(CH_2)_2N(CH_3)(CH_2)_2$—, $HO(CH_2)_2N(CH_2CH_3)(CH_2)_2$—, $(HO(CH_2)_2)_2N(CH_2)_2$—, $CH_3O(CH_2)_2N(CH_3)(CH_2)_2$—, $(CH_3)_2N(CH_2)_3SC(O)O(CH_2)_2$—, $(CH_3)_2N(CH_2)_3SC(O)$—, $CH_3NH(CH_2)_2N(CH_3)(CH_2)_2$—, or $CH_3CH_2NH(CH_2)_2$—. For example, YK-201 with the structure of formula III-I or YK-202 with the structure of formula III-II (see patent CN115677518B).

In some preferred embodiments, the cationic lipid is a compound with the structure of formula IV, or an N-oxide, a solvate, a pharmaceutically acceptable salt, or a stereoisomer thereof, wherein $G_1$ is $C_1$-s alkylene; $G_2$ is $C_{2-8}$ alkylene; $R_1$ is $C_{6-25}$ linear or branched alkyl; $R_2$ is $C_{12-25}$ linear or branched alkyl; $G_3$ is $HO(CH_2)_2N(R_3)CH_2CH(OH)CH_2$—, wherein $R_3$ is —$CH_3$, —$CH_2CH_3$, or —$CH_2CH_2OH$. For example, YK-305 with the structure of formula IV-I or YK-310 with the structure of formula IV-II (see patent CN115745820B3).

formula III

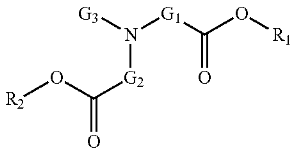

formula III-I

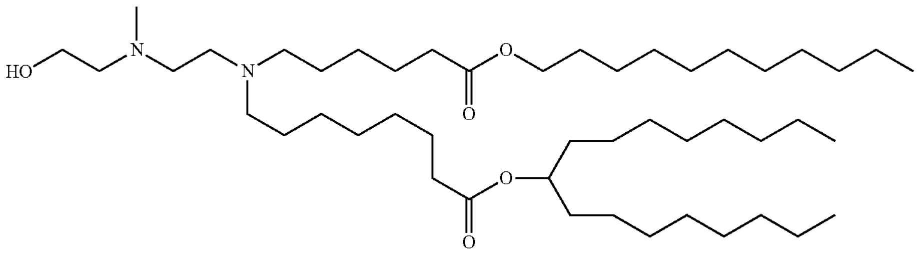

YK-201 formula III-II

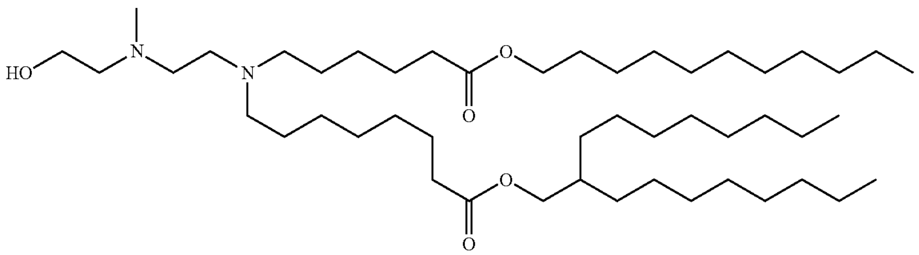

YK-202 formula IV

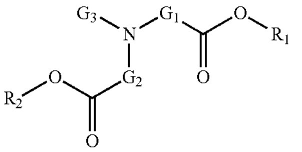

formula IV-I

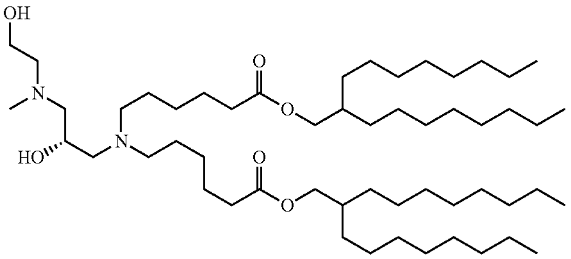

YK-305 formula IV-II

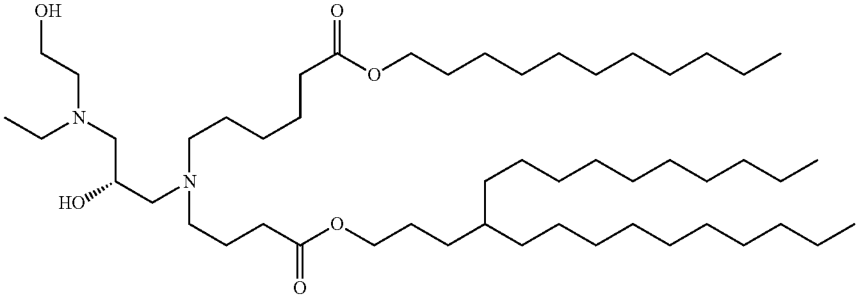

YK-310

In some preferred embodiments, the cationic lipid is a compound with the structure of formula V, or an N-oxide, a solvate, a pharmaceutically acceptable salt, or a stereoisomer thereof, wherein $G^1$ and $G^2$ are each independently unsubstituted $C_6$-$C_{10}$ alkylene; G is unsubstituted $C_1$-$C_{12}$ alkylene; $R^1$ and $R^2$ are each independently $C_6$-$C_{24}$ alkyl or $C_6$-$C_{24}$ alkenyl; $R^3$ is $OR^5$, N, —C(═O)$OR^4$, —OC(═O)$R^4$, or —$NR^5C$(═O)$R^4$; $R^4$ is $C_1$-$C_{12}$ hydrocarbyl; and $R^5$ is H or $C_1$-$C_6$ hydrocarbyl; for example, ALC0315 with the structure of formula V-I (see patent CN108368028B).

In some preferred embodiments, the cationic lipid is a compound with the structure of formula VI, or an N-oxide, a solvate, a pharmaceutically acceptable salt, or a stereoisomer thereof, wherein $R_4$ is selected from —$(CH_2)_n$Q and —$(CH_2)_n$CHQR; Q is selected from the group consisting of —OR, —OH, —$O(CH_2)_nN(R)_2$, —OC(O)R, —$CX_3$, —CN, —N(R)C(O)R, —N(H)C(O)R, —$N(R)S(O)_2R$, —$N(H)S(O)_2R$, —$N(R)C(O)N(R)_2$, —$N(H)C(O)N(R)_2$, —N(H)C(O)N(H)(R), —$N(R)C(S)N(R)_2$, —$N(H)C(S)N(R)_2$, —N(H)C(S)N(H)(R), —$N(R)S(O)_2R_8$, and heterocycle; n is 1, 2, or 3; for example, SM102 with the structure of formula VI-I (see patent CN110520409A).

formula V

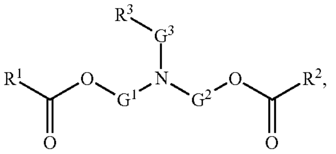

see (CN108368028B, ALC0315)

formula V-I

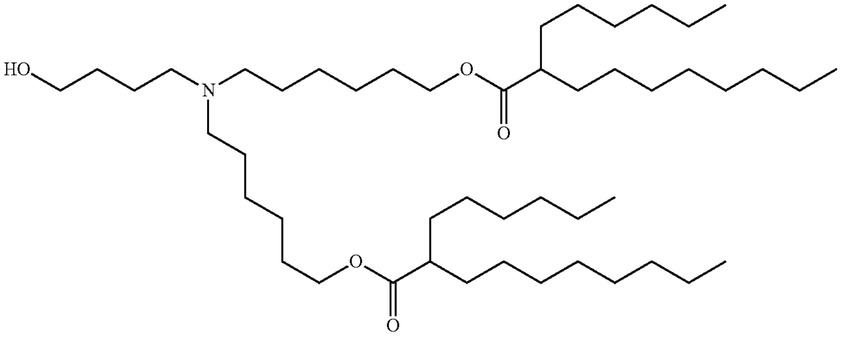

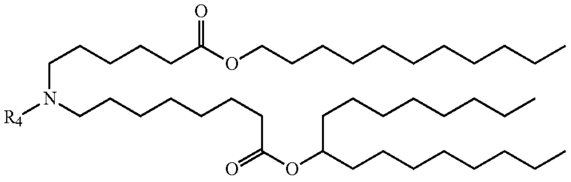

formula VI, see (CN110520409A, SM102)

(OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-formula VI-I

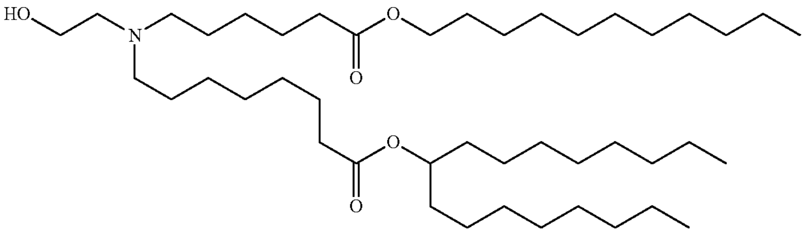

In some preferred embodiments, the cationic lipid is a compound with the structure of formula VII, or an N-oxide, a solvate, a pharmaceutically acceptable salt, or a stereoisomer thereof.

didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), dis-

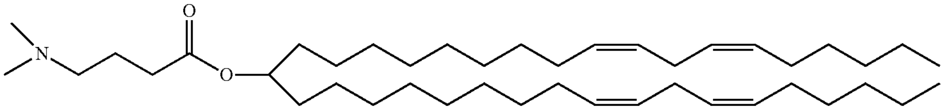 [SMILES: CCCCC/C=C\C/C=C\CCCCCCCCC(CCCCCCCC/C=C\C/C=C\CCCCC)OC(=O)CCCN(C)C]

formula VII, see (CN102625696B, DLIN-MC3-DMA)

In some more preferred embodiments, the cationic lipid comprises YK-009, YK-401, YK-305, ALC0315, SM102, and DLIN-MC3-DMA.

In some preferred embodiments, the molar ratio of the cationic lipid to the neutral lipid is (1 to 10):1.

In some preferred embodiments, the molar ratio of the cationic lipid to the structural lipid is (1 to 5):1.

In some preferred embodiments, the molar ratio of the cationic lipid, the neutral lipid, the structural lipid, and the polymer-conjugated lipid is (25 to 75):(5 to 25):(15 to 65):(0.5 to 10).

In some preferred embodiments, the molar ratio of the cationic lipid, the neutral lipid, the structural lipid, and the polymer-conjugated lipid is (35 to 49):(7.5 to 15):(35 to 55):(1 to 5), such as 49:10:43.5:1.5.

In some preferred embodiments, the neutral lipid includes one or more of phosphatidylcholine, phosphatidylethanolamine, sphingomyelin, ceramide, sterol, and derivatives thereof.

In some more preferred embodiments, the neutral lipid is selected from one or more of the following: 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine tearoyl-phosphatidyl-ethanolamine (DSPE), dipalmitoyl phosphatidylethanolamine (DPPE), dimyristoyl phosphoethanolamine (DMPE), 1-stearoyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), or mixtures thereof.

In some more preferred embodiments, the neutral lipid is DOPE and/or DSPC.

In some preferred embodiments, the structural lipid is selected from one or more of the following: cholesterol, nonsterol, sitosterol, ergosterol, campesterol, stigmasterol, brassinosterol, tomatine, ursolic acid, α-tocopherol, or corticosteroid.

In some more preferred embodiments, the structural lipid is cholesterol.

In some preferred embodiments, the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, or PEG-modified dialkylglycerol.

In some more preferred embodiments, the polymer-conjugated lipid is selected from one or more of distearoyl phosphatidylethanolamine polyethylene glycol 2000 (DSPE-PEG2000), dimyristoylglycero-3-methoxypolyethylene glycol 2000 (DMG-PEG2000), or methoxypolyethylene glycol ditetradecylacetamide (ALC-0159).

Pharmaceutical preparation: Provided herein are compositions (e.g., pharmaceutical compositions), methods, kits, and reagents for the prevention or treatment of varicella-zoster virus in humans and other mammals, for example. The compositions provided herein can be used as therapeutic or prophylactic agents. They can be used in medications to prevent and/or treat herpes zoster.

In some embodiments, a herpes zoster vaccine containing RNA as described herein can be administered to a subject (e.g., a mammalian subject, such as a human subject), and the RNA polynucleotide is translated in vivo to produce an antigenic polypeptide (antigen).

An "effective amount" of a composition (e.g., comprising RNA) is based at least in part on the target tissue, target cell type, mode of administration, physical characteristics of the RNA (e.g., length, nucleotide composition, and/or degree of modified nucleosides), other components of the vaccine, and other determinants, such as age, body weight, height, sex, and general health of the subject. Typically, an effective amount of a composition provides an induced or boosted immune response as a function of antigen production in the cells of the subject. In some embodiments, an effective amount of a composition containing an RNA polynucleotide having at least one chemical modification is more efficient than a composition containing a corresponding unmodified polynucleotide encoding the same antigen or peptide antigen. Increased antigen production may be evidenced by increased cell transfection (the percentage of cells transfected with the RNA vaccine), increased protein translation and/or expression from the polynucleotide, decreased nucleic acid degradation (e.g., as evidenced by increased duration of protein translation from a modified polynucleotide), or altered antigen-specific immune response of the host cell.

The term "pharmaceutical composition" refers to the combination of an active agent with an inert or active carrier, making the composition particularly suitable for diagnostic or therapeutic use in vivo or ex vivo. A "pharmaceutically acceptable carrier" does not cause undesirable physiological effects after or during administration to a subject. The carrier in the pharmaceutical composition must also be "acceptable" in the sense that it is compatible with and capable of stabilizing the active ingredient. One or more solubilizers can be used as pharmaceutical carriers for delivery of the active agent.

In some embodiments, the composition (comprising a polynucleotide and the polypeptide it encodes) according to the present disclosure can be used to treat or prevent herpes zoster. The composition may be administered prophylactically or therapeutically to healthy individuals as part of an active immunization scheme or early in infection during the incubation phase or during active infection after onset of symptoms. In some embodiments, the amount of RNA provided to the cell, tissue, or subject may be an amount effective for immunoprophylaxis.

In some embodiments, the composition may be administered intramuscularly.

The composition can be used in a variety of settings depending on the prevalence of infection or the degree or level of unmet medical need. As a non-limiting example, RNA vaccines can be used to treat and/or prevent a variety of infectious diseases. RNA vaccines have superior properties in that they produce much larger antibody titers, better neutralizing immunity, produce more durable immune responses, and/or produce responses earlier than commercially available vaccines.

Provided herein are pharmaceutical compositions comprising RNA and/or complexes, optionally in combination with one or more pharmaceutically acceptable excipients. In addition to traditional excipients (e.g., any and all solvents, dispersion media, diluents or other liquid vehicles, dispersion or suspension aids, surfactants, isotonic agents, thickeners or emulsifiers, preservatives), excipients may include, but are not limited to, lipidoids, liposomes, lipid nanoparticles, polymers, lipid complexes, core-shell nanoparticles, peptides, proteins, cells transfected with RNA (e.g., for transplantation into a subject), hyaluronidase, nanoparticle mimics, and combinations thereof.

The RNA may be formulated or administered alone or in combination with one or more other components. For example, an immunizing composition may comprise other components including, but not limited to, adjuvants.

The relative amounts of the active ingredient, the pharmaceutically acceptable excipient, and/or any additional ingredients in the pharmaceutical composition according to the present disclosure will vary depending upon the identity, size, and/or condition of the subject being treated and further depending upon the route by which the composition is to be administered. Byway of example, the composition may comprise between 0.1% and 100%, e.g., between 0.5% and 50%, between 1% and 30%, between 5% and 80%, or at least 80% (w/w) of the active ingredient.

In some embodiments, an RNA is formulated using one or more excipients to increase mRNA stability, increase cell transfection efficiency and protein translation efficiency, alter the biodistribution of mRNA to target specific tissues or cell types, etc.

Dosing/administration: Provided herein are immunizing compositions (e.g., RNA vaccines), methods, kits, and reagents for the prevention of varicella-zoster virus in humans and other mammals. Immunizing compositions can be used as therapeutic or prophylactic agents. In some embodiments, immunizing compositions are used to provide prophylactic protection against herpes zoster.

A subject may be any mammal, including non-human primate and human subjects.

In some embodiments, an immunizing composition (e.g., RNA vaccine) is administered to a subject (e.g., a mammalian subject, such as a human subject) in an effective amount to induce an antigen-specific immune response. The RNA encoding the VZV gE antigen is expressed and translated in vivo to produce the antigen, which then stimulates an immune response in the subject.

Prophylactic protection against herpes zoster can be achieved following administration of the immunizing composition (e.g., RNA vaccine) of the present disclosure. The immunizing composition may be administered once, twice, three times, four times or more, but it is possible that a single vaccine administration is sufficient (optionally followed by a single booster).

A method for eliciting an immune response against a varicella-zoster virus antigen (or multiple antigens) in a subject is provided in an aspect of the present disclosure. In some embodiments, the method comprises administering to a subject an immunizing composition comprising an RNA (e.g., mRNA) having an open reading frame encoding a VZV gE glycoprotein, thereby inducing an immune response specific to the varicella-zoster virus antigen in the subject, wherein anti-antigen antibody titer in the subject is increased following vaccination relative to anti-antigen antibody titer in a subject vaccinated with a traditional vaccine (e.g., recombinant subunit vaccine from GSK). An "anti-antigen antibody" is a serum antibody that binds specifically to an antigen.

A prophylactically effective dose is an effective dose that prevents viral infection at a clinically acceptable level. In some embodiments, the effective dose is a dose listed in a package insert for the vaccine. As used herein, the traditional vaccine refers to a vaccine other than the mRNA vaccines of the present disclosure. For example, the traditional vaccine includes, but is not limited to, live microorganism vaccines, killed microorganism vaccines, subunit vaccines, protein antigen vaccines, DNA vaccines, virus-like particle (VLP) vaccines, etc. In exemplary embodiments, the traditional vaccine is a vaccine that has achieved regulatory approval and/or is registered by a national drug regulatory body, such as the U.S. Food and Drug Administration (FDA) or the European Medicines Agency (EMA).

A method for eliciting an immune response against a varicella-zoster virus in a subject is provided in other aspects of the present disclosure. The method comprises administering to a subject an immunizing composition (e.g., RNA vaccine) comprising an RNA polynucleotide comprising an open reading frame encoding a VZV gE antigen, thereby inducing an immune response specific to the varicella-zoster virus in the subject.

In other embodiments, the immune response is assessed by determining the protein (antibody titer) in the subject. In other embodiments, the ability of serum or antibody from an immunized subject to neutralize viral uptake or reduce varicella-zoster virus transformation of human B lymphocytes is tested. In other embodiments, the ability to promote a robust T cell response is measured using techniques recognized in the art.

Also provided herein is a method for eliciting an immune response against a varicella-zoster virus in a subject by administering to the subject an RNA having an open reading frame encoding a first antigen, wherein the RNA does not comprise a stabilizing element, and wherein an adjuvant is not co-formulated or co-administered with the vaccine.

The immunizing composition (e.g., RNA vaccine) may be administered by any route that results in a therapeutically effective outcome. These routes include, but are not limited to, intradermal, intramuscular, or subcutaneous administration. The present disclosure provides a method comprising administering an RNA vaccine to a subject in need thereof. The exact amount required will vary from subject to subject, depending on the species, age, and general condition of the subject, the severity of the disease, the particular composition, its mode of administration, its mode of activity, etc. The RNA is typically formulated in dosage unit form for ease of administration and uniformity of dosage. However, it should be understood that the total daily dosage of the RNA may be determined by the attending physician within the scope of sound medical judgment. The specific therapeutically effective, prophylactically effective, or appropriate imaging dose level for any particular patient will depend upon a variety of factors, including the disorder being treated and the severity of the disorder; the activity of the specific compound employed; the specific composition employed; the age, body weight, general health, sex, and diet of the patient; the time of administration, route of administration, and excretion rate of the specific compound employed; the duration of the treatment; medications used in combination or concurrently with the specific compound employed; and similar factors well known in the medical art.

The effective amount of the RNA as provided herein may be as low as 5 μg, administered for example as a single dose or as two 2.5 μg doses. In some embodiments, the effective amount is a total dose of 5 μg to 200 μg. For example, the effective amount may be a total dose of 5 μg, 10 μg, 20 μg, 25 μg, 30 μg, 35 μg, 40 ag, 45 ag, 50 μg, 55 μg, 60 μg, 65 g, 70 μg, 75 μg, 80 μg, 85 μg, 90 μg, 95 μg, 100 μg, 110 μg, 120 μg, 130 μg, 140 μg, 150 μg, 160 μg, 170 μg, 180 μg, 190 μg, or 200 g. In some embodiments, the effective amount is a total dose of 5 μg to 200 μg. In some embodiments, the effective amount is a total dose of 10 μg. In some embodiments, the effective amount is a total dose of 20 μg. In some embodiments, the effective amount is a total dose of 75 μg. In some embodiments, the effective amount is a total dose of 150 μg. In some embodiments, the effective amount is a total dose of 200 μg.

Vaccine Efficacy

Some aspects of the present disclosure provide a preparation of the immunizing composition (e.g., RNA vaccine), wherein the RNA is formulated in an effective amount to produce an antigen-specific immune response in a subject (e.g., to produce an antibody specific to a varicella-zoster virus antigen). An "effective amount" is a dose of the RNA effective to produce an antigen-specific immune response. Also provided herein is a method for inducing an antigen-specific immune response in a subject.

As used herein, the immune response to the vaccine or LNP of the present disclosure is the generation of a humoral and/or a cellular immune response in a subject to (one or more) varicella-zoster virus proteins present in the vaccine. For purposes of the present disclosure, the "humoral" immune response refers to an immune response mediated by antibody molecules, including, for example, secretory (IgA) or IgG molecules, while the "cellular" immune response refers to an immune response mediated by T lymphocytes (e.g., $CD4^+$ helper and/or $CD8^+$ T cells, such as CTLs) and/or other leukocytes. One important aspect of cellular immunity involves an antigen-specific response by cytolytic T lymphocytes (CTLs). CTLs have specificity for peptide antigens that are presented in association with proteins encoded by the major histocompatibility complex (MHC) and expressed on the cell surface. CTLs help induce and promote the destruction of intracellular microorganisms or the lysis of cells infected with such microorganisms. Another aspect of cellular immunity involves an antigen-specific response by helper T cells. Helper T cells serve to help stimulate the function, and focus the activity of non-specific effector cells on cells that display peptide antigens in association with MHC molecules on their surface. The cellular immune response also leads to the production of cytokines (e.g., IFN-γ, IL-2, TNF-β), chemokines, and other such molecules produced by activated T cells and/or other leukocytes.

In some embodiments, the antigen-specific immune response is characterized by measuring an anti-varicella-zoster virus antigen antibody titer produced in a subject administered the immunizing composition as provided herein. Antibody titer is a measurement of the amount of antibodies within a subject, for example, antibodies that are specific to a particular antigen (e.g., an anti-VZV gE glycoprotein) or an epitope of the antigen. Antibody titer is typically expressed as the reciprocal of the maximum dilution that provides a positive result. For example, enzyme-linked immunosorbent assay (ELISA) is a common assay for determining antibody titers.

In some embodiments, antibody titers are used to assess whether a subject has been infected or to determine whether immunization is required. In some embodiments, antibody titers are used to determine the strength of an autoimmune response, to determine whether a booster immunization is needed, to determine whether a prior vaccine is effective, and to identify any recent or prior infections. According to the present disclosure, antibody titers can be used to determine the strength of an immune response induced in a subject by an immunizing composition (e.g., RNA vaccine).

In some embodiments, the anti-VZV gE antigen antibody titer produced in the subject is increased by at least 1 log relative to a control (unvaccinated subject). For example, the anti-VZV gE antigen antibody titer produced in the subject may be increased by at least 1.5, at least 2, at least 2.5, at least 3, at least 3.5, or at least 4 log relative to a control. In some embodiments, the anti-VZV gE antigen antibody titer produced in the subject is increased by 1, 1.5, 2, 2.5, or 3 log relative to a control. In some embodiments, the anti-VZV gE antigen antibody titer produced in the subject is increased by 1 to 4 log relative to a control. For example, the anti-VZV gE antigen antibody titer produced in the subject may be increased by 1 to 1.5, 1 to 2, 1 to 2.5, 1 to 3, 1.5 to 2, 1.5 to 2.5, 1.5 to 3, 2 to 2.5, 2 to 3, or 2.5 to 4 log relative to a control.

In some embodiments, the anti-VZV gE antigen antibody titer produced in the subject is increased by at least 2-fold relative to a control (vaccinated with the traditional vaccine Shingrix® from GSK). For example, the anti-VZV gE antigen antibody titer produced in the subject may be increased by at least 1-fold, at least 1.5-fold, at least 2-fold, at least 2.5-fold, at least 3-fold, or at least 3.5-fold relative to control GSK.

In some embodiments, the control is an anti-varicella-zoster virus antigen antibody titer produced in a subject not administered an immunizing composition (e.g., RNA vaccine). In some embodiments, the control is an anti-varicella-zoster virus antigen antibody titer produced in a subject administered the recombinant subunit vaccine Shingrix®.

In some embodiments, the ability of an immunizing composition (e.g., RNA vaccine) to be effective is measured in a murine model. For example, the immunizing composition can be administered to a murine model and the murine model can be assayed for induction of neutralizing antibody titers. Viral challenge studies can also be used to assess the efficacy of the vaccines of the present disclosure. For example, the immunizing composition can be administered to a murine model, the murine model can be challenged with virus, and the murine model can be assayed for survival and/or immune response (e.g., T cell response, such as cytokine response).

The present disclosure also relates to the following embodiments:

1. An immunogenic composition, comprising a ribonucleic acid (RNA) of a varicella-zoster virus (VZV) encoding a wild-type VZV gE glycoprotein or a variant thereof,
 wherein the sequence of the wild-type VZV gE glycoprotein is SEQ ID NO: 3.

2. The composition according to embodiment 1, wherein the variant of the VZV gE glycoprotein comprises one or more of the following mutations relative to the wild-type VZV gE glycoprotein: a sequence truncation, a site mutation, and a sequence deletion.

3. The composition according to embodiment 2, wherein the sequence truncation comprises a lack of a carboxy-terminal tail domain.

4. The composition according to any one of embodiments 1 to 3, wherein the sequence truncation is selected from any one of the group consisting of:
 1) truncation of amino acids 540 to 623 at the C-terminal of gE protein; i.e., retention of amino acids 1 to 539 of VZV gE protein;
 2) truncation of amino acids 569 to 623 at the C-terminal of gE protein; i.e., retention of amino acids 1 to 568 of VZV gE protein;
 3) truncation of amino acids 574 to 623 at the C-terminal of gE protein; i.e., retention of amino acids 1 to 573 of VZV gE protein;
 4) truncation of amino acids 588 to 623 at the C-terminal of gE protein; i.e., retention of amino acids 1 to 587 of VZV gE protein;
 5) truncation of amino acids 602 to 623 at the C-terminal of gE protein; i.e., retention of amino acids 1 to 601 of VZV gE protein.

5. The composition according to any one of embodiments 2 to 4, wherein the variant of the VZV gE glycoprotein comprises a site mutation selected from: a mutation in a motif associated with ER retention and endocytosis of gE protein, and/or at least one site mutation in at least one motif associated with localization to Golgi or trans Golgi network, and at least one site mutation in a phosphorylated acidic motif at the C-terminal of gE;
 wherein the motif associated with ER retention and endocytosis of gE protein includes a "$Y_{582}A_{583}G_{584}L_{585}$" motif (e.g., a mutation in the "$Y_{582}A_{583}G_{584}L_{585}$" motif can prevent endocytosis of gE protein and reduce gE antigen localization to trans Golgi network, such as mutation site Y582A, YK-VZV-013 (SEQ ID NO: 43));
 the motif associated with gE protein localization to Golgi or trans Golgi network includes an "$A_{568}Y_{569}$R570$V_{571}$" motif (e.g., the "$A_{568}Y_{569}$R570$V_{571}$" motif, with a specific mutant antigen sequence such as YK-VZV-011 (SEQ ID NO: 35));
 the phosphorylated acidic motif at the C-terminal of gE includes an "$S_{593}E_{594}S_{595}T_{596}D_{597}T_{598}$" motif (e.g., a mutation of the "$S_{593}E_{594}S_{595}T_{596}D_{597}T_{598}$" motif to an "$A_{593}E_{594}A_{595}A_{596}D_{597}A_{598}$" motif can reduce gE antigen localization to trans Golgi network, with a specific mutant antigen sequence such as YK-VZV-010 (SEQ ID NO: 31)).

6. The composition according to any one of embodiments 2 to 5, wherein the variant of the VZV gE glycoprotein comprises a site mutation selected from: A568D, Y569K, Y569A, R570E, V571K, Y582A, S593A, S595A, T596A, and T598A; for example, selected from A568D, Y569K, R570E, and V571K; for example, selected from A568D and Y569K.

7. The composition according to any one of embodiments 2 to 6, wherein the variant of the VZV gE glycoprotein comprises a site mutation selected from:
 1) A568D; Y569K; R570E; V571K; (YK-VZV-023, YK-VZV-011)
 2) A568D; Y569A; R570E; V571K; (YK-VZV-024)
 3) Y569K; R570E; V571K; (YK-VZV-025)
 4) A568D; Y569K; R570E; V571K; Y582A; (YK-VZV-030, YK-VZV-013)
 5) A568D; Y569K; R570E; V571K; Y582G; (YK-VZV-031, YK-VZV-038)
 6) A568D; Y582A; (YK-VZV-032)
 7) Y569K; Y582A; (YK-VZV-033, YK-VZV-009)
 8) R570E; Y582A; (YK-VZV-034)
 9) V571K; Y582A; (YK-VZV-035)
 10) S593A; S595A; T596A; T598A; (YK-VZV-016, YK-VZV-044)
 11) Y582A; S593A; S595A; T596A; T598A; (YK-VZV-037)
 12) A568D; Y569K; R570E; V571K; Y582G; S593A; S595A; T596A; T598A; (YK-VZV-039)
 13) A568D; Y569K; R570E; V571K; Y582A; S593A; S595A; T596A; T598A; (YK-VZV-014)
 14) Y582G; S593A; S595A; T596A; T598A; (YK-VZV-040)

15) Y569K; Y582A; S593A; S595A; T596A; T598A; (YK-VZV-010)

16) A568D; Y569K; R570E; V571K; S593A; S595A; T596A; T598A; (YK-VZV-012)

17) Y582G; (YK-VZV-029)

18) A568D; (YK-VZV-018)

19) Y569K; (YK-VZV-020)

20) R570E; (YK-VZV-021)

21) V571K; and (YK-VZV-022)

22) Y582A; (YK-VZV-028, YK-VZV-036).

8. The composition according to any one of embodiments 2 to 7, wherein the variant of the VZV gE glycoprotein comprises a site mutation selected from:

1) A568D; Y569K; R570E; V571K; (YK-VZV-011)

2) A568D; Y569A; R570E; V571K; (YK-VZV-024)

4) A568D; Y569K; R570E; V571K; Y582A; (YK-VZV-030, YK-VZV-013)

5) A568D; Y569K; R570E; V571K; Y582G; (YK-VZV-031, YK-VZV-038)

7) Y569K; Y582A; (YK-VZV-009)

13) A568D; Y569K; R570E; V571K; Y582A; S593A; S595A; T596A; T598A; (YK-VZV-014);

15) Y569K; Y582A; S593A; S595A; T596A; T598A; (YK-VZV-010)

16) A568D; Y569K; R570E; V571K; S593A; S595A; T596A; T598A; (YK-VZV-012)

18) A568D; (YK-VZV-018)

19) Y569K; (YK-VZV-020)

20) R570E; (YK-VZV-021); and

22) Y582A; (YK-VZV-028).

9. The composition according to any one of embodiments 2 to 8, wherein the variant of the VZV gE glycoprotein comprises a sequence deletion selected from:

1) $A_{568}$;

2) $Y_{569}$RVDKSPYNQS$_{579}$; and

3) $Y_{569}$RVDKSPYNQSMYYAGLPV$_{587}$.

10. The composition according to any one of embodiments 1 to 9, wherein the variant of the VZV gE glycoprotein comprises a combination of a site mutation, a sequence truncation, and a sequence deletion selected from:

| Name | Sequence truncation | Site mutation | Sequence deletion |
|---|---|---|---|
| YK-VZV-018 | gE (1 to 573) | A568D | No sequence deletion |
| YK-VZV-020 | gE (1 to 573) | Y569K | No sequence deletion |
| YK-VZV-021 | gE (1 to 573) | R570E | No sequence deletion |
| YK-VZV-024 | gE (1 to 573) | A568D; Y569A; R570E; V571K | No sequence deletion |
| YK-VZV-028 | gE (1 to 587) | Y582A | -$Y_{569}$RVDKSPYNQS$_{579}$- |
| YK-VZV-030 | gE (1 to 587) | A568D; Y569K; R570E; V571K; Y582A | No sequence deletion |
| YK-VZV-031 | gE (1 to 587) | A568D; Y569K; R570E; V571K; Y582G | No sequence deletion |
| YK-VZV-038 | No sequence truncation | A568D; Y569K; R570E; V571K; Y582G | No sequence deletion |
| YK-VZV-009 | No sequence truncation | Y569K; Y582A | No sequence deletion |
| YK-VZV-010 | No sequence truncation | Y569K; Y582A; S593A; S595A; T596A; T598A | No sequence deletion |
| YK-VZV-011 | No sequence truncation | A568D; Y569K; R570E; V571K | No sequence deletion |
| YK-VZV-012 | No sequence truncation | A568D; Y569K; R570E; V571K; S593A; S595A; T596A; T598A | No sequence deletion |
| YK-VZV-013 | No sequence truncation | A568D; Y569K; R570E; V571K; Y582A | No sequence deletion |
| YK-VZV-014 | No sequence truncation | A568D; Y569K; R570E; V571K; Y582A; S593A; S595A; T596A; T598A | No sequence deletion |

11. The composition according to any one of embodiments 1 to 10, wherein the variant of the VZV gE glycoprotein comprises a combination of a site mutation, a sequence truncation, and/or a sequence deletion selected from:

| Name | Sequence truncation | Site mutation | Sequence deletion |
|---|---|---|---|
| YK-VZV-018 | gE (1 to 573) | A568D | No sequence deletion |
| YK-VZV-020 | gE (1 to 573) | Y569K | No sequence deletion |
| YK-VZV-010 | No sequence truncation | Y569K; Y582A; S593A; S595A; T596A; T598A | No sequence deletion |
| YK-VZV-011 | No sequence truncation | A568D; Y569K; R570E; V571K | No sequence deletion |
| YK-VZV-013 | No sequence truncation | A568D; Y569K; R570E; V571K; Y582A | No sequence deletion |

12. The composition according to any one of embodiments 1 to 11, wherein the variant of the VZV gE glycoprotein comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% identity to the sequence of SEQ ID NO: 27, 31, 35, 39, 43, 47, 63, 71, 75, 87, 103, 111, 115, or 143.

13. The composition according to any one of embodiments 1 to 12, wherein the variant of the VZV gE glycoprotein comprises SEQ ID NO: 31, 35, 43, 63, or 71.

14. The composition according to any one of embodiments 1 to 13, wherein the RNA of VZV has an open reading frame (ORF) encoding a VZV gE glycoprotein or a variant thereof, wherein the open reading frame comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 26, 30, 34, 38, 42, 46, 62, 70, 74, 86, 102, 110, 114, or 142.

15. The composition according to embodiment 14, wherein the open reading frame comprises a sequence of SEQ ID NO: 30, 34, 42, 62, or 70.

16. The composition according to any one of embodiments 1 to 15, wherein the RNA of the VZV further comprises a 5' untranslated region (UTR).

17. The composition according to embodiment 16, wherein the 5' UTR comprises a sequence as shown in SEQ ID NO: 173, 174, 175, 176, or 177.

18. The composition according to embodiment 17, wherein the 5' UTR comprises a sequence as shown in SEQ ID NO: 174.

19. The composition according to any one of embodiments 1 to 18, wherein the RNA of the VZV further comprises a 3' untranslated region (UTR).

20. The composition according to embodiment 19, wherein the 3' UTR comprises a sequence as shown in SEQ ID NO: 178, 179, 180, or 181.

21. The composition according to embodiment 20, wherein the 3' UTR comprises a sequence as shown in SEQ ID NO: 178.

22. The composition according to any one of embodiments 1 to 21, wherein the RNA of VZV further comprises a poly(A) tail.

23. The composition according to embodiment 22, wherein the poly(A) tail has a length of 50 to 150 nucleotides.

24. The composition according to any one of embodiments 1 to 23, wherein the RNA of the VZV further comprises a 5' terminal cap.

25. The composition according to embodiment 24, wherein the 5' terminal cap is 7mG(5')ppp(5')NlmpNp.

26. The composition according to any one of embodiments 14 to 25, wherein the sequence of the open reading frame is codon-optimized.

27. The composition according to embodiment 26, wherein the sequence of the open reading frame comprises at least one base modification.

28. The composition according to embodiment 27, wherein the base modification is selected from one or more of the following: pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyluridine.

29. The composition according to embodiment 28, wherein the base modification comprises replacement of uracil by pseudouridine and/or N1-methylpseudouridine.

30. The composition according to embodiment 27, 28, or 29, wherein the base modification is 1 to 100% base modification, such as 1% base modification, 2% base modification, 3% base modification, 4% base modification, 5% base modification, 6% base modification, 7% base modification, 8% base modification, 9% base modification, 10% base modification, 15% base modification, 20% base modification, 25% base modification, 30% base modification, 35% base modification, 40% base modification, 45% base modification, 50% base modification, 55% base modification, 60% base modification, 65% base modification, 70% base modification, 75% base modification, 80% base modification, 85% base modification, 90% base modification, 95% base modification, and 100% base modification; and a range with any of the above values as endpoints.

31. The composition according to any one of embodiments 1 to 30, wherein the RNA of the VZV comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 28, 32, 36, 40, 44, 48, 64, 72, 76, 88, 104, 112, 116, or 144.

32. The composition according to embodiment 31, wherein the RNA of the VZV comprises a sequence as shown in SEQ ID NO: 32, 36, 44, 64, or 72.

33. The composition according to any one of embodiments 1 to 32, wherein the RNA of the VZV is mRNA.

34. The composition according to any one of embodiments 1 to 33, wherein the RNA encoding the VZV gE glycoprotein comprises an RNA sequence corresponding to a DNA sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 25, 29, 33, 37, 41, 45, 61, 69, 73, 85, 101, 109, 113, or 141.

35. The composition according to embodiment 34, wherein the RNA encoding the VZV gE glycoprotein comprises an RNA sequence corresponding to the DNA sequence as shown in SEQ ID NO: 29, 33, 41, 61, or 69.

36. A method for preparing the composition according to any one of embodiments 1 to 35, comprising:

- providing a template that can transcribe the RNA of the VZV;
- transcribing the RNA using the template under conditions suitable for transcription.

37. The method according to embodiment 36, further comprising a purification step selected from: lithium chloride precipitation, affinity chromatography, ultrafiltration exchange, and cellulose chromatography.

38. The composition according to any one of embodiments 1 to 35, wherein the composition is a vaccine, and further comprises a pharmaceutically acceptable carrier.

39. The composition according to embodiment 38, wherein the carrier comprises a lipid mixture, such as a lipid nanoparticle (LNP).

40. The composition according to embodiment 38 or 39, wherein the vaccine is an mRNA vaccine.

41. The composition according to embodiment 39 or 40, wherein the lipid mixture is a lipid nanoparticle (LNP), for example, comprising a cationic lipid, a neutral lipid, a structural lipid, and a polymer-conjugated lipid.

42. The composition according to embodiment 41, wherein the cationic lipid is a compound with the structure of formula I, or an N-oxide, a solvate, a pharmaceutically acceptable salt, or a stereoisomer thereof, wherein $G_1$ is $C_{1-6}$ alkylene; $G_2$ is $C_{2-8}$ alkylene; $G_3$ is $C_{1-3}$ alkylene; $L_1$ is $C_{6-15}$ linear alkyl; $L_2$ is $C_{12-25}$ branched alkyl; for example, the cationic lipid is YK-009 with the structure of formula I-I.

formula I

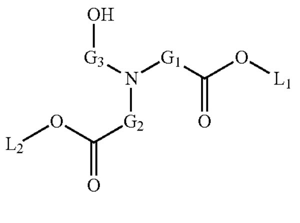

-continued formula I-I

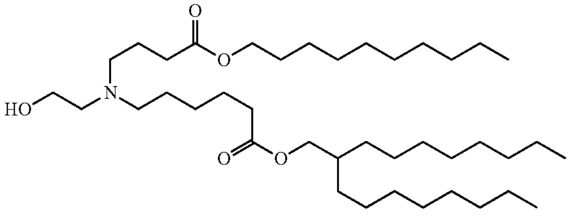

YK-009

43. The composition according to embodiment 41, wherein the cationic lipid is a compound with the structure of formula II, or an N-oxide, a solvate, a pharmaceutically acceptable salt, or a stereoisomer thereof, wherein $G_1$ is $C_{2-8}$ alkylene; $G_2$ is $C_{2-8}$ alkylene; $L_1$ is —C(O)O— or —OC(O)—; $L_2$ is —C(O)O— or —OC(O)—; $R_1$ is $C_{6-25}$ linear or branched alkyl; $R_2$ is $C_{6-25}$ linear or branched alkyl; $G_3$ is $HO(CH_2)_2$— or $HO(CH_2)_3$—; $G_4$ is $HO(CH_2)_2$— or $HO(CH_2)_3$—; L is $(CH_2)_2$—, —$(CH_2)_3$—, or —$(CH_2)_4$—; for example, the cationic lipid is YK-401 with the structure of formula II-I or YK-402 with the structure of formula II-II.

formula II

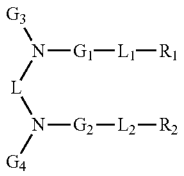

-continued formula II-I

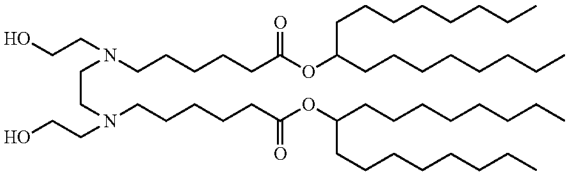

YK-401 formula II-II

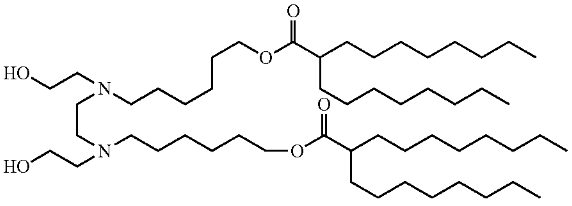

YK-402

44. The composition according to embodiment 41, wherein the cationic lipid is a compound with the structure of formula III, or an N-oxide, a solvate, a pharmaceutically acceptable salt, or a stereoisomer thereof, wherein $G_1$ is $C_{1-6}$ alkylene; $G_2$ is $C_{2-8}$ alkylene; $R_1$ is $C_{6-20}$ linear or branched alkyl; $R_2$ is $C_{12-25}$ branched alkyl; $G_3$ is $HO(CH_2)_2N(CH_3)(CH_2)_2$—, $HO(CH_2)_2N(CH_2CH_3)(CH_2)_2$—, $(HO(CH_2)_2)_2N(CH_2)_2$—, $CH_{30}(CH_2)_2N(CH_3)(CH_2)_2$—, $(CH_3)_2N(CH_2)_3SC(O)O(CH_2)_2$—, $(CH_3)_2N(CH_2)_3SC(O)$—, $CH_3NH(CH_2)_2N(CH_3)(CH_2)_2$—, or $CH_3CH_2NH(CH_2)_2$—; for example, YK-201 with the structure of formula III-I or YK-202 with the structure of formula III-II.

formula III

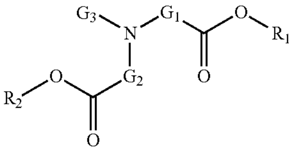

formula III-I

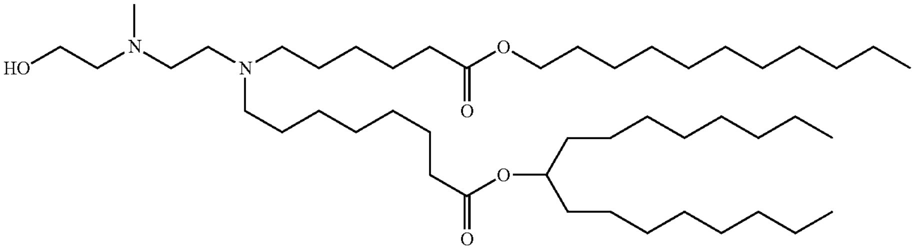

YK-201

-continued formula III-II

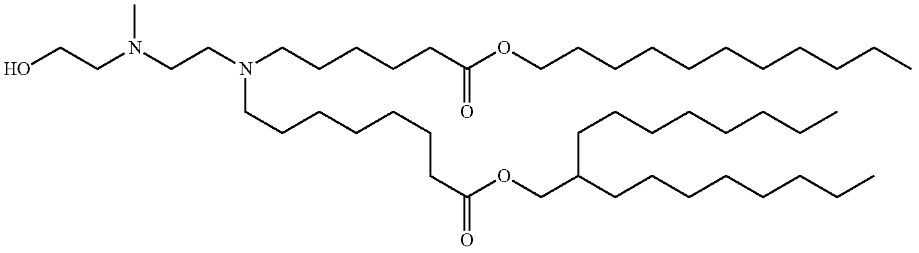

YK-202

45. The composition according to embodiment 41, wherein the cationic lipid is a compound with the structure of formula IV, or an N-oxide, a solvate, a pharmaceutically acceptable salt, or a stereoisomer thereof, wherein $G_1$ is $C_{1-8}$ alkylene; $G_2$ is $C_{2-8}$ alkylene; $R_1$ is $C_{6-25}$ linear or branched alkyl; $R_2$ is $C_{12-25}$ linear or branched alkyl; $G_3$ is $HO(CH_2)_2N(R_3)CH_2CH(OH)CH_2$—, wherein $R_3$ is —$CH_3$, —$CH_2CH_3$, or —$CH_2CH_2OH$; for example, YK-305 with the structure of formula IV-I or YK-310 with the structure of formula IV-II.

46. The composition according to embodiment 41, wherein the cationic lipid is a compound with the structure of formula V, or an N-oxide, a solvate, a pharmaceutically acceptable salt, or a stereoisomer thereof, wherein $G^1$ and $G^2$ are each independently unsubstituted $C_6$-$C_{10}$ alkylene; $G^3$ is unsubstituted $C_1$-$C_{12}$ alkylene; $R^1$ and $R^2$ are each independently $C_6$-$C_{24}$ alkyl or $C_6$-$C_{24}$ alkenyl; $R^3$ is $OR^5$, N, —C(═O)$OR^4$, —OC(═O)$R^4$, or —$NR^5$C(═O)$R^4$; $R^4$ is $C_1$-$C_{12}$ hydrocarbyl; and $R^5$ is H or $C_1$-$C_6$ hydrocarbyl; for example, ALC0315 with the structure of formula V-I.

formula IV

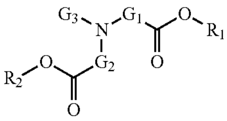

formula IV-I

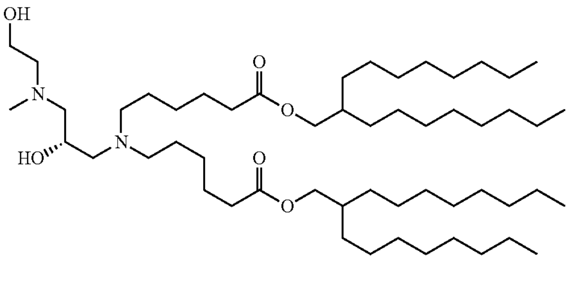

YK-305 formula IV-II

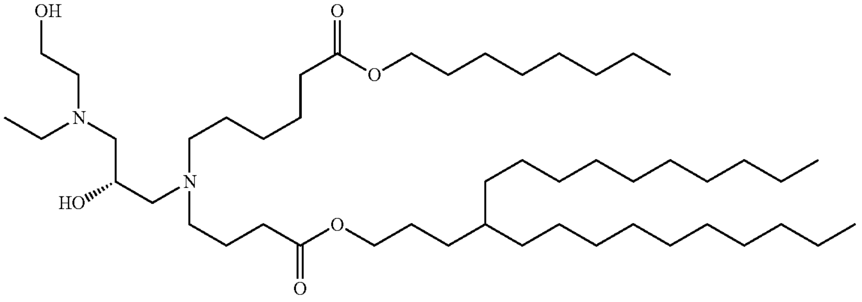

YK-310 formula V

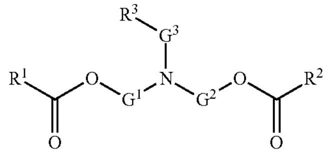

formula V-I

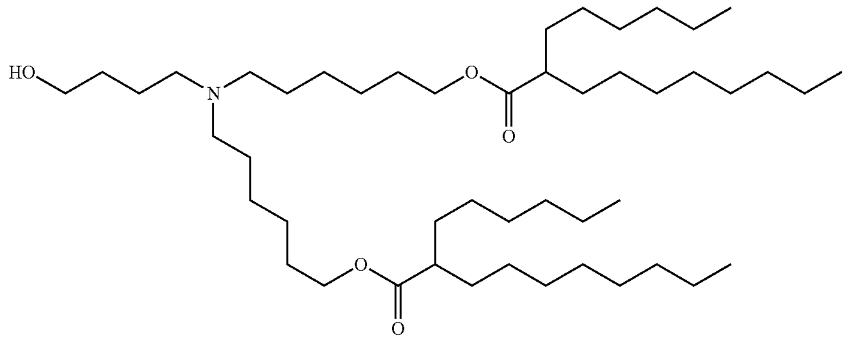

47. The composition according to embodiment 41, wherein the cationic lipid is a compound with the structure of formula VI, or an N-oxide, a solvate, a pharmaceutically acceptable salt, or a stereoisomer thereof, wherein $R_4$ is selected from $—(CH_2)_nQ$ and $—(CH_2)_nCHQR$; Q is selected from the group consisting of —OR, —OH, $—O(CH_2)_nN(R)_2$, —OC(O)R, $—CX_3$, —CN, —N(R)C(O)R, —N(H)C(O)R, $—N(R)S(O)_2R$, $—N(H)S(O)_2R$, $—N(R)C(O)N(R)_2$, $—N(H)C(O)N(R)_2$, —N(H)C(O)N(H)(R), $—N(R)C(S)N(R)_2$, $—N(H)C(S)N(R)_2$, —N(H)C(S)N(H)(R), $—N(R)S(O)_2R_8$, and heterocycle; n is 1, 2, or 3; for example, SM102 with the structure of formula VI-I.

formula VI

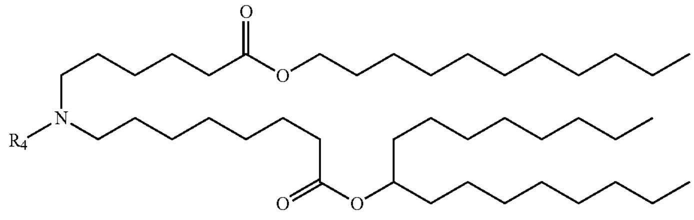

formula VI-I

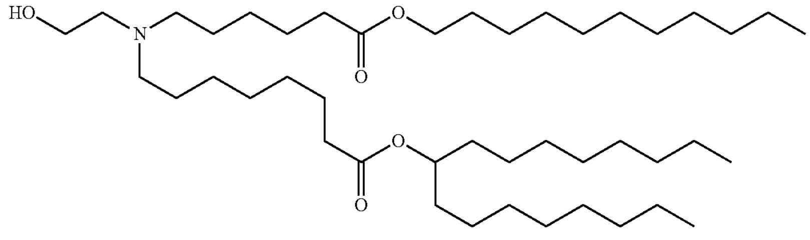

48. The composition according to embodiment 41, wherein the cationic lipid is a compound with the structure of formula VII, or an N-oxide, a solvate, a pharmaceutically acceptable salt, or a stereoisomer thereof.

formula VII

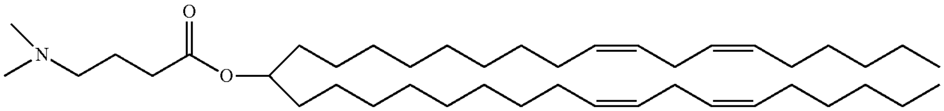

49. The composition according to embodiment 41, wherein the cationic lipid is selected from YK-009, YK-401, YK-305, ALC0315, SM102, and DLIN-MC3-DMA.

50. The composition according to any one of embodiments 41 to 49, wherein the molar ratio of the cationic lipid to the neutral lipid is (1 to 10):1.

51. The composition according to any one of embodiments 41 to 50, wherein the molar ratio of the cationic lipid to the structural lipid is (1 to 5):1.

52. The composition according to any one of embodiments 41 to 51, wherein the molar ratio of the cationic lipid, the neutral lipid, the structural lipid, and the polymer-conjugated lipid is (25 to 65):(5 to 25):(25 to 45):(0.5 to 5).

53. The composition according to embodiment 52, wherein the molar ratio of the cationic lipid, the neutral lipid, the structural lipid, and the polymer-conjugated lipid is (49 to 50):10:(38.5 to 39.5):1.5, such as 50:10:38.5:1.5 or 49:10:39.5:1.5.

54. The composition according to any one of embodiments 41 to 53, wherein the neutral lipid is selected from phosphatidylcholine, phosphatidylethanolamine, sphingomyelin, ceramide, sterol, derivatives thereof, and any combination thereof.

55. The composition according to any one of embodiments 41 to 54, wherein the neutral lipid is selected from: 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearoyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), and mixtures thereof.

56. The composition according to any one of embodiments 41 to 55, wherein the neutral lipid is DOPE and/or DSPC.

57. The composition according to any one of embodiments 41 to 56, wherein the structural lipid is selected from: sterol, cholesterol, nonsterol, sitosterol, ergosterol, campesterol, stigmasterol, brassinosterol, tomatine, ursolic acid, α-tocopherol, corticosteroid, and any combination thereof.

58. The composition according to embodiment 57, wherein the structural lipid comprises cholesterol; for example, the structural lipid is cholesterol.

59. The composition according to any one of embodiments 41 to 56, wherein the polymer-conjugated lipid is selected from: PEG-modified phosphatidylethanolamine, PEG-modified phosphatidic acid, PEG-modified ceramide, PEG-modified dialkylamine, PEG-modified diacylglycerol, PEG-modified dialkylglycerol, and any combination thereof.

60. The composition according to embodiment 59, wherein the polymer-conjugated lipid is selected from: distearoyl phosphatidylethanolamine polyethylene glycol 2000 (DSPE-PEG2000), dimyristoylglycero-3-methoxypolyethylene glycol 2000 (DMG-PEG2000), methoxypolyethylene glycol ditetradecylacetamide (ALC-0159), and any combination thereof.

61. The composition according to any one of embodiments 38 to 60, wherein the RNA of the VZV has an effective dose of 25 g to 200 g; preferably 50 μg to 100 μg.

62. The composition according to any one of embodiments 38 to 60, wherein the vaccine is an injection, such as a liquid preparation or a lyophilized preparation.

63. A method for preparing the composition according to any one of embodiments 38 to 60, comprising: mixing the RNA of the VZV with the pharmaceutically acceptable carrier, for example to encapsulate at least a portion of the RNA in lipid nanoparticles.

64. The method according to embodiment 63, further comprising a purification step of removing an unencapsulated component, such as dialysis and/or filtration.

65. The method according to embodiment 64, wherein the unencapsulated component is selected from: unencapsulated RNA, a non-aqueous solvent, and bacteria.

66. A use of the composition according to any one of embodiments 1 to 62 in the preparation of a medicament for inducing a protective immune response against VZV in a subject, wherein the protective immune response comprises, for example, the production of a neutralizing antibody.

66a. The composition according to any one of embodiments 1 to 62, for use in inducing a protective immune response against VZV in a subject in need thereof, wherein the protective immune response comprises, for example, the production of a neutralizing antibody.

66b. A method for inducing a protective immune response against VZV in a subject in need thereof, comprising administering to the subject the composition according to any one of embodiments 1 to 62, wherein the protective immune response comprises, for example, the production of a neutralizing antibody.

67. The use, composition, or method according to embodiment 66, 66a, or 66b, wherein the subject is immunocompromised.

68. The use, composition, or method according to embodiment 66, 66a, 66b, or 67, wherein the subject is 10 years of age or older, such as 50, 60, 70, 80 years of age or older.

69. The use, composition, or method according to any one of embodiments 66 to 68, wherein the protective immune response further comprises a cellular immune response.

70. The use, composition, or method according to any one of embodiments 66 to 69, wherein the inducing a protective immune response is for the prevention of VZV infection.

71. The use, composition, or method according to any one of embodiments 66 to 69, wherein the inducing a protective immune response is for the prevention of VZV-related pain.

Example 1: VZV gE Mutant Antigen Design

As a highly glycosylated type I membrane protein, gE can be transported between the endoplasmic reticulum (ER), trans Golgi network (TGN), and endosomes. gE proteins have a number of important domains related to their primary functions.

(1) TM transmembrane domain, which consists of amino acids 539 to 559;

(2) $A_{568}YRV_{571}$ motif, which mediates gE transport between the endoplasmic reticulum (ER), trans Golgi network (TGN), and endosomes;

(3) $Y_{582}AGL_{585}$ motif, which mediates gE transport between the endoplasmic reticulum (ER), trans Golgi network (TGN), and endosomes;

(4) $S_{593}ES_{595}T_{596}DT_{598}$ motif, which is an important glycosylation site and mediates gE transport between the endoplasmic reticulum (ER), trans Golgi network (TGN), and endosomes.

The intracellular carboxyl terminus of gE plays a decisive role in the intracellular transport of gE. Based on the important domains of gE proteins and their functions, a series of mRNA antigens targeting mutations in key structural/functional domains of gE and mutations in different truncated forms were designed (as shown in FIG. 1).

Using the wild-type sequence of the gE gene of VZV (with reference to NCBI strain sequence number QXN54923.1), a series of 43 different gE variant mRNA sequences were designed:

Table 1 summarizes the mRNAs encoding variant gE antigens with different C-terminal sequences, in which YK-VZV-004, YK-VZV-006, YK-VZV-045, and YK-VZV-007 correspond to the sequences of mutations or combinations of mutations in the disclosed patents (U.S. Ser. No. 11/643, 441B1, CN114081943A, US20230233671A1, and CN108472309A), respectively.

TABLE 1

Herpes zoster mRNA vaccine antigens

| SEQ ID NO: | Name | Sequence truncation: (truncated to) | Site mutation | Sequence deletion |
|---|---|---|---|---|
| 7 | YK-VZV-002 | gE (1 to 539) | Wild-type (WT) | / |
| 11 | YK-VZV-003 | gE (1 to 568) | WT | / |
| 59 | YK-VZV-017 | gE (1 to 573) | WT | / |
| 15 | YK-VZV-004 | | Y569A (Comparative Example 1) | / |
| 63 | YK-VZV-018 | | A568D | / |
| 67 | YK-VZV-019 | | | $A_{568}$ |
| 71 | YK-VZV-020 | | Y569K | / |
| 75 | YK-VZV-021 | | R570E | / |
| 79 | YK-VZV-022 | | V571K | / |
| 83 | YK-VZV-023 | | A568D; Y569K; R570E; V571K | / |
| 87 | YK-VZV-024 | | A568D; Y569A; R570E; V571K | / |
| 91 | YK-VZV-025 | | Y569K; R570E; V571K | $-A_{568}-$ |
| 95 | YK-VZV-026 | gE (1 to 587) | WT | |
| 99 | YK-VZV-027 | | | $Y_{569}RVDKSPYNQS_{579}$ |
| 103 | YK-VZV-028 | | Y582A | $Y_{569}RVDKSPYNQS_{579}$ |
| 107 | YK-VZV-029 | | Y582G | $Y_{569}RVDKSPYNQS_{579}$ |
| 111 | YK-VZV-030 | | A568D; Y569K; R570E; V571K; Y582A | / |
| 115 | YK-VZV-031 | | A568D; Y569K; R570E; V571K; Y582G | / |
| 119 | YK-VZV-032 | | A568D; Y582A | / |
| 123 | YK-VZV-033 | | Y569K; Y582A | / |
| 127 | YK-VZV-034 | | R570E; Y582A | / |
| 131 | YK-VZV-035 | | V571K; Y582A | / |
| 171 | YK-VZV-045 | gE (1 to 623) | Y582A (Comparative Example 3) | / |
| 3 | YK-VZV-001 | full-length | WT full-length | |
| 51 | YK-VZV-015 | | | $Y_{569}RVDKSPYNQS_{579}$ |
| 55 | YK-VZV-016 | | S593A; S595A; T596A; T598A | $Y_{569}RVDKSPYNQS_{579}$ |
| 135 | YK-VZV-036 | | Y582A | $Y_{569}RVDKSPYNQS_{579}$ |
| 139 | YK-VZV-037 | | Y582A; S593A; S595A; T596A; T598A | $Y_{569}RVDKSPYNQS_{579}$ |
| 143 | YK-VZV-038 | | A568D; Y569K; R570E; V571K; Y582G | / |
| 147 | YK-VZV-039 | | A568D; Y569K; R570E; V571K; Y582G; S593A; S595A; T596A; T598A | / |
| 19 | YK-VZV-006 | | Y569A; S593A; S595A; T596A; T598A (Comparative Example 2) | / |
| 23 | YK-VZV-007 | | Y582A; S593A; S595A; T596A; T598A (Comparative Example 4) | / |

TABLE 1-continued

| Herpes zoster mRNA vaccine antigens | | | | |
|---|---|---|---|---|
| SEQ ID NO: | Name | Sequence truncation: (truncated to) | Site mutation | Sequence deletion |
| 151 | YK-VZV-040 | | Y582G; S593A; S595A; T596A; T598A | / |
| 27 | YK-VZV-009 | | Y569K; Y582A | / |
| 31 | YK-VZV-010 | | Y569K; Y582A; S593A; S595A; T596A; T598A | / |
| 35 | YK-VZV-011 | | A568D; Y569K; R570E; V571K | / |
| 39 | YK-VZV-012 | | A568D; Y569K; R570E; V571K; S593A; S595A; T596A; T598A | / |
| 43 | YK-VZV-013 | | A568D; Y569K; R570E; V571K; Y582A | / |
| 47 | YK-VZV-014 | | A568D; Y569K; R570E; V571K; Y582A; S593A; S595A; T596A; T598A | / |
| 163 | YK-VZV-043 | | / | $Y_{569}$RVDKSPYNQSMYYAGLP$V_{587}$ |
| 167 | YK-VZV-044 | | S593A; S595A; T596A; T598A | $Y_{569}$RVDKSPYNQSMYYAGLP$V_{587}$ |
| 155 | YK-VZV-041 | gE (1 to 601) | / | $Y_{569}$RVDKSPYNQSMYYAGLP$V_{587}$ |
| 159 | YK-VZV-042 | | / | $Y_{569}$RVDKSPYNQSMYYAGLP$V_{587}$ |

Example 2: Preparation of VZV gE Antigen mRNA Vaccine

Preparation of Transcription Template Linearized Plasmid

All antigen gene fragments were artificially synthesized and cloned into pVAX vector (purchased from Thermo Fisher Scientific) by GenScript Biotech Corporation, resulting in a successfully constructed circular plasmid.

The template was prepared by linearizing the plasmid using BsaI restriction endonuclease (purchased from Shanghai Beyotime Biotechnology Co., Ltd.). The digestion system included the supercoiled plasmid inserted into the target gene corresponding to Example 1, 10× digestion buffer, BsaI restriction endonuclease, and RNase-free $ddH_2O$. The digestion reaction was conducted at 37° C. for 3 hours, and the digestion system is shown in Table 2.

TABLE 2

| Digestion reaction system | |
|---|---|
| Component | Amount |
| pDNA | 1 to 2 μg |
| 10x digestion buffer | 5.0 μL |
| BsaI (10 U/μL) | 1.0 μL |
| RNase-free $ddH_2O$ | Up to 50 μL |

After the digestion reaction was completed, the linearized product was recovered using a DNA product purification kit (purchased from Yeasen Biotechnology (Shanghai) Co., Ltd.). The product concentration was measured using an ultra-micro UV-Vis spectrophotometer (Denovix), and the length and status of the linearized plasmid template were detected by agarose gel electrophoresis.

Preparation of mRNA Stock Solution

The in vitro co-transcriptional capping reaction is a process that assembles modified or natural nucleoside triphosphates (NTPs) according to the base sequence of the template to prepare an mRNA polynucleotide, during which Clean Cap is added to generate an mRNA with a Cap1 structure through a one-step transcription reaction. The conventional reaction system consists of the following components (all purchased from Suzhou Novoprotein Scientific Co., Ltd.):

TABLE 3

| In vitro co-transcriptional capping reaction system | |
|---|---|
| Component | Amount |
| Template cDNA | 1.0 μg |
| 10× transcription buffer | 2.0 μL |
| NTP (100 mM each) | 2.0 μL each |
| Cap1-GAG (100 mM) | 2.0 μL |
| RNase inhibitor | 0.5 μL |
| T7 RNA polymerase | 2.0 μL |
| RNase-free $ddH_2O$ | Up to 20 μL |
| Incubation at 37° C. for 2 hours | |

After transcription was completed, 1 μL of DNase I (2 U/μL) was added, mixed well, and incubated at 37° C. for 20 minutes to remove template DNA. The transcription product was then purified by lithium chloride precipitation.

1) 30 μL of RNase-free $H_2O$ and 7.5 M lithium chloride (with a final concentration of 2.8 M) were added to 20 μL of reaction mixture.

2) After mixing well, the mixture was allowed to stand at −20° C. for 2 hours, followed by centrifugation at 12,000 rpm for 15 minutes, and the supernatant was discarded. The RNA pellet was washed with 500 μL of 70% ethanol, followed by centrifugation at 12,000 rpm for 5 minutes, which was repeated once to collect the pellet.

3) After drying, the mRNA pellet was dissolved in 100 μL of enzyme-free water, and the purified RNA solution was stored at −80° C. The concentration and integrity of the mRNA was determined.

Preparation of mRNA-LNP (mRNA Vaccine)

20 mg each of cationic lipid, DSPC, cholesterol, and DMG-PEG2000 were accurately weighed and dissolved in anhydrous ethanol to prepare a solution with a concentration of 10 mg/mL, which was formulated into a carrier mixture in a molar ratio of 49:10:39.5:1.5 as the organic phase for later use.

VZV mRNA was dissolved in 50 mM citrate buffer (pH 4.0) and diluted to prepare a solution with a concentration of 0.15 mg/mL as the aqueous phase for later use. The LNP intermediate solution was prepared in a microfluidic device by drawing 2 mL of the organic phase using a BD (brand name, Bidi in Chinese, the same below) 3 mL syringe and 7 mL of the aqueous phase using a BD 10 mL syringe, with the organic phase on the left pump and the aqueous phase on the right pump.

The volume of preparation was 9.0 mL; the flow rate of the organic phase was 5.0 mL/min; the flow rate of the aqueous phase was 15 mL/min; the LNP intermediate solution was collected.

The LNP intermediate solution was diluted by adding 9 times the volume of PBS and concentrated by ultrafiltration on a small-scale ultrafiltration device with an ultrafiltration membrane pore size of 50 kD. The mixture was further diluted by adding 4 times the volume of PBS and concentrated on the ultrafiltration device when it was concentrated to around 10 mL. The ultrafiltration was stopped when the final concentrated volume was less than 5 mL.

Example 3: Detection of Antigen Expression of Herpes Zoster mRNA Vaccine by Western Blot To verify whether the designed antigen mRNA sequence can be expressed in cells and to assess the expression efficiency of different antigen sequences, cells were first transfected with the mRNA sequence, and the expression of antigen mRNA in cells was detected using Western Blot.

Experimental Materials

TABLE 4

Main experimental materials and sources

| Material name | Source |
|---|---|
| 293T cells | Purchased from ATCC |
| Series of mRNA vaccines | Prepared in Example 2 |
| RIPA lysis buffer | Thermo Fisher Scientific |
| BCA kit | Thermo Fisher Scientific |
| Primary antibody (anti-VZV gE protein antibody, mouse mAb) | Abcam |
| Secondary antibody (goat anti-mouse IgG) | ACRO |

Experimental Steps

Cell culture and transfection: 293T cells were inoculated into a 12-well plate at a density of $2.5\times10^5$ cells/well. The volume of mRNA preparation required for 500 ng of mRNA was calculated, and the corresponding volume of mRNA preparation sample was directly added to the cells and mixed well.

Experimental group: a mixture of protein samples obtained by lysis of cells transfected with a series of mRNA vaccines prepared in Example 2;

negative control (NC): RIPA lysis buffer;

positive control (PC): purified gE protein;

internal reference protein loading control: glyceraldehyde 3-phosphate dehydrogenase (GAPDH);

Protein sample preparation: (i) After 16 hours of transfection, the cells were removed from the incubator and pipetted repeatedly so that the cells were detached from the bottom of the plate, then transferred to a 1.5 mL centrifuge tube, and centrifuged at 1,500 rpm for 3 minutes at 25° C. (ii) The supernatant was discarded. The cells were pipetted and resuspended in 1 mL of PBS, and centrifuged at 1500 rpm for 3 minutes at 25° C. (iii) The previous step was repeated twice. (iv) 50 μL of RIPA lysis buffer was added to each tube of cells (with 0.5 μL of 100× protease inhibitor added before the use of RIPA lysis buffer) and placed on ice for 30 minutes, during which the samples were vortexed for 30 seconds every 5 minutes. (v) The centrifuge was pre-cooled. After the cells were fully lysed, the samples were centrifuged at 12000 rpm for 10 minutes at 4° C. The supernatant was pipetted and transferred to a new 1.5 mL centrifuge tube to obtain protein samples to be tested.

Development and analysis: The concentration of protein samples was quantified using a BCA kit, and 200 μL of BCA working solution and 10 μL of the sample to be tested were added. 10 μg of protein samples were pipetted into a 1.5 mL centrifuge tube and added with water to prepare a 24 μL system. 6 μL of 5× loading buffer was added, and the volume was made up to 30 μL with purified water. The total proteins were boiled for denaturation. 3 μg of sample (9 μL) was pipetted for spotting, alongside 4 μL of marker, and subjected to electrophoresis at 200 V for 30 minutes. The membrane transfer was performed using a dry transmembrane instrument. The gel was removed, and a transfer membrane "sandwich" was prepared. The negative plate was covered, and the membrane transfer was performed at 21 V, 23 V, and 25 V for 1, 4, and 2 minutes, respectively. The membrane was then blocked at room temperature for 1 hour. Primary antibody incubation: The membrane was incubated at room temperature for 1 hour. Antibody preparation (diluted at 1:2000): 7.5 μL of antibody was pipetted, and 15 mL of primary antibody (anti-VZV gE protein antibody, mouse mAb) dilution buffer was added.

Membrane washing: The membrane was washed 3 times for 5 minutes each using 1×TBST buffer. Secondary antibody incubation: The membrane was incubated at room temperature for 1 hour. Antibody preparation (diluted at 1:1000): 30 μL of antibody was pipetted, and 30 mL of secondary antibody (goat anti-mouse IgG) dilution buffer was added. Membrane washing: The membrane was washed 3 times for 5 minutes each using 1×TBST buffer diluted with distilled water. Color development: 1 mL each of developing solution and fixing solution were mixed at a ratio of 1:1. The mixture was added dropwise to the membrane for color development and photographed.

Figure 2:
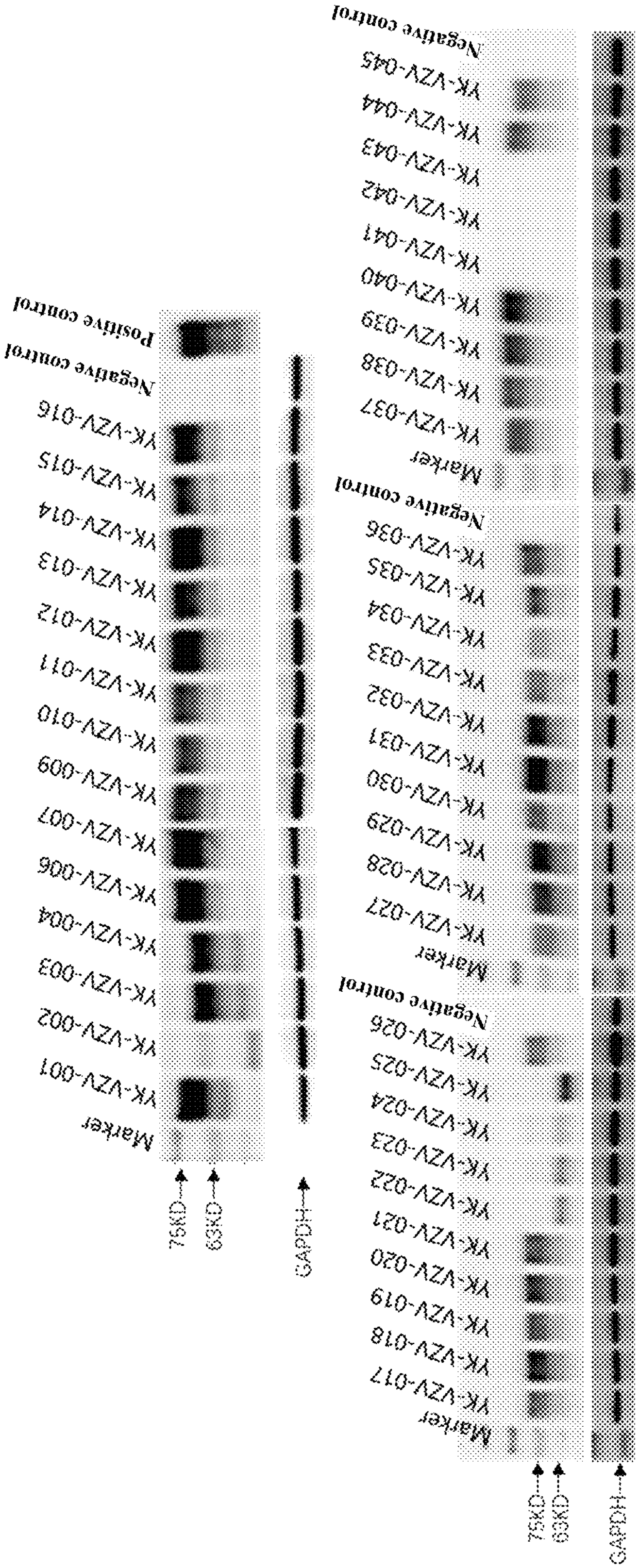
FIG. 2 shows the antigen expression of YK-VZV-001 to YK-VZV-045.

Internal reference protein GAPDH: The relative intensity was consistent, indicating an equal loading amount across all samples, on the basis of which the expression levels were compared between different samples. Negative control (NC): Only the inner reference had corresponding bands, and there was no corresponding band in the target protein region, which met the requirements of negative control. Positive control (PC) (purified gE protein): There were corresponding bands within the target size range, and the inner reference had corresponding bands, which met the requirements of positive control. Under the conditions where the positive and negative controls were appropriately set and the bands were clearly defined, the expression of experimental samples and the level of relative expression were determined. The Western Blot results of the mixture of protein samples obtained by lysis of cells transfected with a series of mRNA vaccines prepared in Example 2 are shown in FIG. 2.

Example 4: Immunization of Balb/c Mice

Experimental Materials

Animals: Balb/c mice, female, 6 to 8 weeks old.

Test substances: 1) mRNA vaccine corresponding to the antigen expressed in Example 3; 2) LNP sample (LNP sample without mRNA prepared in Example 2); 3) recombinant subunit vaccine (Shingrix®) from GSK.

Grouping: Mice were randomly grouped according to body weight, with 5 mice per group.

Animal immunization: On day 0 and day 28, mice were immunized with vehicle or test substance (liquid mRNA vaccine prepared in Example 2) via intramuscular injection into the gastrocnemius muscle. The volumes and doses are shown in the table below.

Sample Collection and Pretreatment

Approximately 0.2 mL of blood was collected from the orbital venous plexus of each animal. Serum was separated (by centrifugation at 4000 rpm for 10 minutes at 4° C.) and stored in a refrigerator at 4° C. for further processing.

Health Monitoring

Twice daily (once in the morning and once in the afternoon), including, but not limited to, observations of death, illness, breathing, secretions, feces, as well as food and water intake.

Humane Endpoint

According to the IACUC protocol, any mouse experiencing more than a 20% body weight loss during the experiment (the body weight on day 0 is used as the baseline body weight before infection, and the body weight on the day of

TABLE 5

Immunization protocol in mice

| | | Immunization | | | | | | |
|---|---|---|---|---|---|---|---|---|
| Group | Number of animals | Vaccine to be tested | Inoculation dose (μg/mouse) | Inoculation volume (μL/mouse) | Route | Frequency | Blood collection time | Euthanasia time |
| 1 | 5 | Vehicle | 0 | 100 | Intramuscular injection (gastrocnemius) | Days 0 and 28 | Blood collection from the orbital vein on days 42 and 56 | Removal of spleen on day 56 |
| 2 | 5 | YK-VZV-001 | 10 | 100 | | | | |
| 3 | 5 | YK-VZV-003 | 10 | 100 | | | | |
| 4 | 5 | YK-VZV-004 | 10 | 100 | | | | |
| 5 | 5 | YK-VZV-006 | 10 | 100 | | | | |
| 6 | 5 | YK-VZV-007 | 10 | 100 | | | | |
| 7 | 5 | YK-VZV-009 | 10 | 100 | | | | |
| 8 | 5 | YK-VZV-010 | 10 | 100 | | | | |
| 9 | 5 | YK-VZV-011 | 10 | 100 | | | | |
| 10 | 5 | YK-VZV-012 | 10 | 100 | | | | |
| 11 | 5 | YK-VZV-013 | 10 | 100 | | | | |
| 12 | 5 | YK-VZV-014 | 10 | 100 | | | | |
| 13 | 5 | YK-VZV-015 | 10 | 100 | | | | |
| 14 | 5 | YK-VZV-016 | 10 | 100 | | | | |
| 15 | 5 | YK-VZV-017 | 10 | 100 | | | | |
| 16 | 5 | YK-VZV-018 | 10 | 100 | | | | |
| 17 | 5 | YK-VZV-019 | 10 | 100 | | | | |
| 18 | 5 | YK-VZV-020 | 10 | 100 | | | | |
| 19 | 5 | YK-VZV-021 | 10 | 100 | | | | |
| 20 | 5 | YK-VZV-022 | 10 | 100 | | | | |
| 21 | 5 | YK-VZV-023 | 10 | 100 | | | | |
| 22 | 5 | YK-VZV-024 | 10 | 100 | | | | |
| 23 | 5 | YK-VZV-025 | 10 | 100 | | | | |
| 24 | 5 | YK-VZV-026 | 10 | 100 | | | | |
| 25 | 5 | YK-VZV-027 | 10 | 100 | | | | |
| 26 | 5 | YK-VZV-028 | 10 | 100 | | | | |
| 27 | 5 | YK-VZV-029 | 10 | 100 | | | | |
| 28 | 5 | YK-VZV-030 | 10 | 100 | | | | |
| 29 | 5 | YK-VZV-031 | 10 | 100 | | | | |
| 30 | 5 | YK-VZV-032 | 10 | 100 | | | | |
| 31 | 5 | YK-VZV-033 | 10 | 100 | | | | |
| 32 | 5 | YK-VZV-034 | 10 | 100 | | | | |
| 33 | 5 | YK-VZV-035 | 10 | 100 | | | | |
| 34 | 5 | YK-VZV-036 | 10 | 100 | | | | |
| 35 | 5 | YK-VZV-037 | 10 | 100 | | | | |
| 36 | 5 | YK-VZV-038 | 10 | 100 | | | | |
| 37 | 5 | YK-VZV-039 | 10 | 100 | | | | |
| 38 | 5 | YK-VZV-040 | 10 | 100 | | | | |
| 39 | 5 | YK-VZV-044 | 10 | 100 | | | | |
| 40 | 5 | YK-VZV-045 | 10 | 100 | | | | |
| 41 | 5 | LNP | 10 | 100 | | | | |
| 42 | 5 | Shingrix ® | 10 | 100 | | | | |

inoculation is used as the baseline body weight after infection) or/and showing signs of imminent death will be euthanized and recorded as a dead animal in the results.

Example 5: Detection of gE Protein-Specific IgG Antibody Titer in Serum of Balb/c Mice by Enzyme-Linked Immunosorbent Assay (ELISA)

Main Experimental Materials and Sources

The varicella-zoster virus (VZV) IgG (human) titer ELISA assay kit (gE protein) was purchased from Beijing ACROBiosystems Co., Ltd., which includes 1× washing buffer, positive control working solution, negative control working solution, dilution buffer, HRP-goat anti-mouse IgG, substrate solution, stop solution, and ELISA plate.

Experimental Steps

Preparation of working solution: Preparation of 1× washing buffer: 50 mL of 10× washing buffer was diluted with ultrapure water or deionized water, and the volume was fixed to 500 mL. Positive control working solution and negative control working solution were prepared.

Pretreatment of samples to be tested: A series of blood samples collected on day 42 and day 56 in Example 4.

Antibody titer assay: The samples to be tested, positive control (PC), and negative control (NC) were diluted with dilution buffer from 1:100 to 1:102400.

Numbering: The diluted samples were numbered corresponding to the wells of the ELISA plate. PC working solution and NC working solution were set for each experiment.

Sample addition: 100 μL of diluted sample, positive control working solution, and negative control working solution were first added to the corresponding plate well. The plate was shaken to mix thoroughly, and incubated at 37° C. for 1.0 hour.

Plate washing: The liquid in the wells was discarded, and the ELISA plate was pat-dried. The plate was washed with 1× washing buffer (300 μL/well, soak for 30 seconds) for a total of 3 times and pat-dried.

Addition of HRP enzyme conjugate: HRP-goat anti-mouse IgG was diluted 1000-fold with dilution buffer, then added to the plate at 100 μL per well, and incubated at 37° C. for 1.0 hour.

Plate washing: The washing step (step 6) was repeated 3 times.

Color development: 100 μL of substrate solution was added to each well and incubated in the dark at 37° C. for 20 minutes.

Termination: 50 μL of stop solution was added to each well, and the plate was shaken to mix thoroughly.

Reading: The absorbance of each well at $OD_{450}$ nm and $OD_{630}$ nm (with 630 nm as the background) was measured using a microplate reader, and read within 3 minutes after termination.

Interpretation of test results: Antibody-positive determination: $OD_{450}$ nm-$OD_{630}$ nm≥0.1.

Example 6: Detection of Percentage of $CD4^+$ T Cells and $CD8^+$ T Cells Secreting IFN-γ and IL-2 in Spleen of Balb/c Mice by Multiparameter Flow Cytometry (FCM)

The role of immune checkpoint inhibitors is to prevent T cell exhaustion. The function of immune cells is assessed by detecting cytokine production in tumor samples. T cells and NK cells produce interferon gamma (IFN-γ) to exert an immune response under inflammatory conditions or host immune defense. $CD8^+$ or $CD4^+$ T cells producing IFN-γ in the spleens of mice were quantified using multiparameter flow cytometry (FCM).

Interferon gamma (IFN-γ) is a soluble dimeric cytokine and the only member of type II interferons. It is mainly secreted by natural killer (NK) cells and natural killer T (NKT) cells, and plays a role in innate immunity; in the process of antigen-specific immunity, it is secreted by CD4 Th1 and CD8 cytotoxic T cells. IFN-γ or type II interferon plays an important role in both innate and adaptive immunity against viral, certain bacterial, and protozoan infections. IFN-γ serves as an important activator of macrophages and an inducer of the expression of major histocompatibility complex class II (MHC II). Interleukin-2 (IL-2) is a cytokine of the chemokine family. It is a cytokine of multicellular origin (mainly produced by activated T cells) with pleiotropic effects (mainly promoting the growth, proliferation, and differentiation of lymphocytes). It plays an important role in the body's immune response and antiviral infection. It can stimulate the proliferation of T cells that have been activated by specific antigens or mitogenic factors; activate T cells and promote cytokine production; stimulate NK cell proliferation, enhance NK killing activity and cytokine production, and induce lymphokine-activated killer (LAK) cell production; promote B cell proliferation and antibody secretion; and activate macrophages.

Detection method: FCM (multiparameter flow cytometry).

Sample for detection: Spleen removed on day 56 from the immunized mouse model in Example 5.

Purpose of detection: To determine the percentage of $CD4^+$ T cells and $CD8^+$ T cells secreting IFN-γ and IL-2 in the spleens of mice.

Detection indicators:

$CD4^+$ (IFN-$\gamma^+$): total number of $CD4^+$ T cells producing IFN-γ;

$CD4^+$ (IL-$2^+$): total number of $CD4^+$ T cells producing IL-2;

$CD4^+$ (IFN-$\gamma^+$ IL-$2^+$): total number of $CD4^+$ T cells producing both IFN-γ and IL-2;

$CD4^+$ (IFN-$\gamma^+$ or IL-$2^+$): total number of $CD4^+$ T cells producing either IFN-γ or IL-2;

$CD8^+$ (IFN-$\gamma^+$): total number of $CD8^+$ T cells producing IFN-γ;

$CD8^+$ (IL-$2^+$): total number of $CD8^+$ T cells producing IL-2;

$CD8^+$ (IFN-$\gamma^+$ IL-$2^+$): total number of $CD8^+$ T cells producing both IFN-γ and IL-2;

$CD8^+$ (IFN-$\gamma^+$ or IL-$2^+$): total number of $CD8^+$ T cells producing either IFN-γ or IL-2.

Experimental Materials

Main Reagent Sources

TABLE 6

Reagents for sample detection

| Name | Manufacturer |
|---|---|
| Fetal bovine serum (FBS) | ExCell Bio |
| RPMI 1640 medium | GIBCO |
| Penicillin-streptomycin mixture | GIBCO |
| Phosphate buffer saline (PBS) | Biotopped |
| 10× RBC Lysis Buffer (Multi-species) | Thermo Fisher |
| Zombie Violet™ Fixable Viability Kit | Biolegend |
| Protein Transport Inhibitor (brefeldin A solution) | Biolegend |
| Fixation and Permeabilization Solution | BD |
| Perm/Wash Buffer | BD |
| Ionomycin | / |

TABLE 6-continued

| Reagents for sample detection | |
|---|---|
| Name | Manufacturer |
| PMA | Sigma |
| PerCP/Cyanine5.5 anti-mouse CD3 | Biolegend |
| FITC anti-mouse CD4 | Biolegend |
| Alexa Fluor ® 700 anti-mouse CD8a | Biolegend |
| APC anti-mouse IFN-γ | Biolegend |
| PE anti-mouse IL-2 | Biolegend |
| Cell Staining Buffer | Biolegend |

Preparation of Test Solution

Each reagent was prepared according to the amount required for the experiment and all reagents were prepared in volume ratio.

FBS inactivation: FBS stored at −20° C. was thawed at 4° C., then inactivated in a water bath at 56° C. for 30 minutes, filtered through a 0.22 μm filter, and stored at 2 to 8° C. with an effective period of 14 days.

Preparation of 1×RBC Lysis Buffer: 10×RBC Lysis Buffer (Multi-species) was diluted into 1×RBC Lysis Buffer with sterile water, and mixed well for later use.

Preparation of complete medium containing 100 dual antibiotics: Complete medium was prepared at a ratio of RPMI-1640: inactivated FBS=9:1.

Complete medium containing 1% dual antibiotics was prepared at a ratio of complete medium:penicillin-streptomycin mixture=99:1, mixed well, and stored at 2 to 8° C. with an effective period of 14 days. The complete medium was equilibrated to room temperature before use.

PMA/ionomycin positive stimulant working solution: 400 μL of PMA working solution and 80 μL of ionomycin (ION) were added to 19.520 mL of complete medium containing 1% dual antibiotics to prepare a positive stimulant working solution, which was ready for use. The final concentration of PMA was 1 μg/mL and the final concentration of ionomycin (ION) was 2 μg/mL.

Negative control: complete medium containing 1% dual antibiotics.

Preparation of peptide working solution: Protein Transport Inhibitor working solution was diluted 50-fold with complete medium containing 1% dual antibiotics.

Live/Dead working solution: Zombie Violet™ Fixable Viability solution was diluted 1000-fold with 1×PBS.

Surface staining antibody: Taking the amount for one well as an example, surface staining antibody was prepared according to the proportions in the table below, mixed well by pipetting, and stored in the dark at 2° C. to 8° C. for later use.

TABLE 7

| Preparation of surface staining antibody | | |
|---|---|---|
| Antibody name | Antibody volume/well | Cell Staining Buffer |
| PerCP/Cyanine5.5 anti-mouse CD3 | 2 μL/test | 45.2 μL |
| FITC anti-mouse CD4 | 2 μL/test | |
| Alexa Fluor ® 700 anti-mouse CD8a | 0.8 μL/test | |

1× Perm/Wash Buffer: 10× Perm/Wash Buffer was diluted 10-fold with ultrapure water.

Intracellular staining antibody: Taking the amount for one well as an example, intracellular staining antibody was prepared according to the proportions in the table below, mixed well by pipetting, and stored in the dark at 2° C. to 8° C. for later use.

TABLE 8

| Preparation of intracellular staining antibody | | |
|---|---|---|
| Antibody name | Antibody volume/well | 1x Perm/ Wash Buffer |
| APC anti-mouse IFN-γ | 2 μL/test | 44 μL |
| PE anti-mouse IL-2 | 2 μL/test | |

Preparation of cryopreservation solution: prepared at a ratio of FBS:DMSO=9:1, ready for use.

Procedure

Isolation of Mouse Spleen Cells

A cell strainer was placed in a 6-well plate containing 4 mL of complete medium containing 1% dual antibiotics. The spleen was then separately placed on the cell strainer, and gently mashed or ground with the plunger end of a syringe. The resulting cell suspension was filtered through the cell strainer and transferred to a 15 mL centrifuge tube. The 6-well plate was rinsed with 1 to 2 mL of complete medium containing 1% dual antibiotics, and the resulting liquid was filtered and transferred to the 15 mL centrifuge tube, which was centrifuged at 500 g for 5 minutes at 20° C. The supernatant was discarded.

The cells were resuspended in 2 mL of 1×RBC Lysis Buffer, lysed for 5±1 minutes, and centrifuged at 500 g for 5 minutes at 20° C. The supernatant was discarded. The cells were washed with 5 mL of complete medium containing 1% dual antibiotics, and centrifuged at 500 g for 5 minutes at 20° C. The supernatant was discarded.

The cells were resuspended in 10 mL of complete medium containing 1% dual antibiotics, mixed well, and 100 μL of cell suspension was immediately added to an EP tube. 10 μL of cell suspension and 10 μL of fluorescent staining solution were then added to the EP tube, mixed well, and 10 μL of mixture was taken for counting with a fluorescence counter. The total number of viable cells and cell viability were counted.

The cells in the 15 mL centrifuge tube were centrifuged at 400 g for 5 minutes at 20° C., and the supernatant was discarded. The cells were resuspended in fresh complete medium containing 1% dual antibiotics, and the concentration of viable cells in each sample was adjusted to $1\times10^7$ cells/mL.

After the samples were plated, the remaining cells were centrifuged at 400 g for 5 minutes at 20° C., and the cell concentration was adjusted to (1 to 2)$\times10^7$ cells/mL with cryopreservation solution. The mixture was aliquoted into pre-labeled cryovials at 1 mL per vial. The cryovials were placed in a programmed cooling box, cryopreserved in a refrigerator below −70° C. for 12 to 24 hours, and transferred to a liquid nitrogen tank for long-term storage.

Stimulation of Mouse Spleen Cells

The stimulation of mouse spleen cells was performed in a 96-well U-shaped plate labeled with the experiment date.

Positive wells, negative wells, and peptide wells were setup based on the experimental requirements. 100 μL/well of negative control was added to the negative wells, 100 μL/well of positive stimulant working solution was added to the positive wells, and 100 μL/well of peptide working solution was added to the peptide wells. 100 μL/well of cell suspension was then added to the positive wells, negative wells, and peptide wells.

The 96-well plate was stimulated in a 5% $CO_2$ incubator at 37° C. for 2 hours±5 minutes, then added with 10 μL/well of Protein Transport Inhibitor working solution, mixed well, and continuously stimulated in the 5% $CO_2$ incubator at 37° C. for an additional 18 hours±10 minutes. The round-bottom 96-well plate was then removed for flow cytometric staining.

Note: All experimental procedures in this section must be conducted in a biosafety cabinet, using sterile reagents.

Cell Staining

Washing stimulated samples: The round-bottom 96-well plate was removed and centrifuged at 500 g for 5 minutes at 4° C., and the supernatant was discarded. 200 μL of PBS was added to each well, resuspended and mixed well, and the plate was centrifuged at 500 g for 5 minutes at 4° C. The supernatant was discarded.

Live/Dead staining: 50 μL of prepared Live/Dead working solution was added to each well, resuspended and mixed well, and stained in the dark at 2° C. to 8° C. for 30 minutes. After staining, 150 μL of PBS was added to each well, and the plate was centrifuged at 500 g for 5 minutes at 4° C. The supernatant was discarded.

Surface staining: 50 μL of surface staining antibody was added to each well, resuspended and mixed well, and stained in the dark at 2° C. to 8° C. for 30 minutes. 150 μL of Cell Staining Buffer was added to each well to terminate the staining, and the plate was centrifuged at 500 g for 5 minutes at 4° C. The supernatant was discarded.

Cell fixation and permeabilization: 100 μL of Fixation and Permeabilization Solution was added to each well, resuspended and mixed well, and incubated in the dark at 4° C. for 20 minutes. 100 μL of 1× Perm/Wash Buffer was added to each well for termination, and the plate was centrifuged at 500 g for 5 minutes at 4° C. The supernatant was discarded.

Intracellular staining: 50 μL of intracellular staining antibody was added to each well, resuspended and mixed well, and incubated in the dark at 4° C. for 50 minutes. 150 μL of 1× Perm/Wash Buffer was added to each well to terminate the staining, and the plate was centrifuged at 500 g for 5 minutes at 4° C. The supernatant was discarded. 200 μL of 1× Perm/Wash Buffer was added to each well, resuspended and mixed well, and the plate was centrifuged at 500 g for 5 minutes at 4° C. The supernatant was discarded.

Filtration: 200 μL of Cell Staining Buffer was added to each well, resuspended and mixed well, and the cell suspension was filtered through a 300-mesh nylon screen and transferred to a new well plate. Example of sample numbering: "01-P-1", where "01" represents the sample number, "P" represents the positive well, and the final "1" represents the well number.

Instrument Detection

Instrument name: Flow cytometer (Cytoflex);

Instrument acquisition parameters: Setting the acquisition flow rate to high speed and recording a total of 100,000 cells collected from the lymphocyte gate.

Data Processing

Data analysis: $CD3^+$ cells were identified, and then $CD4^+$ and $CD8^+$ cells were separately identified. $CD4^+$ (IFN-$\gamma^+$) and $CD4^+$ (IL-$2^+$) subpopulations were identified from the $CD4^+$ cells; $CD8^+$ (IFN-$\gamma^+$) and $CD8^+$ (IL-$2^+$) subpopulations were identified from the $CD8^+$ cells.

Data calculation formula: All values from this assay were calculated as percentages; effective value=mean of peptide wells−mean of negative wells. All values were retained to one decimal place.

Example 7: Detection of IFN-γ and IL-2 Cytokine Secretion from Spleen Cells of Balb/c Mice by Enzyme-Linked Immunospot Assay (ELISPOT)

Enzyme-linked immunospot assay (ELISPOT) is a highly sensitive detection method in cellular immunology research, which can detect antibody-secreting cells (ASCs) and cytokine (CK)-secreting cells at the single-cell level. It offers greater sensitivity than ELISA and limited dilution methods and can detect one protein-secreting cell from 200,000 to 300,000 cells. Moreover, the method allows for functional assessment of viable cells stimulated by antigens, demonstrating high specificity, high intuitive reliability, and operability, making it widely used in the detection of CK-secreting cells or ASC assay in the immunology field both domestic and abroad. Upon antigen stimulation, lymphocytes locally produce cytokines, which are captured by specific monoclonal antibodies (pre-coated) on the PVDF membrane at the bottom of the ELISPOT plate. After removing the cells, the captured cytokines bind to biotin-labeled monoclonal antibodies and subsequently to alkaline phosphatase- or horseradish peroxidase-labeled avidin. After adding substrate for color development, purple or reddish-brown spots appear on the PVDF membrane, indicating cytokine production by cells. The spots are automatically counted and analyzed by an ELISPOT reader.

The spleen removed from the mouse model in Example 6 was used to detect the levels of IFN-γ and IL-2 secreted by spleen cells after peptide library stimulation on day 56 post-immunization.

Sample processing: Follow the procedure for isolation and cryopreservation of mouse spleen cells.

ELISPOT method: Detect the levels of IFN-γ and IL-2 in the supernatant of spleen cells after peptide library stimulation.

Main Reagents

TABLE 9

Reagents for sample detection

| Name | Source |
| --- | --- |
| Mouse spleen cells | Medleader |
| FBS | ExCell Bio |
| RPMI-1640 medium | GIBCO |
| DMSO | Sigma |
| Phosphate buffer saline (1× PBS) | Biotopped |
| Phosphate buffer saline (20× PBS) | Solarbio |
| Phorbol 12-myristate 13-acetate (PMA) | Sigma |
| Ionomycin (ION) | Sigma |
| Penicillin-streptomycin mixture | Gibco |
| ELISpot Plus: Mouse IFN-γ (HRP) | MabTech |
| ELISpot Plus: Mouse IL-2 (HRP) | MabTech |

Preparation of Test Solution

1) FBS inactivation: FBS stored at −20° C. was thawed at 4° C., then inactivated in a water bath at 56° C. for 30 minutes, filtered through a 0.22 m filter, and stored at 2 to 8° C. with an effective period of 30 days.

2) Preparation of PMA working solution: 1 mL of DMSO was added to a PMA reagent bottle to dissolve the PMA powder, and the mixture was transferred to a 15 mL centrifuge tube. The PMA reagent bottle was rinsed with 1 mL of DMSO, and the rinse solution was transferred to the 15 mL centrifuge tube. 8 mL of DMSO was then added to the 15 mL centrifuge tube and mixed well to prepare a PMA working solution with a concentration of 100 μg/mL, which was stored in the dark in a refrigerator at −20° C.

3) Preparation of ION working solution: 2 mL of DMSO was added to an ION reagent bottle to dissolve the ION powder, and the mixture was transferred to a 15 mL centrifuge tube. The ION reagent bottle was rinsed with 1 mL of DMSO, then the rinsing step was repeated twice more (a total of 3 times, each with 1 mL), and the rinse solution was transferred to the 15 mL centrifuge tube. 5 mL of DMSO was then added to the 15 mL centrifuge tube and mixed well to prepare an ION working solution with a concentration of 1 mg/mL, which was stored in a refrigerator at −20° C.

4) Preparation of complete medium containing 1% dual antibiotics: Complete medium was prepared at a ratio of RPMI-1640: inactivated FBS=9:1. Complete medium containing 1% dual antibiotics was prepared at a ratio of complete medium:penicillin-streptomycin mixture=99:1, mixed well, and stored at 2 to 8° C. with an effective period of 14 days. The complete medium was equilibrated to room temperature before use.

5) Preparation of positive stimulant working solution: 400 μL of PMA working solution and 80 μL of ionomycin (ION) were added to 19.520 mL of complete medium to prepare a positive stimulant working solution, which was ready for use. The final concentration of PMA was 2 μg/mL and the final concentration of ION was 4 μg/mL.

6) Preparation of peptide working solution:

(i) Preparation of gE Peptide Library Solution

100 μL of DMSO was added to each tube of lyophilized powder. After dissolution, the peptide concentration in each tube was 1 mg/mL per peptide. 900 μL of PBS was added to the dissolved peptide solution to adjust the gE peptide library concentration to 100 μg/mL per peptide.

(ii) Preparation of gE Working Solution gE working solution was prepared at a ratio of gE peptide library solution:complete medium containing 1% dual antibiotics=1:50, resulting in a concentration of 2 μg/mL per peptide.

Negative control: complete medium containing 1% dual antibiotics.

7) Preparation of 1×PBS solution:prepared at a ratio of 20×PBS:pure water=1:19, stored at room temperature, ready for use.

8) Preparation of PBS containing FBS: prepared at a ratio of PBS (Biotopped):inactivated FBS=200:1, ready for use.

9) Antibody preparation:

(i) Preparation of $R_{4-6}$A2-biotin: prepared at a ratio of $R_4$-6A2-biotin:PBS containing FBS=1:1000, ready for use.

(ii) Preparation of 5H4-biotin: prepared at a ratio of 5H4-biotin:PBS containing FBS=1:1000, ready for use.

Experimental Steps

1) The spleen removed from the mouse model in Example 6 was used to detect the levels of IFN-γ and IL-2 secreted by spleen cells after peptide library stimulation on day 56 post-immunization, as well as $CD4^+$ and $CD8^+$ T cells producing IFN-γ and IL-2.

2) Sample for detection: Spleen removed on day 56, cryopreserved at −80° C.

Resuscitation of Mouse Spleen Cells

Preparation: Before cell resuscitation, the temperature of the thermostatic water bath was adjusted to 37° C., and complete medium containing 1% dual antibiotics was preheated at 37° C.

Sampling: Mouse spleen cells cryopreserved in the liquid nitrogen tank were removed by a sample administrator and transferred to a box containing liquid nitrogen. The cryovials were removed from the box, sprayed with 75% ethanol, and then placed in a transfer window of the cell culture room.

Resuscitation: The cryovials were immediately removed from the transfer window by a validator and rapid thawed in the thermostatic water bath at 37° C. Once fully thawed, the cells were aseptically transferred to a 15 mL centrifuge tube containing 9 mL of complete medium containing 1% dual antibiotics.

Rinsing: 1 mL of complete medium containing 1% dual antibiotics was added to a cryovial, then the cryovial was rinsed, and the rinse solution was transferred back to the 15 mL centrifuge tube.

Centrifugation: The cells were centrifuged at 400 g for 10 minutes at 18 to 20° C.

Counting: The supernatant was discarded. The cells were resuspended in 10 mL of complete medium containing 1% dual antibiotics, mixed well, and 100 μL of cell suspension was added to an EP tube. 10 μL from 100 μL of cell suspension was then added to an EP tube containing 10 μL of fluorescent staining solution, mixed well, and 10 μL of mixture was taken for counting with a fluorescence counter. The total number of viable cells and cell viability were counted (if viability is below 50%, repeat counting with the fluorescence counter once and the results of the second counting shall prevail).

Re-centrifugation: The remaining cells in the 15 mL centrifuge tube were centrifuged at 400 g for 5 minutes at 18 to 20° C.

Resuspension: The supernatant was discarded. The cells were resuspended in complete medium containing 1% dual antibiotics, and the concentration of viable cells was adjusted to A0: $4\times10^6$ cells/mL and A1: $4\times10^5$ cells/mL.

Stimulation of Mouse Spleen Cells

Plate washing: IFN-γ and IL-2 plates were washed with 200 μL/well of PBS (PBS used throughout the experiment was sterile) for a total of 4 times.

Blocking: PBS in the wells was discarded, and the plate was tapped (to the greatest extent remove the residual liquid in the wells). 200 μL/well of complete medium containing 1% dual antibiotics was added, and the plate was left at room temperature for at least 30 minutes (record the exact time).

Plating: Complete medium containing 1% dual antibiotics in the well plate was discarded, and the plate was tapped (to the greatest extent remove the residual liquid in the wells); 100 μL/well of positive stimulant working solution was added to the positive wells; 100 μL/well of negative control was added to the negative wells; 100 μL/well of peptide working solution was added to the peptide wells; 200 μL/well of negative control was added to the blank wells without cells.

Addition of cells: 100 μL/well of A0 cell suspension was added to the negative wells and peptide wells, and 100 μL/well of A1 cell suspension was added to the positive wells.

Incubation: The plate was covered with aluminum foil and stimulated in a 5% $CO_2$ incubator at 37° C. for 21 hours±30 minutes.

Note: All experimental procedures in this section must be conducted in a biosafety cabinet, using sterile reagents.

Cytokine Detection

Plate washing: The next day, the original liquid in the well plate was discarded. The plate was tapped (to the greatest extent remove the residual liquid in the wells) and washed with 200 μL/well of PBS for a total of 5 times.

Addition of secondary antibody: PBS in the wells was discarded, and the plate was tapped (to the greatest extent remove the residual liquid in the wells). IFN-γ: R4-6A2-biotin working solution was added at 100 μL/well. IL-2:

5H4-biotin working solution was added at 100 µL/well. The plate was incubated at room temperature for 2 hours±5 minutes.

Plate washing: The original liquid in the well plate was discarded. The plate was tapped (to the greatest extent remove the residual liquid in the wells) and washed with 200 µL/well of PBS for a total of 5 times.

Addition of tertiary antibody: Streptavidin-HRP working solution was added at 100 µL/well. The plate was incubated at room temperature for 1 hour±2 minutes, and the liquid in the well plate was discarded. The plate was tapped (to the greatest extent remove the residual liquid in the wells) and washed with 200 µL/well of PBS for a total of 5 times.

Plate washing: The original liquid in the well plate was discarded. The plate was tapped (to the greatest extent remove the residual liquid in the wells) and washed with 200 µL/well of PBS for a total of 5 times.

Color development: TMB substrate solution, which had been brought to room temperature, was added at 100 µL/well. After color development at room temperature for 15±1 minutes, the liquid in the well plate was discarded, and the plate was washed with pure water to terminate the color development. The bottom plate was removed from the well plate, and the bottom surface of the well plate was rinsed.

Reading: After the well plate was completely dried at room temperature in the dark, an ELISPOT analyzer was used for photographing and reading. Camera parameters: Shutter (Exposure): 400; Gain: 25. Counting parameters: IFN-γ-Mouse-Mab/L-2-Mouse-MabT: Size: 30; Intensity (threshold for optical density): 30; TNTC: 80%.

Example 8: Distribution of VZV gE Antigen in *Chorocebus sabaeus* Kidney Cells (Vero)

Figure 3:
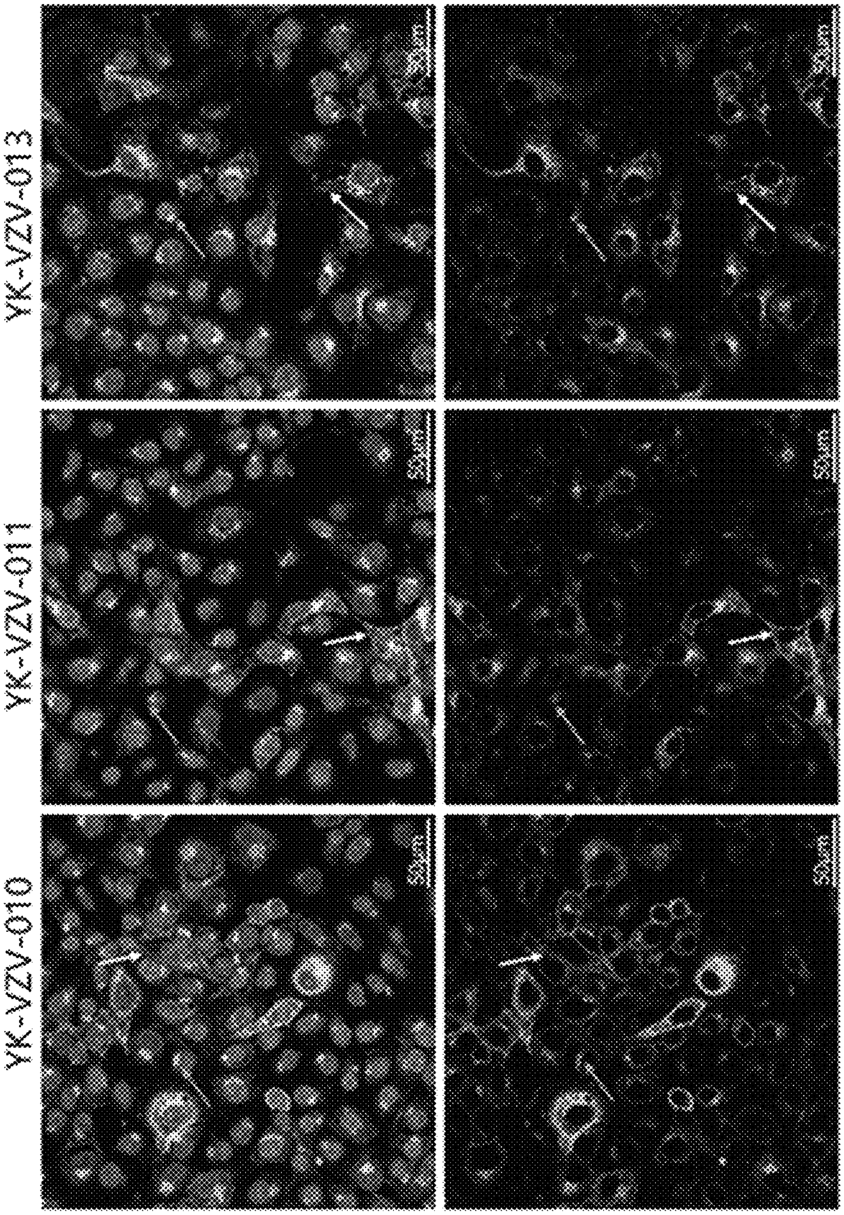
FIG. 3 shows the cellular localization of VZV gE antigens of YK-VZV-010, YK-VZV-011, and YK-VZV-013.
Figure 4:
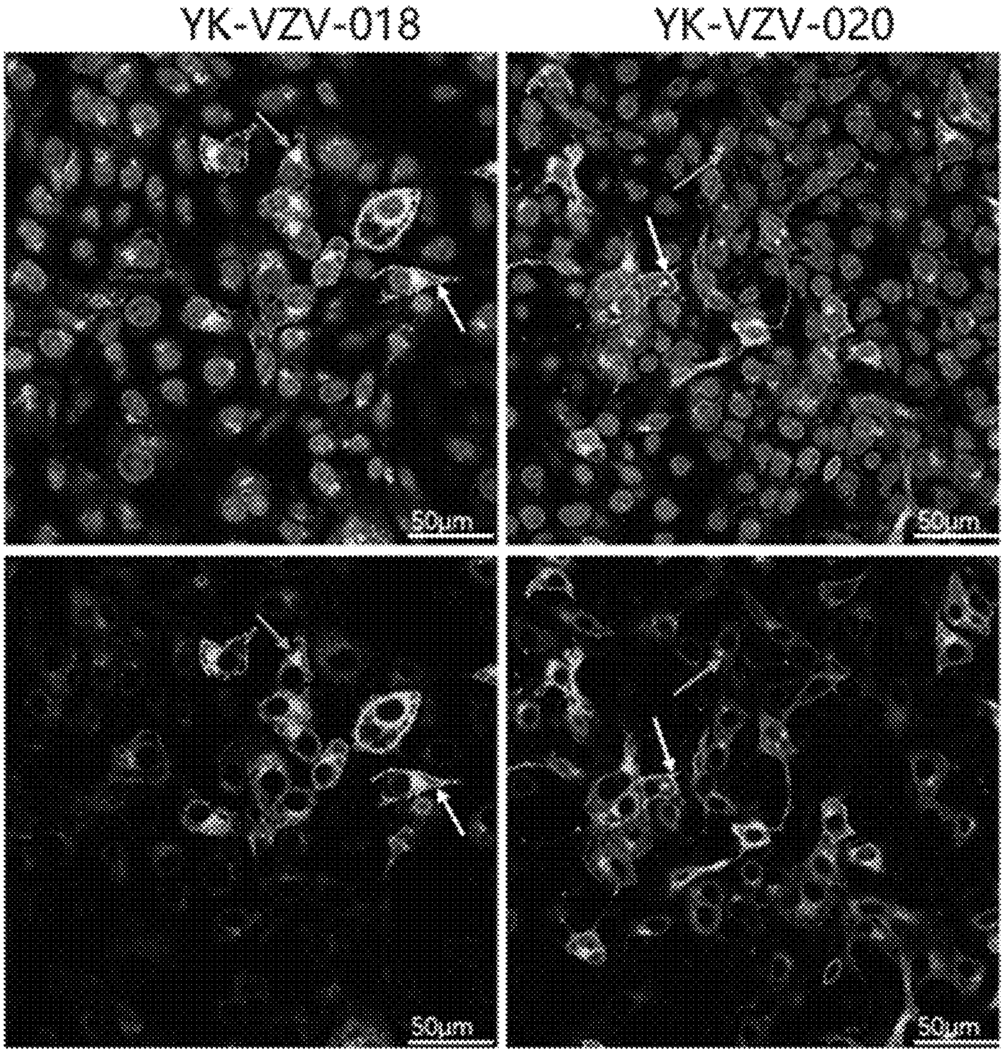
FIG. 4 shows the cellular localization of VZV gE antigens of YK-VZV-018 and YK-VZV-020, in which green represents gE antigen; yellow and red represent GM130 and TGN46, respectively; white arrow represents cell membrane; and orange arrow represents Golgi.

Vero cells area lineage of cells used in cell cultures. The "Vero" lineage was isolated from kidney epithelial cells extracted from *Chorocebus sabaeus*. Vero cells were transfected with different gE antigen variants constructed herein (YK-VZV-010, YK-VZV-011, YK-VZV-013, YK-VZV-018, and YK-VZV-020). The transfected cells were stained with antibodies for gE antigen labeling and Golgi-labeled GM130/TGN46 antibodies, and antigen localization was observed using confocal microscopy. The results are shown in FIGS. 3 and 4.

Preparation Off Reagents and Consumables

TABLE 10

| Reagents and consumables for sample detection | |
|---|---|
| Name | Source |
| u-Slide 8 Well incubation box with light protection | ibidi |
| Anti-VZV gE protein antibody | Abcam |
| 488 donkey anti-mouse secondary antibody | Yeasen Biotechnology (Shanghai) Co., Ltd. |
| Anti-fluorescence quenching sealing agent (containing DAPI) | Beyotime Biotechnology Co., Ltd. |
| Phosphate buffer saline (1× PBS) | Beyotime Biotechnology Co., Ltd. |
| Phosphate buffer saline (20× PBS) | Beyotime Biotechnology Co., Ltd. |
| Immunostaining permeabilization buffer (Triton X-100) | Beyotime Biotechnology Co., Ltd. |
| 4% paraformaldehyde fix solution | Beyotime Biotechnology Co., Ltd. |
| QuickBlock ™ primary antibody dilution buffer for immunostaining | Beyotime Biotechnology Co., Ltd. |
| QuickBlock ™ blocking buffer for immunostaining | Beyotime Biotechnology Co., Ltd. |
| QuickBlock ™ secondary antibody dilution buffer for immunofluorescence | Beyotime Biotechnology Co., Ltd. |
| 647-conjugated GOLGA2/GM130 antibody | Proteintech |
| CoraLite ® 594-conjugated TGN46 antibody | Proteintech |

Experimental Steps

1) Cell inoculation: Vero cells (purchased from Beyotime Biotechnology Co., Ltd.) were inoculated in a confocal petri dish, and the number of inoculated cells was recorded when the cell inoculation density was observed to be around 30% under a microscope. The cells were incubated overnight.

2) Transfection: The cells were transfected with overexpression stock solution (50 ng/well) and incubated for 48 hours.

3) Washing: The confocal petri dish was removed and the medium inside was discarded. The petri dish was washed with PBS 1 to 3 times, avoiding vigorous shaking.

4) Fixation: The cells were fixed with 200 µL of 4% paraformaldehyde solution, left at room temperature for 15 minutes, and washed with 1×PBS three times, leaving at room temperature for 5 minutes each time.

5) Permeabilization: The cells were permeabilized with 200 µL of 0.3% Triton X-100 (diluted with 1×PBS) for 10 minutes, and washed with 1×PBS three times, leaving at room temperature for 5 minutes each time.

6) Blocking: The cells were blocked with 200 µL of immunostaining blocking buffer and incubated at room temperature for 2 hours.

7) Primary antibody binding: 100 µL of primary antibody diluted with antibody dilution buffer was added, with the specific antibodies and dilution ratios as follows. VZV gE antibody was diluted 1:100, 647-conjugated GOLGA2/GM130 antibody was diluted 1:100, and CoraLite® 594-conjugated TGN46 antibody was diluted 1:100. The mixture was incubated in the dark at 4° C. overnight, and primary antibody was aspirated (can be reused).

8) Primary antibody washing: The mixture was washed with 1×PBS three times for 5 minutes each to remove unbound primary antibody.

9) Secondary antibody incubation: 200 µL of fluorescent secondary antibody diluted with antibody dilution buffer at a ratio of 1:300 was added. The mixture was incubated in the dark at room temperature for 1.5 hours.

10) Secondary antibody washing: The mixture was washed with 1×PBS three times for 5 minutes each to remove unbound secondary antibody, preventing non-specific staining.

11) Nuclear staining and sealing: The frame was removed, and a drop of DAPI staining solution was added to each well. The petri dish was covered with a lid and stored in the dark at 4° C.

12) A confocal microscope was used for photographing and observation.

Control Setting

The present disclosure set the following controls:

LNP: Blank LNP without mRNA vaccine;

Shingrix®: Recombinant protein subunit vaccine Shingrix® produced and marketed by GSK, consisting of the extracellular region of VZV gE protein, amino acids 1 to 539, without mutations.

Comparative Example 1

Based on the herpes zoster mRNA vaccine antigen sequence reported in the literature (Morgan A, et al. 2020) and Moderna patent (U.S. Ser. No. 11/643,441B1), it was found that the antigen developed by the patent is gE (1-573aa) Y569A, based on which YK-VZV-004 (SEQ ID NO: 15) was designed in the present disclosure, which retains the same mutation site and truncation length as the herpes zoster mRNA vaccine antigen sequence gE (1-573aa) Y569A reported in Moderna patent (U.S. Ser. No. 11/643, 441B1). YK-VZV-004: gE (1-573aa) Y569A was used as one of the positive controls for antigen screening, together with the sequences of mutations or combinations of mutations newly designed in the present disclosure for immunogenicity evaluation of the vaccine. The specific results are shown in examples.

Comparative Example 2

Based on the herpes zoster mRNA vaccine antigen sequence reported in the patent (CN114081943A), it was found that the full-length polypeptide of VZV gE developed by the patent comprises a combination of mutations (Y569A, S593A, S595A, T596A, and T598A), based on which YK-VZV-006 (SEQ ID NO: 19) was designed in the present disclosure, which retains the same combination of mutation sites (Y569A, S593A, S595A, T596A, and T598A) as SEQ ID NO: 2 mentioned in the patent (CN114081943A). YK-VZV-006: gE(1-623aa) (Y569A, S593A, S595A, T596A, and T598A) was also used as one of the controls for antigen screening in the present disclosure, together with the sequences of mutations or combinations of mutations newly designed in the present disclosure for immunogenicity evaluation of the vaccine. The specific results are shown in examples.

Comparative Example 3

Based on the herpes zoster mRNA vaccine antigen sequence reported in US20230233671A1, it was found that the patent discloses mutant VZV gE protein Y582A, based on which YK-VZV-045 (SEQ ID NO: 171) was designed in the present disclosure, which retains the same combination of mutation sites (Y582A) as the mRNA vaccine antigen sequence mentioned in US20230233671A1. YK-VZV-045 was also used as one of the controls for antigen screening in the present disclosure, together with the sequences of mutations or combinations of mutations newly designed in the present disclosure for immunogenicity evaluation of the vaccine. The specific results are shown in examples.

Comparative Example 4

Based on the herpes zoster mRNA vaccine antigen sequence reported in CN108472309A, it was found that the patent discloses mutant VZV gE protein Y582A, based on which YK-VZV-007 (SEQ ID NO: 23) was designed in the present disclosure, which retains the same combination of mutation sites (Y582A, S593A, S595A, T596A, and T598A) as the mRNA vaccine antigen sequence mentioned in CN108472309A. YK-VZV-007 was also used as one of the controls for antigen screening in the present disclosure, together with the sequences of mutations or combinations of mutations newly designed in the present disclosure for immunogenicity evaluation of the vaccine. The specific results are shown in examples.

Summary and Analysis of Results

In Vitro Expression Results of VZV gE Antigen Variants

The results of Western Blot detection of 43 VZV gE antigen variants (FIG. 2) show that YK-VZV-002 exhibits extremely low or almost no antigenic protein expression; YK-VZV-041, YK-VZV-042, and YK-VZV-043 show negative results with no antigenic protein expression. Consequently, these four sequences could not be used as candidate antigens for the herpes zoster mRNA vaccine and were therefore excluded.

All other antigen variants exhibit significant protein expression, with the size of the expressed protein ranging from approximately 63 kDa to 75 kDa, which is consistent with the theoretical design of the antigen. These antigen variants can be used as effective candidate antigens for subsequent immunogenicity screening and evaluation.

As shown by the results from the above Western blot experiments, all the 39 antigen sequences of YK-VZV-001, YK-VZV-003, YK-VZV-004 (Comparative Example 1), YK-VZV-006 (Comparative Example 2), YK-VZV-007 (Comparative Example 4), YK-VZV-009, YK-VZV-010, YK-VZV-011, YK-VZV-012, YK-VZV-013, YK-VZV-014, YK-VZV-015, YK-VZV-016, YK-VZV-017, YK-VZV-018, YK-VZV-019 YK-VZV-020, YK-VZV-021, YK-VZV-022, YK-VZV-023, YK-VZV-024, YK-VZV-025, YK-VZV-026, YK-VZV-027, YK-VZV-028, YK-VZV-029, YK-VZV-030, YK-VZV-031, YK-VZV-032, YK-VZV-033, YK-VZV-034, YK-VZV-035, YK-VZV-036, YK-VZV-037, YK-VZV-038, YK-VZV-039, YK-VZV-040, YK-VZV-044, and YK-VZV-045 (Comparative Example 3) exhibit significant protein expression and can be used as effective candidate antigens for subsequent immunogenicity screening and evaluation. Therefore, gE-specific antibody IgG titer assay was conducted on these antigens.

Results of gE Protein-Specific IgG Antibody Titers of VZV gE Antigen Variants in Serum of Balb/c Mice (D42)

As shown in Example 5, the gE protein-specific IgG antibody titers in the serum of mice were measured on day 42 post-immunization by ELISA. The test results are shown in Table 11.

TABLE 11

VZV gE protein-specific IgG antibody titers in serum of mice (day 42)

| Test substance | Antibody GMT (× $10^4$) | Antibody GMT of test substance/antibody GMT of Shingrix ® (times) | Antibody GMT of test substance/antibody GMT of YK-VZV-007 (times) |
|---|---|---|---|
| YK-VZV-009 | 1000 | 5.3 | 2.8 |
| YK-VZV-010 | 1000 | 5.3 | 2.8 |
| YK-VZV-013 | 1000 | 5.3 | 2.8 |
| YK-VZV-014 | 1000 | 5.3 | 2.8 |
| YK-VZV-011 | 950 | 5.0 | 2.6 |
| YK-VZV-012 | 944 | 5.0 | 2.6 |
| YK-VZV-018 | 870 | 4.6 | 2.4 |
| YK-VZV-020 | 800 | 4.2 | 2.2 |
| YK-VZV-030 | 662 | 3.5 | 1.8 |
| YK-VZV-031 | 659 | 3.5 | 1.8 |
| YK-VZV-038 | 654 | 3.4 | 1.8 |
| YK-VZV-021 | 650 | 3.4 | 1.8 |
| YK-VZV-024 | 640 | 3.4 | 1.8 |
| YK-VZV-028 | 630 | 3.3 | 1.8 |
| YK-VZV-003 | 560 | 2.9 | 1.6 |
| YK-VZV-001 | 540 | 2.8 | 1.5 |
| YK-VZV-016 | 530 | 2.8 | 1.5 |
| YK-VZV-015 | 520 | 2.7 | 1.4 |
| YK-VZV-017 | 510 | 2.7 | 1.4 |
| YK-VZV-023 | 190 | 1.0 | 0.5 |
| YK-VZV-022 | 163 | 0.9 | 0.5 |
| YK-VZV-026 | 163 | 0.9 | 0.5 |
| YK-VZV-027 | 163 | 0.9 | 0.5 |
| YK-VZV-033 | 163 | 0.9 | 0.5 |
| YK-VZV-037 | 163 | 0.9 | 0.5 |
| YK-VZV-039 | 163 | 0.9 | 0.5 |
| YK-VZV-044 | 163 | 0.9 | 0.5 |
| YK-VZV-040 | 162 | 0.9 | 0.5 |
| YK-VZV-032 | 160 | 0.8 | 0.4 |
| YK-VZV-034 | 154 | 0.8 | 0.4 |
| YK-VZV-025 | 151 | 0.8 | 0.4 |
| YK-VZV-035 | 150 | 0.8 | 0.4 |
| YK-VZV-036 | 136 | 0.7 | 0.4 |
| YK-VZV-029 | 102 | 0.5 | 0.3 |
| LNP | 0 | 0.0 | 0.0 |
| Shingrix ® | 190 | 1.0 | 0.5 |
| YK-VZV-004 (Comparative Example 1) | 400 | 2.1 | 1.1 |
| YK-VZV-006 (Comparative Example 2) | 360 | 1.9 | 1.0 |
| YK-VZV-045 (Comparative Example 3) | 352 | 1.9 | 1.0 |
| YK-VZV-007 (Comparative Example 4) | 360 | 1.9 | 1.0 |

As shown by the gE-specific antibody IgG titer results on day 42, the Shingrix® positive control had a titer result of 190×$10^4$, while the following variants outperformed Shingrix®, including YK-VZV-009, YK-VZV-011, YK-VZV-013, YK-VZV-014, YK-VZV-010, YK-VZV-012, YK-VZV-018, YK-VZV-020, YK-VZV-030, YK-VZV-031, YK-VZV-038, YK-VZV-021, YK-VZV-024, YK-VZV-028, YK-VZV-003, YK-VZV-001, YK-VZV-016, YK-VZV-015, YK-VZV-017, YK-VZV-004 (Comparative Example 1), YK-VZV-006 (Comparative Example 2), YK-VZV-045 (Comparative Example 3), and YK-VZV-007 (Comparative Example 4), whose titer result was 2.7 to 5.3 times that of the Shingrix® positive control.

Using the Shingrix® positive control as a standard, and on the basis that the above gE-specific antibody IgG titer result was also 1.8 to 2.8 times better than that of the YK-VZV-007 sequence (Comparative Example 4), a total of 14 variants were further extracted, including YK-VZV-009, YK-VZV-011, YK-VZV-013, YK-VZV-014, YK-VZV-010, YK-VZV-012, YK-VZV-018, YK-VZV-020, YK-VZV-030, YK-VZV-031, YK-VZV-038, YK-VZV-021, YK-VZV-024, YK-VZV-028, as well as 4 control sequences including YK-VZV-004 (Comparative Example 1), YK-VZV-006 (Comparative Example 2), YK-VZV-045 (Comparative Example 3), and YK-VZV-007 (Comparative Example 4) for subsequent testing.

Results of Cellular Immunity of VZV gE Antigen Variants (FCM)

Cellular immunity, particularly T cell immunity, plays a crucial role in the process of VZV infection. Studies have shown that the cell-mediated immune response is an important indicator for the evaluation of the immune effect of the herpes zoster vaccine. To further evaluate the specific cellular immune response induced by immunization of mice with the above antigen variant mRNA, the specific $CD4^+$ and $CD8^+$ T cell immune responses induced by immunization of mice with VZV gE antigen mRNA were detected by FCM in Example 6.

Using the Shingrix® positive control as a standard, and on the basis that the above gE-specific antibody IgG titer result was also better than that of the YK-VZV-007 sequence, a total of 14 variants were further extracted, including the spleens of immunized mice on day 56 of YK-VZV-009, YK-VZV-011, YK-VZV-013, YK-VZV-014, YK-VZV-010, YK-VZV-012, YK-VZV-018, YK-VZV-020, YK-VZV-030, YK-VZV-031, YK-VZV-038, YK-VZV-021, YK-VZV-024, YK-VZV-028, as well as 4 control sequences including YK-VZV-004 (Comparative Example 1), YK-VZV-006 (Comparative Example 2), YK-VZV-045 (Comparative Example 3), and YK-VZV-007 (Comparative Example 4), and the percentage of $CD4^+$ T cells and $CD8^+$ T cells secreting IFN-γ and IL-2 in the spleens of mice was measured according to the detection method in Example 6.

$CD4^+$ T Cells

The immune effect of $CD4^+$ T cells plays a crucial role in the recovery of VZV infection and the immune effect of the vaccine. It is one of the most important indicators for the evaluation of the immune effect of the vaccine. The spleens of immunized mice were removed on day 56, and the percentage of $CD4^+$ T cells secreting IFN-γ and IL-2 in the spleens of mice was measured. The specific results are shown in the table below.

TABLE 12

Summary of $CD4^+$ T cell assay results

| Test substance | $CD4^+$ (IFN-$\gamma^+$) | | | $CD4^+$ (IL-$2^+$) | | | $CD4^+$ (IFN-$\gamma^+$ or IL-$2^+$) | | |
|---|---|---|---|---|---|---|---|---|---|
| | $CD4^+$ (IFN-$\gamma^+$) | Compared to Shingrix ® (times) | Compared to YK-VZV-007 (times) | $CD4^+$ (IL-$2^+$) | Compared to Shingrix ® (times) | Compared to YK-VZV-007 (times) | $CD4^+$ (IFN-$\gamma^+$ or IL-$2^+$) | Compared to Shingrix ® (times) | Compared to YK-VZV-007 (times) |
| YK-VZV-010 | 2.00% | 6.7 | 4.4 | 3.70% | 12.3 | 7.4 | 4.20% | 7.0 | 5.3 |
| YK-VZV-013 | 1.70% | 5.7 | 3.8 | 1.30% | 4.3 | 2.6 | 1.90% | 3.2 | 2.4 |
| YK-VZV-011 | 1.60% | 5.3 | 3.6 | 1.20% | 4.0 | 2.4 | 1.60% | 2.7 | 2.0 |
| YK-VZV-020 | 1.60% | 5.3 | 3.6 | 2.50% | 8.3 | 5.0 | 3.10% | 5.2 | 3.9 |
| YK-VZV-012 | 1.40% | 4.7 | 3.1 | 1.20% | 4.0 | 2.4 | 1.70% | 2.8 | 2.1 |
| YK-VZV-018 | 1.20% | 4.0 | 2.7 | 1.10% | 3.7 | 2.2 | 1.40% | 2.3 | 1.8 |
| YK-VZV-028 | 1.20% | 4.0 | 2.7 | 1.30% | 4.3 | 2.6 | 1.70% | 2.8 | 2.1 |
| YK-VZV-014 | 1.10% | 3.7 | 2.4 | 0.80% | 2.7 | 1.6 | 1.10% | 1.8 | 1.4 |
| YK-VZV-038 | 1.10% | 3.7 | 2.4 | 1.40% | 4.7 | 2.8 | 1.90% | 3.2 | 2.4 |
| YK-VZV-031 | 1.00% | 3.3 | 2.2 | 1.40% | 4.7 | 2.8 | 1.70% | 2.8 | 2.1 |
| YK-VZV-021 | 0.90% | 3.0 | 2.0 | 1.10% | 3.7 | 2.2 | 1.50% | 2.5 | 1.9 |
| YK-VZV-009 | 0.80% | 2.7 | 1.8 | 1.10% | 3.7 | 2.2 | 1.40% | 2.3 | 1.8 |
| YK-VZV-024 | 0.70% | 2.3 | 1.6 | 0.60% | 2.0 | 1.2 | 0.90% | 1.5 | 1.1 |
| YK-VZV-030 | 0.60% | 2.0 | 1.3 | 0.80% | 2.7 | 1.6 | 1.10% | 1.8 | 1.4 |
| LNP | 0.10% | 0.3 | 0.2 | 0.10% | 0.3 | 0.2 | 0.20% | 0.3 | 0.3 |
| Shingrix ® | 0.30% | 1.0 | 0.7 | 0.30% | 1.0 | 0.6 | 0.60% | 1.0 | 0.8 |
| YK-VZV-004 (Comparative Example 1) | 0.55% | 1.8 | 1.2 | 0.55% | 1.8 | 1.1 | 0.95% | 1.6 | 1.2 |
| YK-VZV-045 (Comparative Example 3) | 0.50% | 1.7 | 1.1 | 0.30% | 1.0 | 0.6 | 0.50% | 0.8 | 0.6 |
| YK-VZV-007 (Comparative Example 4) | 0.45% | 1.5 | 1.0 | 0.50% | 1.7 | 1.0 | 0.80% | 1.3 | 1.0 |

Note:
Shingrix ® is a recombinant protein vaccine from GSK.

Total percentage of IFN-$\gamma^+$ $CD4^+$ T cells and IL-$2^+$ $CD4^+$ T cells

A) Based on the above results, the mRNA vaccines prepared from test substances YK-VZV-010, YK-VZV-020, YK-VZV-013, YK-VZV-038, YK-VZV-012, YK-VZV-028, YK-VZV-031, YK-VZV-011, YK-VZV-021, YK-VZV-018, and YK-VZV-009 (11 in total) were screened out. The total percentage of IFN-$\gamma^+$ $CD4^+$ T cells and IL-$2^+$ $CD4^+$ T cells secreted by these mRNA vaccines was 2 times or more and up to 7 times that of the Shingrix® positive control vaccine, and 1.8 to 5.3 times that of YK-VZV-007 (Comparative Example 4). Moreover, the results were significantly better than those of YK-VZV-004 (Comparative Example 1) and YK-VZV-045 (Comparative Example 3).

Specifically, the total percentage of IFN-$\gamma^+$ $CD4^+$ T cells and IL-$2^+$ $CD4^+$ T cells secreted by the mRNA vaccines prepared from YK-VZV-010, YK-VZV-020, YK-VZV-013, YK-VZV-011, and YK-VZV-018 was 7.0, 5.2, 3.2, 2.7, and 2.3 times that of the Shingrix® positive control vaccine, respectively; 5.3, 3.9, 2.4, 2.0, and 1.8 times that of YK-VZV-007 (Comparative Example 4), respectively; and significantly higher than that of YK-VZV-004 (Comparative Example 1) and YK-VZV-045 (Comparative Example 3).

The details are shown in the table below.

TABLE 13

Total percentage of IFN-$\gamma^+$ $CD4^+$ T cells and IL-$2^+$ $CD4^+$ T cells induced by mRNA vaccines - 1

| Test substance | $CD4^+$ (IFN-$\gamma^+$ or IL-$2^+$) | Compared to Shingrix ® (times) | Compared to YK-VZV-007 (times) |
|---|---|---|---|
| YK-VZV-010 | 4.20% | 7.0 | 5.3 |
| YK-VZV-020 | 3.10% | 5.2 | 3.9 |
| YK-VZV-013 | 1.90% | 3.2 | 2.4 |

TABLE 13-continued

Total percentage of IFN-$\gamma^+$ $CD4^+$ T cells and IL-$2^+$ $CD4^+$ T cells induced by mRNA vaccines - 1

| Test substance | $CD4^+$ (IFN-$\gamma^+$ or IL-$2^+$) | Compared to Shingrix ® (times) | Compared to YK-VZV-007 (times) |
|---|---|---|---|
| YK-VZV-038 | 1.90% | 3.2 | 2.4 |
| YK-VZV-012 | 1.70% | 2.8 | 2.1 |

TABLE 13-continued

Total percentage of IFN-γ$^+$ CD4$^+$ T cells and IL-2$^+$ CD4$^+$ T cells induced by mRNA vaccines - 1

| Test substance | CD4$^+$ (IFN-γ$^+$ or IL-2$^+$) | Compared to Shingrix ® (times) | Compared to YK-VZV-007 (times) |
|---|---|---|---|
| YK-VZV-028 | 1.70% | 2.8 | 2.1 |
| YK-VZV-031 | 1.70% | 2.8 | 2.1 |
| YK-VZV-011 | 1.60% | 2.7 | 2.0 |
| YK-VZV-021 | 1.50% | 2.5 | 1.9 |
| YK-VZV-018 | 1.40% | 2.3 | 1.8 |
| YK-VZV-009 | 1.40% | 2.3 | 1.8 |
| LNP | 0.20% | 0.3 | 0.3 |
| Shingrix ® | 0.60% | 1.0 | 0.8 |
| YK-VZV-004 (Comparative Example 1) | 0.95% | 1.6 | 1.2 |
| YK-VZV-045 (Comparative Example 3) | 0.50% | 0.8 | 0.6 |
| YK-VZV-007 (Comparative Example 4) | 0.80% | 1.3 | 1.0 |

B) However, the total percentage of IFN-γ$^+$ CD4$^+$ T cells and IL-2$^+$ CD4$^+$ T cells secreted by the mRNA vaccines prepared from test substances YK-VZV-014, YK-VZV-030, and YK-VZV-024 was less than 2 times that of the Shingrix® positive control vaccine and less than 1.5 times that of Comparative Example 4 (YK-VZV-007), so that these sequences were excluded. The specific results are shown in the table below.

TABLE 14

Total percentage of IFN-γ$^+$ CD4$^+$ T cells and IL-2$^+$ CD4+ T cells induced by mRNA vaccines - 2

| Test substance | CD4$^+$ (IFN-γ$^+$ or IL-2$^+$) | Compared to Shingrix ® (times) | Compared to YK-VZV-007 (times) |
|---|---|---|---|
| YK-VZV-014 | 1.10% | 1.8 | 1.4 |
| YK-VZV-030 | 1.10% | 1.8 | 1.4 |
| YK-VZV-024 | 0.90% | 1.5 | 1.1 |
| LNP | 0.20% | 0.3 | 0.3 |
| Shingrix ® | 0.60% | 1.0 | 0.8 |
| YK-VZV-004 (Comparative Example 1) | 0.95% | 1.6 | 1.2 |
| YK-VZV-045 (Comparative Example 3) | 0.50% | 0.8 | 0.6 |
| YK-VZV-007 (Comparative Example 4) | 0.80% | 1.3 | 1.0 |

Percentage of IFN-γ+ CD4+ T cells

A) The mRNA vaccines prepared from test substances YK-VZV-010, YK-VZV-013, YK-VZV-011, YK-VZV-020, YK-VZV-012, YK-VZV-018, YK-VZV-028, YK-VZV-014, YK-VZV-038, and YK-VZV-031 were screened out. The percentage of IFN-γ$^+$ CD4$^+$ T cells secreted by these mRNA vaccines was optimal at 1.00 to 2.00%, which was significantly higher than that of the comparative examples (YK-VZV-004, YK-VZV-045, and YK-VZV-007); which was 3 times or more and up to 6.7 times that of the Shingrix® positive control vaccine; and which was approximately 2.2 to 4.4 times that of Comparative Example 4 (YK-VZV-007).

Specifically, the percentage of IFN-γ$^+$ CD4$^+$ T cells secreted by the mRNA vaccines corresponding to YK-VZV-010, YK-VZV-013, YK-VZV-011, YK-VZV-020, and YK-VZV-018 was 6.7, 5.7, 5.3, 5.3, and 4.0 times that of the Shingrix® positive control vaccine, respectively; 4.4, 3.8, 3.6, 3.6, and 2.7 times that of Comparative Example 4 (YK-VZV-007), respectively; and significantly higher than that of Comparative Example 1 (YK-VZV-004) and Comparative Example 3 (YK-VZV-045).

The specific results are shown in the table below.

TABLE 15

IFN-γ$^+$ CD4$^+$ T cells induced by mRNA vaccines-1

| Test substance | CD4$^+$ IFN-γ$^+$ | Compared to Shingrix ® (times) | Compared to YK-VZV-007 (times) |
|---|---|---|---|
| YK-VZV-010 | 2.00% | 6.7 | 4.4 |
| YK-VZV-013 | 1.70% | 5.7 | 3.8 |
| YK-VZV-011 | 1.60% | 5.3 | 3.6 |
| YK-VZV-020 | 1.60% | 5.3 | 3.6 |
| YK-VZV-012 | 1.40% | 4.7 | 3.1 |
| YK-VZV-018 | 1.20% | 4.0 | 2.7 |
| YK-VZV-028 | 1.20% | 4.0 | 2.7 |
| YK-VZV-014 | 1.10% | 3.7 | 2.4 |
| YK-VZV-038 | 1.10% | 3.7 | 2.4 |
| YK-VZV-031 | 1.00% | 3.3 | 2.2 |
| LNP | 0.10% | 0.3 | 0.2 |
| Shingrix ® | 0.30% | 1.0 | 0.7 |
| YK-VZV-004 (Comparative Example 1) | 0.55% | 1.8 | 1.2 |
| YK-VZV-045 (Comparative Example 3) | 0.50% | 1.7 | 1.1 |
| YK-VZV-007 (Comparative Example 4) | 0.45% | 1.5 | 1.0 |

B) Since the percentage of IFN-γ$^+$ CD4$^+$ T cells secreted by the mRNA vaccines prepared from test substances YK-VZV-021, YK-VZV-009, YK-VZV-024, and YK-VZV-030 was less than 1.4, which was significantly lower than the optimal and relatively optimal percentage of (cells secreted by the mRNA vaccines (1.0 to 2.00), only 2 to 3 times that of the Shingrix® positive control vaccine, and approximately 1 to 2 times that of Comparative Example 4 (YK-VZV-007), YK-VZV-021, YK-VZV-009, YK-VZV-024, and YK-VZV-030 were excluded from the candidate sequences. The specific results are shown in the table below.

TABLE 16

IFN-γ$^+$ CD4$^+$ T cells induced by mRNA vaccines-2

| Test substance | CD4$^+$ IFN-γ$^+$ | Compared to Shingrix ® (times) | Compared to YK-VZV-007 (times) |
|---|---|---|---|
| YK-VZV-021 | 0.90% | 3.0 | 2.0 |
| YK-VZV-009 | 0.80% | 2.7 | 1.8 |
| YK-VZV-024 | 0.70% | 2.3 | 1.6 |
| YK-VZV-030 | 0.60% | 2.0 | 1.3 |
| LNP | 0.10% | 0.3 | 0.2 |
| Shingrix ® | 0.30% | 1.0 | 0.7 |
| YK-VZV-004 (Comparative Example 1) | 0.55% | 1.8 | 1.2 |
| YK-VZV-045 (Comparative Example 3) | 0.50% | 1.7 | 1.1 |
| YK-VZV-007 (Comparative Example 4) | 0.45% | 1.5 | 1.0 |

IL-2+ CD4+ T Cells

A) The mRNA vaccines corresponding to test substances YK-VZV-010, YK-VZV-020, YK-VZV-038, YK-VZV-031, YK-VZV-013, YK-VZV-028, YK-VZV-011, YK-VZV-012, YK-VZV-018, YK-VZV-021, and YK-VZV-009 were screened out. The percentage of IL-2$^+$ CD4$^+$ T cells secreted by these mRNA vaccines was optimal at 1.10 to 3.70%, which was significantly higher than that of comparative example mRNA vaccines (YK-VZV-004, YK-VZV-045, and YK-VZV-007); which was 3.7 times or more that of the Shingrix® positive control vaccine and 2.2 times or more that of YK-VZV-007; and which was significantly higher than that of Comparative Example 1 (YK-VZV-004) and Comparative Example 3 (YK-VZV-045).

Specifically, the percentage of IL-$2^+$ $CD4^+$ T cells secreted by the mRNA vaccines prepared from YK-VZV-010, YK-VZV-020, YK-VZV-013, YK-VZV-011, and YK-VZV-018 was 12.3, 8.3, 4.3, 4.0, and 3.7 times that of the Shingrix® positive control vaccine, respectively; 7.4, 5.0, 2.6, 2.4, and 2.2 times that of YK-VZV-007 (Comparative Example 4), respectively; and significantly higher than that of YK-VZV-004 (Comparative Example 1) and YK-VZV-045 (Comparative Example 3).

The specific results are shown in the table below.

TABLE 17

IL-$2^+$ $CD4^+$ T cells induced by mRNA vaccines-1

| Test substance | $CD4^+$ IL-$2^+$ | Compared to Shingrix ® (times) | Compared to YK-VZV-007 (times) |
|---|---|---|---|
| YK-VZV-010 | 3.70% | 12.3 | 7.4 |
| YK-VZV-020 | 2.50% | 8.3 | 5.0 |
| YK-VZV-038 | 1.40% | 4.7 | 2.8 |
| YK-VZV-031 | 1.40% | 4.7 | 2.8 |
| YK-VZV-013 | 1.30% | 4.3 | 2.6 |
| YK-VZV-028 | 1.30% | 4.3 | 2.6 |
| YK-VZV-011 | 1.20% | 4.0 | 2.4 |
| YK-VZV-012 | 1.20% | 4.0 | 2.4 |
| YK-VZV-018 | 1.10% | 3.7 | 2.2 |
| YK-VZV-021 | 1.10% | 3.7 | 2.2 |
| YK-VZV-009 | 1.10% | 3.7 | 2.2 |
| LNP | 0.10% | 0.3 | 0.2 |
| Shingrix | 0.30% | 1.0 | 0.6 |
| YK-VZV-004 (Comparative Example 1) | 0.55% | 1.8 | 1.1 |
| YK-VZV-045 (Comparative Example 3) | 0.30% | 1.0 | 0.6 |
| YK-VZV-007 (Comparative Example 4) | 0.50% | 1.7 | 1.0 |

B) Since the percentage of IL-$2^+$ $CD4^+$ T cells secreted by the mRNA vaccines prepared from test substances YK-VZV-014, YK-VZV-030, and YK-VZV-024 was less than 1.0%, which was significantly lower than the optimal and relatively optimal percentage of cells secreted by the mRNA vaccines (more than 1.00), 3 times or less that of the Shingrix® positive control vaccine, and less than two times that of YK-VZV-007 (Comparative Example 4), YK-VZV-014, YK-VZV-030, and YK-VZV-024 were excluded from the candidate sequences. The specific results are shown in the table below.

TABLE 18

IL-$2^+$ $CD4^+$ T cells induced by mRNA vaccines-2

| Test substance | $CD4^+$ IL-$2^+$ | Compared to Shingrix ® (times) | Compared to YK-VZV-007 (times) |
|---|---|---|---|
| YK-VZV-014 | 0.80% | 2.7 | 1.6 |
| YK-VZV-030 | 0.80% | 2.7 | 1.6 |
| YK-VZV-024 | 0.60% | 2.0 | 1.2 |
| LNP | 0.10% | 0.3 | 0.2 |
| Shingrix ® | 0.30% | 1.0 | 0.6 |
| YK-VZV-004 (Comparative Example 1) | 0.55% | 1.8 | 1.1 |
| YK-VZV-045 (Comparative Example 3) | 0.30% | 1.0 | 0.6 |
| YK-VZV-007 (Comparative Example 4) | 0.50% | 1.7 | 1.0 |

iv) Conclusion

A) After immunizing mice with the mRNA vaccines prepared from the selected sequences, the percentage of immune cells in the spleens of mice is as follows:

the total percentage of IFN-$\gamma^+$ $CD4^+$ T cells and IL-$2^+$ $CD4^+$ T cells was 2 times or more and up to 7 times that of the Shingrix® positive control, and 1.8 to 5.3 times that of YK-VZV-007 (Comparative Example 4);

the percentage of IFN-$\gamma^+$ $CD4^+$ T cells was 1.00 to 2.00%), which was 3 times or more and up to 6.7 times that of the Shingrix® positive control vaccine, and approximately 2.2 to 4.4 times that of Comparative Example 4 (YK-VZV-007);

the percentage of IL-$2^+$ $CD4^+$ T cells was more than 10, which was 3.7 times or more that of the Shingrix® positive control vaccine and 2.2 times or more that of YK-VZV-007; the details are as follows:

TABLE 19

$CD4^+$ T cells producing IFN-$\gamma^+$ or IL-$2^+$ induced by mRNA vaccines

| | $CD4^+$ (IFN-$\gamma^+$) | | | $CD4^+$ (IL-$2^+$) | | | $CD4^+$ (IFN-$\gamma^+$ or IL-$2^+$) | | |
|---|---|---|---|---|---|---|---|---|---|
| Test substance | $CD4^+$ (IFN-$\gamma^+$) | Compared to Shingrix ® (times) | Compared to YK-VZV-007 (times) | $CD4^+$ (IL-$2^+$) | Compared to Shingrix ® (times) | Compared to YK-VZV-007 (times) | $CD4^+$ (IFN-$\gamma^+$ or IL-$2^+$) | Compared to Shingrix ® (times) | Compared to YK-VZV-007 (times) |
| YK-VZV-010 | 2.00% | 6.7 | 4.4 | 3.70% | 12.3 | 7.4 | 4.20% | 7.0 | 5.3 |
| YK-VZV-013 | 1.70% | 5.7 | 3.8 | 1.30% | 4.3 | 2.6 | 1.90% | 3.2 | 2.4 |
| YK-VZV-011 | 1.60% | 5.3 | 3.6 | 1.20% | 4.0 | 2.4 | 1.60% | 2.7 | 2.0 |
| YK-VZV-020 | 1.60% | 5.3 | 3.6 | 2.50% | 8.3 | 5.0 | 3.10% | 5.2 | 3.9 |
| YK-VZV-012 | 1.40% | 4.7 | 3.1 | 1.20% | 4.0 | 2.4 | 1.70% | 2.8 | 2.1 |
| YK-VZV-018 | 1.20% | 4.0 | 2.7 | 1.10% | 3.7 | 2.2 | 1.40% | 2.3 | 1.8 |
| YK-VZV-028 | 1.20% | 4.0 | 2.7 | 1.30% | 4.3 | 2.6 | 1.70% | 2.8 | 2.1 |
| YK-VZV-038 | 1.10% | 3.7 | 2.4 | 1.40% | 4.7 | 2.8 | 1.90% | 3.2 | 2.4 |
| YK-VZV-031 | 1.00% | 3.3 | 2.2 | 1.40% | 4.7 | 2.8 | 1.70% | 2.8 | 2.1 |
| LNP | 0.10% | 0.3 | 0.2 | 0.10% | 0.3 | 0.2 | 0.20% | 0.3 | 0.3 |
| Shingrix ® | 0.30% | 1.0 | 0.7 | 0.30% | 1.0 | 0.6 | 0.60% | 1.0 | 0.8 |

TABLE 19-continued

CD4+ T cells producing IFN-γ+ or IL-2+ induced by mRNA vaccines

| Test substance | CD4+ (IFN-γ+) | | | CD4+ (IL-2+) | | | CD4+ (IFN-γ+ or IL-2+) | | |
|---|---|---|---|---|---|---|---|---|---|
| | CD4+ (IFN-γ+) | Compared to Shingrix® (times) | Compared to YK-VZV-007 (times) | CD4+ (IL-2+) | Compared to Shingrix® (times) | Compared to YK-VZV-007 (times) | CD4+ (IFN-γ+ or IL-2+) | Compared to Shingrix® (times) | Compared to YK-VZV-007 (times) |
| YK-VZV-004 (Comparative Example 1) | 0.55% | 1.8 | 1.2 | 0.55% | 1.8 | 1.1 | 0.95% | 1.6 | 1.2 |
| YK-VZV-045 (Comparative Example 3) | 0.50% | 1.7 | 1.1 | 0.30% | 1.0 | 0.6 | 0.50% | 0.8 | 0.6 |
| YK-VZV-007 (Comparative Example 4) | 0.45% | 1.5 | 1.0 | 0.50% | 1.7 | 1.0 | 0.80% | 1.3 | 1.0 |

Among the above sequences, the percentage of IFN-$\gamma^+$ $CD4^+$ T cells and IL-$2^+$ $CD4^+$ T cells induced by YK-VZV-010 in spleen cells was more than 2%, which was approximately 6 to 12 times that of the Shingrix® positive control vaccine, indicating the best immune effect.

B) The percentage of immune cells secreted by the mRNA vaccines prepared from the excluded sequences is as follows:

the total percentage of IFN-$\gamma^+$ $CD4^+$ T cells and IL-$2^+$ $CD4^+$ T cells was less than 2 times that of the Shingrix® positive control vaccine and less than 1.5 times that of Comparative Example 4 (YK-VZV-007);

or the percentage of FN-$\gamma^+$ $CD4^+$ T cells secreted by the mRNA vaccines was less than 1.0%, which was only 2 to 3 times that of the Shingrix® positive control vaccine and approximately 1 to 2 times that of Comparative Example 4 (YK-VZV-007);

or the percentage of IL-$2^+$ $CD4^+$ T cells was less than 1.0%, which was 3 times or less that of the Shingrix® positive control vaccine and less than 2 times that of YK-VZV-007 (Comparative Example 4); the details are as follows:

The percentage of $CD4^+$ T cells producing IFN-γ or IL-2 induced by the above mRNA vaccines in spleen cells was less than 1%, and the total percentage of IFN-$\gamma^+$ $CD4^+$ T cells and IL-$2^+$ $CD4^+$ T cells was less than 2.0 times that of Shingrix®, indicating a poor immune-boosting effect. Therefore, these sequences were not suitable as candidate sequences for the herpes zoster vaccine as compared to the sequences in part A above.

In summary, the mRNA vaccines prepared from test substances YK-VZV-010, YK-VZV-013, YK-VZV-011, YK-VZV-020, YK-VZV-012, YK-VZV-018, YK-VZV-028, YK-VZV-038, and YK-VZV-031 were selected. IFN-$\gamma^+$ CD4 T cells and LL-$2^+$ $CD4^+$ T cells induced by these mRNA vaccines had an excellent effect. Therefore, the above sequences as well as YK-VZV-004 (Comparative Example 1), YK-VZV-006 (Comparative Example 2), YK-VZV-045 (Comparative Example 3), and YK-VZV-007 (Comparative Example 4) were used for subsequent $CD8^+$ T cell immunoassays.

TABLE 20

CD4+ T cells producing IFN-γ+ or IL-2+ induced by mRNA vaccines

| Test substance | CD4+ (IFN-γ+) | | | CD4+ (IL-2+) | | | CD4+ (IFN-γ+ or IL-2+) | | |
|---|---|---|---|---|---|---|---|---|---|
| | CD4+ (IFN-γ+) | Compared to Shingrix® (times) | Compared to YK-VZV-007 (times) | CD4+ (IL-2+) | Compared to Shingrix® (times) | Compared to YK-VZV-007 (times) | CD4+ (IFN-γ+ or IL-2+) | Compared to Shingrix® (times) | Compared to YK-VZV-007 (times) |
| YK-VZV-014 | 1.10% | 3.7 | 2.4 | 0.80% | 2.7 | 1.6 | 1.10% | 1.8 | 1.4 |
| YK-VZV-021 | 0.90% | 3.0 | 2.0 | 1.10% | 3.7 | 2.2 | 1.50% | 2.5 | 1.9 |
| YK-VZV-009 | 0.80% | 2.7 | 1.8 | 1.10% | 3.7 | 2.2 | 1.40% | 2.3 | 1.8 |
| YK-VZV-024 | 0.70% | 2.3 | 1.6 | 0.60% | 2.0 | 1.2 | 0.90% | 1.5 | 1.1 |
| YK-VZV-030 | 0.60% | 2.0 | 1.3 | 0.80% | 2.7 | 1.6 | 1.10% | 1.8 | 1.4 |
| LNP | 0.10% | 0.3 | 0.2 | 0.10% | 0.3 | 0.2 | 0.20% | 0.3 | 0.3 |
| Shingrix | 0.30% | 1.0 | 0.7 | 0.30% | 1.0 | 0.6 | 0.60% | 1.0 | 0.8 |
| YK-VZV-004 (Comparative Example 1) | 0.55% | 1.8 | 1.2 | 0.55% | 1.8 | 1.1 | 0.95% | 1.6 | 1.2 |
| YK-VZV-045 (Comparative Example 3) | 0.50% | 1.7 | 1.1 | 0.30% | 1.0 | 0.6 | 0.50% | 0.8 | 0.6 |
| YK-VZV-007 (Comparative Example 4) | 0.45% | 1.5 | 1.0 | 0.50% | 1.7 | 1.0 | 0.80% | 1.3 | 1.0 |

CD8+ T cells

Based on the results for CD4+ T cells, test substances YK-VZV-010, YK-VZV-013, YK-VZV-011, YK-VZV-020, YK-VZV-012, YK-VZV-018, YK-VZV-028, YK-VZV-038, YK-VZV-031, YK-VZV-004 (Comparative Example 1), YK-VZV-006 (Comparative Example 2), YK-VZV-045 (Comparative Example 3), and YK-VZV-007 (Comparative Example 4) were assayed, and the number of CD8+ T cells producing IL-2/IFN-γ induced by these sequences was measured. The specific results are shown in the table below.

TABLE 21

Summary of CD8+ T cell assay results

| Test substance | CD8+ (IFN-γ+) | | | CD8+ (IL-2+) | | | CD8+ (IFN-γ+ or IL-2+) | | |
|---|---|---|---|---|---|---|---|---|---|
| | CD8+ (IFN-γ+) | Compared to Shingrix ® (times) | Compared to YK-VZV-007 (times) | CD8+ (IL-2+) | Compared to Shingrix ® (times) | Compared to YK-VZV-007 (times) | CD8+ (IFN-γ+ or IL-2+) | Compared to Shingrix ® (times) | Compared to YK-VZV-007 (times) |
| YK-VZV-010 | 8.10% | 7.36 | 4.26 | 0.50% | 4.17 | 2.78 | 7.90% | 7.18 | 4.94 |
| YK-VZV-013 | 6.90% | 6.27 | 3.63 | 0.40% | 3.33 | 2.22 | 7.10% | 6.45 | 4.44 |
| YK-VZV-020 | 5.60% | 5.09 | 2.95 | 0.30% | 2.50 | 1.67 | 5.60% | 5.09 | 3.50 |
| YK-VZV-018 | 5.20% | 4.73 | 2.74 | 0.40% | 3.33 | 2.22 | 5.20% | 4.73 | 3.25 |
| YK-VZV-011 | 5.00% | 4.55 | 2.63 | 0.40% | 3.33 | 2.22 | 5.10% | 4.64 | 3.19 |
| YK-VZV-012 | 4.20% | 3.82 | 2.21 | 0.10% | 0.83 | 0.56 | 4.20% | 3.82 | 2.63 |
| YK-VZV-028 | 3.10% | 2.82 | 1.63 | 0.40% | 3.33 | 2.22 | 3.10% | 2.82 | 1.94 |
| YK-VZV-038 | 2.40% | 2.18 | 1.26 | 0.20% | 1.67 | 1.11 | 2.30% | 2.09 | 1.44 |
| YK-VZV-031 | 1.80% | 1.64 | 0.95 | 0.10% | 0.83 | 0.56 | 1.90% | 1.73 | 1.19 |
| LNP | 0.00% | — | — | 0.00% | — | — | 0.00% | — | — |
| Shingrix ® | 1.10% | 1.00 | 0.58 | 0.12% | 1.00 | 0.67 | 1.10% | 1.00 | 0.69 |
| YK-VZV-004 (Comparative Example 1) | 2.80% | 2.55 | 1.47 | 0.21% | 1.75 | 1.17 | 2.70% | 2.45 | 1.69 |
| YK-VZV-006 (Comparative Example 2) | 1.90% | 1.73 | 1.00 | 0.20% | 1.67 | 1.11 | 1.50% | 1.36 | 0.94 |
| YK-VZV-045 (Comparative Example 3) | 1.50% | 1.36 | 0.79 | 0.16% | 1.33 | 0.89 | 1.40% | 1.27 | 0.88 |
| YK-VZV-007 (Comparative Example 4) | 1.90% | 1.73 | 1.00 | 0.18% | 1.50 | 1.00 | 1.60% | 1.45 | 1.00 |

Note:
Shingrix ® is a recombinant protein vaccine from GSK.

Total percentage of IFN-γ+ CD8+ T cells and IL-2+ CD8+ T cells

A) Based on the above results, the mRNA vaccines prepared from test substances YK-VZV-010, YK-VZV-013, YK-VZV-020, YK-VZV-018, and YK-VZV-011 were screened out. The total percentage of IFN-γ+ CD8+ T cells and IL-2+ CD8+ T cells induced by these mRNA vaccines was 4 to 7 times or more that of the Shingrix® positive control vaccine and approximately 3 to 5 times that of YK-VZV-007 (Comparative Example 4). The specific results are shown in the table below.

TABLE 22

Total percentage of IFN-γ+ CD8+ T cells and IL-2+ CD8+ T cells induced by mRNA vaccines-1

| Test substance | CD8+ (IFN-γ+ or IL-2+) | Compared to Shingrix ® (times) | Compared to YK-VZV-007 (times) |
|---|---|---|---|
| YK-VZV-010 | 7.90% | 7.18 | 4.94 |
| YK-VZV-013 | 7.10% | 6.45 | 4.44 |
| YK-VZV-020 | 5.60% | 5.09 | 3.50 |
| YK-VZV-018 | 5.20% | 4.73 | 3.25 |
| YK-VZV-011 | 5.10% | 4.64 | 3.19 |
| LNP | 0.00% | — | — |
| Shingrix ® | 1.10% | 1.00 | 0.69 |
| YK-VZV-004 (Comparative Example 1) | 2.70% | 2.45 | 1.69 |
| YK-VZV-006 (Comparative Example 2) | 1.50% | 1.36 | 0.94 |
| YK-VZV-045 (Comparative Example 3) | 1.40% | 1.27 | 0.88 |
| YK-VZV-007 (Comparative Example 4) | 1.60% | 1.45 | 1.00 |

B) However, the total percentage of IFN-γ+ CD8+ T cells and IL-2+ CD8+ T cells secreted by the mRNA vaccines prepared from test substances YK-VZV-012, YK-VZV-028, YK-VZV-038, and YK-VZV-031 was less than 4 times that of the Shingrix® positive control vaccine and 3 times or less that of YK-VZV-007 (Comparative Example 4). The specific results are shown in the table below.

TABLE 23

| Total percentage of IFN-$\gamma^+$ CD8$^+$ T cells and IL-2$^+$ CD8$^+$ T cells induced by mRNA vaccines-2 | | | |
|---|---|---|---|
| Test substance | CD8$^+$ (IFN-$\gamma^+$ or IL-2$^+$) | Compared to Shingrix ® (times) | Compared to YK-VZV-007 (times) |
| YK-VZV-012 | 4.20% | 3.82 | 2.63 |
| YK-VZV-028 | 3.10% | 2.82 | 1.94 |
| YK-VZV-038 | 2.30% | 2.09 | 1.44 |
| YK-VZV-031 | 1.90% | 1.73 | 1.19 |
| LNP | 0.00% | — | — |
| Shingrix ® | 1.10% | 1.00 | 0.69 |
| YK-VZV-004 (Comparative Example 1) | 2.70% | 2.45 | 1.69 |
| YK-VZV-006 (Comparative Example 2) | 1.50% | 1.36 | 0.94 |
| YK-VZV-045 (Comparative Example 3) | 1.40% | 1.27 | 0.88 |
| YK-VZV-007 (Comparative Example 4) | 1.60% | 1.45 | 1.00 |

IFN-$\gamma^+$ CD8$^+$ T Cells

A) The mRNA vaccines prepared from test substances YK-VZV-010, YK-VZV-013, YK-VZV-020, YK-VZV-018, and YK-VZV-11 were screened out. The percentage of IFN-$\gamma^+$ CD8$^+$ T cells secreted by these mRNA vaccines was optimal at 5.0% or more, with the percentage of YK-VZV-010 the highest at 8.10%, which was significantly higher than that of Comparative Examples 1 to 4 (YK-VZV-004, YK-VZV-006, YK-VZV-045, and YK-VZV-007). The percentage of these five sequences was 4.5 to 7.0 times or more that of the Shingrix® positive control vaccine and approximately 2.5 to 4.5 times that of YK-VZV-007. The specific results are shown in the table below.

TABLE 24

| IFN-$\gamma^+$ CD8$^+$ T cells induced by mRNA vaccines-1 | | | |
|---|---|---|---|
| Test substance | CD8$^+$ (IFN-$\gamma^+$) | Compared to Shingrix ® (times) | Compared to YK-VZV-007 (times) |
| YK-VZV-010 | 8.10% | 7.36 | 4.26 |
| YK-VZV-013 | 6.90% | 6.27 | 3.63 |
| YK-VZV-020 | 5.60% | 5.09 | 2.95 |
| YK-VZV-018 | 5.20% | 4.73 | 2.74 |
| YK-VZV-011 | 5.00% | 4.55 | 2.63 |
| LNP | 0.00% | — | — |
| Shingrix ® | 1.10% | 1.00 | 0.58 |
| YK-VZV-004 (Comparative Example 1) | 2.80% | 2.55 | 1.47 |
| YK-VZV-006 (Comparative Example 2) | 1.90% | 1.73 | 1.00 |
| YK-VZV-045 (Comparative Example 3) | 1.50% | 1.36 | 0.79 |
| YK-VZV-007 (Comparative Example 4) | 1.90% | 1.73 | 1.00 |

B) Since the percentage of IFN-$\gamma^+$ CD8$^+$ T cells secreted by the mRNA vaccines prepared from test substances YK-VZV-012, YK-VZV-028, YK-VZV-038, and YK-VZV-031 was less than 50, which was significantly lower than the optimal percentage of cells secreted by the mRNA vaccines (5.00 to 8.10%), only 4 times or less that of the Shingrix® positive control vaccine, and approximately 1 to 2 times that of YK-VZV-007, these sequences were excluded. The specific results are shown in the table below.

TABLE 25

| IFN-$\gamma^+$ CD8$^+$ T cells induced by mRNA vaccines-2 | | | |
|---|---|---|---|
| Test substance | CD8$^+$ (IFN-$\gamma^+$) | Compared to Shingrix ® (times) | Compared to YK-VZV-007 (times) |
| YK-VZV-012 | 4.20% | 3.82 | 2.21 |
| YK-VZV-028 | 3.10% | 2.82 | 1.63 |
| YK-VZV-038 | 2.40% | 2.18 | 1.26 |
| YK-VZV-031 | 1.80% | 1.64 | 0.95 |
| LNP | 0.00% | — | — |
| Shingrix ® | 1.10% | 1.00 | 0.58 |
| YK-VZV-004 (Comparative Example 1) | 2.80% | 2.55 | 1.47 |
| YK-VZV-006 (Comparative Example 2) | 1.90% | 1.73 | 1.00 |
| YK-VZV-045 (Comparative Example 3) | 1.50% | 1.36 | 0.79 |
| YK-VZV-007 (Comparative Example 4) | 1.90% | 1.73 | 1.00 |

IL-2$^+$ CD8$^+$ T Cells

A) The mRNA vaccines prepared from test substances YK-VZV-010, YK-VZV-013, YK-VZV-018, YK-VZV-011, YK-VZV-028, and YK-VZV-020 were screened out. The percentage of IL-2$^+$ CD8$^+$ T cells secreted by these mRNA vaccines was optimal at 0.3 to 0.5%, which was significantly higher than that of the comparative examples (YK-VZV-004, YK-VZV-006, YK-VZV-045, and YK-VZV-007); and which was 2.5 to 4.0 times or more that of the Shingrix® positive control vaccine and approximately 1.5 to 3.0 times that of YK-VZV-007. The specific results are shown in the table below.

TABLE 26

| IL-2$^+$ CD8$^+$ T cells induced by mRNA vaccines-1 | | | |
|---|---|---|---|
| Test substance | CD8$^+$ (IL-2$^+$) | Compared to Shingrix ® (times) | Compared to YK-VZV-007 (times) |
| YK-VZV-010 | 0.50% | 4.17 | 2.78 |
| YK-VZV-013 | 0.40% | 3.33 | 2.22 |
| YK-VZV-018 | 0.40% | 3.33 | 2.22 |
| YK-VZV-011 | 0.40% | 3.33 | 2.22 |
| YK-VZV-028 | 0.40% | 3.33 | 2.22 |
| YK-VZV-020 | 0.30% | 2.50 | 1.67 |
| LNP | 0.00% | — | — |
| Shingrix ® | 0.12% | 1.00 | 0.67 |
| YK-VZV-004 (Comparative Example 1) | 0.21% | 1.75 | 1.17 |
| YK-VZV-006 (Comparative Example 2) | 0.20% | 1.67 | 1.11 |
| YK-VZV-045 (Comparative Example 3) | 0.16% | 1.33 | 0.89 |
| YK-VZV-007 (Comparative Example 4) | 0.18% | 1.50 | 1.00 |

B) Since the percentage of 11-2$^+$ CD8$^+$ T cells secreted by the mRNA vaccines prepared from test substances YK-VZV-038, YK-VZV-012, and YK-VZV-031 was only 0.2 or less, whose effect was not significantly different from or worse than that of the Shingrix® positive control vaccine and YK-VZV-007, and which was only approximately 0.8 to 1.6 times that of the Shingrix® positive control vaccine and approximately 0.5 to 1.0 times that of YK-VZV-007, these sequences were excluded. The specific results are shown in the table below.

TABLE 27

| IL-2$^+$ CD8$^+$ T cells induced by mRNA vaccines-2 | | | |
|---|---|---|---|
| Test substance | CD8$^+$ (IL-2$^+$) | Compared to Shingrix ® (times) | Compared to YK-VZV-007 (times) |
| YK-VZV-038 | 0.20% | 1.67 | 1.11 |
| YK-VZV-012 | 0.10% | 0.83 | 0.56 |
| YK-VZV-031 | 0.10% | 0.83 | 0.56 |
| LNP | 0.00% | — | — |
| Shingrix ® | 0.12% | 1.00 | 0.67 |
| YK-VZV-004 (Comparative Example 1) | 0.21% | 1.75 | 1.17 |
| YK-VZV-006 (Comparative Example 2) | 0.20% | 1.67 | 1.11 |
| YK-VZV-045 (Comparative Example 3) | 0.16% | 1.33 | 0.89 |
| YK-VZV-007 (Comparative Example 4) | 0.18% | 1.50 | 1.00 |

Conclusion:

Based on the results from (i) to (iii) above, the candidate vaccines were screened out, and the percentage of immune cells in the spleens of mice induced by these vaccines is as follows:

A) the total percentage of IFN-γ$^+$ CD8$^+$ T cells and IL-2$^+$ CD8$^+$ T cells was 4 to 7 times or more that of the Shingrix® vaccine and approximately 3 to 5 times that of YK-VZV-007 (Comparative Example 4);

the percentage of IFN-γ$^+$ CD8$^+$ T cells was optimal at 5.0% or more, which was 4.5 to 7 times or more that of the Shingrix® positive control vaccine and approximately 2.5 to 4.5 times that of YK-VZV-007;

the percentage of IL-2$^+$ CD8$^+$ T cells was optimal at 0.3 to 0.5%, which was 2.5 to 4 times or more that of the Shingrix® positive control vaccine and approximately 1.5 to 3 times that of YK-VZV-007;

the results were significantly higher than those of the comparative examples (YK-VZV-004, YK-VZV-006, YK-VZV-045, and YK-VZV-007); the details are as follows:

TABLE 28

| CD8$^+$ T cells producing IFN-γ$^+$ or IL-2$^+$ induced by mRNA vaccines—1 | | | | | | | | | |
|---|---|---|---|---|---|---|---|---|---|
| | CD8$^+$ (IFN-γ$^+$) | | | CD8$^+$ (IL-2$^+$) | | | CD8$^+$ (IFN-γ$^+$ or IL-2$^+$) | | |
| Test substance | CD8$^+$ (IFN-γ$^+$) | Compared to Shingrix ® (times) | Compared to YK-VZV-007 (times) | CD8$^+$ (IL-2$^+$) | Compared to Shingrix ® (times) | Compared to YK-VZV-007 (times) | CD8$^+$ (IFN-γ$^+$ or IL-2$^+$) | Compared to Shingrix ® (times) | Compared to YK-VZV-007 (times) |
| YK-VZV-010 | 8.10% | 7.36 | 4.26 | 0.50% | 4.17 | 2.78 | 7.90% | 7.18 | 4.94 |
| YK-VZV-013 | 6.90% | 6.27 | 3.63 | 0.40% | 3.33 | 2.22 | 7.10% | 6.45 | 4.44 |
| YK-VZV-020 | 5.60% | 5.09 | 2.95 | 0.30% | 2.50 | 1.67 | 5.60% | 5.09 | 3.50 |
| YK-VZV-018 | 5.20% | 4.73 | 2.74 | 0.40% | 3.33 | 2.22 | 5.20% | 4.73 | 3.25 |
| YK-VZV-011 | 5.00% | 4.55 | 2.63 | 0.40% | 3.33 | 2.22 | 5.10% | 4.64 | 3.19 |
| LNP | 0.00% | — | — | 0.00% | — | — | 0.00% | — | — |
| Shingrix ® | 1.10% | 1.00 | 0.58 | 0.12% | 1.00 | 0.67 | 1.10% | 1.00 | 0.69 |
| YK-VZV-004 (Comparative Example 1) | 2.80% | 2.55 | 1.47 | 0.21% | 1.75 | 1.17 | 2.70% | 2.45 | 1.69 |
| YK-VZV-006 (Comparative Example 2) | 1.90% | 1.73 | 1.00 | 0.20% | 1.67 | 1.11 | 1.50% | 1.36 | 0.94 |
| YK-VZV-045 (Comparative Example 3) | 1.50% | 1.36 | 0.79 | 0.16% | 1.33 | 0.89 | 1.40% | 1.27 | 0.88 |
| YK-VZV-007 (Comparative Example 4) | 1.90% | 1.73 | 1.00 | 0.18% | 1.50 | 1.00 | 1.60% | 1.45 | 1.00 |

B) The percentage of immune cells in the spleens of mice induced by the vaccines prepared from the excluded test substances is as follows:

the total percentage of IFN-γ$^+$ CD8$^+$ T cells and IL-2 CD8$^+$ T cells was less than 4 times that of the Shingrix® vaccine and 3 times or less that of YK-VZV-007 (Comparative Example 4);

or, the percentage of IFN-γ$^+$ CD8$^+$ T cells was less than 5, which was significantly lower than the optimal percentage of cells secreted by the mRNA vaccines (5.20 to 8.10%), only 4 times or less that of the Shingrix® positive control vaccine, and approximately 1 to 2 times that of YK-VZV-007;

or, the percentage of IL-2$^+$ CD8$^+$ T cells was only 0.2.8 or less, whose effect was not significantly different from or worse than that of the Shingrix® positive control vaccine and YK-VZV-007, and which was only approximately 0.8 to 1.6 times that of the Shingrix® positive control vaccine and approximately 0.5 to 1.0 times that of YK-VZV-007, so that these sequences were excluded;

the details are as follows:

TABLE 29

CD8+ T cells producing IFN-γ+ or IL-2+ induced by mRNA vaccines—2

| | CD8+ (IFN-γ+) | | | CD8+ (IL-2+) | | | CD8+ (IFN-γ+ or IL-2+) | | |
|---|---|---|---|---|---|---|---|---|---|
| Test substance | CD8+ (IFN-γ+) | Compared to Shingrix ® (times) | Compared to YK-VZV-007 (times) | CD8+ (IL-2+) | Compared to Shingrix ® (times) | Compared to YK-VZV-007 (times) | CD8+ (IFN-γ+ or IL-2+) | Compared to Shingrix ® (times) | Compared to YK-VZV-007 (times) |
| YK-VZV-012 | 4.20% | 3.82 | 2.21 | 0.10% | 0.83 | 0.56 | 4.20% | 3.82 | 2.63 |
| YK-VZV-028 | 3.10% | 2.82 | 1.63 | 0.40% | 3.33 | 2.22 | 3.10% | 2.82 | 1.94 |
| YK-VZV-038 | 2.40% | 2.18 | 1.26 | 0.20% | 1.67 | 1.11 | 2.30% | 2.09 | 1.44 |
| YK-VZV-031 | 1.80% | 1.64 | 0.95 | 0.10% | 0.83 | 0.56 | 1.90% | 1.73 | 1.19 |
| LNP | 0.00% | — | — | 0.00% | — | — | 0.00% | — | — |
| Shingrix ® | 1.10% | 1.00 | 0.58 | 0.12% | 1.00 | 0.67 | 1.10% | 1.00 | 0.69 |
| YK-VZV-004 (Comparative Example 1) | 2.80% | 2.55 | 1.47 | 0.21% | 1.75 | 1.17 | 2.70% | 2.45 | 1.69 |
| YK-VZV-006 (Comparative Example 2) | 1.90% | 1.73 | 1.00 | 0.20% | 1.67 | 1.11 | 1.50% | 1.36 | 0.94 |
| YK-VZV-045 (Comparative Example 3) | 1.50% | 1.36 | 0.79 | 0.16% | 1.33 | 0.89 | 1.40% | 1.27 | 0.88 |
| YK-VZV-007 (Comparative Example 4) | 1.90% | 1.73 | 1.00 | 0.18% | 1.50 | 1.00 | 1.60% | 1.45 | 1.00 |

The percentage of $CD8^+$ T cells producing IL-$2^+$ induced by the mRNA vaccines prepared from YK-VZV-012 and YK-VZV-031 was less than that of the Shingrix® vaccine and YK-VZV-007 (Comparative Example 4). Therefore, these sequences were excluded.

The total percentage of $CD8^+$ T cells producing IFN-$\gamma^+$ and $CD8^+$ T cells producing IFN-$\gamma^+$ and IL-$2^+$ induced by the mRNA vaccines prepared from YK-VZV-028 and YK-VZV-038 was only approximately 2 times that of the Shingrix® vaccine, which was significantly lower than that of the sequences designed in part A above (up to 7 times or more), indicating a poor immune effect. Therefore, these sequences were not suitable as candidate sequences for the herpes zoster vaccine.

Therefore, based on the above results, the sequences with significant advantages in overall immune effect include: YK-VZV-010, YK-VZV-013, YK-VZV-011, YK-VZV-020, and YK-VZV-018, with YK-VZV-010 showing the best effect.

Results of gE Protein-Specific IgG Antibody Titers of VZV gE Antigen Variants in Serum of Balb/c Mice (D56)

To verify the consistency of some of the above IgG antibody titers and some of the cellular immunoassay results of VZV gE antigen variants, some of the following test substances (including YK-VZV-009, YK-VZV-010, YK-VZV-011, YK-VZV-013, YK-VZV-020, YK-VZV-014, YK-VZV-012, YK-VZV-018, YK-VZV-021, YK-VZV-024, YK-VZV-028, YK-VZV-030, YK-VZV-031, YK-VZV-038, YK-VZV-004 (Comparative Example 1), YK-VZV-045 (Comparative Example 3), and YK-VZV-007 (Comparative Example 4)) were further used. Serum samples from immunized mice on day 56 were determined, and the VZV binding-gE antibody IgG titers in the serum were measured according to the detection method in Example 5. The test results are shown in the table below.

TABLE 30

VZV binding-gE antibody IgG titers in serum (day 56)

| Test substance | Antibody GMT ($\times 10^4$) | Antibody GMT of test substance/antibody GMT of Shingrix ® | Antibody GMT of test substance/antibody GMT of YK-VZV-007 |
|---|---|---|---|
| YK-VZV-010 | 750 | 5.00 | 2.68 |
| YK-VZV-011 | 710 | 4.73 | 2.54 |
| YK-VZV-018 | 698 | 4.65 | 2.49 |
| YK-VZV-020 | 690 | 4.60 | 2.46 |
| YK-VZV-013 | 669 | 4.46 | 2.39 |
| YK-VZV-031 | 480 | 3.20 | 1.71 |
| YK-VZV-030 | 454 | 3.03 | 1.62 |
| YK-VZV-038 | 445 | 2.97 | 1.59 |
| YK-VZV-009 | 420 | 2.80 | 1.50 |
| YK-VZV-014 | 410 | 2.73 | 1.46 |
| YK-VZV-012 | 405 | 2.70 | 1.45 |
| YK-VZV-021 | 373 | 2.49 | 1.33 |
| YK-VZV-028 | 357 | 2.38 | 1.28 |
| YK-VZV-024 | 274 | 1.83 | 0.98 |
| LNP | 0 | 0.00 | 0.00 |
| Shingrix ® | 150 | 1.00 | 0.54 |

TABLE 30-continued

| VZV binding-gE antibody IgG titers in serum (day 56) | | | |
|---|---|---|---|
| Test substance | Antibody GMT ($\times 10^4$) | Antibody GMT of test substance/antibody GMT of Shingrix ® | Antibody GMT of test substance/antibody GMT of YK-VZV-007 |
| YK-VZV-004 (Comparative Example 1) | 330 | 2.20 | 1.18 |
| YK-VZV-045 (Comparative Example 3) | 170 | 1.13 | 0.61 |
| YK-VZV-007 (Comparative Example 4) | 280 | 1.87 | 1.00 |

Based on the above results, on day 56, the gE-specific antibody IgG titers of the above mRNA vaccines were all superior to the Shingrix® positive control, being approximately 1.8 to 5.0 times that of the Shingrix® vaccine, with the antibody GMT ranging from 270 to $750\times10^4$. Specifically, the antibody GMT of YK-VZV-010, YK-VZV-011, YK-VZV-018, YK-VZV-020, and YK-VZV-013 could reach $650\times10^4$ or more, being 4.0 to 5.0 times or more that of the Shingrix® vaccine and 2 times or more that of YK-VZV-007 (Comparative Example 4). Moreover, the results were significantly better than those of YK-VZV-004 (Comparative Example 1) and YK-VZV-045 (Comparative Example 3).

Based on the IgG antibody titers as well as $CD4^+$ T cell and $CD8^+$ T cell assay results, the five antigens YK-VZV-010, YK-VZV-013, YK-VZV-011, YK-VZV-020, and YK-VZV-018 exhibited the best effect of cellular immunity, making them suitable candidate antigens for further detection and analysis by ELISPOT.

Results of Cellular Immune Factors of VZV gE Antigen Variants (ELISOPT)

ELISOPT is the gold standard for screening and evaluating the immune effects of candidate vaccine antigen-specific T cells and can be used to differentiate between subpopulations of activated T cells through cytokines, such as T helper (Th) type 1 cells (producing IFN-γ, IL-2, IL-6, IL-12, IL-21, and TNF-α cytokines), Th2 cells (producing IL-4, IL-5, IL-10, and IL-13 cytokines), and Th17 cells (producing IL-17 cytokines).

Through the comprehensive analysis of IgG and cytokine assay results, a total of 5 optimal antigen sequences (including YK-VZV-010, YK-VZV-013, YK-VZV-011, YK-VZV-020, and YK-VZV-018) were screened out and further detected by ELISPOT together with Comparative Example 1 (YK-VZV-004), Comparative Example 2 (YK-VZV-006), Comparative Example 3 (YK-VZV-045), and Comparative Example 4 (YK-VZV-007), using LNP and Shingrix® as controls. The results are as follows:

1) The amount of cytokine IFN-γ secreted by T cells stimulated by the mRNA vaccine was 500 SFU or more, with a maximum close to 600 SFU, which was approximately 16 to 19 times that of the Shingrix® positive control and 2.5 to 3.0 times that of Comparative Example 4 (YK-VZV-007); and which was significantly better than that of the cytokine secreted and stimulated by the mRNA vaccine corresponding to Comparative Example 1 (YK-VZV-004), Comparative Example 2 (YK-VZV-006), or Comparative Example 3 (YK-VZV-045).

Specifically, the mRNA vaccine prepared from the YK-VZV-010 sequence reached a maximum of 598.8 SFU, which was 18.7 times that of the Shingrix® positive control and nearly 3 times that of the YK-VZV-007 control.

The IFN-γ secretion levels from high to low were YK-VZV-010, YK-VZV-018, YK-VZV-011, YK-VZV-020, and YK-VZV-013, with no significant difference between the groups, indicating a good and significant immune effect.

TABLE 31

| IFN-$\gamma^+$ secretion from spleen cells induced by mRNA vaccines | | | |
|---|---|---|---|
| Test substance | IFN-$\gamma^+$ (SFU) | Compared to Shingrix ® (times) | Compared to YK-VZV-007 (times) |
| YK-VZV-010 | 598.8 | 18.71 | 2.99 |
| YK-VZV-018 | 565 | 17.66 | 2.82 |
| YK-VZV-011 | 561.7 | 17.55 | 2.80 |
| YK-VZV-020 | 522.4 | 16.33 | 2.61 |
| YK-VZV-013 | 511.0 | 15.97 | 2.55 |
| LNP | 1.2 | 0.04 | 0.01 |
| Shingrix ® | 32.0 | 1.00 | 0.16 |
| YK-VZV-004 (Comparative Example 1) | 280.3 | 8.76 | 1.40 |
| YK-VZV-006 (Comparative Example 2) | 220.3 | 6.88 | 1.10 |
| YK-VZV-045 (Comparative Example 3) | 200.1 | 6.25 | 1.00 |
| YK-VZV-007 (Comparative Example 4) | 200.3 | 6.26 | 1.00 |

2) The amount of cytokine IL-2 secreted by T cells stimulated by the mRNA vaccine was 400 to 600 SFU or more, which was 10 to 16 times that of the Shingrix® positive control and 2.0 to 3.0 times that of the YK-VZV-007 control; and which was significantly better than that of the cytokine secreted and stimulated by the mRNA vaccine corresponding to Comparative Example 1 (YK-VZV-004), Comparative Example 2 (YK-VZV-006), or Comparative Example 3 (YK-VZV-045).

Specifically, the mRNA vaccine prepared from the YK-VZV-10 sequence reached a maximum of 614.5 SFU, which was 16.00 times that of the Shingrix® positive control and 3 times or more that of the YK-VZV-007 control.

The IL-2 secretion levels from high to low were YK-VZV-010, YK-VZV-011, YK-VZV-018, YK-VZV-013, and YK-VZV-020, with no significant difference between the groups, indicating a good and significant immune effect.

TABLE 32

| IL-$2^+$ secretion from spleen cells induced by mRNA vaccines | | | |
|---|---|---|---|
| Test substance | IL-$2^+$ (SFU) | Compared to Shingrix ® (times) | Compared to YK-VZV-007 (times) |
| YK-VZV-010 | 614.5 | 16.00 | 3.07 |
| YK-VZV-011 | 490.3 | 12.77 | 2.45 |
| YK-VZV-018 | 452.3 | 11.78 | 2.26 |

TABLE 32-continued

| IL-2$^+$ secretion from spleen cells induced by mRNA vaccines | | | |
|---|---|---|---|
| Test substance | IL-2$^+$ (SFU) | Compared to Shingrix ® (times) | Compared to YK-VZV-007 (times) |
| YK-VZV-013 | 441.6 | 11.50 | 2.20 |
| YK-VZV-020 | 418.9 | 10.91 | 2.09 |
| LNP | 16.1 | 0.42 | 0.08 |
| Shingrix ® | 38.4 | 1.00 | 0.19 |
| YK-VZV-004 (Comparative Example 1) | 274.7 | 7.15 | 1.37 |
| YK-VZV-006 (Comparative Example 2) | 230.3 | 6.00 | 1.15 |
| YK-VZV-045 (Comparative Example 3) | 205.3 | 5.35 | 1.02 |
| YK-VZV-007 (Comparative Example 4) | 200.4 | 5.22 | 1.00 |

cytosis motif (SEQ ID NO: 185). The results of Example 8 showed that any combination of "$A_{568}Y_{569}$R570$V_{571}$" or "$Y_{582}A_{583}G_{584}L_{585}$" mutated motifs resulted in gE antigen expression on the cell membrane.

3) Reduction of Localization of Full-Length gE Variants with "$A_{593}E_{594}A_{595}A_{596}D_{597}A_{598}$" Mutated Motif and Y569K and Y582A Mutations to Trans Golgi Network YK-VZV-010 (SEQ ID NO: 31) encodes a full-length gE polypeptide, with the $A_{593}E_{594}A_{595}A_{596}D_{597}A_{598}$ sequence (SEQ ID NO: 183) replacing the "$S_{593}E_{594}S_{595}T_{596}D_{597}T_{598}$" motif (SEQ ID NO: 182). YK-VZV-010 replaces the Ser/Thr-rich "SSTT" acidic cluster with an Ala-rich sequence. In addition, the YK-VZV-010 mRNA vaccine also has Y569K and Y582A mutations. The results of Example 8 showed that the gE polypeptide of YK-VZV-010 showed enhanced cell membrane expression.

These variants are each modified to reduce the localization of the encoded gE protein to the trans Golgi network and enhance transport to the plasma membrane.

TABLE 33

| Antigen localization results of different antigen sequences of VZV on Vero cells | | | | |
|---|---|---|---|---|
| Mutation site | Antigen sequence | SEQ ID NO | Expression | Cellular localization |
| full-length gE; Y569K; Y582A; S593A; S595A; T596A; T598A | YK-VZV-010 | 31 | +++ | Showing localization in Golgi and cell membrane |
| full-length gE; A568D; Y569K; R570E; V571K | YK-VZV-011 | 35 | ++ | Showing localization in Golgi and cell membrane |
| full-length gE; A568D; Y569K; R570E; V571K; Y582A | YK-VZV-013 | 43 | ++ | Showing localization in Golgi, cytoplasm, and cell membrane |
| gE (1-573aa); A568D | YK-VZV-018 | 63 | +++ | Showing localization in Golgi, cytoplasm, and cell membrane |
| gE (1-573aa); Y569K | YK-VZV-020 | 71 | +++ | Showing localization in Golgi, cytoplasm, and cell membrane |

Results of Cellular Localization of VZV gE Antigen Variants

1) Reduction of gE Antigen Localization to Trans Golgi Network by C-Terminal Truncation and Mutations in "$A_{568}Y_{569}$R570$V_{571}$" Motif The "$A_{568}Y_{569}$R570$V_{571}$" motif (SEQ ID NO: 184) is a transport motif that targets the gE polypeptide to the trans Golgi network. YK-VZV-018 (SEQ ID NO: 63) and YK-VZV-020 (SEQ ID NO: 71) encode a truncated polypeptide with terminal 50 amino acids deleted from the C-terminal region (retaining 1-573aa) and mutations at any site of the $A_{568}Y_{569}$R570$V_{571}$ sequence (e.g., mutations at A568D and Y569K). The results of Example 8 showed that both YK-VZV-018 and YK-VZV-020 variants led to reduced localization of the gE polypeptide to the trans Golgi network and enhanced cell membrane expression.

2) Reduction of gE Antigen Localization to Trans Golgi Network by any Combination of "$A_{568}Y_{569}$R570$V_{571}$" or "$Y_{582}A_{583}G_{584}L_{585}$" Mutated Motifs YK-VZV-011 (SEQ ID NO: 35) and YK-VZV-013 (SEQ ID NO: 43) encode a full-length gE polypeptide with mutations at each site of the "$A_{568}Y_{569}$R570$V_{571}$" motif (SEQ ID NO: 184). In addition, YK-VZV-013 also has mutations (e.g., Y582A) in the "$Y_{582}A_{583}G_{584}L_{585}$" endo-

SUMMARY

In conclusion, the present disclosure designed 43 antigen sequences encoding VZV gE protein variants and screened out several sequences with excellent performance, including those at least outperformed the Shingrix® vaccine as well as YK-VZV-004 (Comparative Example 1), YK-VZV-006 (Comparative Example 2), YK-VZV-045 (Comparative Example 3), and YK-VZV-007 (Comparative Example 4), which is quite surprising. Among these sequences, the mutation combinations of YK-VZV-010 (full-length gE; Y569K; Y582A; S593A; S595A; T596A; T598A), YK-VZV-011 (full-length gE; A568D; Y569K; R570E; V571K), YK-VZV-013 (full-length gE; A568D; Y569K; R570E; V571K; Y582A), YK-VZV-018 (gE 1-573aa, A568D), and YK-VZV-020 (gE 1-573aa, Y569K) were preferred. The following table shows the complete sequence information and numbering of the present disclosure. For example, in the antigen sequences of YK-VZV-1N1, SEQ ID NO: 2 and 3 represent the nucleic acid sequence ("ORF-NT") and amino acid sequence ("ORF-AA") of the open reading frame for antigen YK-VZV-01, respectively; SEQ ID NO: 1 and 4 represent the DNA sequence ("DNA") and mRNA sequence ("mRNA") for antigen YK-VZV-001, respectively.

TABLE 34

| Sequence listing | | |
|---|---|---|
| SEQ ID NO: | Name | Sequence type |
| 1 | YK-VZV-001-DNA | DNA |
| 2 | YK-VZV-001-ORF-NT | ORF-NT |
| 3 | YK-VZV-001-ORF-AA | ORF-AA |
| 4 | YK-VZV-001-mRNA | mRNA |
| 5 | YK-VZV-002-DNA | DNA |
| 6 | YK-VZV-002-ORF-NT | ORF-NT |
| 7 | YK-VZV-002-ORF-AA | ORF-AA |
| 8 | YK-VZV-002-mRNA | mRNA |
| 9 | YK-VZV-003-DNA | DNA |
| 10 | YK-VZV-003-ORF-NT | ORF-NT |
| 11 | YK-VZV-003-ORF-AA | ORF-AA |
| 12 | YK-VZV-003-mRNA | mRNA |
| 13 | YK-VZV-004-DNA | DNA |
| 14 | YK-VZV-004-ORF-NT | ORF-NT |
| 15 | YK-VZV-004-ORF-AA | ORF-AA |
| 16 | YK-VZV-004-mRNA | mRNA |
| 17 | YK-VZV-006-DNA | DNA |
| 18 | YK-VZV-006-ORF-NT | ORF-NT |
| 19 | YK-VZV-006-ORF-AA | ORF-AA |
| 20 | YK-VZV-006-mRNA | mRNA |
| 21 | YK-VZV-007-DNA | DNA |
| 22 | YK-VZV-007-ORF-NT | ORF-NT |
| 23 | YK-VZV-007-ORF-AA | ORF-AA |
| 24 | YK-VZV-007-mRNA | mRNA |
| 25 | YK-VZV-009-DNA | DNA |
| 26 | YK-VZV-009-ORF-NT | ORF-NT |
| 27 | YK-VZV-009-ORF-AA | ORF-AA |
| 28 | YK-VZV-009-mRNA | mRNA |
| 29 | YK-VZV-010-DNA | DNA |
| 30 | YK-VZV-010-ORF-NT | ORF-NT |
| 31 | YK-VZV-010-ORF-AA | ORF-AA |
| 32 | YK-VZV-010-mRNA | mRNA |
| 33 | YK-VZV-011-DNA | DNA |
| 34 | YK-VZV-011-ORF-NT | ORF-NT |
| 35 | YK-VZV-011-ORF-AA | ORF-AA |
| 36 | YK-VZV-011-mRNA | mRNA |
| 37 | YK-VZV-012-DNA | DNA |
| 38 | YK-VZV-012-ORF-NT | ORF-NT |

TABLE 34-continued

| Sequence listing | | |
|---|---|---|
| SEQ ID NO: | Name | Sequence type |
| 39 | YK-VZV-012-ORF-AA | ORF-AA |
| 40 | YK-VZV-012-mRNA | mRNA |
| 41 | YK-VZV-013-DNA | DNA |
| 42 | YK-VZV-013-ORF-NT | ORF-NT |
| 43 | YK-VZV-013-ORF-AA | ORF-AA |
| 44 | YK-VZV-013-mRNA | mRNA |
| 45 | YK-VZV-014-DNA | DNA |
| 46 | YK-VZV-014-ORF-NT | ORF-NT |
| 47 | YK-VZV-014-ORF-AA | ORF-AA |
| 48 | YK-VZV-014-mRNA | mRNA |
| 49 | YK-VZV-015-DNA | DNA |
| 50 | YK-VZV-015-ORF-NT | ORF-NT |
| 51 | YK-VZV-015-ORF-AA | ORF-AA |
| 52 | YK-VZV-015-mRNA | mRNA |
| 53 | YK-VZV-016-DNA | DNA |
| 54 | YK-VZV-016-ORF-NT | ORF-NT |
| 55 | YK-VZV-016-ORF-AA | ORF-AA |
| 56 | YK-VZV-016-mRNA | mRNA |
| 57 | YK-VZV-017-DNA | DNA |
| 58 | YK-VZV-017-ORF-NT | ORF-NT |
| 59 | YK-VZV-017-ORF-AA | ORF-AA |
| 60 | YK-VZV-017-mRNA | mRNA |
| 61 | YK-VZV-018-DNA | DNA |
| 62 | YK-VZV-018-ORF-NT | ORF-NT |
| 63 | YK-VZV-018-ORF-AA | ORF-AA |
| 64 | YK-VZV-018-mRNA | mRNA |
| 65 | YK-VZV-019-DNA | DNA |
| 66 | YK-VZV-019-ORF-NT | ORF-NT |
| 67 | YK-VZV-019-ORF-AA | ORF-AA |
| 68 | YK-VZV-019-mRNA | mRNA |
| 69 | YK-VZV-020-DNA | DNA |
| 70 | YK-VZV-020-ORF-NT | ORF-NT |
| 71 | YK-VZV-020-ORF-AA | ORF-AA |
| 72 | YK-VZV-020-mRNA | mRNA |
| 73 | YK-VZV-021-DNA | DNA |
| 74 | YK-VZV-021-ORF-NT | ORF-NT |
| 75 | YK-VZV-021-ORF-AA | ORF-AA |

TABLE 34-continued

| Sequence listing | | |
|---|---|---|
| SEQ ID NO: | Name | Sequence type |
| 76 | YK-VZV-021-mRNA | mRNA |
| 77 | YK-VZV-022-DNA | DNA |
| 78 | YK-VZV-022-ORF-NT | ORF-NT |
| 79 | YK-VZV-022-ORF-AA | ORF-AA |
| 80 | YK-VZV-022-mRNA | mRNA |
| 81 | YK-VZV-023-DNA | DNA |
| 82 | YK-VZV-023-ORF-NT | ORF-NT |
| 83 | YK-VZV-023-ORF-AA | ORF-AA |
| 84 | YK-VZV-023-mRNA | mRNA |
| 85 | YK-VZV-024-DNA | DNA |
| 86 | YK-VZV-024-ORF-NT | ORF-NT |
| 87 | YK-VZV-024-ORF-AA | ORF-AA |
| 88 | YK-VZV-024-mRNA | mRNA |
| 89 | YK-VZV-025-DNA | DNA |
| 90 | YK-VZV-025-ORF-NT | ORF-NT |
| 91 | YK-VZV-025-ORF-AA | ORF-AA |
| 92 | YK-VZV-025-mRNA | mRNA |
| 93 | YK-VZV-026-DNA | DNA |
| 94 | YK-VZV-026-ORF-NT | ORF-NT |
| 95 | YK-VZV-026-ORF-AA | ORF-AA |
| 96 | YK-VZV-026-mRNA | mRNA |
| 97 | YK-VZV-027-DNA | DNA |
| 98 | YK-VZV-027-ORF-NT | ORF-NT |
| 99 | YK-VZV-027-ORF-AA | ORF-AA |
| 100 | YK-VZV-027-mRNA | mRNA |
| 101 | YK-VZV-028-DNA | DNA |
| 102 | YK-VZV-028-ORF-NT | ORF-NT |
| 103 | YK-VZV-028-ORF-AA | ORF-AA |
| 104 | YK-VZV-028-mRNA | mRNA |
| 105 | YK-VZV-029-DNA | DNA |
| 106 | YK-VZV-029-ORF-NT | ORF-NT |
| 107 | YK-VZV-029-ORF-AA | ORF-AA |
| 108 | YK-VZV-029-mRNA | mRNA |
| 109 | YK-VZV-030-DNA | DNA |
| 110 | YK-VZV-030-ORF-NT | ORF-NT |
| 111 | YK-VZV-030-ORF-AA | ORF-AA |
| 112 | YK-VZV-030-mRNA | mRNA |
| 113 | YK-VZV-031-DNA | DNA |

TABLE 34-continued

| Sequence listing | | |
|---|---|---|
| SEQ ID NO: | Name | Sequence type |
| 114 | YK-VZV-031-ORF-NT | ORF-NT |
| 115 | YK-VZV-031-ORF-AA | ORF-AA |
| 116 | YK-VZV-031-mRNA | mRNA |
| 117 | YK-VZV-032-DNA | DNA |
| 118 | YK-VZV-032-ORF-NT | ORF-NT |
| 119 | YK-VZV-032-ORF-AA | ORF-AA |
| 120 | YK-VZV-032-mRNA | mRNA |
| 121 | YK-VZV-033-DNA | DNA |
| 122 | YK-VZV-033-ORF-NT | ORF-NT |
| 123 | YK-VZV-033-ORF-AA | ORF-AA |
| 124 | YK-VZV-033-mRNA | mRNA |
| 125 | YK-VZV-034-DNA | DNA |
| 126 | YK-VZV-034-ORF-NT | ORF-NT |
| 127 | YK-VZV-034-ORF-AA | ORF-AA |
| 128 | YK-VZV-034-mRNA | mRNA |
| 129 | YK-VZV-035-DNA | DNA |
| 130 | YK-VZV-035-ORF-NT | ORF-NT |
| 131 | YK-VZV-035-ORF-AA | ORF-AA |
| 132 | YK-VZV-035-mRNA | mRNA |
| 133 | YK-VZV-036-DNA | DNA |
| 134 | YK-VZV-036-ORF-NT | ORF-NT |
| 135 | YK-VZV-036-ORF-AA | ORF-AA |
| 136 | YK-VZV-036-mRNA | mRNA |
| 137 | YK-VZV-037-DNA | DNA |
| 138 | YK-VZV-037-ORF-NT | ORF-NT |
| 139 | YK-VZV-037-ORF-AA | ORF-AA |
| 140 | YK-VZV-037-mRNA | mRNA |
| 141 | YK-VZV-038-DNA | DNA |
| 142 | YK-VZV-038-ORF-NT | ORF-NT |
| 143 | YK-VZV-038-ORF-AA | ORF-AA |
| 144 | YK-VZV-038-mRNA | mRNA |
| 145 | YK-VZV-039-DNA | DNA |
| 146 | YK-VZV-039-ORF-NT | ORF-NT |
| 147 | YK-VZV-039-ORF-AA | ORF-AA |
| 148 | YK-VZV-039-mRNA | mRNA |
| 149 | YK-VZV-040-DNA | DNA |
| 150 | YK-VZV-040-ORF-NT | ORF-NT |

TABLE 34-continued

Sequence listing

| SEQ ID NO: | Name | Sequence type |
|---|---|---|
| 151 | YK-VZV-040-ORF-AA | ORF-AA |
| 152 | YK-VZV-040-mRNA | mRNA |
| 153 | YK-VZV-041-DNA | DNA |
| 154 | YK-VZV-041-ORF-NT | ORF-NT |
| 155 | YK-VZV-041-ORF-AA | ORF-AA |
| 156 | YK-VZV-041-mRNA | mRNA |
| 157 | YK-VZV-042-DNA | DNA |
| 158 | YK-VZV-042-ORF-NT | ORF-NT |
| 159 | YK-VZV-042-ORF-AA | ORF-AA |
| 160 | YK-VZV-042-mRNA | mRNA |
| 161 | YK-VZV-043-DNA | DNA |
| 162 | YK-VZV-043-ORF-NT | ORF-NT |
| 163 | YK-VZV-043-ORF-AA | ORF-AA |
| 164 | YK-VZV-043-mRNA | mRNA |
| 165 | YK-VZV-044-DNA | DNA |
| 166 | YK-VZV-044-ORF-NT | ORF-NT |
| 167 | YK-VZV-044-ORF-AA | ORF-AA |
| 168 | YK-VZV-044-mRNA | mRNA |
| 169 | YK-VZV-045-DNA | DNA |
| 170 | YK-VZV-045-ORF-NT | ORF-NT |
| 171 | YK-VZV-045-ORF-AA | ORF-AA |
| 172 | YK-VZV-045-mRNA | mRNA |
| 173 | 5' UTR | Artificially synthesized |
| 174 | 5' UTR | C3 (complement component 3) |
| 175 | 5' UTR | Artificially synthesized |
| 176 | 5' UTR | Artificially synthesized |
| 177 | 5' UTR | Artificially synthesized |
| 178 | 3' UTR | Homo sapiens hemoglobin β-globin gene 1 (TA) |
| 179 | 3' UTR | Homo sapiens hemoglobin β-globin gene |
| 180 | 3' UTR | PCBP4 gene |
| 181 | 3' UTR | CYBA_1.5x |
| 182 | $S_{593}ES_{595}T_{596}DT_{598}$ motif | Amino acid sequence |
| 183 | $A_{593}EA_{595}A_{596}DA_{598}$ motif | Amino acid sequence |
| 184 | $A_{568}YRV_{571}$ motif | Amino acid sequence |
| 185 | $Y_{582}AGL_{585}$ motif | Amino acid sequence |
| 186 | $Y_{569}RVDKSPYNQS_{579}$ motif | Amino acid sequence |
| 187 | $Y_{569}RVDKSPYNQSMYYAGLPV_{587}$ motif | Amino acid sequence |
| 188 | SSTT motif | Amino acid sequence |
| 189 | AYRVYAGLSSTT | Amino acid sequence |
| 190 | YAGLSSTT | Amino acid sequence |
| 191 | AYRVYAGL | Amino acid sequence |

SEQ ID NO: 1

YK-VZV-001-DNA
AGAAATAAGAGAGAAAAGAAGAGTAAGAAGAAATATAAGAGCCACCATG
GGCACCGTGAACAAGCCTGTTGTGGGCGTGCTGATGGGCTTCGGCATCATCACAG
GCACCCTGCGGATCACCAATCCTGTGCGGGCTAGCGTGCTGAGATACGACGACTT
CCACATCGACGAGGACAAGCTGGACACCAACAGCGTGTACGAGCCCTACTACCAC
AGCGATCACGCCGAGTCTAGCTGGGTCAACAGAGGCGAGAGCAGCAGAAAGGCC
TACGACCACAACAGCCCCTACATCTGGCCCCGGAACGACTACGATGGCTTCCTGG
AAAATGCCCACGAGCACCACGGCGTGTACAATCAAGGCAGAGGCATCGACAGCG
GCGAGAGACTGATGCAGCCTACACAGATGAGCGCCCAAGAGGACCTGGGAGATG
ATACCGGCATCCACGTGATCCCCACACTGAACGGCGACGACAGACACAAGATCGT
GAACGTGGACCAGCGGCAGTACGGCGACGTGTTCAAGGGCGACCTGAATCCTAA
GCCTCAGGGCCAGCGCCTGATCGAGGTGTCCGTGGAAGAGAATCACCCCTTCACA
CTGAGAGCCCCTATCCAGAGAATCTACGGCGTGCGCTATACCGAGACATGGTCCTT
TCTGCCCAGCCTGACATGTACCGGGGATGCCGCTCCTGCCATCCAGCACATTTGCC
TGAAGCACACCACCTGTTTCCAGGACGTGGTGGTGGATGTGGACTGCGCCGAGA
ACACCAAAGAGGATCAGCTGGCCGAGATCAGCTACCGGTTCCAGGGAAAGAAAG
AGGCCGACCAGCCTTGGATCGTGGTCAACACCAGCACACTGTTCGACGAGCTGG
AACTGGACCCTCCTGAGATTGAACCCGGGGTGCTGAAGGTGCTGAGAACCGAGA
AGCAGTACCTGGGAGTGTACATCTGGAACATGAGAGGCAGCGACGGCACCTCTAC
CTACGCCACCTTTCTGGTCACATGGAAGGGCGACGAGAAAACACGGAACCCCAC
ACCAGCTGTGACCCCTCAACCTAGAGGCGCCGAGTTTCACATGTGGAATTACCAC
AGCCACGTGTTCAGCGTGGGCGATACCTTTAGCCTGGCCATGCATCTGCAGTACAA
GATCCACGAGGCCCCTTTCGACCTGCTGCTGGAATGGCTGTACGTGCCCATCGATC

-continued

CTACCTGCCAGCCTATGCGGCTGTACTCCACCTGTCTGTATCACCCCAACGCTCCC
CAGTGCCTGAGCCACATGAATAGCGGCTGCACCTTCACAAGCCCTCACCTGGCTC
AGCGAGTGGCCAGCACAGTGTACCAGAATTGCGAGCACGCCGACAATTACACCG
CCTACTGTCTGGGCATCAGCCACATGGAACCTAGCTTCGGCCTGATCCTGCACGAT
GGCGGCACAACCCTGAAGTTCGTGGATACCCCTGAGAGCCTGAGCGGCCTGTATG
TGTTCGTGGTGTACTTCAACGGCCACGTGGAAGCCGTGGCCTACACCGTGGTGTC
TACCGTGGACCACTTCGTGAACGCCATCGAGGAAAGAGGCTTCCCTCCAACTGCT
GGACAGCCTCCTGCCACCACCAAGCCTAAAGAAATCACACCCGTGAATCCCGGCA
CAAGCCCACTGCTTAGATACGCCGCTTGGACAGGCGGACTGGCTGCTGTTGTTCT
GCTGTGCCTGGTCATCTTCCTGATCTGCACCGCCAAGCGGATGAGAGTGAAGGCC
TACAGAGTGGACAAGAGCCCTTACAACCAGAGCATGTACTACGCCGGCCTGCCTG
TGGACGACTTCGAGGATAGCGAGAGCACCGACACCGAGGAAGAGTTCGGCAACG
CCATTGGAGGATCTCACGGCGGCAGCAGCTATACCGTGTACATCGACAAGACCCG
GTGAGCTGGAGCCTCGGTGGCCATGCTTCTTGCCCCTTGGGCCTCCCCCCAGCCC
CTCCTCCCCTTCCTGCACCCGTACCCCCGTGGTCTTTGAATAAAGTCTGAGTGGGC
GGCAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAA
AAAAAAAAA

SEQ ID NO: 2

YK-VZV-001-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCTACAGAGTGGACAAGAGCCCTTACAACCAGAGCATGTACTACGCCGGCCT
GCCTGTGGACGACTTCGAGGATAGCGAGAGCACCGACACCGAGGAAGAGTTCGG
CAACGCCATTGGAGGATCTCACGGCGGCAGCAGCTATACCGTGTACATCGACAAG
ACCCGGTGA

SEQ ID NO: 3

YK-VZV-001-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AYRVDKSPYNQSMYYAGLPVDDFEDSESTDTEEEFGNAIGGSHGGSSYTVYIDKTR

SEQ ID NO: 4

YK-VZV-001-mRNA
AGAAAUAAGAGAGAAAAGAAGAGUAAGAAGAAAUAUAAGAGCCACCA
UGGGCACCGUGAACAAGCCUGUUGUGGGCGUGCUGAUGGGCUUCGGCAUCAUC
ACAGGCACCCUGCGGAUCACCAAUCCUGUGCGGGCUAGCGUGCUGAGAUACGA
CGACUUCCACAUCGACGAGGACAAGCUGGACACCAACAGCGUGUACGAGCCCU
ACUACCACAGCGAUCACGCCGAGUCUAGCUGGGUCAACAGAGGCGAGAGCAGC
AGAAAGGCCUACGACCACAACAGCCCCUACAUCUGGCCCCGGAACGACUACGA
UGGCUUCCUGGAAAAUGCCCACGAGCACCACGGCGUGUACAAUCAAGGCAGAG
GCAUCGACAGCGGCGAGAGACUGAUGCAGCCUACACAGAUGAGCGCCCAAGAG

-continued

GACCUGGGAGAUGAUACCGGCAUCCACGUGAUCCCCACACUGAACGGCGACGA
CAGACACAAGAUCGUGAACGUGGACCAGCGGCAGUACGGCGACGUGUUCAAGG
GCGACCUGAAUCCUAAGCCUCAGGGCCAGCGCCUGAUCGAGGUGUCCGUGGAA
GAGAAUCACCCCUUCACACUGAGAGCCCCUAUCCAGAGAAUCUACGGCGUGCG
CUAUACCGAGACAUGGUCCUUUCUGCCCAGCCUGACAUGUACCGGGGAUGCCG
CUCCUGCCAUCCAGCACAUUUGCCUGAAGCACACCACCUGUUUCCAGGACGUG
GUGGUGGAUGUGGACUGCGCCGAGAACACCAAAGAGGAUCAGCUGGCCGAGA
UCAGCUACCGGUUCCAGGGAAAGAAAGAGGCCGACCAGCCUUGGAUCGUGGUC
AACACCAGCACACUGUUCGACGAGCUGGAACUGGACCCUCCUGAGAUUGAACC
CGGGGUGCUGAAGGUGCUGAGAACCGAGAAGCAGUACCUGGGAGUGUACAUC
UGGAACAUGAGAGGCAGCGACGGCACCUCUACCUACGCCACCUUUCUGGUCAC
AUGGAAGGGCGACGAGAAAACACGGAACCCCACACCAGCUGUGACCCCUCAAC
CUAGAGGCGCCGAGUUUCACAUGUGGAAUUACCACAGCCACGUGUUCAGCGUG
GGCGAUACCUUUAGCCUGGCCAUGCAUCUGCAGUACAAGAUCCACGAGGCCCC
UUUCGACCUGCUGCUGGAAUGGCUGUACGUGCCCAUCGAUCCUACCUGCCAGC
CUAUGCGGCUGUACUCCACCUGUCUGUAUCACCCCAACGCUCCCCAGUGCCUG
AGCCACAUGAAUAGCGGCUGCACCUUCACAAGCCCUCACCUGGCUCAGCGAGU
GGCCAGCACAGUGUACCAGAAUUGCGAGCACGCCGACAAUUACACCGCCUACU
GUCUGGGCAUCAGCCACAUGGAACCUAGCUUCGGCCUGAUCCUGCACGAUGGC
GGCACAACCCUGAAGUUCGUGGAUACCCCUGAGAGCCUGAGCGGCCUGUAUGU
GUUCGUGGUGUACUUCAACGGCCACGUGGAAGCCGUGGCCUACACCGUGGUGU
CUACCGUGGACCACUUCGUGAACGCCAUCGAGGAAAGAGGCUUCCCUCCAACU
GCUGGACAGCCUCCUGCCACCACCAAGCCUAAAGAAAUCACACCCGUGAAUCC
CGGCACAAGCCCACUGCUUAGAUACGCCGCUUGGACAGGCGGACUGGCUGCUG
UUGUUCUGCUGUGCCUGGUCAUCUUCCUGAUCUGCACCGCCAAGCGGAUGAGA
GUGAAGGCCUACAGAGUGGACAAGAGCCCUUACAACCAGAGCAUGUACUACGC
CGGCCUGCCUGUGGACGACUUCGAGGAUAGCGAGAGCACCGACACCGAGGAAG
AGUUCGGCAACGCCAUUGGAGGAUCUCACGGCGGCAGCAGCUAUACCGUGUAC
AUCGACAAGACCCGGUGAGCUGGAGCCUCGGUGGCCAUGCUUCUUGCCCCUUG
GGCCUCCCCCCAGCCCCUCCUCCCCUUCCUGCACCCGUACCCCCGUGGUCUUUG
AAUAAAGUCUGAGUGGGCGGCAAAAAAAAAAAAAAAAAAAAAAAAAAAAAAAA
AAAAAAAAAAAAAAAAAAAAAAAAAAAAAAAAAAAAAAAAAAAAAAAAAAAAA
AAAAAAAAAAAAAAAAAAAAAAAAAAA

SEQ ID NO: 5

YK-VZV-002-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTCAGATATGCCTGAGCTGGAGC
CTCGGTGGCCATGCTTCTTGCCCCTTGGGCCTCCCCCCAGCCCCTCCTCCCCTTCC
TGCACCCGTACCCCCGTGGTCTTTGAATAAAGTCTGAGTGGGCGGCAAAAAAAAA
AAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAA

SEQ ID NO: 6

YK-VZV-002-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT

-continued

GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTCAGATATGCCTGA

SEQ ID NO: 7

YK-VZV-002-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYA

SEQ ID NO: 8

YK-VZV-002-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUCAGAUAUGCCUGAGC
UGGAGCCUCGGUGGCCAUGCUUCUUGCCCCUUGGGCCUCCCCCCAGCCCCUCC
UCCCCUUCCUGCACCCGUACCCCCGUGGUCUUUGAAUAAAGUCUGAGUGGGCG
GCAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAA
AAAAAAAA

SEQ ID NO: 9

YK-VZV-003-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA

-continued

TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAAGCCTGAgctggagcctcggtggccatgcttcttgccccttgggcctccccccagccc
ctcctccccttcctgcacccgtacccccgtggtctttgaataaagtctgagtgggcggcAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAA

SEQ ID NO: 10

YK-VZV-003-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AAGCCTGA

-continued

SEQ ID NO: 11

YK-VZV-003-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
A

SEQ ID NO: 12

YK-VZV-003-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAAGCCUGAGcUggagccUcggUggccaUgcUUcUU
gccccUUgggccUccccccagccccUccUccccUUccUgcacccgUacccccgUggUcUUUgaaUaaagUcU
gagUgggcggcAAAAAAAAAAAAAAAAAAAAAAAAAAAAAAAAAAAAAAAAAAAAA

SEQ ID NO: 13

YK-VZV-004-DNA
AGAAATAAGAGAGAAAAGAAGAGTAAGAAGAAATATAAGAGCCACCATG
GGCACCGTGAACAAGCCTGTTGTGGGCGTGCTGATGGGCTTCGGCATCATCACAG
GCACCCTGCGGATCACCAATCCTGTGCGGGCTAGCGTGCTGAGATACGACGACTT
CCACATCGACGAGGACAAGCTGGACACCAACAGCGTGTACGAGCCCTACTACCAC
AGCGATCACGCCGAGTCTAGCTGGGTCAACAGAGGCGAGAGCAGCAGAAAGGCC
TACGACCACAACAGCCCCTACATCTGGCCCCGGAACGACTACGATGGCTTCCTGG
AAAATGCCCACGAGCACCACGGCGTGTACAATCAAGGCAGAGGCATCGACAGCG
GCGAGAGACTGATGCAGCCTACACAGATGAGCGCCCAAGAGGACCTGGGAGATG
ATACCGGCATCCACGTGATCCCCACACTGAACGGCGACGACAGACACAAGATCGT
GAACGTGGACCAGCGGCAGTACGGCGACGTGTTCAAGGGCGACCTGAATCCTAA
GCCTCAGGGCCAGCGCCTGATCGAGGTGTCCGTGGAAGAGAATCACCCCTTCACA
CTGAGAGCCCCTATCCAGAGAATCTACGGCGTGCGCTATACCGAGACATGGTCCTT
TCTGCCCAGCCTGACATGTACCGGGGATGCCGCTCCTGCCATCCAGCACATTTGCC
TGAAGCACACCACCTGTTTCCAGGACGTGGTGGTGGATGTGGACTGCGCCGAGA
ACACCAAAGAGGATCAGCTGGCCGAGATCAGCTACCGGTTCCAGGGAAAGAAAG
AGGCCGACCAGCCTTGGATCGTGGTCAACACCAGCACACTGTTCGACGAGCTGG
AACTGGACCCTCCTGAGATTGAACCCGGGGTGCTGAAGGTGCTGAGAACCGAGA
AGCAGTACCTGGGAGTGTACATCTGGAACATGAGAGGCAGCGACGGCACCTCTAC
CTACGCCACCTTTCTGGTCACATGGAAGGGCGACGAGAAAACACGGAACCCCAC
ACCAGCTGTGACCCCTCAACCTAGAGGCGCCGAGTTTCACATGTGGAATTACCAC
AGCCACGTGTTCAGCGTGGGCGATACCTTTAGCCTGGCCATGCATCTGCAGTACAA
GATCCACGAGGCCCCTTTCGACCTGCTGCTGGAATGGCTGTACGTGCCCATCGATC
CTACCTGCCAGCCTATGCGGCTGTACTCCACCTGTCTGTATCACCCCAACGCTCCC
CAGTGCCTGAGCCACATGAATAGCGGCTGCACCTTCACAAGCCCTCACCTGGCTC

-continued

AGCGAGTGGCCAGCACAGTGTACCAGAATTGCGAGCACGCCGACAATTACACCG
CCTACTGTCTGGGCATCAGCCACATGGAACCTAGCTTCGGCCTGATCCTGCACGAT
GGCGGCACAACCCTGAAGTTCGTGGATACCCCTGAGAGCCTGAGCGGCCTGTATG
TGTTCGTGGTGTACTTCAACGGCCACGTGGAAGCCGTGGCCTACACCGTGGTGTC
TACCGTGGACCACTTCGTGAACGCCATCGAGGAAAGAGGCTTCCCTCCAACTGCT
GGACAGCCTCCTGCCACCACCAAGCCTAAAGAAATCACACCCGTGAATCCCGGCA
CAAGCCCACTGCTTAGATACGCCGCTTGGACAGGCGGACTGGCTGCTGTTGTTCT
GCTGTGCCTGGTCATCTTCCTGATCTGCACCGCCAAGCGGATGAGAGTGAAAGCC
GCCAGAGTGGACAAGTGAgctggagcctcggtggccatgcttcttgccccttgggcctccccccagcccctcctccc
cttcctgcacccgtacccccgtggtctttgaataaagtctgagtgggcggcAAAAAAAAAAAAAAAAAAAAA
AAAAAAAAAAAAAAAAAAAAAAAAAAAAAAAAAAAAAAAAAAAAAAAAAAA
AAAAAAAAAAAAAAAAAAAAAAAAAAAAAAAAAAA

SEQ ID NO: 14

YK-VZV-004-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AAGCCGCCAGAGTGGACAAGTGA

SEQ ID NO: 15

YK-VZV-004-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AARVDK

SEQ ID NO: 16

YK-VZV-004-mRNA
AGAAAUAAGAGAGAAAAGAAGAGUAAGAAGAAAUAUAAGAGCCACCA
UGGGCACCGUGAACAAGCCUGUUGUGGGCGUGCUGAUGGGCUUCGGCAUCAUC
ACAGGCACCCUGCGGAUCACCAAUCCUGUGCGGGCUAGCGUGCUGAGAUACGA
CGACUUCCACAUCGACGAGGACAAGCUGGACACCAACAGCGUGUACGAGCCCU
ACUACCACAGCGAUCACGCCGAGUCUAGCUGGGUCAACAGAGGCGAGAGCAGC
AGAAAGGCCUACGACCACAACAGCCCCUACAUCUGGCCCCGGAACGACUACGA
UGGCUUCCUGGAAAAUGCCCACGAGCACCACGGCGUGUACAAUCAAGGCAGAG
GCAUCGACAGCGGCGAGAGACUGAUGCAGCCUACACAGAUGAGCGCCCAAGAG
GACCUGGGAGAUGAUACCGGCAUCCACGUGAUCCCCACACUGAACGGCGACGA
CAGACACAAGAUCGUGAACGUGGACCAGCGGCAGUACGGCGACGUGUUCAAGG
GCGACCUGAAUCCUAAGCCUCAGGGCCAGCGCCUGAUCGAGGUGUCCGUGGAA
GAGAAUCACCCCUUCACACUGAGAGCCCCUAUCCAGAGAAUCUACGGCGUGCG
CUAUACCGAGACAUGGUCCUUUCUGCCCAGCCUGACAUGUACCGGGGAUGCCG
CUCCUGCCAUCCAGCACAUUUGCCUGAAGCACACCACCUGUUUCCAGGACGUG
GUGGUGGAUGUGGACUGCGCCGAGAACACCAAAGAGGAUCAGCUGGCCGAGA
UCAGCUACCGGUUCCAGGGAAAGAAAGAGGCCGACCAGCCUUGGAUCGUGGUC
AACACCAGCACACUGUUCGACGAGCUGGAACUGGACCCUCCUGAGAUUGAACC

-continued

CGGGGUGCUGAAGGUGCUGAGAACCGAGAAGCAGUACCUGGGAGUGUACAUC
UGGAACAUGAGAGGCAGCGACGGCACCUCUACCUACGCCACCUUUCUGGUCAC
AUGGAAGGGCGACGAGAAAACACGGAACCCCACACCAGCUGUGACCCCUCAAC
CUAGAGGCGCCGAGUUUCACAUGUGGAAUUACCACAGCCACGUGUUCAGCGUG
GGCGAUACCUUUAGCCUGGCCAUGCAUCUGCAGUACAAGAUCCACGAGGCCCC
UUUCGACCUGCUGCUGGAAUGGCUGUACGUGCCCAUCGAUCCUACCUGCCAGC
CUAUGCGGCUGUACUCCACCUGUCUGUAUCACCCCAACGCUCCCCAGUGCCUG
AGCCACAUGAAUAGCGGCUGCACCUUCACAAGCCCUCACCUGGCUCAGCGAGU
GGCCAGCACAGUGUACCAGAAUUGCGAGCACGCCGACAAUUACACCGCCUACU
GUCUGGGCAUCAGCCACAUGGAACCUAGCUUCGGCCUGAUCCUGCACGAUGGC
GGCACAACCCUGAAGUUCGUGGAUACCCCUGAGAGCCUGAGCGGCCUGUAUGU
GUUCGUGGUGUACUUCAACGGCCACGUGGAAGCCGUGGCCUACACCGUGGUGU
CUACCGUGGACCACUUCGUGAACGCCAUCGAGGAAAGAGGCUUCCCUCCAACU
GCUGGACAGCCUCCUGCCACCACCAAGCCUAAAGAAAUCACACCCGUGAAUCC
CGGCACAAGCCCACUGCUUAGAUACGCCGCUUGGACAGGCGGACUGGCUGCUG
UUGUUCUGCUGUGCCUGGUCAUCUUCCUGAUCUGCACCGCCAAGCGGAUGAGA
GUGAAAGCCGCCAGAGUGGACAAGUGAgcUggagccUcggUggccaUgcUUcUUgccccU
UgggccUccccccagccccUccUccccUUccUgcacccgUacccccgUggUcUUUgaaUaaagUcUgagUgg
gcggcAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAA

SEQ ID NO: 17

YK-VZV-006-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCGCGAGAGTGGACAAGAGCCCTTACAACCAGAGCA
TGTACTACGCCGGCCTGCCTGTGGACGATTTCGAGGATGCTGAAGCCGCCGATGC
CGAGGAAGAGTTTGGCAACGCCATTGGCGGATCTCACGGCGGCAGCAGCTATACC
GTGTACATCGACAAGACCCGGTGAgctggagcctcggtggccatgcttcttgccccttgggcctccccccagcc
cctcctccccttcctgcacccgtacccccgtggtctttgaataaagtctgagtgggcggcAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAA

SEQ ID NO: 18

YK-VZV-006-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA

-continued

CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCGCGAGAGTGGACAAGAGCCCTTACAACCAGAGCATGTACTACGCCGGCC
TGCCTGTGGACGATTTCGAGGATGCTGAAGCCGCCGATGCCGAGGAAGAGTTTGG
CAACGCCATTGGCGGATCTCACGGCGGCAGCAGCTATACCGTGTACATCGACAAG
ACCCGGTGA

SEQ ID NO: 19

YK-VZV-006-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AARVDKSPYNQSMYYAGLPVDDFEDAEAADAEEEFGNAIGGSHGGSSYTVYIDKTR

SEQ ID NO: 20

YK-VZV-006-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCGCUAGAGUGGACAAGAGCCCUUAC
AACCAGAGCAUGUACUACGCCGGCCUGCCUGUGGACGAUUUCGAGGAUGCUGA
AGCCGCCGAUGCCGAGGAAGAGUUUGGCAACGCCAUUGGCGGAUCUCACGGCG
GCAGCAGCUAUACCGUGUACAUCGACAAGACCCGGUGAgcUggagccUcggUggccaU
gcUUcUUgccccUUgggccUccccccagccccUccUccccUUccUgcacccgUacccccgUggUcUUUgaa
UaaagUcUgagUgggcggcAAAAAAAAAAAAAAAAAAAAAAAAAAAAAAAAAAAAAAAAAAAAAAAAAAA
AAAAaAAAAAAAAAAAAAAAAAAAAAAAAAAAAAAAAAAAAAAAAAAAAAA
AAAAAAAAAAAAAAAAAAAA -continued

SEQ ID NO: 21

YK-VZV-007-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCTACAGAGTGGACAAGAGCCCTTACAACCAGTCTAT
GTATGCCGCCGGACTGCCCGTGGACGATTTTGAGGATGCTGAAGCCGCCGACGCC
GAGGAAGAATTTGGCAACGCCATTGGCGGAAGCCACGGCGGCAGTAGCTATACCG
TGTACATCGACAAGACCCGGTGAgctggagcctcggtggccatgcttcttgccccttgggcctcccccagccc
ctcctccccttcctgcacccgtaccccgtggtctttgaataaagtctgagtgggcggcAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAA

SEQ ID NO: 22

YK-VZV-007-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCTACAGAGTGGACAAGAGCCCTTACAACCAGTCTATGTATGCCGCCGGACT
GCCCGTGGACGATTTTGAGGATGCTGAAGCCGCCGACGCCGAGGAAGAATTTGGC
AACGCCATTGGCGGAAGCCACGGCGGCAGTAGCTATACCGTGTACATCGACAAGA
CCCGGTGA

-continued

SEQ ID NO: 23

YK-VZV-007-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AYRVDKSPYNQSMYAAGLPVDDFEDAEAADAEEEFGNAIGGSHGGSSYTVYIDKTR

SEQ ID NO: 24

YK-VZV-007-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCUACAGAGUGGACAAGAGCCCUUAC
AACCAGUCUAUGUAUGCCGCCGGACUGCCCGUGGACGAUUUUGAGGAUGCUGA
AGCCGCCGACGCCGAGGAAGAAUUUGGCAACGCCAUUGGCGGAAGCCACGGCG
GCAGUAGCUAUACCGUGUACAUCGACAAGACCCGGUGAgcUggagccUcggUggccaU
gcUUcUUgccccUUgggccUccccccagccccUccUccccUUccUgcacccgUacccccgUggUcUUUgaa
UaaagUcUgagUgggcggcAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAA

SEQ ID NO: 25

YK-VZV-009-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT

-continued

GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCAAGAGAGTGGACAAGAGCCCTTACAACCAGTCTA
TGTATGCCGCCGGACTGCCCGTGGACGATTTCGAGGATAGCGAGAGCACCGACAC
CGAGGAAGAGTTCGGCAACGCCATTGGAGGATCTCACGGCGGCAGCAGCTATACC
GTGTACATCGACAAGACCCGGTGAgctggagcctcggtggccatgcttcttgccccttgggcctccccccagcc
cctcctccccttcctgcacccgtacccccgtggtctttgaataaagtctgagtgggcggcAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAA

SEQ ID NO: 26

YK-VZV-009-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCAAGAGAGTGGACAAGAGCCCTTACAACCAGTCTATGTATGCCGCCGGACT
GCCCGTGGACGATTTCGAGGATAGCGAGAGCACCGACACCGAGGAAGAGTTCGG
CAACGCCATTGGAGGATCTCACGGCGGCAGCAGCTATACCGTGTACATCGACAAG
ACCCGGTGA

SEQ ID NO: 27

YK-VZV-009-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AKRVDKSPYNQSMYAAGLPVDDFEDSESTDTEEEFGNAIGGSHGGSSYTVYIDKTR

SEQ ID NO: 28

YK-VZV-009-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU

-continued

ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCAAGAGAGUGGACAAGAGCCCUUAC
AACCAGUCUAUGUAUGCCGCCGGACUGCCCGUGGACGAUUUCGAGGAUAGCGA
GAGCACCGACACCGAGGAAGAGUUCGGCAACGCCAUUGGAGGAUCUCACGGCG
GCAGCAGCUAUACCGUGUACAUCGACAAGACCCGGUGAgcUggagccUcggUggccaU
gcUUcUUgccccUUgggccUcccccagccccUccUccccUUccUgcacccgUacccccgUggUcUUUgaa
UaaagUcUgagUgggcggcAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAA

SEQ ID NO: 29

YK-VZV-010-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCAAGAGAGTGGACAAGAGCCCTTACAACCAGTCTA
TGTATGCCGCCGGACTGCCCGTGGACGATTTTGAGGATGCTGAAGCCGCCGACGC
CGAGGAAGAATTTGGCAACGCCATTGGCGGAAGCCACGGCGGCAGTAGCTATACC
GTGTACATCGACAAGACCCGGTGAGCTGGAGCCTCGGTGGCCATGCTTCTTGCCC
CTTGGGCCTCCCCCCAGCCCCTCCTCCCCTTCCTGCACCCGTACCCCCGTGGTCTT
TGAATAAAGTCTGAGTGGGCGGCAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAA

SEQ ID NO: 30

YK-VZV-010-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC

-continued

GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCAAGAGAGTGGACAAGAGCCCTTACAACCAGTCTATGTATGCCGCCGGACT
GCCCGTGGACGATTTTGAGGATGCTGAAGCCGCCGACGCCGAGGAAGAATTTGGC
AACGCCATTGGCGGAAGCCACGGCGGCAGTAGCTATACCGTGTACATCGACAAGA
CCCGGTGA

SEQ ID NO: 31

YK-VZV-010-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AKRVDKSPYNQSMYAAGLPVDDFEDAEAADAEEEFGNAIGGSHGGSSYTVYIDKTR

SEQ ID NO: 32

YK-VZV-010-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA

-continued

GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCAAGAGAGUGGACAAGAGCCCUUAC
AACCAGUCUAUGUAUGCCGCCGGACUGCCCGUGGACGAUUUUGAGGAUGCUGA
AGCCGCCGACGCCGAGGAAGAAUUUGGCAACGCCAUUGGCGGAAGCCACGGCG
GCAGUAGCUAUACCGUGUACAUCGACAAGACCCGGUGAGCUGGAGCCUCGGUG
GCCAUGCUUCUUGCCCCUUGGGCCUCCCCCCAGCCCCUCCUCCCCUUCCUGCAC
CCGUACCCCCGUGGUCUUUGAAUAAAGUCUGAGUGGGCGGCAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAA

SEQ ID NO: 33

YK-VZV-011-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGCGCGTGAAGGACAAAGAGAAGGACAAGTCCCCTTACAACCAGAGCA
TGTACTACGCCGGCCTGCCTGTGGACGACTTCGAGGATAGCGAGAGCACCGACAC
CGAGGAAGAGTTCGGCAACGCCATTGGAGGATCTCACGGCGGCAGCAGCTATACC
GTGTACATCGACAAGACCCGGTGAGCTGGAGCCTCGGTGGCCATGCTTCTTGCCC
CTTGGGCCTCCCCCCAGCCCCTCCTCCCCTTCCTGCACCCGTACCCCCGTGGTCTT
TGAATAAAGTCTGAGTGGGCGGCAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAA

SEQ ID NO: 34

YK-VZV-011-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT

-continued

GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGCGCGTGA
AGGACAAAGAGAAGGACAAGTCCCCTTACAACCAGAGCATGTACTACGCCGGCC
TGCCTGTGGACGACTTCGAGGATAGCGAGAGCACCGACACCGAGGAAGAGTTCG
GCAACGCCATTGGAGGATCTCACGGCGGCAGCAGCTATACCGTGTACATCGACAA
GACCCGGTGA

SEQ ID NO: 35

YK-VZV-011-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DKEKDKSPYNQSMYYAGLPVDDFEDSESTDTEEEFGNAIGGSHGGSSYTVYIDKTR

SEQ ID NO: 36

YK-VZV-011-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGCGCGUGAAGGACAAAGAGAAGGACAAGUCCCCUUAC
AACCAGAGCAUGUACUACGCCGGCCUGCCUGUGGACGACUUCGAGGAUAGCGA
GAGCACCGACACCGAGGAAGAGUUCGGCAACGCCAUUGGAGGAUCUCACGGCG
GCAGCAGCUAUACCGUGUACAUCGACAAGACCCGGUGAGCUGGAGCCUCGGUG
GCCAUGCUUCUUGCCCCUUGGGCCUCCCCCCAGCCCCUCCUCCCCUUCCUGCAC
CCGUACCCCCGUGGUCUUUGAAUAAAGUCUGAGUGGGCGGCAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAA

SEQ ID NO: 37

YK-VZV-012-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT

-continued

CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGCGCGTGAAGGACAAAGAGAAGGACAAGTCCCCTTACAACCAGAGCA
TGTACTACGCCGGCCTGCCTGTGGACGATTTCGAGGATGCTGAAGCCGCCGATGC
CGAGGAAGAGTTTGGCAACGCCATTGGCGGATCTCACGGCGGCAGCAGCTATACC
GTGTACATCGACAAGACCCGGTGAgctggagcctcggtggccatgcttcttgccccttgggcctccccccagcc
cctcctccccttcctgcacccgtacccccgtggtctttgaataaagtctgagtgggcggcAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAA

SEQ ID NO: 38

YK-VZV-012-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGCGCGTGA
AGGACAAAGAGAAGGACAAGTCCCCTTACAACCAGAGCATGTACTACGCCGGCC
TGCCTGTGGACGATTTCGAGGATGCTGAAGCCGCCGATGCCGAGGAAGAGTTTGG
CAACGCCATTGGCGGATCTCACGGCGGCAGCAGCTATACCGTGTACATCGACAAG
ACCCGGTGA

SEQ ID NO: 39

YK-VZV-012-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DKEKDKSPYNQSMYYAGLPVDDFEDAEAADAEEEFGNAIGGSHGGSSYTVYIDKTR

-continued

SEQ ID NO: 40

YK-VZV-012-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGCGCGUGAAGGACAAAGAGAAGGACAAGUCCCCUUAC
AACCAGAGCAUGUACUACGCCGGCCUGCCUGUGGACGAUUUCGAGGAUGCUGA
AGCCGCCGAUGCCGAGGAAGAGUUUGGCAACGCCAUUGGCGGAUCUCACGGCG
GCAGCAGCUAUACCGUGUACAUCGACAAGACCCGGUGAgcUggagccUcgg Uggcca U
gcUUcUUgccccUUgggccUccccccagccccUccUccccUUccUgcacccgUacccccgUggUcUUUgaa
UaaagUcUgagUgggcggcAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAA

SEQ ID NO: 41

YK-VZV-013-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGCGCGTGAAGGACAAAGAGAAGGACAAGTCCCCTTACAACCAGTCTA
TGTATGCCGCCGGACTGCCCGTGGACGATTTCGAGGATAGCGAGAGCACCGACAC

-continued
CGAGGAAGAGTTCGGCAACGCCATTGGAGGATCTCACGGCGGCAGCAGCTATACC
GTGTACATCGACAAGACCCGGTGAGCTGGAGCCTCGGTGGCCATGCTTCTTGCCC
CTTGGGCCTCCCCCCAGCCCCTCCTCCCCTTCCTGCACCCGTACCCCCGTGGTCTT
TGAATAAAGTCTGAGTGGGCGGCAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAA

SEQ ID NO: 42

YK-VZV-013-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGCGCGTGA
AGGACAAAGAGAAGGACAAGTCCCCTTACAACCAGTCTATGTATGCCGCCGGACT
GCCCGTGGACGATTTCGAGGATAGCGAGAGCACCGACACCGAGGAAGAGTTCGG
CAACGCCATTGGAGGATCTCACGGCGGCAGCAGCTATACCGTGTACATCGACAAG
ACCCGGTGA

SEQ ID NO: 43

YK-VZV-013-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DKEKDKSPYNQSMYAAGLPVDDFEDSESTDTEEEFGNAIGGSHGGSSYTVYIDKTR

SEQ ID NO: 44

YK-VZV-013-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC

-continued

ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGCGCGUGAAGGACAAAGAGAAGGACAAGUCCCCUUAC
AACCAGUCUAUGUAUGCCGCCGGACUGCCCGUGGACGAUUUCGAGGAUAGCGA
GAGCACCGACACCGAGGAAGAGUUCGGCAACGCCAUUGGAGGAUCUCACGGCG
GCAGCAGCUAUACCGUGUACAUCGACAAGACCCGGUGAGCUGGAGCCUCGGUG
GCCAUGCUUCUUGCCCCUUGGGCCUCCCCCCAGCCCCUCCUCCCCUUCCUGCAC
CCGUACCCCCGUGGUCUUUGAAUAAAGUCUGAGUGGGCGGCAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAA

SEQ ID NO: 45

YK-VZV-014-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGOGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGCGCGTGAAGGACAAAGAGAAGGACAAGTCCCCTTACAACCAGTCTA
TGTATGCCGCCGGACTGCCCGTGGACGATTTTGAGGATGCTGAAGCCGCCGACGC
CGAGGAAGAATTTGGCAACGCCATTGGCGGAAGCCACGGCGGCAGTAGCTATACC
GTGTACATCGACAAGACCCGGTGAgctggagcctcggtggccatgcttcttgccccttgggcctccccccagcc
cctcctccccttcctgcacccgtacccccgtggtctttgaataaagtctgagtgggggcAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAA

SEQ ID NO: 46

YK-VZV-014-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA

-continued

CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGCGCGTGA
AGGACAAAGAGAAGGACAAGTCCCCTTACAACCAGTCTATGTATGCCGCCGGACT
GCCCGTGGACGATTTTGAGGATGCTGAAGCCGCCGACGCCGAGGAAGAATTTGGC
AACGCCATTGGCGGAAGCCACGGCGGCAGTAGCTATACCGTGTACATCGACAAGA
CCCGGTGA

SEQ ID NO: 47

YK-VZV-014-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DKEKDKSPYNQSMYAAGLPVDDFEDAEAADAEEEFGNAIGGSHGGSSYTVYIDKTR

SEQ ID NO: 48

YK-VZV-014-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGCGCGUGAAGGACAAAGAGAAGGACAAGUCCCCUUAC
AACCAGUCUAUGUAUGCCGCCGGACUGCCCGUGGACGAUUUUGAGGAUGCUGA
AGCCGCCGACGCCGAGGAAGAAUUUGGCAACGCCAUUGGCGGAAGCCACGGCG
GCAGUAGCUAUACCGUGUACAUCGACAAGACCCGGUGAgcUggagccUcggUggccaU
gcUUcUUgccccUUgggccUcccccagccccUccUccccUUccUgcacccgUacccccgUggUcUUUgaa
UaaagUcUgagUgggcggcAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAA
AAAAAAAAAAAAAAAAAAAA -continued

SEQ ID NO: 49

YK-VZV-015-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCATGTACTATGCCGGCCTGCCTGTGGACGACTTCGA
GGATAGCGAGAGCACCGACACCGAGGAAGAGTTCGGCAACGCCATTGGAGGATC
TCACGGCGGCAGCAGCTATACCGTGTACATCGACAAGACCCGGTGAgctggagcctcggt
ggccatgcttcttgccccttgggcctccccccagcccctcctccccttcctgcacccgtacccccgtggtctttgaataaagtctgagtg
ggcggcAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAA
AAAAAAAAAA

SEQ ID NO: 50

YK-VZV-015-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCATGTACTATGCCGGCCTGCCTGTGGACGACTTCGAGGATAGCGAGAGCAC
CGACACCGAGGAAGAGTTCGGCAACGCCATTGGAGGATCTCACGGCGGCAGCAG
CTATACCGTGTACATCGACAAGACCCGGTGA

-continued

SEQ ID NO: 51

YK-VZV-015-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AMYYAGLPVDDFEDSESTDTEEEFGNAIGGSHGGSSYTVYIDKTR

SEQ ID NO: 52

YK-VZV-015-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCAUGUACUAUGCCGGCCUGCCUGUG
GACGACUUCGAGGAUAGCGAGAGCACCGACACCGAGGAAGAGUUCGGCAACGC
CAUUGGAGGAUCUCACGGCGGCAGCAGCUAUACCGUGUACAUCGACAAGACCC
GGUGAgcUggagccUcggUggccaUgcUUcUUgccccUUgggccUccccccagccccUccUccccUUcc
UgcacccgUacccccgUggUcUUUgaaUaaagUcUgagUgggcggcAAAAAAAAAAAAAAAAA
AAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAA

SEQ ID NO: 53

YK-VZV-016-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT

-continued

GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCATGTACTATGCCGGCCTGCCTGTGGACGATTTCGA
AGATGCTGAAGCCGCCGACGCCGAGGAAGAGTTTGGAAACGCCATTGGCGGAAG
CCACGGCGGCAGCAGCTACACTGTGTACATCGACAAGACCCGGTGAgctggagcctoggt
ggccatgcttcttgccccttgggcctccccccagcccctcctccccttcctgcacccgtacccccgtggtctttgaataaagtctgagtg
ggcggcAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAA
AAAAAAAAAA

SEQ ID NO: 54

YK-VZV-016-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCATGTACTATGCCGGCCTGCCTGTGGACGATTTCGAAGATGCTGAAGCCGC
CGACGCCGAGGAAGAGTTTGGAAACGCCATTGGCGGAAGCCACGGCGGCAGCAG
CTACACTGTGTACATCGACAAGACCCGGTGA

SEQ ID NO: 55

YK-VZV-016-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AMYYAGLPVDDFEDAEAADAEEEFGNAIGGSHGGSSYTVYIDKTR

SEQ ID NO: 56

YK-VZV-016-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC

-continued

AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCAUGUACUAUGCCGGCCUGCCUGUG
GACGAUUUCGAAGAUGCUGAAGCCGCCGACGCCGAGGAAGAGUUUGGAAACG
CCAUUGGCGGAAGCCACGGCGGCAGCAGCUACACUGUGUACAUCGACAAGACC
CGGUGAgcUggagccUcggUggccaUgcUUcUUgccccUUgggccUcccccagccccUccUccccUUc
cUgcacccgUacccccgUggUcUUUgaaUaaagUcUgagUgggcggcAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAA

SEQ ID NO: 57

YK-VZV-017-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCTACAGAGTGGACAAGTGATAATAGgctggagcctcggtgg
ccatgcttcttgccccttgggcctccccccagcccctcctccccttcctgcacccgtacccccgtggtctttgaataaagtctgagtgggc
ggcAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAA

SEQ ID NO: 58

YK-VZV-017-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC

-continued

AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCTACAGAGTGGACAAGTGA

SEQ ID NO: 59

YK-VZV-017-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AYRVDK

SEQ ID NO: 60

YK-VZV-017-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA

-continued

GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCUACAGAGUGGACAAGUGAUAAUA
GgcUggagccUcggUggccaUgcUUcUUgccccUUgggccUccccccagccccUccUccccUUccUgcaccc
gUacccccgUggUcUUUgaaUaaagUcUgagUgggcggcAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAA

SEQ ID NO: 61

YK-VZV-018-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGACTACAGAGTGGACAAGTGATAATAGgctggagcctcggtgg
ccatgcttcttgccccttgggcctccccccagcccctcctccccttcctgcacccgtacccccgtggtctttgaataaagtctgagtgggc
ggcAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAA

SEQ ID NO: 62

YK-VZV-018-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC

-continued

CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGACTACAGAGTGGACAAGTGA

SEQ ID NO: 63

YK-VZV-018-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DYRVDK

SEQ ID NO: 64

YK-VZV-018-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGACUACAGAGUGGACAAGUGAUAAUA
GgcUggagccUcggUggccaUgcUUcUUgccccUUgggccUccccccagccccUccUccccUUccUgcaccc
gUacccccgUggUcUUUgaaUaaagUcUgagUgggcggcAAAAAAAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAA

SEQ ID NO: 65

YK-VZV-019-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT

-continued

GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGTACAGAGTGGACAAGTGATAATAGgctggagcctcggtggccatg
cttcttgccccttgggcctccccccagcccctcctccccttcctgcacccgtacccccgtggtctttgaataaagtctgagtgggcggc
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAA

SEQ ID NO: 66

YK-VZV-019-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGTACAGAGTGGACAAGTGA

SEQ ID NO: 67

YK-VZV-019-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
YRVDK

SEQ ID NO: 68

YK-VZV-019-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU

-continued

CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGUACAGAGUGGACAAGUGAUAAUAGgcU
ggagccUcggUggccaUgcUUcUUgccccUUgggccUccccccagccccUccUccccUUccUgcacccgUac
ccccgUggUcUUUgaaUaaagUcUgagUgggcggcAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAA

SEQ ID NO: 69

YK-VZV-020-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCAAGAGAGTGGACAAGTGATAATAGgetggagcctcggtgg
ccatgcttcttgccccttgggcctcccccagcccctcctccccttcctgcacccgtacccccgtggtctttgaataaagtctgagtgggc
ggcAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAA

SEQ ID NO: 70

YK-VZV-020-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG

-continued

AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCAAGAGAGTGGACAAGTGA

SEQ ID NO: 71

YK-VZV-020-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AKRVDK

SEQ ID NO: 72

YK-VZV-020-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCAAGAGAGUGGACAAGUGAUAAUA
GGcUggagccUeggUggccaUgcUUcUUgccccUUgggccUccccccagccccUccUccccUUccUgcaccc
gUacccccgUggUcUUUgaaUaaagUcUgagUgggcggcAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAA -continued SEQ ID NO: 73
YK-VZV-021-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCTATGAGGTGGACAAGTGATAATAGgctggagcctcggtggc
catgcttcttgccccttgggcctccccccagcccctcctccccttcctgcacccgtacccccgtggtctttgaataaagtctgagtgggc
ggcAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAA
AAAAAAAA SEQ ID NO: 74
YK-VZV-021-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCTATGAGGTGGACAAGTGA SEO ID NO: 75
YK-VZV-021-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH -continued TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AYEVDK

SEQ ID NO: 76

YK-VZV-021-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCUAUGAGGUGGACAAGUGAUAAUA
GGcUGgagccUcggUggccaUgcUUcUUgccccUUgggccUccccccagccccUccUccccUUccUgcaccc
gUacccccgUggUcUUUgaaUaaagUcUgagUgggcggcAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAA

SEQ ID NO: 77

YK-VZV-022-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA

-continued

TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCTACCGGAAGGACAAGTGATAATAGgctggagcctcggtgg
ccatgcttcttgccccttgggcctccccccagcccctcctccccttcctgcacccgtacccccgtggtcttgaataaagtctgagtgggc
ggcAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAA
AAAAAAAA

SEQ ID NO: 78

YK-VZV-022-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCTACCGGAAGGACAAGTGA

SEQ ID NO: 79

YK-VZV-022-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AYRKDK

SEQ ID NO: 80

YK-VZV-022-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG

-continued
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCUACCGGAAGGACAAGUGAUAAUA
GGcUggagccUcggUggccaUgcUUcUUgccccUUgggccUccccccagccccUccUccccUUccUgcaccc
gUacccccgUggUcUUUgaaUaaagUcUgagUgggcggcAAAAAAAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAA

SEQ ID NO: 81

YK-VZV-023-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGCGCGTGAAGGACAAAGAGAAGGACAAGTGATAATAGgctggagcctcggtgg
ccatgcttcttgccccttgggcctccccccagcccctcctccccttcctgcacccgtacccccgtggtctttgaataaagtctgagtgggc
ggcAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAA

SEQ ID NO: 82

YK-VZV-023-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA

-continued

ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGCGCGTGA
AGGACAAAGAGAAGGACAAGTGA

SEQ ID NO: 83

YK-VZV-023-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DKEKDK

SEQ ID NO: 84

YK-VZV-023-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGCGCGUGAAGGACAAAGAGAAGGACAAGUGAUAAUA
GGcUGgagccUcgGUggccaUgcUUcUUgccccUUgggccUcccccagccccUccUccccUUccUgcaccc
gUacccccgUggUcUUUgaaUaaagUcUgagUgggcggcAAAAAAAAAAAAAAAAAAAAAA
AAAAAAAAAAAAAAAAAAAAAAAAAAAAAAAAAAAAAAAAAAAAAAAAAAAAA
AAAAAAAAAAAAAAAAAAAAAAAAAAAAAAAAAAAA

SEQ ID NO: 85

YK-VZV-024-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT

-continued

CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGACGCCGAGAAGGACAAGTGATAATAGgctggagcctcggtgg
ccatgcttcttgccccttgggcctccccccagcccctcctccccttcctgcacccgtacccccgtggtctttgaataaagtctgagtgggc
ggcAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAA

SEQ ID NO: 86

YK-VZV-024-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGACGCCGAGAAGGACAAGTGA

SEQ ID NO: 87

YK-VZV-024-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DAEKDK

SEQ ID NO: 88

YK-VZV-024-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG

-continued

GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGACGCCGAGAAGGACAAGUGAUAAUA
GgcUggagccUcggUggccaUgcUUcUUgccccUUgggccUccccccagccccUccUccccUUccUgcaccc
gUacccccgUggUcUUUgaaUaaagUcUgagUgggcggcAAAAAAAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAA

SEQ ID NO: 89

YK-VZV-025-DNA

AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGCGCGTGAAGAAAGAGAAGGACAAGTGATAATAGgctggagcctcggtggccatg
cttcttgccccttgggcctccccccagcccctcctccccttcctgcacccgtacccccgtggtctttgaataaagtctgagtgggggc
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAA
AAAAAA

SEQ ID NO: 90

YK-VZV-025-ORF-NT

ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG

-continued

GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGCGCGTGA
AGAAAGAGAAGGACAAGTGA

SEQ ID NO: 91

YK-VZV-025-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
KEKDK

SEQ ID NO: 92

YK-VZV-025-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG

-continued

AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGCGCGUGAAGAAAGAGAAGGACAAGUGAUAAUAGgcU
ggagccUcggUggccaUgcUUcUUgccccUUgggccUccccccagccccUccUccccUUccUgcacccgUac
ccccgUggUcUUUgaaUaaagUcUgagUgggcggcAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAA

SEQ ID NO: 93

YK-VZV-026-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCTACAGAGTGGACAAGAGCCCTTACAACCAGAGCA
TGTACTACGCCGGCCTGCCTGTTTGATAATAGgctggagcctcggtggccatgcttcttgccccttgggcc
tccccccagcccctcctccccttcctgcacccgtacccccgtggtctttgaataaagtctgagtgggcggcAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAA

SEQ ID NO: 94

YK-VZV-026-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA

-continued

ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCTACAGAGTGGACAAGAGCCCTTACAACCAGAGCATGTACTACGCCGGCCT
GCCTGTTTGA

SEQ ID NO: 95

YK-VZV-026-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AYRVDKSPYNQSMYYAGLPV

SEQ ID NO: 96

YK-VZV-026-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCUACAGAGUGGACAAGAGCCCUUAC
AACCAGAGCAUGUACUACGCCGGCCUGCCUGUUUGAUAAUAGGcUggagccUcggU
ggccaUgcUUcUUgccccUUgggccUccccccagccccUccUccccUUccUgcacccgUacccccgUggUcU
UUgaaUaaagUcUgagUgggcggcAAAAAAAAAAAAAAAAAAAAAAAAAAAAAAAAAAA
AAAAAAAAAAAAAAAAAAAAAAAAAAAAAAAAAAAAAAAAAAAAAAAAAAA
AAAAAAAAAAAAAAAAAAAAAAAA

SEQ ID NO: 97

YK-VZV-027-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT

-continued

GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCATGTACTATGCCGGCCTGCCTGTTTGATAATAGgctg
gagcctcggtggccatgcttcttgccccttgggcctccccccagcccctcctccccttcctgcacccgtacccccgtggtctttgaataa
agtctgagtgggcggcAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAA
AAAAAAAAAAAAAAAA

SEQ ID NO: 98

YK-VZV-027-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCATGTACTATGCCGGCCTGCCTGTTTGA

SEQ ID NO: 99

YK-VZV-027-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AMYYAGLPV

SEQ ID NO: 100

YK-VZV-027-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU

-continued

CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCAUGUACUAUGCCGGCCUGCCUGUU
UGAUAAUAGgcUggagccUcggUggccaUgcUUcUUgccccUUgggccUcccccagccccUccUcccc
UUccUgcacccgUacccccgUggUcUUUgaaUaaagUcUgagUgggcggcAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAA

SEQ ID NO: 101

YK-VZV-028-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCTATGTATGCCGCCGGACTGCCTGTTTGATAATAGgctg
gagcctcggtggccatgcttcttgccccttgggcctcccccagcccctcctccccttcctgcacccgtacccccgtggtctttgaataa
agtctgagtgggcggcAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAA

SEQ ID NO: 102

YK-VZV-028-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG

-continued

AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCTATGTATGCCGCCGGACTGCCTGTTTGA

SEQ ID NO: 103

YK-VZV-028-ORF-AA

MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AMYAAGLPV

SEQ ID NO: 104

YK-VZV-028-mRNA

AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA

-continued

GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCUAUGUAUGCCGCCGGACUGCCUGUU
UGAUAAUAGgcUggagccUcggUggccaUgcUUcUUgccccUUgggccUccccccagccccUccUcccc
UUccUgcacccgUacccccgUggUcUUUgaaUaaagUcUgagUgggcggcAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAA

SEQ ID NO: 105

YK-VZV-029-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCTATGTATGGCGCCGGACTGCCTGTTTGATAATAGGctg
gagcctcggtggccatgcttcttgccccttgggcctccccccagcccctcctccccttcctgcacccgtacccccgtggtctttgaataa
agtctgagtgggcggcAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAA

SEQ ID NO: 106

YK-VZV-029-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT

-continued

TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCTATGTATGGCGCCGGACTGCCTGTTTGA

SEQ ID NO: 107

YK-VZV-029-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AMYGAGLPV

SEQ ID NO: 108

YK-VZV-029-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCUAUGUAUGGCGCCGGACUGCCUGUU
UGAUAAUAGGcUggagccUcggUggccaUgcUUcUUgccccUUgggccUccccccagccccUccUcccc
UUccUgcacccgUacccccgUggUcUUUgaaUaaagUcUgagUgggcggcAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAA

SEQ ID NO: 109

YK-VZV-030-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT

-continued

ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGCGCGTGAAGGACAAAGAGAAGGACAAGTCCCCTTACAACCAGTCTA
TGTATGCCGCCGGACTGCCCGTTTGATAATAGgctggagcctcggtggccatgcttcttgccccttgggcc
tccccccagcccctcctccccttcctgcacccgtacccccgtggtctttgaataaagtctgagtgggcggcAAAAAAAAA
AAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAA

SEQ ID NO: 110

YK-VZV-030-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGCGCGTGA
AGGACAAAGAGAAGGACAAGTCCCCTTACAACCAGTCTATGTATGCCGCCGGACT
GCCCGTTTGA

SEQ ID NO: 111

YK-VZV-030-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DKEKDKSPYNQSMYAAGLPV

SEQ ID NO: 112

YK-VZV-030-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU

-continued

CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGCGCGUGAAGGACAAAGAGAAGGACAAGUCCCCUUAC
AACCAGUCUAUGUAUGCCGCCGGACUGCCCGUUUGAUAAUAGgcUggagccUcggU
ggccaUgcUUcUUgccccUUgggccUccccccagccccUccUccccUUccUgcacccgUacccccgUggUcU
UUgaaUaaagUcUgagUgggcggcAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAA

SEQ ID NO: 113

YK-VZV-031-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGCGCGTGAAGGACAAAGAGAAGGACAAGTCCCCTTACAACCAGTCTA
TGTATGGCGCCGGACTGCCCGTTTGATAATAGgctggagcctcggtggccatgcttcttgccccttgggcc
tccccccagcccctcctccccttcctgcacccgtacccccgtggtctttgaataaagtctgagtgggcggcAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAA

SEQ ID NO: 114

YK-VZV-031-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG

-continued

GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGCGCGTGA
AGGACAAAGAGAAGGACAAGTCCCCTTACAACCAGTCTATGTATGGCGCCGGACT
GCCCGTTTGA

SEQ ID NO: 115

YK-VZV-031-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DKEKDKSPYNQSMYGAGLPV

SEQ ID NO: 116

YK-VZV-031-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGCGCGUGAAGGACAAAGAGAAGGACAAGUCCCCUUAC
AACCAGUCUAUGUAUGGCGCCGGACUGCCCGUUUGAUAAUAGGcUggagccUcggU
ggccaUgcUUcUUgccccUUgggccUccccccagccccUccUccccUUccUgcacccgUacccccgUggUcU -continued UUgaaUaaagUcUgagUgggcggcAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAA

SEQ ID NO: 117

YK-VZV-032-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGACTACAGAGTGGACAAGAGCCCTTACAACCAGTCTA
TGTATGCCGCCGGACTGCCCGTTTGATAATAGgctggagcctcggtggccatgcttcttgccccttgggcc
tccccccagcccctcctccccttcctgcacccgtacccccgtggtctttgaataaagtctgagtgggcggcAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAA

SEQ ID NO: 118

YK-VZV-032-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC

-continued

CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGACTACAGAGTGGACAAGAGCCCTTACAACCAGTCTATGTATGCCGCCGGACT
GCCCGTTTGA

SEQ ID NO: 119
YK-VZV-032-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DYRVDKSPYNQSMYAAGLPV

SEQ ID NO: 120
YK-VZV-032-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGACUACAGAGUGGACAAGAGCCCUUAC
AACCAGUCUAUGUAUGCCGCCGGACUGCCCGUUUGAUAAUAGGcUggagccUcggU
ggccaUgcUUcUUgccccUUgggccUccccccagccccUccUccccUUccUgcacccgUacccccgUggUcU
UUgaaUaaagUcUgagUgggcggcAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAA SEQ ID NO: 121
YK-VZV-033-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG -continued AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCAAGAGAGTGGACAAGAGCCCTTACAACCAGTCTA
TGTATGCCGCCGGACTGCCCGTTTGATAATAGgctggagcctcggtggccatgcttcttgccccttgggcc
tccccccagcccctcctccccttcctgcacccgtacccccgtggtctttgaataaagtctgagtgggcggcAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAA

SEQ ID NO: 122

YK-VZV-033-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCAAGAGAGTGGACAAGAGCCCTTACAACCAGTCTATGTATGCCGCCGGACT
GCCCGTTTGA

SEQ ID NO: 123

YK-VZV-033-ORF-AA
MGTVNKPVVGVLMGFGIITGTLRITNPVRASVLRYDDFHIDEDKLDINSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AKRVDKSPYNQSMYAAGLPV

SEQ ID NO: 124

YK-VZV-033-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU

-continued

CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCAAGAGAGUGGACAAGAGCCCUUAC
AACCAGUCUAUGUAUGCCGCCGGACUGCCCGUUUGAUAAUAGGcUggagccUcggU
ggccaUgcUUcUUgccccUUgggccUcccccccagccccUccUccccUUccUgcacccgUacccccgUggUcU
UUgaaUaaagUcUgagUgggcggcAAAAAAAAAAAAAAAAAAAAAAAAAAAAAAA
AAAAAAAAAAAAAAAAAAAAAAAAAAAAAAAAAAAAAAAAAAAAAAA
AAAAAAAAAAAAAAAAAAAAAA

SEQ ID NO: 125

YK-VZV-034-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCTATGAGGTGGACAAGAGCCCTTACAACCAGTCTAT
GTATGCCGCCGGACTGCCCGTTTGATAATAGgctggagcctcggtggccatgcttcttgccccttgggcctc
cccccagcccctcctccccttcctgcacccgtacccccgtggtctttgaataaagtctgagtgggggcAAAAAAAAAA
AAAAAAAAAAAAAAAAAAAAAAAAAAAAAAAAAAAAAAAAAAAAAAA
AAAAAAAAAAAAAAAAAAAAAAAAAAAAAAAAAAAAAAAAAAA

SEQ ID NO: 126

YK-VZV-034-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC

-continued

AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCTATGAGGTGGACAAGAGCCCTTACAACCAGTCTATGTATGCCGCCGGACT
GCCCGTTTGA

SEQ ID NO: 127

YK-VZV-034-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AYEVDKSPYNQSMYAAGLPV

SEQ ID NO: 128

YK-VZV-034-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCUAUGAGGUGGACAAGAGCCCUUAC
AACCAGUCUAUGUAUGCCGCCGGACUGCCCGUUUGAUAAUAGgcUggagccUcggU
ggccaUgcUUcUUgccccUUgggccUccccccagccccUccUccccUUccUgcacccgUacccccgUggUcU
UUgaaUaaagUcUgagUgggcggcAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAA -continued

SEQ ID NO: 129

YK-VZV-035-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCTACCGGAAGGACAAGAGCCCTTACAACCAGTCTA
TGTATGCCGCCGGACTGCCCGTTTGATAATAGgctggagcctcggtggccatgcttcttgccccttgggcc
tccccccagcccctcctccccttcctgcacccgtacccccgtggtctttgaataaagtctgagtgggcggcAAAAAAAAA
AAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAA

SEQ ID NO: 130

YK-VZV-035-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCTACCGGAAGGACAAGAGCCCTTACAACCAGTCTATGTATGCCGCCGGACT
GCCCGTTTGA

SEQ ID NO: 131

YK-VZV-035-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI

-continued

DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AYRKDKSPYNQSMYAAGLPV

SEQ ID NO: 132

YK-VZV-035-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCUACCGGAAGGACAAGAGCCCUUAC
AACCAGUCUAUGUAUGCCGCCGGACUGCCCGUUUGAUAAUAGgcUggagccUcggU
ggccaUgcUUcUUgccccUUgggccUccccccagccccUccUccccUUccUgcacccgUacccccgUggUcU
UUgaaUaaagUcUgagUgggcggcAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAA

SEQ ID NO: 133

YK-VZV-036-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG

-continued
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCTATGTATGCCGCCGGACTGCCCGTGGACGATTTCGA
GGATAGCGAGAGCACCGACACCGAGGAAGAGTTCGGCAACGCCATTGGAGGATC
TCACGGCGGCAGCAGCTATACCGTGTACATCGACAAGACCCGGTGATAATAGgctgga
gcctcggtggccatgcttcttgccccttgggcctccccccagcccctcctccccttcctgcacccgtacccccgtggtctttgaataaagt
ctgagtgggcggcAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAA

SEQ ID NO: 134

YK-VZV-036-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCTATGTATGCCGCCGGACTGCCCGTGGACGATTTCGAGGATAGCGAGAGCAC
CGACACCGAGGAAGAGTTCGGCAACGCCATTGGAGGATCTCACGGCGGCAGCAG
CTATACCGTGTACATCGACAAGACCCGGTGA

SEQ ID NO: 135

YK-VZV-036-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AMYAAGLPVDDFEDSESTDTEEEFGNAIGGSHGGSSYTVYIDKTR

SEQ ID NO: 136

YK-VZV-036-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA

-continued

AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCUAUGUAUGCCGCCGGACUGCCCGUG
GACGAUUUCGAGGAUAGCGAGAGCACCGACACCGAGGAAGAGUUCGGCAACGC
CAUUGGAGGAUCUCACGGCGGCAGCAGCUAUACCGUGUACAUCGACAAGACCC
GGUGAUAAUAGgcUggagccUcggUggccaUgcUUcUUgccccUUgggccUccccccagccccUccU
ccccUUccUgcacccgUacccccgUggUcUUUgaaUaaagUcUgagUgggcggcAAAAAAAAAAA
AAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAA

SEQ ID NO: 137

YK-VZV-037-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCTATGTATGCCGCCGGACTGCCCGTGGACGATTTTGA
GGATGCTGAAGCCGCCGACGCCGAGGAAGAATTTGGCAACGCCATTGGCGGAAG
CCACGGCGGCAGTAGCTATACCGTGTACATCGACAAGACCCGGTGATAATAGgctgga
gcctcggtggccatgcttcttgccccttgggcctccccccagcccctcctccccttcctgcacccgtacccccgtggtctttgaataaagt
ctgagtgggcggcAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAA
AAAAAAAAAAAAAA

SEQ ID NO: 138

YK-VZV-037-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC

-continued

ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCTATGTATGCCGCCGGACTGCCCGTGGACGATTTTGAGGATGCTGAAGCCGC
CGACGCCGAGGAAGAATTTGGCAACGCCATTGGCGGAAGCCACGGCGGCAGTAG
CTATACCGTGTACATCGACAAGACCCGGTGA

SEQ ID NO: 139

YK-VZV-037-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AMYAAGLPVDDFEDAEAADAEEEFGNAIGGSHGGSSYTVYIDKTR

SEQ ID NO: 140

YK-VZV-037-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCUAUGUAUGCCGCCGGACUGCCCGUG
GACGAUUUUGAGGAUGCUGAAGCCGCCGACGCCGAGGAAGAAUUUGGCAACG
CCAUUGGCGGAAGCCACGGCGGCAGUAGCUAUACCGUGUACAUCGACAAGACC
CGGUGAUAAUAGGcUggagccUcggUggccaUgcUUcUUgccccUUgggccUccccccagccccUcc
UccccUUccUgcacccgUacccccgUggUcUUUgaaUaaagUcUgagUgggcggcAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAA -continued

SEQ ID NO: 141

YK-VZV-038-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGCGCGTGAAGGACAAAGAGAAGGACAAGTCCCCTTACAACCAGTCTA
TGTATGGCGCCGGACTGCCCGTGGACGATTTCGAGGATAGCGAGAGCACCGACAC
CGAGGAAGAGTTCGGCAACGCCATTGGAGGATCTCACGGCGGCAGCAGCTATACC
GTGTACATCGACAAGACCCGGTGATAATAGgctggagcctcggtggccatgcttcttgccccttgggcctc
cccccagcccctcctccccttcctgcacccgtacccccgtggtctttgaataaagtctgagtgggcggcAAAAAAAAAA
AAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA

SEQ ID NO: 142

YK-VZV-038-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT

-continued

TGTTCTGCTGTGCCTGGTCATCTTCCTGATCTGCACCGCCAAGCGGATGCGCGTGA
AGGACAAAGAGAAGGACAAGTCCCCTTACAACCAGTCTATGTATGGCGCCGGACT
GCCCGTGGACGATTTCGAGGATAGCGAGAGCACCGACACCGAGGAAGAGTTCGG
CAACGCCATTGGAGGATCTCACGGCGGCAGCAGCTATACCGTGTACATCGACAAG
ACCCGGTGA

SEQ ID NO: 143

YK-VZV-038-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DKEKDKSPYNQSMYGAGLPVDDFEDSESTDTEEEFGNAIGGSHGGSSYTVYIDKTR

SEQ ID NO: 144

YK-VZV-038-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGCGCGUGAAGGACAAAGAGAAGGACAAGUCCCCUUAC
AACCAGUCUAUGUAUGGCGCCGGACUGCCCGUGGACGAUUUCGAGGAUAGCGA
GAGCACCGACACCGAGGAAGAGUUCGGCAACGCCAUUGGAGGAUCUCACGGCG
GCAGCAGCUAUACCGUGUACAUCGACAAGACCCGGUGAUAAUAGgcUggagccUcg
gUggccaUgcUUcUUgccccUUgggccUccccccagccccUccUccccUUccUgcacccgUacccccgUggU
cUUUgaaUaaagUcUgagUgggcggcAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAA

SEQ ID NO: 145

YK-VZV-039-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT

-continued

ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGCGCGTGAAGGACAAAGAGAAGGACAAGTCCCCTTACAACCAGTCTA
TGTATGGCGCCGGACTGCCCGTGGACGATTTTGAGGATGCTGAAGCCGCCGACGC
CGAGGAAGAATTTGGCAACGCCATTGGCGGAAGCCACGGCGGCAGTAGCTATACC
GTGTACATCGACAAGACCCGGTGATAATAGgctggagcctcggtggccatgcttcttgccccttgggcctc
cccccagcccctcctccccttcctgcacccgtacccccgtggtctttgaataaagtctgagtgggcggcAAAAAAAAAA
AAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAA

SEQ ID NO: 146

YK-VZV-039-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGCGCGTGA
AGGACAAAGAGAAGGACAAGTCCCCTTACAACCAGTCTATGTATGGCGCCGGACT
GCCCGTGGACGATTTTGAGGATGCTGAAGCCGCCGACGCCGAGGAAGAATTTGGC
AACGCCATTGGCGGAAGCCACGGCGGCAGTAGCTATACCGTGTACATCGACAAGA
CCCGGTGA

SEQ ID NO: 147

YK-VZV-039-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
DKEKDKSPYNQSMYGAGLPVDDFEDAEAADAEEEFGNAIGGSHGGSSYTVYIDKTR

SEQ ID NO: 148

YK-VZV-039-mRNA
AGACUCCUCCCCAUCCUCUCCCUCUGUCCCUCUGUCCCCUCUGACCCUGC
ACUGUCCCAGCACCGCCACCAUGGGCACCGUGAACAAGCCUGUUGUGGGCGUG

-continued

CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGCGCGUGAAGGACAAAGAGAAGGACAAGUCCCCUUAC
AACCAGUCUAUGUAUGGCGCCGGACUGCCCGUGGACGAUUUUGAGGAUGCUG
AAGCCGCCGACGCCGAGGAAGAAUUUGGCAACGCCAUUGGCGGAAGCCACGGC
GGCAGUAGCUAUACCGUGUACAUCGACAAGACCCGGUGAUAAUAGgcUggagccU
cggUggccaUgcUUcUUgccccUUgggccUccccccagccccUccUccccUUccUgcacccgUacccccgUg
gUcUUUgaaUaaagUcUgagUgggcggcAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAA

SEQ ID NO: 149

YK-VZV-040-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCTACAGAGTGGACAAGAGCCCTTACAACCAGTCTAT
GTATGGCGCCGGACTGCCCGTGGACGATTTTGAGGATGCTGAAGCCGCCGACGCC
GAGGAAGAATTTGGCAACGCCATTGGCGGAAGCCACGGCGGCAGTAGCTATACCG
TGTACATCGACAAGACCCGGTGATAATAGgctggagcctcggtggccatgcttcttgccccttgggcctccc
cccagcccctcctccccttcctgcacccgtacccccgtggtctttgaataaagtctgagtgggcggcAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAA -continued

SEQ ID NO: 150

YK-VZV-040-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCTACAGAGTGGACAAGAGCCCTTACAACCAGTCTATGTATGGCGCCGGACT
GCCCGTGGACGATTTTGAGGATGCTGAAGCCGCCGACGCCGAGGAAGAATTTGGC
AACGCCATTGGCGGAAGCCACGGCGGCAGTAGCTATACCGTGTACATCGACAAGA
CCCGGTGA

SEQ ID NO: 151

YK-VZV-040-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AYRVDKSPYNQSMYGAGLPVDDFEDAEAADAEEEFGNAIGGSHGGSSYTVYIDKTR

SEQ ID NO: 152

YK-VZV-040-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC

-continued

CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCUACAGAGUGGACAAGAGCCCUUAC
AACCAGUCUAUGUAUGGCGCCGGACUGCCCGUGGACGAUUUUGAGGAUGCUG
AAGCCGCCGACGCCGAGGAAGAAUUUGGCAACGCCAUUGGCGGAAGCCACGGC
GGCAGUAGCUAUACCGUGUACAUCGACAAGACCCGGUGAUAAUAGgcUggagccU
cggUggccaUgcUUcUUgccccUUgggccUcccccagccccUccUccccUUccUgcacccgUacccccgUg
gUcUUUgaaUaaagUcUgagUgggcggcAAAAAAAAAAAAAAAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAA

SEQ ID NO: 153

YK-VZV-041-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCGACGATTTCGAGGACAGCGAGAGCACCGATACCG
AGGAAGAATGATAATAGgctggagcctcggtggccatgcttcttgccccttgggcctccccccagcccctcctcccctt
cctgcacccgtacccccgtggtctttgaataaagtctgagtgggcggcAAAAAAAAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAA

SEQ ID NO: 154

YK-VZV-041-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA

-continued

CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCGACGATTTCGAGGACAGCGAGAGCACCGATACCGAGGAAGAATGA

SEQ ID NO: 155

YK-VZV-041-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYONCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
ADDFEDSESTDTEEE

SEQ ID NO: 156

YK-VZV-041-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCGACGAUUUCGAGGACAGCGAGAGC
ACCGAUACCGAGGAAGAAUGAUAAUAGGcUggagccUcggUggccaUgcUUcUUgccccU
UgggccUccccccagccccUccUccccUUccUgcacccgUacccccgUggUcUUUgaaUaaagUcUgagUgg
gcggcAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAA

SEQ ID NO: 157

YK-VZV-042-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT

-continued

CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCGACGATTTCGAGGATGCCGAGGCCGCCGATGCTG
AGGAAGAATGATAATAGgctggagcctcggtggccatgcttcttgccccttgggcctccccccagcccctcctcccctt
cctgcacccgtacccccgtggtctttgaataaagtctgagtgggcggcAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAA

SEQ ID NO: 158

YK-VZV-042-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCGACGATTTCGAGGATGCCGAGGCCGCCGATGCTGAGGAAGAATGA

SEQ ID NO: 159

YK-VZV-042-ORF-AA
MGTVNKPVVGVLMGFGIITGTLRITNPVRASVLRYDDFHIDEDKLDINSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
ADDFEDAEAADAEEE

SEQ ID NO: 160

YK-VZV-042-mRNA
AGACUCCUCCCCAUCCUCUCCCUCUGUCCCUCUGUCCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG

-continued

GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCGACGAUUUCGAGGAUGCCGAGGCC
GCCGAUGCUGAGGAAGAAUGAUAAUAGgcUggagccUcggUggccaUgcUUcUUgccccU
UgggccUccccccagccccUccUccccUUccUgcacccgUacccccgUggUcUUUgaaUaaagUcUgagUgg
gcggcAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAA

SEQ ID NO: 161

YK-VZV-043-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCGACGATTTCGAGGACAGCGAGAGCACCGATACCG
AGGAAGAGTTCGGCAACGCCATTGGCGGATCTCACGGCGGCAGCAGCTATACCGT
GTACATCGACAAGACCCGGTGATAATAGgctggagcctcggtggccatgcttcttgccccttgggcctcccc
ccagcccctcctccccttcctgcacccgtacccccgtggtctttgaataaagtctgagtgggggcAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAA

SEQ ID NO: 162

YK-VZV-043-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC

-continued
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCGACGATTTCGAGGACAGCGAGAGCACCGATACCGAGGAAGAGTTCGGCA
ACGCCATTGGCGGATCTCACGGCGGCAGCAGCTATACCGTGTACATCGACAAGAC
CCGGTGA SEQ ID NO: 163
YK-VZV-043-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
ADDFEDSESTDTEEEFGNAIGGSHGGSSYTVYIDKTR SEQ ID NO: 164
YK-VZV-043-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU -continued GCACCGCCAAGCGGAUGAGAGUGAAGGCCGACGAUUUCGAGGACAGCGAGAGC
ACCGAUACCGAGGAAGAGUUCGGCAACGCCAUUGGCGGAUCUCACGGCGGCAG
CAGCUAUACCGUGUACAUCGACAAGACCCGGUGAUAAUAGgcUggagccUcggUggc
caUgcUUcUUgccccUUgggccUccccccagccccUccUccccUUccUgcacccgUacccccgUggUcUUU
gaaUaaagUcUgagUgggcggcAAAAAAAAAAAAAAAAAAAAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAA

SEQ ID NO: 165

YK-VZV-044-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT
GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCGACGATTTCGAGGATGCCGAGGCCGCCGATGCTG
AGGAAGAATTTGGCAACGCCATTGGCGGCTCTCACGGCGGCAGTAGCTATACCGT
GTACATCGACAAGACCCGGTGATAATAGgctggagcctcggtggccatgcttcttgccccttgggcctcccc
ccagcccctcctccccttcctgcacccgtacccccgtggtctttgaataaagtctgagtgggggcAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAA

SEQ ID NO: 166

YK-VZV-044-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT

-continued
TGTTCTGCTGTGCCTGGTCATCTTCCTGATCTGCACCGCCAAGCGGATGAGAGTGA
AGGCCGACGATTTCGAGGATGCCGAGGCCGCCGATGCTGAGGAAGAATTTGGCA
ACGCCATTGGCGGCTCTCACGGCGGCAGTAGCTATACCGTGTACATCGACAAGAC
CCGGTGA SEQ ID NO: 167
YK-VZV-044-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGOPPATTKPKEITPVNPGTSPLLRYAAWTGGLAAVVLLCLVIFLICTAKRMRVK
ADDFEDAEAADAEEEFGNAIGGSHGGSSYTVYIDKTR SEQ ID NO: 168
YK-VZV-044-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA
CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCGACGAUUUCGAGGAUGCCGAGGCC
GCCGAUGCUGAGGAAGAAUUUGGCAACGCCAUUGGCGGCUCUCACGGCGGCAG
UAGCUAUACCGUGUACAUCGACAAGACCCGGUGAUAAUAGgcUggagccUcggUggc
caUgcUUcUUgccccUUgggccUccccccagccccUccUccccUUccUgcacccgUacccccgUggUcUUU
gaaUaaagUcUgagUgggcggcAAAAAAAAAAAAAAAAAAAAAAAAAAAAAAAAAAAAAA
AAAAAAAAAAAAAAAAAAAAAAAAAAAAAAAAAAAAAAAAAAAAAAAAAAA
AAAAAAAAAAAAAAAAAAAAAA SEQ ID NO: 169
YK-VZV-045-DNA
AGACTCCTCCCCATCCTCTCCCTCTGTCCCTCTGTCCCTCTGACCCTGCAC
TGTCCCAGCACCGCCACCATGGGCACCGTGAACAAGCCTGTTGTGGGCGTGCTGA
TGGGCTTCGGCATCATCACAGGCACCCTGCGGATCACCAATCCTGTGCGGGCTAG
CGTGCTGAGATACGACGACTTCCACATCGACGAGGACAAGCTGGACACCAACAG
CGTGTACGAGCCCTACTACCACAGCGATCACGCCGAGTCTAGCTGGGTCAACAGA
GGCGAGAGCAGCAGAAAGGCCTACGACCACAACAGCCCCTACATCTGGCCCCGG
AACGACTACGATGGCTTCCTGGAAAATGCCCACGAGCACCACGGCGTGTACAATC
AAGGCAGAGGCATCGACAGCGGCGAGAGACTGATGCAGCCTACACAGATGAGCG
CCCAAGAGGACCTGGGAGATGATACCGGCATCCACGTGATCCCCACACTGAACGG
CGACGACAGACACAAGATCGTGAACGTGGACCAGCGGCAGTACGGCGACGTGTT
CAAGGGCGACCTGAATCCTAAGCCTCAGGGCCAGCGCCTGATCGAGGTGTCCGTG
GAAGAGAATCACCCCTTCACACTGAGAGCCCCTATCCAGAGAATCTACGGCGTGC
GCTATACCGAGACATGGTCCTTTCTGCCCAGCCTGACATGTACCGGGGATGCCGCT
CCTGCCATCCAGCACATTTGCCTGAAGCACACCACCTGTTTCCAGGACGTGGTGG
TGGATGTGGACTGCGCCGAGAACACCAAAGAGGATCAGCTGGCCGAGATCAGCT
ACCGGTTCCAGGGAAAGAAAGAGGCCGACCAGCCTTGGATCGTGGTCAACACCA
GCACACTGTTCGACGAGCTGGAACTGGACCCTCCTGAGATTGAACCCGGGGTGCT -continued GAAGGTGCTGAGAACCGAGAAGCAGTACCTGGGAGTGTACATCTGGAACATGAG
AGGCAGCGACGGCACCTCTACCTACGCCACCTTTCTGGTCACATGGAAGGGCGAC
GAGAAAACACGGAACCCCACACCAGCTGTGACCCCTCAACCTAGAGGCGCCGAG
TTTCACATGTGGAATTACCACAGCCACGTGTTCAGCGTGGGCGATACCTTTAGCCT
GGCCATGCATCTGCAGTACAAGATCCACGAGGCCCCTTTCGACCTGCTGCTGGAAT
GGCTGTACGTGCCCATCGATCCTACCTGCCAGCCTATGCGGCTGTACTCCACCTGT
CTGTATCACCCCAACGCTCCCCAGTGCCTGAGCCACATGAATAGCGGCTGCACCTT
CACAAGCCCTCACCTGGCTCAGCGAGTGGCCAGCACAGTGTACCAGAATTGCGA
GCACGCCGACAATTACACCGCCTACTGTCTGGGCATCAGCCACATGGAACCTAGC
TTCGGCCTGATCCTGCACGATGGCGGCACAACCCTGAAGTTCGTGGATACCCCTG
AGAGCCTGAGCGGCCTGTATGTGTTCGTGGTGTACTTCAACGGCCACGTGGAAGC
CGTGGCCTACACCGTGGTGTCTACCGTGGACCACTTCGTGAACGCCATCGAGGAA
AGAGGCTTCCCTCCAACTGCTGGACAGCCTCCTGCCACCACCAAGCCTAAAGAAA
TCACACCCGTGAATCCCGGCACAAGCCCACTGCTTAGATACGCCGCTTGGACAGG
CGGACTGGCTGCTGTTGTTCTGCTGTGCCTGGTCATCTTCCTGATCTGCACCGCCA
AGCGGATGAGAGTGAAGGCCTACAGAGTGGACAAGAGCCCTTACAACCAGAGCA
TGTACGCTGCCGGCCTGCCTGTGGACGACTTCGAGGATAGCGAGAGCACCGACAC
CGAGGAAGAGTTCGGCAACGCCATTGGAGGATCTCACGGCGGCAGCAGCTATACC
GTGTACATCGACAAGACCCGGTGAgctggagcctcggtggccatgcttcttgccccttgggcctccccccagcc
cctcctccccttcctgcacccgtacccccgtggtctttgaataaagtctgagtgggcggcAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAA

SEQ ID NO: 170

YK-VZV-045-ORF-NT
ATGGGCACCGTGAACAAGCCTGTTGTGGGCGTGCTGATGGGCTTCGGCAT
CATCACAGGCACCCTGCGGATCACCAATCCTGTGCGGGCTAGCGTGCTGAGATAC
GACGACTTCCACATCGACGAGGACAAGCTGGACACCAACAGCGTGTACGAGCCC
TACTACCACAGCGATCACGCCGAGTCTAGCTGGGTCAACAGAGGCGAGAGCAGC
AGAAAGGCCTACGACCACAACAGCCCCTACATCTGGCCCCGGAACGACTACGATG
GCTTCCTGGAAAATGCCCACGAGCACCACGGCGTGTACAATCAAGGCAGAGGCAT
CGACAGCGGCGAGAGACTGATGCAGCCTACACAGATGAGCGCCCAAGAGGACCT
GGGAGATGATACCGGCATCCACGTGATCCCCACACTGAACGGCGACGACAGACAC
AAGATCGTGAACGTGGACCAGCGGCAGTACGGCGACGTGTTCAAGGGCGACCTG
AATCCTAAGCCTCAGGGCCAGCGCCTGATCGAGGTGTCCGTGGAAGAGAATCACC
CCTTCACACTGAGAGCCCCTATCCAGAGAATCTACGGCGTGCGCTATACCGAGAC
ATGGTCCTTTCTGCCCAGCCTGACATGTACCGGGGATGCCGCTCCTGCCATCCAGC
ACATTTGCCTGAAGCACACCACCTGTTTCCAGGACGTGGTGGTGGATGTGGACTG
CGCCGAGAACACCAAAGAGGATCAGCTGGCCGAGATCAGCTACCGGTTCCAGGG
AAAGAAAGAGGCCGACCAGCCTTGGATCGTGGTCAACACCAGCACACTGTTCGA
CGAGCTGGAACTGGACCCTCCTGAGATTGAACCCGGGGTGCTGAAGGTGCTGAG
AACCGAGAAGCAGTACCTGGGAGTGTACATCTGGAACATGAGAGGCAGCGACGG
CACCTCTACCTACGCCACCTTTCTGGTCACATGGAAGGGCGACGAGAAAACACGG
AACCCCACACCAGCTGTGACCCCTCAACCTAGAGGCGCCGAGTTTCACATGTGGA
ATTACCACAGCCACGTGTTCAGCGTGGGCGATACCTTTAGCCTGGCCATGCATCTG
CAGTACAAGATCCACGAGGCCCCTTTCGACCTGCTGCTGGAATGGCTGTACGTGC
CCATCGATCCTACCTGCCAGCCTATGCGGCTGTACTCCACCTGTCTGTATCACCCCA
ACGCTCCCCAGTGCCTGAGCCACATGAATAGCGGCTGCACCTTCACAAGCCCTCA
CCTGGCTCAGCGAGTGGCCAGCACAGTGTACCAGAATTGCGAGCACGCCGACAAT
TACACCGCCTACTGTCTGGGCATCAGCCACATGGAACCTAGCTTCGGCCTGATCCT
GCACGATGGCGGCACAACCCTGAAGTTCGTGGATACCCCTGAGAGCCTGAGCGGC
CTGTATGTGTTCGTGGTGTACTTCAACGGCCACGTGGAAGCCGTGGCCTACACCGT
GGTGTCTACCGTGGACCACTTCGTGAACGCCATCGAGGAAAGAGGCTTCCCTCCA
ACTGCTGGACAGCCTCCTGCCACCACCAAGCCTAAAGAAATCACACCCGTGAATC
CCGGCACAAGCCCACTGCTTAGATACGCCGCTTGGACAGGCGGACTGGCTGCTGT
TGTTCTGCTGTGCCTGGTCATCTTCCTGATCTGCACCGCCAAGCGGATGAGAGTGA
AGGCCTACAGAGTGGACAAGAGCCCTTACAACCAGAGCATGTACGCTGCCGGCCT
GCCTGTGGACGACTTCGAGGATAGCGAGAGCACCGACACCGAGGAAGAGTTCGG
CAACGCCATTGGAGGATCTCACGGCGGCAGCAGCTATACCGTGTACATCGACAAG
ACCCGGTGA

SEQ ID NO: 171

YK-VZV-045-ORF-AA
MGTVNKPVVGVLMGFGIITGTLRITNPVRASVLRYDDFHIDEDKLDTNSVYE
PYYHSDHAESSWVNRGESSRKAYDHNSPYIWPRNDYDGFLENAHEHHGVYNQGRGI
DSGERLMQPTQMSAQEDLGDDTGIHVIPTLNGDDRHKIVNVDQRQYGDVFKGDLNP
KPQGQRLIEVSVEENHPFTLRAPIQRIYGVRYTETWSFLPSLTCTGDAAPAIQHICLKH
TTCFQDVVVDVDCAENTKEDQLAEISYRFQGKKEADQPWIVVNTSTLFDELELDPPE
IEPGVLKVLRTEKQYLGVYIWNMRGSDGTSTYATFLVTWKGDEKTRNPTPAVTPQPR
GAEFHMWNYHSHVFSVGDTFSLAMHLQYKIHEAPFDLLLEWLYVPIDPTCQPMRLY
STCLYHPNAPQCLSHMNSGCTFTSPHLAQRVASTVYQNCEHADNYTAYCLGISHMEP
SFGLILHDGGTTLKFVDTPESLSGLYVFVVYFNGHVEAVAYTVVSTVDHFVNAIEERG
FPPTAGQPPATTKPKEITPVNPGTSPLLRYAAWTGGLAAVVLLCLVIFLICTAKRMRVK
AYRVDKSPYNQSMYAAGLPVDDFEDSESTDTEEEFGNAIGGSHGGSSYTVYIDKTR

SEQ ID NO: 172

YK-VZV-045-mRNA
AGACUCCUCCCCAUCCUCUCCCUCUGUCCCUCUGUCCCUCUGACCCUGC
ACUGUCCCAGCACCGCCACCAUGGGCACCGUGAACAAGCCUGUUGUGGGCGUG
CUGAUGGGCUUCGGCAUCAUCACAGGCACCCUGCGGAUCACCAAUCCUGUGCG
GGCUAGCGUGCUGAGAUACGACGACUUCCACAUCGACGAGGACAAGCUGGACA

-continued

CCAACAGCGUGUACGAGCCCUACUACCACAGCGAUCACGCCGAGUCUAGCUGG
GUCAACAGAGGCGAGAGCAGCAGAAAGGCCUACGACCACAACAGCCCCUACAU
CUGGCCCCGGAACGACUACGAUGGCUUCCUGGAAAAUGCCCACGAGCACCACG
GCGUGUACAAUCAAGGCAGAGGCAUCGACAGCGGCGAGAGACUGAUGCAGCCU
ACACAGAUGAGCGCCCAAGAGGACCUGGGAGAUGAUACCGGCAUCCACGUGAU
CCCCACACUGAACGGCGACGACAGACACAAGAUCGUGAACGUGGACCAGCGGC
AGUACGGCGACGUGUUCAAGGGCGACCUGAAUCCUAAGCCUCAGGGCCAGCGC
CUGAUCGAGGUGUCCGUGGAAGAGAAUCACCCCUUCACACUGAGAGCCCCUAU
CCAGAGAAUCUACGGCGUGCGCUAUACCGAGACAUGGUCCUUUCUGCCCAGCC
UGACAUGUACCGGGGAUGCCGCUCCUGCCAUCCAGCACAUUUGCCUGAAGCAC
ACCACCUGUUUCCAGGACGUGGUGGUGGAUGUGGACUGCGCCGAGAACACCAA
AGAGGAUCAGCUGGCCGAGAUCAGCUACCGGUUCCAGGGAAAGAAAGAGGCC
GACCAGCCUUGGAUCGUGGUCAACACCAGCACACUGUUCGACGAGCUGGAACU
GGACCCUCCUGAGAUUGAACCCGGGGUGCUGAAGGUGCUGAGAACCGAGAAGC
AGUACCUGGGAGUGUACAUCUGGAACAUGAGAGGCAGCGACGGCACCUCUACC
UACGCCACCUUUCUGGUCACAUGGAAGGGCGACGAGAAAACACGGAACCCCAC
ACCAGCUGUGACCCCUCAACCUAGAGGCGCCGAGUUUCACAUGUGGAAUUACC
ACAGCCACGUGUUCAGCGUGGGCGAUACCUUUAGCCUGGCCAUGCAUCUGCAG
UACAAGAUCCACGAGGCCCCUUUCGACCUGCUGCUGGAAUGGCUGUACGUGCC
CAUCGAUCCUACCUGCCAGCCUAUGCGGCUGUACUCCACCUGUCUGUAUCACC
CCAACGCUCCCCAGUGCCUGAGCCACAUGAAUAGCGGCUGCACCUUCACAAGC
CCUCACCUGGCUCAGCGAGUGGCCAGCACAGUGUACCAGAAUUGCGAGCACGC
CGACAAUUACACCGCCUACUGUCUGGGCAUCAGCCACAUGGAACCUAGCUUCG
GCCUGAUCCUGCACGAUGGCGGCACAACCCUGAAGUUCGUGGAUACCCCUGAG
AGCCUGAGCGGCCUGUAUGUGUUCGUGGUGUACUUCAACGGCCACGUGGAAGC
CGUGGCCUACACCGUGGUGUCUACCGUGGACCACUUCGUGAACGCCAUCGAGG
AAAGAGGCUUCCCUCCAACUGCUGGACAGCCUCCUGCCACCACCAAGCCUAAA
GAAAUCACACCCGUGAAUCCCGGCACAAGCCCACUGCUUAGAUACGCCGCUUG
GACAGGCGGACUGGCUGCUGUUGUUCUGCUGUGCCUGGUCAUCUUCCUGAUCU
GCACCGCCAAGCGGAUGAGAGUGAAGGCCUACAGAGUGGACAAGAGCCCUUAC
AACCAGAGCAUGUACGCUGCCGGCCUGCCUGUGGACGACUUCGAGGAUAGCGA
GAGCACCGACACCGAGGAAGAGUUCGGCAACGCCAUUGGAGGAUCUCACGGCG
GCAGCAGCUAUACCGUGUACAUCGACAAGACCCGGUGAgcUggagccUcggUggccaU
gcUUcUUgccccUUgggccUcccccagccccUccUccccUUccUgcacccgUacccccgUggUcUUUgaa
UaaagUcUgagUgggcggcAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAA

SEQ ID NO: 173

5' UTR
5'AGAAATAAGAGAGAAAAGAAGAGTAAGAAGAAATATAAGAGCCACC3'

SEQ ID NO: 174

5' UTR
S'AGACTCCTCCCCATCCTCTCCCTCTGTCCCTCTGTCCCTCTGACCCTGCA
CTGTCCCAGCACCGCCACC3'

SEQ ID NO: 175

5'UTR
5'AGCATTCTGTGGTCTGATCATCCTGTGGTTTCGTCGCCGCCATCCTCGTC
GCGACACGCTGTTTTCGGTTCTCGGCCCGACGAGCCATCGCCATCCTACAGC3'

SEQ ID NO: 176

5' UTR
5'AGCACTCGCGCTGCCATCACTCTTCCGCCGTCTTCGCCGCCATCCTCGGC
GCGACTCGCTTCTTTCGGTTCTACCAGGTAGAGTCCGCCGCCATCCTCCACC3'

SEQ ID NO: 177

5' UTR
5'AGCTTGTCTCGCTCCGGGGAACGCTCGGAAACTCCCGGCCGCCGCCAC
CCGCGTCTGTTCTGTTACACAAGGGAAGAAAAGCCGCTGCCGCACTCCGAGTGT3'

SEQ ID NO: 178

3' UTR
5'gctggagcctcggtggccatgcttcttgccccttgggcctccccccagcccctcctccccttcctgcacccgtaccccc
gtggtctttgaataaagtctgagtgggcggc3'

SEQ ID NO: 179

3' UTR
5'GCTCGCTTTCTTGCTGTCCAATTTCTATTAAAGGTTCCTTTGTTCCCTAAG
TCCAACTACTAAACTGGGGGATATTATGAAGGGCCTTGAGCATCTGGATTCTGCCT
AATAAAAAACATTTATTTTCATTGC3'

SEQ ID NO: 180

3' UTR
5'TTCTGGACTTCTGGACTTCTGGACTTCTGGACTTCTGGACTTCTGGACTT
CTGGACTTCTGGACTTCTGGACTTCTGGACTTCTGGAC3'

-continued

SEQ ID NO: 181

3' UTR
5'CCTCGCCCCGGACCTGCCCTCCCGCCAGGTGCACCCACCTGCAATAAAT
GCAGCGAAGCCGGGACCTCGCCCCGGACCTGCCCTCCCGCCAGGTGCACCCACC
TGCAATAAATGC3'

SEQ ID NO: 182

$S_{593}ES_{595}T_{596}DT_{598}$

SEQ ID NO: 183

$A_{593}EA_{595}A_{596}DA_{598}$

SEQ ID NO: 184

$A_{568}YRV_{571}$

SEQ ID NO: 185

$Y_{522}AGL_{525}$

SEQ ID NO: 186

$Y_{569}$RVDKSPYNQ$S_{579}$

SEQ ID NO: 187

$Y_{569}$RVDKSPYNQSMYYAGLP$V_{587}$

SEQ ID NO: 188

SSTT

SEQ ID NO: 189 a sequence in FIG. 1
AYRVYAGLSSTT

SEQ ID NO: 190 a sequence in FIG. 1
YAGLSSTT

SEQ ID NO: 191 a sequence in FIG. 1
AYRVYAGL

SEQUENCE LISTING

```
Sequence total quantity: 191
SEQ ID NO: 1            moltype = DNA  length = 2138
FEATURE                 Location/Qualifiers
source                  1..2138
                        mol_type = genomic DNA
                        organism = Varicella-Zoster Virus
SEQUENCE: 1
agaaataaga gagaaaagaa gagtaagaag aaatataaga gccaccatgg gcaccgtgaa  60
caagcctgtt gtgggcgtgc tgatgggctt cggcatcatc acaggcaccc tgcggatcac  120
caatcctgtg cgggctagcg tgctgagata cgacgacttc cacatcgacg aggacaagct  180
ggacaccaac agcgtgtacg agccctacta ccacagcgat cacgccgagt ctagctgggt  240
caacagaggc gagagcagca gaaaggccta cgaccacaac agcccctaca tctggccccg  300
gaacgactac gatggcttcc tggaaaatgc ccacgagcac cacggcgtgt acaatcaagg  360
cagaggcatc gacagcggcg agagactgat gcagcctaca cagatgagcg cccaagagga  420
cctgggagat gataccggca tccacgtgat ccccacactg aacggcgacg acagacacaa  480
gatcgtgaac gtggaccagc ggcagtacgg cgacgtgttc aagggcgacc tgaatcctaa  540
gcctcagggc cagcgcctga tcgaggtgtc cgtggaagag aatcacccct tcacactgag  600
agcccctatc cagagaatct acggcgtgcg ctataccgag acatggtcct ttctgcccag  660
cctgacatgt accggggatg ccgctcctgc catccagcac atttgcctga agcacaccac  720
ctgtttccag gacgtggtgg tggatgtgga ctgcgccgag aacaccaaag aggatcagct  780
ggccgagatc agctaccggt tccagggaaa gaaagaggcc gaccagcctt ggatcgtggt  840
caacaccagc acactgttcg acgagctgga actggaccct cctgagattg aacccggggt  900
gctgaaggtg ctgagaaccg agaagcagta cctgggagtg tacatctgga acatgagagg  960
cagcgacggc acctctacct acgccacctt tctggtcaca tggaagggcg acgagaaaac  1020
acggaacccc acaccagctg tgacccctca acctagaggc gccgagtttc acatgtggaa  1080
ttaccacagc cacgtgttca gcgtgggcga tacctttagc ctggccatgc atctgcagta  1140
caagatccac gaggcccctt tcgacctgct gctggaatgg ctgtacgtgc ccatcgatcc  1200
tacctgccag cctatgcggc tgtactccac ctgtctgtat caccccaacg ctccccagtg  1260
cctgagccac atgaatagcg gctgcacctt cacaagccct cacctggctc agcgagtggc  1320
cagcacagtg taccagaatt gcgagcacgc cgacaattac accgcctact gtctgggcat  1380
cagccacatg gaacctagct tcggcctgat cctgcacgat ggcggcacaa ccctgaagtt  1440
cgtggatacc cctgagagcc tgagcggcct gtatgtgttc gtggtgtact tcaacggcca  1500
cgtggaagcc gtggcctaca ccgtggtgtc taccgtggac cacttcgtga acgccatcga  1560
ggaaagaggc ttccctccaa ctgctggaca gcctcctgcc accaccaagc ctaaagaaat  1620
cacacccgtg aatcccggca caagcccact gcttagatac gccgcttgga caggcggact  1680
ggctgctgtt gttctgctgt gcctggtcat cttcctgatc tgcaccgcca agcggatgag  1740
```

```
agtgaaggcc tacagagtgg acaagagccc ttacaaccag agcatgtact acgccggcct  1800
gcctgtggac gacttcgagg atagcgagag caccgacacc gaggaagagt tcggcaacgc  1860
cattggagga tctcacggcg gcagcagcta taccgtgtac atcgacaaga cccggtgagc  1920
tggagcctcg gtggccatgc ttcttgcccc ttgggcctcc ccccagcccc tcctcccctt  1980
cctgcacccg tacccccgtg gtctttgaat aaagtctgag tgggcggcaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaaaaaa                          2138

SEQ ID NO: 2           moltype = DNA  length = 1872
FEATURE                Location/Qualifiers
source                 1..1872
                       mol_type = other DNA
                       organism = Varicella-Zoster Virus
SEQUENCE: 2
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggcctacaga gtggacaaga gcccttacaa ccagagcatg  1740
tactacgccg gcctgcctgt ggacgacttc gaggatagcg agagcaccga caccgaggaa  1800
gagttcggca acgccattgg aggatctcac ggcggcagca gctataccgt gtacatcgac  1860
aagacccggt ga                                                      1872

SEQ ID NO: 3           moltype = AA  length = 623
FEATURE                Location/Qualifiers
source                 1..623
                       mol_type = protein
                       organism = Varicella-Zoster Virus
SEQUENCE: 3
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR VDKSPYNQSM YYAGLPVDDF EDSESTDTEE  600
EFGNAIGGSH GGSSYTVYID KTR                                          623

SEQ ID NO: 4           moltype = RNA  length = 2138
FEATURE                Location/Qualifiers
source                 1..2138
                       mol_type = mRNA
                       organism = Varicella-Zoster Virus
SEQUENCE: 4
agaaataaga gagaaaagaa gagtaagaag aaatataaga gccaccatgg gcaccgtgaa  60
caagcctgtt gtgggcgtgc tgatgggctt cggcatcatc acaggcaccc tgcggatcac  120
caatcctgtg cgggctagcg tgctgagata cgacgacttc cacatcgacg aggacaagct  180
ggacaccaac agcgtgtacg agccctacta ccacagcgat cacgccgagt ctagctgggt  240
caacagaggc gagagcagca gaaaggccta cgaccacaac agcccctaca tctggccccg  300
gaacgactac gatggcttcc tggaaaatgc ccacgagcac cacggcgtgt acaatcaagg  360
cagaggcatc gacagcggcg agagactgat gcagcctaca cagatgagcg cccaagagga  420
cctgggagat gataccggca tccacgtgat ccccacactg aacggcgacg acagacacaa  480
```

```
gatcgtgaac gtggaccagc ggcagtacgg cgacgtgttc aagggcgacc tgaatcctaa  540
gcctcagggc cagcgcctga tcgaggtgtc cgtggaagag aatcacccct tcacactgag  600
agcccctatc cagagaatct acggcgtgcg ctataccgag acatggtcct ttctgcccag  660
cctgacatgt accggggatg ccgctcctgc catccagcac atttgcctga agcacaccac  720
ctgtttccag gacgtggtgg tggatgtgga ctgcgccgag aacaccaaag aggatcagct  780
ggccgagatc agctaccggt tccagggaaa gaaagaggcc gaccagcctt ggatcgtggt  840
caacaccagc acactgttcg acgagctgga actggaccct cctgagattg aacccggggt  900
gctgaaggtg ctgagaaccg agaagcagta cctgggagtg tacatctgga acatgagagg  960
cagcgacggc acctctacct acgccacctt tctggtcaca tggaagggcg acgagaaaac  1020
acggaacccc acaccagctg tgacccctca acctagaggc gccgagtttc acatgtggaa  1080
ttaccacagc cacgtgttca gcgtgggcga tacctttagc ctggccatgc atctgcagta  1140
caagatccac gaggcccctt tcgacctgct gctggaatgg ctgtacgtgc ccatcgatcc  1200
tacctgccag cctatgcggc tgtactccac ctgtctgtat caccccaacg ctccccagtg  1260
cctgagccac atgaatagcg gctgcacctt cacaagccct cacctggctc agcgagtggc  1320
cagcacagtg taccagaatt gcgagcacgc cgacaattac accgcctact gtctgggcat  1380
cagccacatg gaacctagct tcggcctgat cctgcacgat ggcggcacaa ccctgaagtt  1440
cgtggatacc cctgagagcc tgagcggcct gtatgtgttc gtggtgtact tcaacggcca  1500
cgtggaagcc gtggcctaca ccgtggtgtc taccgtggac cacttcgtga acgccatcga  1560
ggaaagaggc ttccctccaa ctgctggaca gcctcctgcc accaccaagc ctaaagaaat  1620
cacacccgtg aatcccggca caagcccact gcttagatac gccgcttgga caggcggact  1680
ggctgctgtt gttctgctgt gcctggtcat cttcctgatc tgcaccgcca agcggatgag  1740
agtgaaggcc tacagagtgg acaagagccc ttacaaccag agcatgtact acgccggcct  1800
gcctgtggac gacttcgagg atagcgagag caccgacacc gaggaagagt tcggcaacgc  1860
cattggagga tctcacggcg gcagcagcta taccgtgtac atcgacaaga cccggtgagc  1920
tggagcctcg gtggccatgc ttcttgcccc ttgggcctcc ccccagcccc tcctcccctt  1980
cctgcacccg tacccccgtg gtctttgaat aaagtctgag tgggcggcaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaaaaa                          2138

SEQ ID NO: 5            moltype = DNA  length = 1909
FEATURE                 Location/Qualifiers
source                  1..1909
                        mol_type = other DNA
                        organism = synthetic construct
SEQUENCE: 5
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgctcaga  1680
tatgcctgag ctggagcctc ggtggccatg cttcttgccc cttgggcctc cccccagccc  1740
ctcctcccct tcctgcaccc gtacccccgt ggtctttgaa taaagtctga gtgggcggca  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaa              1909

SEQ ID NO: 6            moltype = DNA  length = 1620
FEATURE                 Location/Qualifiers
source                  1..1620
                        mol_type = other DNA
                        organism = synthetic construct
SEQUENCE: 6
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
```

-continued

```
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aacacggaac ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgctcag atatgcctga  1620

SEQ ID NO: 7           moltype = AA  length = 539
FEATURE                Location/Qualifiers
source                 1..539
                       mol_type = protein
                       organism = synthetic construct
SEQUENCE: 7
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYA   539

SEQ ID NO: 8           moltype = RNA  length = 1909
FEATURE                Location/Qualifiers
source                 1..1909
                       mol_type = other RNA
                       organism = synthetic construct
SEQUENCE: 8
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgctcaga  1680
tatgcctgag ctggagcctc ggtggccatg cttcttgccc cttgggcctc cccccagccc  1740
ctcctcccct tcctgcaccc gtacccccgt ggtctttgaa taaagtctga gtgggcggca  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaa              1909

SEQ ID NO: 9           moltype = DNA  length = 1996
```

```
FEATURE                Location/Qualifiers
source                 1..1996
                       mol_type = other DNA
                       organism = synthetic construct
SEQUENCE: 9
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcaccccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaaa gcctgagctg gagcctcggt ggccatgctt  1800
cttgcccctt gggcctcccc ccagcccctc ctccccttcc tgcacccgta cccccgtggt  1860
ctttgaataa agtctgagtg ggcggcaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaa                                                 1996

SEQ ID NO: 10          moltype = DNA  length = 1707
FEATURE                Location/Qualifiers
source                 1..1707
                       mol_type = other DNA
                       organism = synthetic construct
SEQUENCE: 10
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa agcctga                                     1707

SEQ ID NO: 11          moltype = AA  length = 568
FEATURE                Location/Qualifiers
source                 1..568
```

```
                        mol_type = protein
                        organism = synthetic construct
SEQUENCE: 11
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKA                                    568

SEQ ID NO: 12           moltype = RNA  length = 1996
FEATURE                 Location/Qualifiers
source                  1..1996
                        mol_type = other RNA
                        organism = synthetic construct
SEQUENCE: 12
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaaa gcctgagctg gagcctcggt ggccatgctt  1800
cttgcccctt gggcctcccc ccagcccctc ctccccttcc tgcacccgta cccccgtggt  1860
ctttgaataa agtctgagtg ggcggcaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaa                                                 1996

SEQ ID NO: 13           moltype = DNA  length = 1988
FEATURE                 Location/Qualifiers
source                  1..1988
                        mol_type = other DNA
                        organism = synthetic construct
SEQUENCE: 13
agaaataaga gagaaaagaa gagtaagaag aaatataaga gccaccatgg gcaccgtgaa  60
caagcctgtt gtgggcgtgc tgatgggctt cggcatcatc acaggcaccc tgcggatcac  120
caatcctgtg cgggctagcg tgctgagata cgacgacttc cacatcgacg aggacaagct  180
ggacaccaac agcgtgtacg agccctacta ccacagcgat cacgccgagt ctagctgggt  240
caacagaggc gagagcagca gaaaggccta cgaccacaac agcccctaca tctggccccg  300
gaacgactac gatggcttcc tggaaaatgc ccacgagcac cacggcgtgt acaatcaagg  360
cagaggcatc gacagcggcg agagactgat gcagcctaca cagatgagcg cccaagagga  420
cctgggagat gataccggca tccacgtgat ccccacactg aacggcgacg acagacacaa  480
gatcgtgaac gtggaccagc ggcagtacgg cgacgtgttc aagggcgacc tgaatcctaa  540
gcctcagggc cagcgcctga tcgaggtgtc cgtggaagag aatcacccct tcacactgag  600
agcccctatc cagagaatct acggcgtgcg ctataccgag acatggtcct ttctgcccag  660
cctgacatgt accggggatg ccgctcctgc catccagcac atttgcctga agcacaccac  720
ctgtttccag gacgtggtgg tggatgtgga ctgcgccgag aacaccaaag aggatcagct  780
ggccgagatc agctaccggt tccagggaaa gaaagaggcc gaccagcctt ggatcgtggt  840
caacaccagc acactgttcg acgagctgga actggaccct cctgagattg aacccggggt  900
gctgaaggtg ctgagaaccg agaagcagta cctgggagtg tacatctgga acatgagagg  960
cagcgacggc acctctacct acgccacctt tctggtcaca tggaagggcg acgagaaaac  1020
acggaacccc acaccagctg tgacccctca acctagaggc gccgagtttc acatgtggaa  1080
```

-continued

```
ttaccacagc cacgtgttca gcgtgggcga tacctttagc ctggccatgc atctgcagta  1140
caagatccac gaggcccctt tcgacctgct gctggaatgg ctgtacgtgc ccatcgatcc  1200
tacctgccag cctatgcggc tgtactccac ctgtctgtat caccccaacg ctccccagtg  1260
cctgagccac atgaatagcg gctgcacctt cacaagccct cacctggctc agcgagtggc  1320
cagcacagtg taccagaatt gcgagcacgc cgacaattac accgcctact gtctgggcat  1380
cagccacatg gaacctagct tcggcctgat cctgcacgat ggcggcacaa ccctgaagtt  1440
cgtggatacc cctgagagcc tgagcggcct gtatgtgttc gtggtgtact tcaacggcca  1500
cgtggaagcc gtggcctaca ccgtggtgtc taccgtggac cacttcgtga acgccatcga  1560
ggaaagaggc ttccctccaa ctgctggaca gcctcctgcc accaccaagc ctaaagaaat  1620
cacacccgtg aatcccggca caagcccact gcttagatac gccgcttgga caggcggact  1680
ggctgctgtt gttctgctgt gcctggtcat cttcctgatc tgcaccgcca agcggatgag  1740
agtgaaagcc gccagagtgg acaagtgagc tggagcctcg gtggccatgc ttcttgcccc  1800
ttgggcctcc ccccagcccc tcctcccctt cctgcacccg tacccccgtg gtctttgaat  1860
aaagtctgag tgggcggcaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaa                                                           1988

SEQ ID NO: 14          moltype = DNA  length = 1722
FEATURE                Location/Qualifiers
source                 1..1722
                       mol_type = other DNA
                       organism = synthetic construct
SEQUENCE: 14
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa agccgccaga gtggacaagt ga                     1722

SEQ ID NO: 15          moltype = AA  length = 573
FEATURE                Location/Qualifiers
source                 1..573
                       mol_type = protein
                       organism = synthetic construct
SEQUENCE: 15
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAAR VDK                                573

SEQ ID NO: 16          moltype = RNA  length = 1988
FEATURE                Location/Qualifiers
source                 1..1988
                       mol_type = other RNA
                       organism = synthetic construct
SEQUENCE: 16
agaaataaga gagaaaagaa gagtaagaag aaatataaga gccaccatgg gcaccgtgaa  60
caagcctgtt gtgggcgtgc tgatgggctt cggcatcatc acaggcaccc tgcggatcac  120
caatcctgtg cgggctagcg tgctgagata cgacgacttc cacatcgacg aggacaagct  180
```

-continued

```
ggacaccaac agcgtgtacg agccctacta ccacagcgat cacgccgagt ctagctgggt  240
caacagaggc gagagcagca gaaaggccta cgaccacaac agcccctaca tctggccccg  300
gaacgactac gatggcttcc tggaaaatgc ccacgagcac cacggcgtgt acaatcaagg  360
cagaggcatc gacagcggcg agagactgat gcagcctaca cagatgagcg cccaagagga  420
cctgggagat gataccggca tccacgtgat ccccacactg aacggcgacg acagacacaa  480
gatcgtgaac gtggaccagc ggcagtacgg cgacgtgttc aagggcgacc tgaatcctaa  540
gcctcagggc cagcgcctga tcgaggtgtc cgtggaagag aatcacccct tcacactgag  600
agcccctatc cagagaatct acggcgtgcg ctataccgag acatggtcct ttctgcccag  660
cctgacatgt accggggatg ccgctcctgc catccagcac atttgcctga agcacaccac  720
ctgtttccag gacgtggtgg tggatgtgga ctgcgccgag aacaccaaag aggatcagct  780
ggccgagatc agctaccggt tccagggaaa gaaagaggcc gaccagcctt ggatcgtggt  840
caacaccagc acactgttcg acgagctgga actggaccct cctgagattg aacccggggt  900
gctgaaggtg ctgagaaccg agaagcagta cctgggagtg tacatctgga acatgagagg  960
cagcgacggc acctctacct acgccacctt tctggtcaca tggaagggcg acgagaaaac  1020
acggaacccc acaccagctg tgacccctca acctagaggc gccgagtttc acatgtggaa  1080
ttaccacagc cacgtgttca gcgtgggcga tacctttagc ctggccatgc atctgcagta  1140
caagatccac gaggcccctt tcgacctgct gctggaatgg ctgtacgtgc ccatcgatcc  1200
tacctgccag cctatgcggc tgtactccac ctgtctgtat caccccaacg ctccccagtg  1260
cctgagccac atgaatagcg gctgcacctt cacaagccct cacctggctc agcgagtggc  1320
cagcacagtg taccagaatt gcgagcacgc cgacaattac accgcctact gtctgggcat  1380
cagccacatg gaacctagct tcggcctgat cctgcacgat ggcggcacaa ccctgaagtt  1440
cgtggatacc cctgagagcc tgagcggcct gtatgtgttc gtggtgtact tcaacggcca  1500
cgtggaagcc gtggcctaca ccgtggtgtc taccgtggac cacttcgtga acgccatcga  1560
ggaaagaggc ttccctccaa ctgctggaca gcctcctgcc accaccaagc ctaaagaaat  1620
cacacccgtg aatcccggca caagcccact gcttagatac gccgcttgga caggcggact  1680
ggctgctgtt gttctgctgt gcctggtcat cttcctgatc tgcaccgcca agcggatgag  1740
agtgaaagcc gccagagtgg acaagtgagc tggagcctcg gtggccatgc ttcttgcccc  1800
ttgggcctcc ccccagcccc tcctcccctt cctgcacccg taccccgtg gtctttgaat  1860
aaagtctgag tgggcggcaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaa                                                           1988

SEQ ID NO: 17          moltype = DNA  length = 2161
FEATURE                Location/Qualifiers
source                 1..2161
                       mol_type = other DNA
                       organism = synthetic construct
SEQUENCE: 17
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccgcgagag tggacaagag cccttacaac  1800
cagagcatgt actacgccgg cctgcctgtg gacgatttcg aggatgctga agccgccgat  1860
gccgaggaag agtttggcaa cgccattggc ggatctcacg gcggcagcag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 18          moltype = DNA  length = 1872
FEATURE                Location/Qualifiers
source                 1..1872
```

```
                         mol_type = other DNA
                         organism = synthetic construct
SEQUENCE: 18
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccgcgaga gtggacaaga gcccttacaa ccagagcatg  1740
tactacgccg gcctgcctgt ggacgatttc gaggatgctg aagccgccga tgccgaggaa  1800
gagtttggca acgccattgg cggatctcac ggcggcagca gctataccgt gtacatcgac  1860
aagacccggt ga                                                     1872

SEQ ID NO: 19            moltype = AA  length = 623
FEATURE                  Location/Qualifiers
source                   1..623
                         mol_type = protein
                         organism = synthetic construct
SEQUENCE: 19
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAAR VDKSPYNQSM YYAGLPVDDF EDAEAADAEE  600
EFGNAIGGSH GGSSYTVYID KTR                                         623

SEQ ID NO: 20            moltype = RNA  length = 2161
FEATURE                  Location/Qualifiers
source                   1..2161
                         mol_type = other RNA
                         organism = synthetic construct
SEQUENCE: 20
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
```

```
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccgctagag tggacaagag cccttacaac  1800
cagagcatgt actacgccgg cctgcctgtg gacgatttcg aggatgctga agccgccgat  1860
gccgaggaag agtttggcaa cgccattggc ggatctcacg gcggcagcag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 21          moltype = DNA  length = 2161
FEATURE                Location/Qualifiers
source                 1..2161
                       mol_type = other DNA
                       organism = synthetic construct
SEQUENCE: 21
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctacagag tggacaagag cccttacaac  1800
cagtctatgt atgccgccgg actgcccgtg gacgattttg aggatgctga agccgccgac  1860
gccgaggaag aatttggcaa cgccattggc ggaagccacg gcggcagtag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 22          moltype = DNA  length = 1872
FEATURE                Location/Qualifiers
source                 1..1872
                       mol_type = other DNA
                       organism = synthetic construct
SEQUENCE: 22
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
```

-continued

```
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggcctacaga gtggacaaga gcccttacaa ccagtctatg  1740
tatgccgccg gactgcccgt ggacgatttt gaggatgctg aagccgccga cgccgaggaa  1800
gaatttggca acgccattgg cggaagccac ggcggcagta gctataccgt gtacatcgac  1860
aagacccggt ga                                                      1872

SEQ ID NO: 23          moltype = AA  length = 623
FEATURE                Location/Qualifiers
source                 1..623
                       mol_type = protein
                       organism = synthetic construct
SEQUENCE: 23
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR VDKSPYNQSM YAAGLPVDDF EDAEAADAEE  600
EFGNAIGGSH GGSSYTVYID KTR                                          623

SEQ ID NO: 24          moltype = RNA  length = 2161
FEATURE                Location/Qualifiers
source                 1..2161
                       mol_type = other RNA
                       organism = synthetic construct
SEQUENCE: 24
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgatacctttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctacagag tggacaagag cccttacaac  1800
cagtctatgt atgccgccgg actgcccgtg gacgattttg aggatgctga agccgccgac  1860
gccgaggaag aatttggcaa cgccattggc ggaagccacg gcggcagtag ctataccgtg  1920
```

-continued

```
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 25          moltype = DNA  length = 2101
FEATURE                Location/Qualifiers
source                 1..2101
                       mol_type = other DNA
                       organism = synthetic construct
SEQUENCE: 25
accgccacca tgggcaccgt gaacaagcct gttgtgggcg tgctgatggg cttcggcatc  60
atcacaggca ccctgcggat caccaatcct gtgcgggcta gcgtgctgag atacgacgac  120
ttccacatcg acgaggacaa gctggacacc aacagcgtgt acgagcccta ctaccacagc  180
gatcacgccg agtctagctg ggtcaacaga ggcgagagca gcagaaaggc ctacgaccac  240
aacagcccct acatctggcc ccggaacgac tacgatggct tcctggaaaa tgcccacgag  300
caccacggcg tgtacaatca aggcagaggc atcgacagcg gcgagagact gatgcagcct  360
acacagatga gcgcccaaga ggacctggga gatgataccg gcatccacgt gatccccaca  420
ctgaacggcg acgacagaca caagatcgtg aacgtggacc agcggcagta cggcgacgtg  480
ttcaagggcg acctgaatcc taagcctcag ggccagcgcc tgatcgaggt gtccgtggaa  540
gagaatcacc ccttcacact gagagcccct atccagagaa tctacggcgt gcgctatacc  600
gagacatggt cctttctgcc cagcctgaca tgtaccgggg atgccgctcc tgccatccag  660
cacatttgcc tgaagcacac cacctgtttc caggacgtgg tggtggatgt ggactgcgcc  720
gagaacacca aagaggatca gctggccgag atcagctacc ggttccaggg aaagaaagag  780
gccgaccagc cttggatcgt ggtcaacacc agcacactgt tcgacgagct ggaactggac  840
cctcctgaga ttgaacccgg ggtgctgaag gtgctgagaa ccgagaagca gtacctggga  900
gtgtacatct ggaacatgag aggcagcgac ggcacctcta cctacgccac ctttctggtc  960
acatggaagg gcgacgagaa aacacggaac ccccacaccag ctgtgacccc tcaacctaga  1020
ggcgccgagt ttcacatgtg gaattaccac agccacgtgt tcagcgtggg cgataccttt  1080
agcctggcca tgcatctgca gtacaagatc cacgaggccc ctttcgacct gctgctggaa  1140
tggctgtacg tgcccatcga tcctacctgc cagcctatgc ggctgtactc cacctgtctg  1200
tatcacccca acgctcccca gtgcctgagc cacatgaata gcggctgcac cttcacaagc  1260
cctcacctgg ctcagcgagt ggccagcaca gtgtaccaga attgcgagca cgccgacaat  1320
tacaccgcct actgtctggg catcagccac atggaaccta gcttcggcct gatcctgcac  1380
gatggcggca caaccctgaa gttcgtggat acccctgaga gcctgagcgg cctgtatgtg  1440
ttcgtggtgt acttcaacgg ccacgtggaa gccgtggcct acaccgtggt gtctaccgtg  1500
gaccacttcg tgaacgccat cgaggaaaga ggcttccctc caactgctgg acagcctcct  1560
gccaccacca agcctaaaga aatcacaccc gtgaatcccg gcacaagccc actgcttaga  1620
tacgccgctt ggacaggcgg actggctgct gttgttctgc tgtgcctggt catcttcctg  1680
atctgcaccg ccaagcggat gagagtgaag gccaagagag tggacaagag cccttacaac  1740
cagtctatgt atgccgccgg actgcccgtg gacgatttcg aggatagcga gagcaccgac  1800
accgaggaag agttcggcaa cgccattgga ggatctcacg gcggcagcag ctataccgtg  1860
tacatcgaca agacccggtg agctggagcc tcggtggcca tgcttcttgc cccttgggcc  1920
tccccccagc ccctcctccc cttcctgcac ccgtaccccc gtggtctttg aataaagtct  1980
gagtgggcgg caaaaaaaaa aaaaaaaaaa aaaaaaaaaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
a                                                                  2101

SEQ ID NO: 26          moltype = DNA  length = 1872
FEATURE                Location/Qualifiers
source                 1..1872
                       mol_type = other DNA
                       organism = synthetic construct
SEQUENCE: 26
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccctgag agcctgagcg gcctgtatgt gttcgtggtg  1440
```

-continued

```
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccaagaga gtggacaaga gcccttacaa ccagtctatg  1740
tatgccgccg gactgcccgt ggacgatttc gaggatagcg agagcaccga caccgaggaa  1800
gagttcggca acgccattgg aggatctcac ggcggcagca gctataccgt gtacatcgac  1860
aagacccggt ga                                                       1872

SEQ ID NO: 27          moltype = AA  length = 623
FEATURE                Location/Qualifiers
source                 1..623
                       mol_type = protein
                       organism = synthetic construct
SEQUENCE: 27
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAKR VDKSPYNQSM YAAGLPVDDF EDSESTDTEE  600
EFGNAIGGSH GGSSYTVYID KTR                                           623

SEQ ID NO: 28          moltype = RNA  length = 2161
FEATURE                Location/Qualifiers
source                 1..2161
                       mol_type = other RNA
                       organism = synthetic construct
SEQUENCE: 28
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccaagagag tggacaagag cccttacaac  1800
cagtctatgt atgccgccgg actgcccgtg gacgatttcg aggatagcga gagcaccgac  1860
accgaggaag agttcggcaa cgccattgga ggatctcacg gcggcagcag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                   2161

SEQ ID NO: 29          moltype = DNA  length = 2161
FEATURE                Location/Qualifiers
source                 1..2161
                       mol_type = other DNA
                       organism = synthetic construct
SEQUENCE: 29
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
```

```
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccaagagag tggacaagag cccttacaac  1800
cagtctatgt atgccgccgg actgcccgtg gacgattttg aggatgctga agccgccgac  1860
gccgaggaag aatttggcaa cgccattggc ggaagccacg gcggcagtag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 30          moltype = DNA  length = 1872
FEATURE                Location/Qualifiers
source                 1..1872
                       mol_type = other DNA
                       organism = synthetic construct
SEQUENCE: 30
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccaagaga gtggacaaga gcccttacaa ccagtctatg  1740
tatgccgccg gactgcccgt ggacgatttt gaggatgctg aagccgccga cgccgaggaa  1800
gaatttggca acgccattgg cggaagccac ggcggcagta gctataccgt gtacatcgac  1860
aagacccggt ga                                                      1872

SEQ ID NO: 31          moltype = AA  length = 623
FEATURE                Location/Qualifiers
source                 1..623
                       mol_type = protein
```

```
                        organism = synthetic construct
SEQUENCE: 31
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAKR VDKSPYNQSM YAAGLPVDDF EDAEAADAEE  600
EFGNAIGGSH GGSSYTVYID KTR                                        623

SEQ ID NO: 32           moltype = RNA  length = 2161
FEATURE                 Location/Qualifiers
source                  1..2161
                        mol_type = other RNA
                        organism = synthetic construct
SEQUENCE: 32
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccaagagag tggacaagag cccttacaac  1800
cagtctatgt atgccgccgg actgcccgtg gacgattttg aggatgctga agccgccgac  1860
gccgaggaag aatttggcaa cgccattggc ggaagccacg gcggcagtag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                2161

SEQ ID NO: 33           moltype = DNA  length = 2161
FEATURE                 Location/Qualifiers
source                  1..2161
                        mol_type = other DNA
                        organism = synthetic construct
SEQUENCE: 33
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
```

-continued

```
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagagcatgt actacgccgg cctgcctgtg gacgacttcg aggatagcga gagcaccgac  1860
accgaggaag agttcggcaa cgccattgga ggatctcacg gcggcagcag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 34          moltype = DNA  length = 1872
FEATURE                Location/Qualifiers
source                 1..1872
                       mol_type = other DNA
                       organism = synthetic construct
SEQUENCE: 34
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgcgcgtgaa ggacaaagag aaggacaagt ccccttacaa ccagagcatg  1740
tactacgccg gcctgcctgt ggacgacttc gaggatagcg agagcaccga caccgaggaa  1800
gagttcggca acgccattgg aggatctcac ggcggcagca gctataccgt gtacatcgac  1860
aagacccggt ga                                                      1872

SEQ ID NO: 35          moltype = AA  length = 623
FEATURE                Location/Qualifiers
source                 1..623
                       mol_type = protein
                       organism = synthetic construct
SEQUENCE: 35
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDKE KDKSPYNQSM YYAGLPVDDF EDSESTDTEE  600
EFGNAIGGSH GGSSYTVYID KTR                                          623
```

```
SEQ ID NO: 36          moltype = RNA  length = 2161
FEATURE                Location/Qualifiers
source                 1..2161
                       mol_type = other RNA
                       organism = synthetic construct
SEQUENCE: 36
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagagcatgt actacgccgg cctgcctgtg gacgacttcg aggatagcga gagcaccgac  1860
accgaggaag agttcggcaa cgccattgga ggatctcacg gcggcagcag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                   2161

SEQ ID NO: 37          moltype = DNA  length = 2161
FEATURE                Location/Qualifiers
source                 1..2161
                       mol_type = other DNA
                       organism = synthetic construct
SEQUENCE: 37
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
```

```
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagagcatgt actacgccgg cctgcctgtg gacgatttcg aggatgctga agccgccgat  1860
gccgaggaag agtttggcaa cgccattggc ggatctcacg gcggcagcag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161
```

```
SEQ ID NO: 38          moltype = DNA  length = 1872
FEATURE                Location/Qualifiers
source                 1..1872
                       mol_type = other DNA
                       organism = synthetic construct
SEQUENCE: 38
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgcgcgtgaa ggacaaagag aaggacaagt ccccttacaa ccagagcatg  1740
tactacgccg gcctgcctgt ggacgatttc gaggatgctg aagccgccga tgccgaggaa  1800
gagtttggca acgccattgg cggatctcac ggcggcagca gctataccgt gtacatcgac  1860
aagacccggt ga                                                     1872
```

```
SEQ ID NO: 39          moltype = AA  length = 623
FEATURE                Location/Qualifiers
source                 1..623
                       mol_type = protein
                       organism = synthetic construct
SEQUENCE: 39
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDKE KDKSPYNQSM YYAGLPVDDF EDAEAADAEE  600
EFGNAIGGSH GGSSYTVYID KTR                                         623
```

```
SEQ ID NO: 40          moltype = RNA  length = 2161
FEATURE                Location/Qualifiers
source                 1..2161
                       mol_type = other RNA
                       organism = synthetic construct
SEQUENCE: 40
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
```

-continued

```
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagagcatgt actacgccgg cctgcctgtg gacgatttcg aggatgctga agccgccgat  1860
gccgaggaag agtttggcaa cgccattggc ggatctcacg gcggcagcag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 41          moltype = DNA  length = 2161
FEATURE                Location/Qualifiers
source                 1..2161
                       mol_type = other DNA
                       organism = synthetic construct
SEQUENCE: 41
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atgccgccgg actgcccgtg gacgatttcg aggatagcga gagcaccgac  1860
accgaggaag agttcggcaa cgccattgga ggatctcacg gcggcagcag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 42          moltype = DNA  length = 1872
FEATURE                Location/Qualifiers
source                 1..1872
```

```
                         mol_type = other DNA
                         organism = synthetic construct
SEQUENCE: 42
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgcgcgtgaa ggacaaagag aaggacaagt ccccttacaa ccagtctatg  1740
tatgccgccg gactgcccgt ggacgatttc gaggatagcg agagcaccga caccgaggaa  1800
gagttcggca acgccattgg aggatctcac ggcggcagca gctataccgt gtacatcgac  1860
aagacccggt ga                                                    1872

SEQ ID NO: 43            moltype = AA  length = 623
FEATURE                  Location/Qualifiers
source                   1..623
                         mol_type = protein
                         organism = synthetic construct
SEQUENCE: 43
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDKE KDKSPYNQSM YAAGLPVDDF EDSESTDTEE  600
EFGNAIGGSH GGSSYTVYID KTR                                        623

SEQ ID NO: 44            moltype = RNA  length = 2161
FEATURE                  Location/Qualifiers
source                   1..2161
                         mol_type = other RNA
                         organism = synthetic construct
SEQUENCE: 44
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
```

```
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atgccgccgg actgcccgtg gacgatttcg aggatagcga gagcaccgac  1860
accgaggaag agttcggcaa cgccattgga ggatctcacg gcggcagcag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 45          moltype = DNA  length = 2161
FEATURE                Location/Qualifiers
source                 1..2161
                       mol_type = other DNA
                       organism = synthetic construct
SEQUENCE: 45
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atgccgccgg actgcccgtg gacgattttg aggatgctga agccgccgac  1860
gccgaggaag aatttggcaa cgccattggc ggaagccacg gcggcagtag ctataccgtg  1920
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 46          moltype = DNA  length = 1872
FEATURE                Location/Qualifiers
source                 1..1872
                       mol_type = other DNA
                       organism = synthetic construct
SEQUENCE: 46
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
```

```
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg ggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgcgcgtgaa ggacaaagag aaggacaagt ccccttacaa ccagtctatg  1740
tatgccgccg gactgcccgt ggacgatttt gaggatgctg aagccgccga cgccgaggaa  1800
gaatttggca acgccattgg cggaagccac ggcggcagta gctataccgt gtacatcgac  1860
aagacccggt ga                                                      1872

SEQ ID NO: 47          moltype = AA  length = 623
FEATURE                Location/Qualifiers
source                 1..623
                       mol_type = protein
                       organism = synthetic construct
SEQUENCE: 47
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDKE KDKSPYNQSM YAAGLPVDDF EDAEAADAEE  600
EFGNAIGGSH GGSSYTVYID KTR                                          623

SEQ ID NO: 48          moltype = RNA  length = 2161
FEATURE                Location/Qualifiers
source                 1..2161
                       mol_type = other RNA
                       organism = synthetic construct
SEQUENCE: 48
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt ccttctctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atgccgccgg actgcccgtg gacgattttg aggatgctga agccgccgac  1860
gccgaggaag aatttggcaa cgccattggc ggaagccacg gcggcagtag ctataccgtg  1920
```

```
tacatcgaca agacccggtg agctggagcc tcggtggcca tgcttcttgc cccttgggcc  1980
tccccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 49          moltype = DNA  length = 2128
FEATURE                Location/Qualifiers
source                 1..2128
                       mol_type = other DNA
                       organism = synthetic construct
SEQUENCE: 49
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccatgtact atgccggcct gcctgtggac  1800
gacttcgagg atagcgagag caccgacacc gaggaagagt tcggcaacgc cattggagga  1860
tctcacggcg gcagcagcta taccgtgtac atcgacaaga cccggtgagc tggagcctcg  1920
gtggccatgc ttcttgcccc ttgggcctcc ccccagcccc tcctcccctt cctgcacccg  1980
tacccccgtg gtctttgaat aaagtctgag tgggcggcaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaa                                    2128

SEQ ID NO: 50          moltype = DNA  length = 1839
FEATURE                Location/Qualifiers
source                 1..1839
                       mol_type = other DNA
                       organism = synthetic construct
SEQUENCE: 50
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
```

```
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccatgtac tatgccggcc tgcctgtgga cgacttcgag  1740
gatagcgaga gcaccgacac cgaggaagag ttcggcaacg ccattggagg atctcacggc  1800
ggcagcagct ataccgtgta catcgacaag acccggtga                          1839

SEQ ID NO: 51          moltype = AA  length = 612
FEATURE                Location/Qualifiers
source                 1..612
                       mol_type = protein
                       organism = synthetic construct
SEQUENCE: 51
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAMY YAGLPVDDFE DSESTDTEEE FGNAIGGSHG  600
GSSYTVYIDK TR                                                       612

SEQ ID NO: 52          moltype = RNA  length = 2128
FEATURE                Location/Qualifiers
source                 1..2128
                       mol_type = other RNA
                       organism = synthetic construct
SEQUENCE: 52
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccatgtact atgccggcct gcctgtggac  1800
gacttcgagg atagcgagag caccgacacc gaggaagagt tcggcaacgc cattggagga  1860
tctcacggcg gcagcagcta taccgtgtac atcgacaaga cccggtgagc tggagcctcg  1920
gtggccatgc ttcttgcccc ttgggcctcc ccccagcccc tcctcccctt cctgcacccg  1980
tacccccgtg gtctttgaat aaagtctgag tgggcggcaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaa                                      2128

SEQ ID NO: 53          moltype = DNA  length = 2128
FEATURE                Location/Qualifiers
source                 1..2128
                       mol_type = other DNA
                       organism = synthetic construct
SEQUENCE: 53
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
```

-continued

```
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca 480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccatgtact atgccggcct gcctgtggac  1800
gatttcgaag atgctgaagc cgccgacgcc gaggaagagt ttggaaacgc cattggcgga  1860
agccacggcg gcagcagcta cactgtgtac atcgacaaga cccggtgagc tggagcctcg  1920
gtggccatgc ttcttgcccc ttgggcctcc ccccagcccc tcctcccctt cctgcacccg  1980
tacccccgtg gtctttgaat aaagtctgag tgggcggcaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaa                                    2128

SEQ ID NO: 54          moltype = DNA  length = 1839
FEATURE                Location/Qualifiers
source                 1..1839
                       mol_type = other DNA
                       organism = synthetic construct
SEQUENCE: 54
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccatgtac tatgccggcc tgcctgtgga cgatttcgaa  1740
gatgctgaag ccgccgacgc cgaggaagag tttggaaacg ccattggcgg aagccacggc  1800
ggcagcagct acactgtgta catcgacaag acccggtga                        1839

SEQ ID NO: 55          moltype = AA  length = 612
FEATURE                Location/Qualifiers
source                 1..612
                       mol_type = protein
                       organism = synthetic construct
SEQUENCE: 55
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
```

-continued

```
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAMY YAGLPVDDFE DAEAADAEEE FGNAIGGSHG  600
GSSYTVYIDK TR                                                     612

SEQ ID NO: 56          moltype = RNA  length = 2128
FEATURE                Location/Qualifiers
source                 1..2128
                       mol_type = other RNA
                       organism = synthetic construct
SEQUENCE: 56
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccatgtact atgccggcct gcctgtggac  1800
gatttcgaag atgctgaagc cgccgacgcc gaggaagagt ttggaaacgc cattggcgga  1860
agccacggcg gcagcagcta cactgtgtac atcgacaaga cccggtgagc tggagcctcg  1920
gtggccatgc ttcttgcccc ttgggcctcc ccccagcccc tcctcccctt cctgcacccg  1980
tacccccgtg gtctttgaat aaagtctgag tgggcggcaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaa                                    2128

SEQ ID NO: 57          moltype = DNA  length = 2017
FEATURE                Location/Qualifiers
source                 1..2017
                       mol_type = other DNA
                       organism = synthetic construct
SEQUENCE: 57
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
```

```
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctacagag tggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                          2017

SEQ ID NO: 58          moltype = DNA  length = 1722
FEATURE                Location/Qualifiers
source                 1..1722
                       mol_type = other DNA
                       organism = synthetic construct
SEQUENCE: 58
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggcctacaga gtggacaagt ga                    1722

SEQ ID NO: 59          moltype = AA  length = 573
FEATURE                Location/Qualifiers
source                 1..573
                       mol_type = protein
                       organism = synthetic construct
SEQUENCE: 59
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR VDK                               573

SEQ ID NO: 60          moltype = RNA  length = 2017
FEATURE                Location/Qualifiers
source                 1..2017
                       mol_type = other RNA
                       organism = synthetic construct
SEQUENCE: 60
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
```

```
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctacagag tggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                           2017

SEQ ID NO: 61           moltype = DNA  length = 2017
FEATURE                 Location/Qualifiers
source                  1..2017
                        mol_type = other DNA
                        organism = synthetic construct
SEQUENCE: 61
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gactacagag tggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                           2017

SEQ ID NO: 62           moltype = DNA  length = 1722
FEATURE                 Location/Qualifiers
source                  1..1722
                        mol_type = other DNA
                        organism = synthetic construct
SEQUENCE: 62
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
```

```
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggactacaga gtggacaagt ga                    1722

SEQ ID NO: 63          moltype = AA  length = 573
FEATURE                Location/Qualifiers
source                 1..573
                       mol_type = protein
                       organism = synthetic construct
SEQUENCE: 63
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDYR VDK                              573

SEQ ID NO: 64          moltype = RNA  length = 2017
FEATURE                Location/Qualifiers
source                 1..2017
                       mol_type = other RNA
                       organism = synthetic construct
SEQUENCE: 64
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
```

```
tacgccgctt ggacaggcgg actggctgct gttgttctgc tgtgcctggt catcttcctg  1740
atctgcaccg ccaagcggat gagagtgaag gactacagag tggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                           2017

SEQ ID NO: 65          moltype = DNA  length = 2014
FEATURE                Location/Qualifiers
source                 1..2014
                       mol_type = other DNA
                       organism = synthetic construct
SEQUENCE: 65
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag tacagagtgg acaagtgata ataggctgga  1800
gcctcggtgg ccatgcttct tgccccttgg gcctcccccc agcccctcct ccccttcctg  1860
cacccgtacc cccgtggtct ttgaataaag tctgagtggg cggcaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaa                              2014

SEQ ID NO: 66          moltype = DNA  length = 1719
FEATURE                Location/Qualifiers
source                 1..1719
                       mol_type = other DNA
                       organism = synthetic construct
SEQUENCE: 66
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
```

-continued

```
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa gtacagagtg gacaagtga                         1719

SEQ ID NO: 67           moltype = AA  length = 572
FEATURE                 Location/Qualifiers
source                  1..572
                        mol_type = protein
                        organism = synthetic construct
SEQUENCE: 67
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKYRV DK                                572

SEQ ID NO: 68           moltype = RNA  length = 2014
FEATURE                 Location/Qualifiers
source                  1..2014
                        mol_type = other RNA
                        organism = synthetic construct
SEQUENCE: 68
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag tacagagtgg acaagtgata ataggctgga  1800
gcctcggtgg ccatgcttct tgccccttgg gcctcccccc agcccctcct ccccttcctg  1860
cacccgtacc cccgtggtct ttgaataaag tctgagtggg cggcaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaa                              2014

SEQ ID NO: 69           moltype = DNA  length = 2017
FEATURE                 Location/Qualifiers
source                  1..2017
                        mol_type = other DNA
                        organism = synthetic construct
SEQUENCE: 69
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
```

-continued

```
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccaagagag tggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                           2017

SEQ ID NO: 70          moltype = DNA  length = 1722
FEATURE                Location/Qualifiers
source                 1..1722
                       mol_type = other DNA
                       organism = synthetic construct
SEQUENCE: 70
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccaagaga gtggacaagt ga                     1722

SEQ ID NO: 71          moltype = AA  length = 573
FEATURE                Location/Qualifiers
source                 1..573
                       mol_type = protein
                       organism = synthetic construct
SEQUENCE: 71
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAKR VDK                                573

SEQ ID NO: 72          moltype = RNA  length = 2017
```

-continued

```
FEATURE                Location/Qualifiers
source                 1..2017
                       mol_type = other RNA
                       organism = synthetic construct
SEQUENCE: 72
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccaagagag tggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                           2017

SEQ ID NO: 73          moltype = DNA  length = 2017
FEATURE                Location/Qualifiers
source                 1..2017
                       mol_type = other DNA
                       organism = synthetic construct
SEQUENCE: 73
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctatgagg tggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
```

-continued

```
aaaaaaaaaa aaaaaaaaaa aaaaaaaaaa aaaaaaa                          2017

SEQ ID NO: 74          moltype = DNA  length = 1722
FEATURE                Location/Qualifiers
source                 1..1722
                       mol_type = other DNA
                       organism = synthetic construct
SEQUENCE: 74
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggcctatgag gtggacaagt ga                    1722

SEQ ID NO: 75          moltype = AA  length = 573
FEATURE                Location/Qualifiers
source                 1..573
                       mol_type = protein
                       organism = synthetic construct
SEQUENCE: 75
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYE VDK                               573

SEQ ID NO: 76          moltype = RNA  length = 2017
FEATURE                Location/Qualifiers
source                 1..2017
                       mol_type = other RNA
                       organism = synthetic construct
SEQUENCE: 76
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
```

```
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctatgagg tggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                           2017

SEQ ID NO: 77          moltype = DNA  length = 2017
FEATURE                Location/Qualifiers
source                 1..2017
                       mol_type = other DNA
                       organism = synthetic construct
SEQUENCE: 77
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctaccgga aggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                           2017

SEQ ID NO: 78          moltype = DNA  length = 1722
FEATURE                Location/Qualifiers
source                 1..1722
                       mol_type = other DNA
                       organism = synthetic construct
SEQUENCE: 78
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
```

```
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggcctaccgg aaggacaagt ga                    1722
```

```
SEQ ID NO: 79          moltype = AA  length = 573
FEATURE                Location/Qualifiers
source                 1..573
                       mol_type = protein
                       organism = synthetic construct
SEQUENCE: 79
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR KDK                               573
```

```
SEQ ID NO: 80          moltype = RNA  length = 2017
FEATURE                Location/Qualifiers
source                 1..2017
                       mol_type = other RNA
                       organism = synthetic construct
SEQUENCE: 80
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctaccgga aggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                           2017
```

```
SEQ ID NO: 81          moltype = DNA  length = 2017
FEATURE                Location/Qualifiers
source                 1..2017
                       mol_type = other DNA
                       organism = synthetic construct
SEQUENCE: 81
```

```
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                          2017

SEQ ID NO: 82           moltype = DNA  length = 1722
FEATURE                 Location/Qualifiers
source                  1..1722
                        mol_type = other DNA
                        organism = synthetic construct
SEQUENCE: 82
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgcgcgtgaa ggacaaagag aaggacaagt ga                    1722

SEQ ID NO: 83           moltype = AA  length = 573
FEATURE                 Location/Qualifiers
source                  1..573
                        mol_type = protein
                        organism = synthetic construct
SEQUENCE: 83
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
```

-continued

```
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDKE KDK                               573

SEQ ID NO: 84          moltype = RNA  length = 2017
FEATURE                Location/Qualifiers
source                 1..2017
                       mol_type = other RNA
                       organism = synthetic construct
SEQUENCE: 84
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                           2017

SEQ ID NO: 85          moltype = DNA  length = 2017
FEATURE                Location/Qualifiers
source                 1..2017
                       mol_type = other DNA
                       organism = synthetic construct
SEQUENCE: 85
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
```

```
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gacgccgaga aggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                           2017

SEQ ID NO: 86           moltype = DNA  length = 1722
FEATURE                 Location/Qualifiers
source                  1..1722
                        mol_type = other DNA
                        organism = synthetic construct
SEQUENCE: 86
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggacgccgag aaggacaagt ga                     1722

SEQ ID NO: 87           moltype = AA  length = 573
FEATURE                 Location/Qualifiers
source                  1..573
                        mol_type = protein
                        organism = synthetic construct
SEQUENCE: 87
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDAE KDK                                573

SEQ ID NO: 88           moltype = RNA  length = 2017
FEATURE                 Location/Qualifiers
source                  1..2017
                        mol_type = other RNA
                        organism = synthetic construct
SEQUENCE: 88
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
```

```
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gacgccgaga aggacaagtg ataataggct  1800
ggagcctcgg tggccatgct tcttgcccct tgggcctccc cccagcccct cctccccttc  1860
ctgcacccgt acccccgtgg tctttgaata aagtctgagt gggcggcaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaa                          2017

SEQ ID NO: 89          moltype = DNA  length = 2014
FEATURE                Location/Qualifiers
source                 1..2014
                       mol_type = other DNA
                       organism = synthetic construct
SEQUENCE: 89
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag aaagagaagg acaagtgata ataggctgga  1800
gcctcggtgg ccatgcttct tgccccttgg gcctcccccc agcccctcct ccccttcctg  1860
cacccgtacc cccgtggtct ttgaataaag tctgagtggg cggcaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaa                             2014

SEQ ID NO: 90          moltype = DNA  length = 1719
FEATURE                Location/Qualifiers
source                 1..1719
                       mol_type = other DNA
                       organism = synthetic construct
SEQUENCE: 90
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
```

-continued

```
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgcgcgtgaa gaaagagaag gacaagtga                        1719

SEQ ID NO: 91          moltype = AA  length = 572
FEATURE                Location/Qualifiers
source                 1..572
                       mol_type = protein
                       organism = synthetic construct
SEQUENCE: 91
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKKEK DK                                572

SEQ ID NO: 92          moltype = RNA  length = 2014
FEATURE                Location/Qualifiers
source                 1..2014
                       mol_type = other RNA
                       organism = synthetic construct
SEQUENCE: 92
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgatacctttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcaccccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag aaagagaagg acaagtgata ataggctgga  1800
gcctcggtgg ccatgcttct tgccccttgg gcctcccccc agcccctcct ccccttcctg  1860
```

-continued

```
cacccgtacc cccgtggtct ttgaataaag tctgagtggg cggcaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaa                              2014

SEQ ID NO: 93          moltype = DNA  length = 2059
FEATURE                Location/Qualifiers
source                 1..2059
                       mol_type = other DNA
                       organism = synthetic construct
SEQUENCE: 93
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctacagag tggacaagag cccttacaac  1800
cagagcatgt actacgccgg cctgcctgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                               2059

SEQ ID NO: 94          moltype = DNA  length = 1764
FEATURE                Location/Qualifiers
source                 1..1764
                       mol_type = other DNA
                       organism = synthetic construct
SEQUENCE: 94
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
```

```
tggacaggcg gactggctgc tgttgttctg ctgtgcctgg tcatcttcct gatctgcacc  1680
gccaagcgga tgagagtgaa ggcctacaga gtggacaaga gcccttacaa ccagagcatg  1740
tactacgccg gcctgcctgt ttga                                          1764

SEQ ID NO: 95          moltype = AA  length = 587
FEATURE                Location/Qualifiers
source                 1..587
                       mol_type = protein
                       organism = synthetic construct
SEQUENCE: 95
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR VDKSPYNQSM YYAGLPV                 587

SEQ ID NO: 96          moltype = RNA  length = 2059
FEATURE                Location/Qualifiers
source                 1..2059
                       mol_type = other RNA
                       organism = synthetic construct
SEQUENCE: 96
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctacagag tggacaagag cccttacaac  1800
cagagcatgt actacgccgg cctgcctgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                                2059

SEQ ID NO: 97          moltype = DNA  length = 2026
FEATURE                Location/Qualifiers
source                 1..2026
                       mol_type = other DNA
                       organism = synthetic construct
SEQUENCE: 97
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
```

-continued

```
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccatgtact atgccggcct gcctgtttga  1800
taataggctg gagcctcggt ggccatgctt cttgcccctt gggcctcccc ccagcccctc  1860
ctccccttcc tgcacccgta cccccgtggt ctttgaataa agtctgagtg ggcggcaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaa                 2026

SEQ ID NO: 98          moltype = DNA  length = 1731
FEATURE                Location/Qualifiers
source                 1..1731
                       mol_type = other DNA
                       organism = synthetic construct
SEQUENCE: 98
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccatgtac tatgccggcc tgcctgtttg a           1731

SEQ ID NO: 99          moltype = AA  length = 576
FEATURE                Location/Qualifiers
source                 1..576
                       mol_type = protein
                       organism = synthetic construct
SEQUENCE: 99
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAMY YAGLPV                            576

SEQ ID NO: 100         moltype = RNA  length = 2026
```

-continued

```
FEATURE                Location/Qualifiers
source                 1..2026
                       mol_type = other RNA
                       organism = synthetic construct
SEQUENCE: 100
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccatgtact atgccggcct gcctgtttga  1800
taataggctg gagcctcggt ggccatgctt cttgcccctt gggcctcccc ccagcccctc  1860
ctccccttcc tgcacccgta cccccgtggt ctttgaataa agtctgagtg ggcggcaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaa                 2026

SEQ ID NO: 101         moltype = DNA  length = 2026
FEATURE                Location/Qualifiers
source                 1..2026
                       mol_type = other DNA
                       organism = synthetic construct
SEQUENCE: 101
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gctatgtatg ccgccggact gcctgtttga  1800
taataggctg gagcctcggt ggccatgctt cttgcccctt gggcctcccc ccagcccctc  1860
ctccccttcc tgcacccgta cccccgtggt ctttgaataa agtctgagtg ggcggcaaaa  1920
aaaaaaaaaa aaaaaaaaaa aaaaaaaaaa aaaaaaaaaa aaaaaaaaaa aaaaaaaaaa  1980
```

-continued

```
aaaaaaaaaa aaaaaaaaaa aaaaaaaaaa aaaaaaaaaa aaaaaa                2026

SEQ ID NO: 102          moltype = DNA  length = 1731
FEATURE                 Location/Qualifiers
source                  1..1731
                        mol_type = other DNA
                        organism = synthetic construct
SEQUENCE: 102
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg ggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggctatgtat gccgccggac tgcctgtttg a          1731

SEQ ID NO: 103          moltype = AA  length = 576
FEATURE                 Location/Qualifiers
source                  1..576
                        mol_type = protein
                        organism = synthetic construct
SEQUENCE: 103
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAMY AAGLPV                            576

SEQ ID NO: 104          moltype = RNA  length = 2026
FEATURE                 Location/Qualifiers
source                  1..2026
                        mol_type = other RNA
                        organism = synthetic construct
SEQUENCE: 104
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
```

```
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gctatgtatg ccgccggact gcctgtttga  1800
taataggctg gagcctcggt ggccatgctt cttgcccctt gggcctcccc ccagcccctc  1860
ctccccttcc tgcacccgta cccccgtggt ctttgaataa agtctgagtg ggcggcaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaa                 2026

SEQ ID NO: 105         moltype = DNA  length = 2026
FEATURE                Location/Qualifiers
source                 1..2026
                       mol_type = other DNA
                       organism = synthetic construct
SEQUENCE: 105
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gctatgtatg gcgccggact gcctgtttga  1800
taataggctg gagcctcggt ggccatgctt cttgcccctt gggcctcccc ccagcccctc  1860
ctccccttcc tgcacccgta cccccgtggt ctttgaataa agtctgagtg ggcggcaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaa                 2026

SEQ ID NO: 106         moltype = DNA  length = 1731
FEATURE                Location/Qualifiers
source                 1..1731
                       mol_type = other DNA
                       organism = synthetic construct
SEQUENCE: 106
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
```

```
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggctatgtat ggcgccggac tgcctgtttg a           1731
```

```
SEQ ID NO: 107          moltype = AA  length = 576
FEATURE                 Location/Qualifiers
source                  1..576
                        mol_type = protein
                        organism = synthetic construct
SEQUENCE: 107
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAMY GAGLPV                            576
```

```
SEQ ID NO: 108          moltype = RNA  length = 2026
FEATURE                 Location/Qualifiers
source                  1..2026
                        mol_type = other RNA
                        organism = synthetic construct
SEQUENCE: 108
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gctatgtatg gcgccggact gcctgtttga  1800
taataggctg gagcctcggt ggccatgctt cttgcccctt gggcctcccc ccagcccctc  1860
ctccccttcc tgcacccgta cccccgtggt ctttgaataa agtctgagtg ggcggcaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaa                 2026
```

```
SEQ ID NO: 109          moltype = DNA  length = 2059
FEATURE                 Location/Qualifiers
source                  1..2059
                        mol_type = other DNA
                        organism = synthetic construct
SEQUENCE: 109
```

-continued

```
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atgccgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                              2059

SEQ ID NO: 110          moltype = DNA  length = 1764
FEATURE                 Location/Qualifiers
source                  1..1764
                        mol_type = other DNA
                        organism = synthetic construct
SEQUENCE: 110
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgcgcgtgaa ggacaaagag aaggacaagt ccccttacaa ccagtctatg  1740
tatgccgccg gactgcccgt ttga                                        1764

SEQ ID NO: 111          moltype = AA  length = 587
FEATURE                 Location/Qualifiers
source                  1..587
                        mol_type = protein
                        organism = synthetic construct
SEQUENCE: 111
```

-continued

```
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDKE KDKSPYNQSM YAAGLPV               587

SEQ ID NO: 112         moltype = RNA  length = 2059
FEATURE                Location/Qualifiers
source                 1..2059
                       mol_type = other RNA
                       organism = synthetic construct
SEQUENCE: 112
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atgccgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                              2059

SEQ ID NO: 113         moltype = DNA  length = 2059
FEATURE                Location/Qualifiers
source                 1..2059
                       mol_type = other DNA
                       organism = synthetic construct
SEQUENCE: 113
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
```

-continued

```
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atggcgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                               2059

SEQ ID NO: 114          moltype = DNA  length = 1764
FEATURE                 Location/Qualifiers
source                  1..1764
                        mol_type = other DNA
                        organism = synthetic construct
SEQUENCE: 114
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgcgcgtgaa ggacaaagag aaggacaagt ccccttacaa ccagtctatg  1740
tatggcgccg gactgcccgt ttga                                         1764

SEQ ID NO: 115          moltype = AA  length = 587
FEATURE                 Location/Qualifiers
source                  1..587
                        mol_type = protein
                        organism = synthetic construct
SEQUENCE: 115
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDKE KDKSPYNQSM YGAGLPV                587

SEQ ID NO: 116          moltype = RNA  length = 2059
FEATURE                 Location/Qualifiers
source                  1..2059
                        mol_type = other RNA
                        organism = synthetic construct
SEQUENCE: 116
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
```

-continued

```
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atggcgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                               2059

SEQ ID NO: 117         moltype = DNA  length = 2059
FEATURE                Location/Qualifiers
source                 1..2059
                       mol_type = other DNA
                       organism = synthetic construct
SEQUENCE: 117
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gactacagag tggacaagag cccttacaac  1800
cagtctatgt atgccgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                               2059

SEQ ID NO: 118         moltype = DNA  length = 1764
FEATURE                Location/Qualifiers
source                 1..1764
                       mol_type = other DNA
```

```
                        organism = synthetic construct
SEQUENCE: 118
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggactacaga gtggacaaga gcccttacaa ccagtctatg  1740
tatgccgccg gactgcccgt ttga                                        1764

SEQ ID NO: 119          moltype = AA  length = 587
FEATURE                 Location/Qualifiers
source                  1..587
                        mol_type = protein
                        organism = synthetic construct
SEQUENCE: 119
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDYR VDKSPYNQSM YAAGLPV                587

SEQ ID NO: 120          moltype = RNA  length = 2059
FEATURE                 Location/Qualifiers
source                  1..2059
                        mol_type = other RNA
                        organism = synthetic construct
SEQUENCE: 120
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
```

-continued

```
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gactacagag tggacaagag cccttacaac  1800
cagtctatgt atgccgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                               2059

SEQ ID NO: 121          moltype = DNA  length = 2059
FEATURE                 Location/Qualifiers
source                  1..2059
                        mol_type = other DNA
                        organism = synthetic construct
SEQUENCE: 121
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccaagagag tggacaagag cccttacaac  1800
cagtctatgt atgccgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                               2059

SEQ ID NO: 122          moltype = DNA  length = 1764
FEATURE                 Location/Qualifiers
source                  1..1764
                        mol_type = other DNA
                        organism = synthetic construct
SEQUENCE: 122
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
```

```
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccaagaga gtggacaaga gcccttacaa ccagtctatg  1740
tatgccgccg gactgcccgt ttga                                        1764

SEQ ID NO: 123          moltype = AA  length = 587
FEATURE                 Location/Qualifiers
source                  1..587
                        mol_type = protein
                        organism = synthetic construct
SEQUENCE: 123
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAKR VDKSPYNQSM YAAGLPV                587

SEQ ID NO: 124          moltype = RNA  length = 2059
FEATURE                 Location/Qualifiers
source                  1..2059
                        mol_type = other RNA
                        organism = synthetic construct
SEQUENCE: 124
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccaagagag tggacaagag cccttacaac  1800
cagtctatgt atgccgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                              2059

SEQ ID NO: 125          moltype = DNA  length = 2059
FEATURE                 Location/Qualifiers
source                  1..2059
                        mol_type = other DNA
                        organism = synthetic construct
SEQUENCE: 125
agactcctcc ccatcctctc cctctgtccc tctgtccctc tgaccctgca ctgtcccagc  60
```

```
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacacag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctatgagg tggacaagag cccttacaac  1800
cagtctatgt atgccgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                              2059

SEQ ID NO: 126         moltype = DNA  length = 1764
FEATURE                Location/Qualifiers
source                 1..1764
                       mol_type = other DNA
                       organism = synthetic construct
SEQUENCE: 126
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggcctatgag gtggacaaga gcccttacaa ccagtctatg  1740
tatgccgccg gactgcccgt ttga                                        1764

SEQ ID NO: 127         moltype = AA  length = 587
FEATURE                Location/Qualifiers
source                 1..587
                       mol_type = protein
                       organism = synthetic construct
SEQUENCE: 127
MGTVNKPVVG VLMGFGIITG TLRITNPVRA SVLRYDDFHI DEDKLDTNSV YEPYYHSDHA  60
```

```
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYE VDKSPYNQSM YAAGLPV                587

SEQ ID NO: 128         moltype = RNA  length = 2059
FEATURE                Location/Qualifiers
source                 1..2059
                       mol_type = other RNA
                       organism = synthetic construct
SEQUENCE: 128
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgatacettt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctatgagg tggacaagag cccttacaac  1800
cagtctatgt atgccgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                               2059

SEQ ID NO: 129         moltype = DNA  length = 2059
FEATURE                Location/Qualifiers
source                 1..2059
                       mol_type = other DNA
                       organism = synthetic construct
SEQUENCE: 129
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgatacettt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
```

-continued

```
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctaccgga aggacaagag cccttacaac  1800
cagtctatgt atgccgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                               2059

SEQ ID NO: 130         moltype = DNA  length = 1764
FEATURE                Location/Qualifiers
source                 1..1764
                       mol_type = other DNA
                       organism = synthetic construct
SEQUENCE: 130
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggcctaccgg aaggacaaga gcccttacaa ccagtctatg  1740
tatgccgccg gactgcccgt ttga                                          1764

SEQ ID NO: 131         moltype = AA  length = 587
FEATURE                Location/Qualifiers
source                 1..587
                       mol_type = protein
                       organism = synthetic construct
SEQUENCE: 131
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR KDKSPYNQSM YAAGLPV                 587

SEQ ID NO: 132         moltype = RNA  length = 2059
FEATURE                Location/Qualifiers
source                 1..2059
                       mol_type = other RNA
                       organism = synthetic construct
SEQUENCE: 132
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
```

-continued

```
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctaccgga aggacaagag cccttacaac  1800
cagtctatgt atgccgccgg actgcccgtt tgataatagg ctggagcctc ggtggccatg  1860
cttcttgccc cttgggcctc cccccagccc ctcctcccct tcctgcaccc gtacccccgt  1920
ggtctttgaa taaagtctga gtgggcggca aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaa                                              2059
```

```
SEQ ID NO: 133         moltype = DNA  length = 2134
FEATURE                Location/Qualifiers
source                 1..2134
                       mol_type = other DNA
                       organism = synthetic construct
SEQUENCE: 133
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gctatgtatg ccgccggact gcccgtggac  1800
gatttcgagg atagcgagag caccgacacc gaggaagagt tcggcaacgc cattggagga  1860
tctcacggcg gcagcagcta taccgtgtac atcgacaaga cccggtgata ataggctgga  1920
gcctcggtgg ccatgcttct tgccccttgg gcctcccccc agcccctcct ccccttcctg  1980
cacccgtacc cccgtggtct ttgaataaag tctgagtggg cggcaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaa                             2134
```

```
SEQ ID NO: 134         moltype = DNA  length = 1839
FEATURE                Location/Qualifiers
source                 1..1839
                       mol_type = other DNA
```

```
                        organism = synthetic construct
SEQUENCE: 134
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggctatgtat gccgccggac tgcccgtgga cgatttcgag  1740
gatagcgaga gcaccgacac cgaggaagag ttcggcaacg ccattggagg atctcacggc  1800
ggcagcagct ataccgtgta catcgacaag acccggtga                        1839

SEQ ID NO: 135          moltype = AA  length = 612
FEATURE                 Location/Qualifiers
source                  1..612
                        mol_type = protein
                        organism = synthetic construct
SEQUENCE: 135
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAMY AAGLPVDDFE DSESTDTEEE FGNAIGGSHG  600
GSSYTVYIDK TR                                                     612

SEQ ID NO: 136          moltype = RNA  length = 2134
FEATURE                 Location/Qualifiers
source                  1..2134
                        mol_type = other RNA
                        organism = synthetic construct
SEQUENCE: 136
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
```

```
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gctatgtatg ccgccggact gcccgtggac  1800
gatttcgagg atagcgagag caccgacacc gaggaagagt tcggcaacgc cattggagga  1860
tctcacggcg gcagcagcta taccgtgtac atcgacaaga cccggtgata ataggctgga  1920
gcctcggtgg ccatgcttct tgccccttgg gcctcccccc agcccctcct ccccttcctg  1980
cacccgtacc cccgtggtct ttgaataaag tctgagtggg cggcaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaa                             2134

SEQ ID NO: 137          moltype = DNA  length = 2134
FEATURE                 Location/Qualifiers
source                  1..2134
                        mol_type = other DNA
                        organism = synthetic construct
SEQUENCE: 137
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gctatgtatg ccgccggact gcccgtggac  1800
gattttgagg atgctgaagc cgccgacgcc gaggaagaat ttggcaacgc cattggcgga  1860
agccacggcg gcagtagcta taccgtgtac atcgacaaga cccggtgata ataggctgga  1920
gcctcggtgg ccatgcttct tgccccttgg gcctcccccc agcccctcct ccccttcctg  1980
cacccgtacc cccgtggtct ttgaataaag tctgagtggg cggcaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaa                             2134

SEQ ID NO: 138          moltype = DNA  length = 1839
FEATURE                 Location/Qualifiers
source                  1..1839
                        mol_type = other DNA
                        organism = synthetic construct
SEQUENCE: 138
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
```

```
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggctatgtat gccgccggac tgcccgtgga cgattttgag  1740
gatgctgaag ccgccgacgc cgaggaagaa tttggcaacg ccattggcgg aagccacggc  1800
ggcagtagct ataccgtgta catcgacaag acccggtga                         1839

SEQ ID NO: 139         moltype = AA  length = 612
FEATURE                Location/Qualifiers
source                 1..612
                       mol_type = protein
                       organism = synthetic construct
SEQUENCE: 139
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAMY AAGLPVDDFE DAEAADAEEE FGNAIGGSHG  600
GSSYTVYIDK TR                                                      612

SEQ ID NO: 140         moltype = RNA  length = 2134
FEATURE                Location/Qualifiers
source                 1..2134
                       mol_type = other RNA
                       organism = synthetic construct
SEQUENCE: 140
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gctatgtatg ccgccggact gcccgtggac  1800
gattttgagg atgctgaagc cgccgacgcc gaggaagaat ttggcaacgc cattggcgga  1860
agccacggcg gcagtagcta taccgtgtac atcgacaaga cccggtgata ataggctgga  1920
gcctcggtgg ccatgcttct tgccccttgg gcctcccccc agcccctcct ccccttcctg  1980
cacccgtacc cccgtggtct ttgaataaag tctgagtggg cggcaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaa                              2134
```

-continued

```
SEQ ID NO: 141         moltype = DNA  length = 2167
FEATURE                Location/Qualifiers
source                 1..2167
                       mol_type = other DNA
                       organism = synthetic construct
SEQUENCE: 141
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atggcgccgg actgcccgtg gacgatttcg aggatagcga gagcaccgac  1860
accgaggaag agttcggcaa cgccattgga ggatctcacg gcggcagcag ctataccgtg  1920
tacatcgaca agacccggtg ataataggct ggagcctcgg tggccatgct tcttgcccct  1980
tgggcctccc cccagcccct cctccccttc ctgcacccgt acccccgtgg tctttgaata  2040
aagtctgagt gggcggcaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaa                                                           2167

SEQ ID NO: 142         moltype = DNA  length = 1872
FEATURE                Location/Qualifiers
source                 1..1872
                       mol_type = other DNA
                       organism = synthetic construct
SEQUENCE: 142
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgcgcgtgaa ggacaaagag aaggacaagt ccccttacaa ccagtctatg  1740
```

-continued

```
tatggcgccg gactgcccgt ggacgatttc gaggatagcg agagcaccga caccgaggaa  1800
gagttcggca acgccattgg aggatctcac ggcggcagca gctataccgt gtacatcgac  1860
aagacccggt ga                                                      1872

SEQ ID NO: 143         moltype = AA  length = 623
FEATURE                Location/Qualifiers
source                 1..623
                       mol_type = protein
                       organism = synthetic construct
SEQUENCE: 143
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDKE KDKSPYNQSM YGAGLPVDDF EDSESTDTEE  600
EFGNAIGGSH GGSSYTVYID KTR                                          623

SEQ ID NO: 144         moltype = RNA  length = 2167
FEATURE                Location/Qualifiers
source                 1..2167
                       mol_type = other RNA
                       organism = synthetic construct
SEQUENCE: 144
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatcccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atggcgccgg actgcccgtg gacgatttcg aggatagcga gagcaccgac  1860
accgaggaag agttcggcaa cgccattgga ggatctcacg gcggcagcag ctataccgtg  1920
tacatcgaca agacccggtg ataataggct ggagcctcgg tggccatgct tcttgcccct  1980
tgggcctccc cccagcccct cctccccttc ctgcacccgt accccccgtgg tctttgaata  2040
aagtctgagt gggcggcaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaa                                                            2167

SEQ ID NO: 145         moltype = DNA  length = 2167
FEATURE                Location/Qualifiers
source                 1..2167
                       mol_type = other DNA
                       organism = synthetic construct
SEQUENCE: 145
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
```

-continued

```
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atggcgccgg actgcccgtg gacgattttg aggatgctga agccgccgac  1860
gccgaggaag aatttggcaa cgccattggc ggaagccacg gcggcagtag ctataccgtg  1920
tacatcgaca agacccggtg ataataggct ggagcctcgg tggccatgct tcttgcccct  1980
tgggcctccc cccagcccct cctccccttc ctgcacccgt acccccgtgg tctttgaata  2040
aagtctgagt gggcggcaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaa                                                            2167
```

```
SEQ ID NO: 146          moltype = DNA  length = 1872
FEATURE                 Location/Qualifiers
source                  1..1872
                        mol_type = other DNA
                        organism = synthetic construct
SEQUENCE: 146
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgcgcgtgaa ggacaaagag aaggacaagt ccccttacaa ccagtctatg  1740
tatggcgccg gactgcccgt ggacgatttt gaggatgctg aagccgccga cgccgaggaa  1800
gaatttggca acgccattgg cggaagccac ggcggcagta gctataccgt gtacatcgac  1860
aagacccggt ga                                                    1872
```

```
SEQ ID NO: 147          moltype = AA  length = 623
FEATURE                 Location/Qualifiers
source                  1..623
                        mol_type = protein
                        organism = synthetic construct
SEQUENCE: 147
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
```

-continued

```
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKDKE KDKSPYNQSM YGAGLPVDDF EDAEAADAEE  600
EFGNAIGGSH GGSSYTVYID KTR                                        623

SEQ ID NO: 148         moltype = RNA  length = 2167
FEATURE                Location/Qualifiers
source                 1..2167
                       mol_type = other RNA
                       organism = synthetic construct
SEQUENCE: 148
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gcgcgtgaag gacaaagaga aggacaagtc cccttacaac  1800
cagtctatgt atggcgccgg actgcccgtg gacgattttg aggatgctga agccgccgac  1860
gccgaggaag aatttggcaa cgccattggc ggaagccacg gcggcagtag ctataccgtg  1920
tacatcgaca agacccggtg ataataggct ggagcctcgg tggccatgct tcttgcccct  1980
tgggcctccc cccagcccct cctccccttc ctgcacccgt acccccgtgg tctttgaata  2040
aagtctgagt gggcggcaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaa                                                           2167

SEQ ID NO: 149         moltype = DNA  length = 2167
FEATURE                Location/Qualifiers
source                 1..2167
                       mol_type = other DNA
                       organism = synthetic construct
SEQUENCE: 149
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
```

-continued

```
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctacagag tggacaagag cccttacaac  1800
cagtctatgt atggcgccgg actgcccgtg gacgattttg aggatgctga agccgccgac  1860
gccgaggaag aatttggcaa cgccattggc ggaagccacg gcggcagtag ctataccgtg  1920
tacatcgaca agacccggtg ataataggct ggagcctcgg tggccatgct tcttgcccct  1980
tgggcctccc cccagcccct cctccccttc ctgcacccgt acccccgtgg tctttgaata  2040
aagtctgagt gggcggcaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaa                                                             2167
```

```
SEQ ID NO: 150         moltype = DNA  length = 1872
FEATURE                Location/Qualifiers
source                 1..1872
                       mol_type = other DNA
                       organism = synthetic construct
SEQUENCE: 150
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggcctacaga gtggacaaga gcccttacaa ccagtctatg  1740
tatggcgccg gactgcccgt ggacgatttt gaggatgctg aagccgccga cgccgaggaa  1800
gaatttggca acgccattgg cggaagccac ggcggcagta gctataccgt gtacatcgac  1860
aagacccggt ga                                                     1872
```

```
SEQ ID NO: 151         moltype = AA  length = 623
FEATURE                Location/Qualifiers
source                 1..623
                       mol_type = protein
                       organism = synthetic construct
SEQUENCE: 151
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR VDKSPYNQSM YGAGLPVDDF EDAEAADAEE  600
EFGNAIGGSH GGSSYTVYID KTR                                         623
```

```
SEQ ID NO: 152         moltype = RNA  length = 2167
FEATURE                Location/Qualifiers
source                 1..2167
                       mol_type = other RNA
```

-continued

```
                         organism = synthetic construct
SEQUENCE: 152
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctacagag tggacaagag cccttacaac  1800
cagtctatgt atggcgccgg actgcccgtg gacgattttg aggatgctga agccgccgac  1860
gccgaggaag aatttggcaa cgccattggc ggaagccacg gcggcagtag ctataccgtg  1920
tacatcgaca agacccggtg ataataggct ggagcctcgg tggccatgct tcttgcccct  1980
tgggcctccc cccagcccct cctccccttc ctgcacccgt acccccgtgg tctttgaata  2040
aagtctgagt gggcggcaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaa                                                             2167

SEQ ID NO: 153           moltype = DNA  length = 2044
FEATURE                  Location/Qualifiers
source                   1..2044
                         mol_type = other DNA
                         organism = synthetic construct
SEQUENCE: 153
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccgacgatt tcgaggacag cgagagcacc  1800
gataccgagg aagaatgata ataggctgga gcctcggtgg ccatgcttct tgccccttgg  1860
gcctccccc agcccctcct ccccttcctg cacccgtacc cccgtggtct ttgaataaag  1920
tctgagtggg cggcaaaaaa aaaaaaaaaa aaaaaaaaaa aaaaaaaaaa aaaaaaaaaa  1980
```

-continued

```
aaaaaaaaaa aaaaaaaaaa aaaaaaaaaa aaaaaaaaaa aaaaaaaaaa aaaaaaaaaa  2040
aaaa                                                               2044

SEQ ID NO: 154          moltype = DNA  length = 1749
FEATURE                 Location/Qualifiers
source                  1..1749
                        mol_type = other DNA
                        organism = synthetic construct
SEQUENCE: 154
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg ggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccgacgat ttcgaggaca gcgagagcac cgataccgag  1740
gaagaatga                                                          1749

SEQ ID NO: 155          moltype = AA  length = 582
FEATURE                 Location/Qualifiers
source                  1..582
                        mol_type = protein
                        organism = synthetic construct
SEQUENCE: 155
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKADD FEDSESTDTE EE                     582

SEQ ID NO: 156          moltype = RNA  length = 2044
FEATURE                 Location/Qualifiers
source                  1..2044
                        mol_type = other RNA
                        organism = synthetic construct
SEQUENCE: 156
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
```

-continued

```
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccgacgatt tcgaggacag cgagagcacc  1800
gataccgagg aagaatgata ataggctgga gcctcggtgg ccatgcttct tgccccttgg  1860
gcctcccccc agcccctcct ccccttcctg cacccgtacc cccgtggtct ttgaataaag  1920
tctgagtggg cggcaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaa                                                                2044

SEQ ID NO: 157          moltype = DNA  length = 2044
FEATURE                 Location/Qualifiers
source                  1..2044
                        mol_type = other DNA
                        organism = synthetic construct
SEQUENCE: 157
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccgacgatt tcgaggatgc cgaggccgcc  1800
gatgctgagg aagaatgata ataggctgga gcctcggtgg ccatgcttct tgccccttgg  1860
gcctcccccc agcccctcct ccccttcctg cacccgtacc cccgtggtct ttgaataaag  1920
tctgagtggg cggcaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaa                                                                2044

SEQ ID NO: 158          moltype = DNA  length = 1749
FEATURE                 Location/Qualifiers
source                  1..1749
                        mol_type = other DNA
                        organism = synthetic construct
SEQUENCE: 158
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
```

```
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccgacgat ttcgaggatg ccgaggccgc cgatgctgag  1740
gaagaatga                                                          1749

SEQ ID NO: 159         moltype = AA  length = 582
FEATURE                Location/Qualifiers
source                 1..582
                       mol_type = protein
                       organism = synthetic construct
SEQUENCE: 159
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKADD FEDAEAADAE EE                    582

SEQ ID NO: 160         moltype = RNA  length = 2044
FEATURE                Location/Qualifiers
source                 1..2044
                       mol_type = other RNA
                       organism = synthetic construct
SEQUENCE: 160
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccgacgatt tcgaggatgc cgaggccgcc  1800
gatgctgagg aagaatgata ataggctgga gcctcggtgg ccatgcttct tgccccttgg  1860
gcctcccccc agcccctcct ccccttcctg cacccgtacc cccgtggtct ttgaataaag  1920
tctgagtggg cggcaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaa                                                               2044
```

-continued

```
SEQ ID NO: 161          moltype = DNA  length = 2110
FEATURE                 Location/Qualifiers
source                  1..2110
                        mol_type = other DNA
                        organism = synthetic construct
SEQUENCE: 161
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccgacgatt tcgaggacag cgagagcacc  1800
gataccgagg aagagttcgg caacgccatt ggcggatctc acggcggcag cagctatacc  1860
gtgtacatcg acaagacccg gtgataatag gctggagcct cggtggccat gcttcttgcc  1920
ccttgggcct ccccccagcc cctcctcccc ttcctgcacc cgtacccccg tggtctttga  1980
ataaagtctg agtgggcggc aaaaaaaaaa aaaaaaaaaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa                                                         2110

SEQ ID NO: 162          moltype = DNA  length = 1815
FEATURE                 Location/Qualifiers
source                  1..1815
                        mol_type = other DNA
                        organism = synthetic construct
SEQUENCE: 162
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccgacgat ttcgaggaca gcgagagcac cgataccgag  1740
gaagagttcg gcaacgccat tggcggatct cacggcggca gcagctatac cgtgtacatc  1800
```

-continued

```
gacaagaccc ggtga                                                  1815

SEQ ID NO: 163          moltype = AA  length = 604
FEATURE                 Location/Qualifiers
source                  1..604
                        mol_type = protein
                        organism = synthetic construct
SEQUENCE: 163
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKADD FEDSESTDTE EEFGNAIGGS HGGSSYTVYI  600
DKTR                                                              604

SEQ ID NO: 164          moltype = RNA  length = 2110
FEATURE                 Location/Qualifiers
source                  1..2110
                        mol_type = other RNA
                        organism = synthetic construct
SEQUENCE: 164
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccgacgatt tcgaggacag cgagagcacc  1800
gataccgagg aagagttcgg caacgccatt ggcggatctc acggcggcag cagctatacc  1860
gtgtacatcg acaagacccg gtgataatag gctggagcct cggtggccat gcttcttgcc  1920
ccttgggcct ccccccagcc cctcctcccc ttcctgcacc cgtacccccg tggtctttga  1980
ataaagtctg agtgggcggc aaaaaaaaaa aaaaaaaaaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa                                                        2110

SEQ ID NO: 165          moltype = DNA  length = 2110
FEATURE                 Location/Qualifiers
source                  1..2110
                        mol_type = other DNA
                        organism = synthetic construct
SEQUENCE: 165
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
```

```
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac ccccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat accccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccgacgatt tcgaggatgc cgaggccgcc  1800
gatgctgagg aagaatttgg caacgccatt ggcggctctc acggcggcag tagctatacc  1860
gtgtacatcg acaagacccg gtgataatag gctggagcct cggtggccat gcttcttgcc  1920
ccttgggcct ccccccagcc cctcctcccc ttcctgcacc cgtacccccg tggtctttga  1980
ataaagtctg agtgggcggc aaaaaaaaaa aaaaaaaaaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa                                                         2110

SEQ ID NO: 166          moltype = DNA  length = 1815
FEATURE                 Location/Qualifiers
source                  1..1815
                        mol_type = other DNA
                        organism = synthetic construct
SEQUENCE: 166
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga tacccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggccgacgat ttcgaggatg ccgaggccgc cgatgctgag  1740
gaagaatttg gcaacgccat tggcggctct cacggcggca gtagctatac cgtgtacatc  1800
gacaagaccc ggtga                                                   1815

SEQ ID NO: 167          moltype = AA  length = 604
FEATURE                 Location/Qualifiers
source                  1..604
                        mol_type = protein
                        organism = synthetic construct
SEQUENCE: 167
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
```

-continued

```
YFNGHVEAVA YTVVSTVDHF VNAIEERGFP PTAGQPPATT KPKEITPVNP GTSPLLRYAA  540
WTGGLAAVVL LCLVIFLICT AKRMRVKADD FEDAEAADAE EEFGNAIGGS HGGSSYTVYI  600
DKTR                                                               604

SEQ ID NO: 168         moltype = RNA  length = 2110
FEATURE                Location/Qualifiers
source                 1..2110
                       mol_type = other RNA
                       organism = synthetic construct
SEQUENCE: 168
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gccgacgatt tcgaggatgc cgaggccgcc  1800
gatgctgagg aagaatttgg caacgccatt ggcggctctc acggcggcag tagctatacc  1860
gtgtacatcg acaagacccg gtgataatag gctggagcct cggtggccat gcttcttgcc  1920
ccttgggcct ccccccagcc cctcctcccc ttcctgcacc cgtacccccg tggtctttga  1980
ataaagtctg agtgggcggc aaaaaaaaaa aaaaaaaaaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa                                                         2110

SEQ ID NO: 169         moltype = DNA  length = 2161
FEATURE                Location/Qualifiers
source                 1..2161
                       mol_type = other DNA
                       organism = synthetic construct
SEQUENCE: 169
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
```

```
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctacagag tggacaagag cccttacaac  1800
cagagcatgt acgctgccgg cctgcctgtg gacgacttcg aggatagcga gagcaccgac  1860
accgaggaag agttcggcaa cgccattgga ggatctcacg gcggcagcag ctataccgtg  1920
tacatcgaca agacccggtg agctggagcc tcggtggcca tgcttcttgc cccttgggcc  1980
tccccccagc ccctcctccc cttcctgcac ccgtacccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 170         moltype = DNA  length = 1872
FEATURE                Location/Qualifiers
source                 1..1872
                       mol_type = other DNA
                       organism = synthetic construct
SEQUENCE: 170
atgggcaccg tgaacaagcc tgttgtgggc gtgctgatgg gcttcggcat catcacaggc  60
accctgcgga tcaccaatcc tgtgcgggct agcgtgctga gatacgacga cttccacatc  120
gacgaggaca agctggacac caacagcgtg tacgagccct actaccacag cgatcacgcc  180
gagtctagct gggtcaacag aggcgagagc agcagaaagg cctacgacca caacagcccc  240
tacatctggc cccggaacga ctacgatggc ttcctggaaa atgcccacga gcaccacggc  300
gtgtacaatc aaggcagagg catcgacagc ggcgagagac tgatgcagcc tacacagatg  360
agcgcccaag aggacctggg agatgatacc ggcatccacg tgatccccac actgaacggc  420
gacgacagac acaagatcgt gaacgtggac cagcggcagt acggcgacgt gttcaagggc  480
gacctgaatc ctaagcctca gggccagcgc ctgatcgagg tgtccgtgga agagaatcac  540
cccttcacac tgagagcccc tatccagaga atctacggcg tgcgctatac cgagacatgg  600
tcctttctgc ccagcctgac atgtaccggg gatgccgctc ctgccatcca gcacatttgc  660
ctgaagcaca ccacctgttt ccaggacgtg gtggtggatg tggactgcgc cgagaacacc  720
aaagaggatc agctggccga gatcagctac cggttccagg gaaagaaaga ggccgaccag  780
ccttggatcg tggtcaacac cagcacactg ttcgacgagc tggaactgga ccctcctgag  840
attgaacccg gggtgctgaa ggtgctgaga accgagaagc agtacctggg agtgtacatc  900
tggaacatga gaggcagcga cggcacctct acctacgcca cctttctggt cacatggaag  960
ggcgacgaga aaacacggaa ccccacacca gctgtgaccc ctcaacctag aggcgccgag  1020
tttcacatgt ggaattacca cagccacgtg ttcagcgtgg gcgatacctt tagcctggcc  1080
atgcatctgc agtacaagat ccacgaggcc cctttcgacc tgctgctgga atggctgtac  1140
gtgcccatcg atcctacctg ccagcctatg cggctgtact ccacctgtct gtatcacccc  1200
aacgctcccc agtgcctgag ccacatgaat agcggctgca ccttcacaag ccctcacctg  1260
gctcagcgag tggccagcac agtgtaccag aattgcgagc acgccgacaa ttacaccgcc  1320
tactgtctgg gcatcagcca catggaacct agcttcggcc tgatcctgca cgatggcggc  1380
acaaccctga agttcgtgga taccccctgag agcctgagcg gcctgtatgt gttcgtggtg  1440
tacttcaacg gccacgtgga agccgtggcc tacaccgtgg tgtctaccgt ggaccacttc  1500
gtgaacgcca tcgaggaaag aggcttccct ccaactgctg gacagcctcc tgccaccacc  1560
aagcctaaag aaatcacacc cgtgaatccc ggcacaagcc cactgcttag atacgccgct  1620
tggacaggcg gactggctgc tgttgttctg ctgtgcctgg tcatcttcct gatctgcacc  1680
gccaagcgga tgagagtgaa ggcctacaga gtggacaaga gcccttacaa ccagagcatg  1740
tacgctgccg gcctgcctgt ggacgacttc gaggatagcg agagcaccga caccgaggaa  1800
gagttcggca acgccattgg aggatctcac ggcggcagca gctataccgt gtacatcgac  1860
aagacccggt ga                                                     1872

SEQ ID NO: 171         moltype = AA  length = 623
FEATURE                Location/Qualifiers
source                 1..623
                       mol_type = protein
                       organism = synthetic construct
SEQUENCE: 171
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR VDKSPYNQSM YAAGLPVDDF EDSESTDTEE  600
EFGNAIGGSH GGSSYTVYID KTR                                         623

SEQ ID NO: 172         moltype = RNA  length = 2161
FEATURE                Location/Qualifiers
source                 1..2161
                       mol_type = other RNA
                       organism = synthetic construct
SEQUENCE: 172
agactcctcc ccatcctctc cctctgtccc tctgtccctc tgaccctgca ctgtcccagc  60
accgccacca tgggcaccgt gaacaagcct gttgtgggcg tgctgatggg cttcggcatc  120
atcacaggca ccctgcggat caccaatcct gtgcgggcta gcgtgctgag atacgacgac  180
ttccacatcg acgaggacaa gctggacacc aacagcgtgt acgagcccta ctaccacagc  240
```

-continued

```
gatcacgccg agtctagctg ggtcaacaga ggcgagagca gcagaaaggc ctacgaccac  300
aacagcccct acatctggcc ccggaacgac tacgatggct tcctggaaaa tgcccacgag  360
caccacggcg tgtacaatca aggcagaggc atcgacagcg gcgagagact gatgcagcct  420
acacagatga gcgcccaaga ggacctggga gatgataccg gcatccacgt gatccccaca  480
ctgaacggcg acgacagaca caagatcgtg aacgtggacc agcggcagta cggcgacgtg  540
ttcaagggcg acctgaatcc taagcctcag ggccagcgcc tgatcgaggt gtccgtggaa  600
gagaatcacc ccttcacact gagagcccct atccagagaa tctacggcgt gcgctatacc  660
gagacatggt cctttctgcc cagcctgaca tgtaccgggg atgccgctcc tgccatccag  720
cacatttgcc tgaagcacac cacctgtttc caggacgtgg tggtggatgt ggactgcgcc  780
gagaacacca aagaggatca gctggccgag atcagctacc ggttccaggg aaagaaagag  840
gccgaccagc cttggatcgt ggtcaacacc agcacactgt tcgacgagct ggaactggac  900
cctcctgaga ttgaacccgg ggtgctgaag gtgctgagaa ccgagaagca gtacctggga  960
gtgtacatct ggaacatgag aggcagcgac ggcacctcta cctacgccac ctttctggtc  1020
acatggaagg gcgacgagaa aacacggaac cccacaccag ctgtgacccc tcaacctaga  1080
ggcgccgagt ttcacatgtg gaattaccac agccacgtgt tcagcgtggg cgataccttt  1140
agcctggcca tgcatctgca gtacaagatc cacgaggccc ctttcgacct gctgctggaa  1200
tggctgtacg tgcccatcga tcctacctgc cagcctatgc ggctgtactc cacctgtctg  1260
tatcacccca acgctcccca gtgcctgagc cacatgaata gcggctgcac cttcacaagc  1320
cctcacctgg ctcagcgagt ggccagcaca gtgtaccaga attgcgagca cgccgacaat  1380
tacaccgcct actgtctggg catcagccac atggaaccta gcttcggcct gatcctgcac  1440
gatggcggca caaccctgaa gttcgtggat acccctgaga gcctgagcgg cctgtatgtg  1500
ttcgtggtgt acttcaacgg ccacgtggaa gccgtggcct acaccgtggt gtctaccgtg  1560
gaccacttcg tgaacgccat cgaggaaaga ggcttccctc caactgctgg acagcctcct  1620
gccaccacca agcctaaaga aatcacaccc gtgaatcccg gcacaagccc actgcttaga  1680
tacgccgctt ggacaggcgg actggctgct gttgttctgc tgtgcctggt catcttcctg  1740
atctgcaccg ccaagcggat gagagtgaag gcctacagag tggacaagag cccttacaac  1800
cagagcatgt acgctgccgg cctgcctgtg gacgacttcg aggatagcga gagcaccgac  1860
accgaggaag agttcggcaa cgccattgga ggatctcacg gcggcagcag ctataccgtg  1920
tacatcgaca agacccggtg agctggagcc tcggtggcca tgcttcttgc cccttgggcc  1980
tcccccagc ccctcctccc cttcctgcac ccgtaccccc gtggtctttg aataaagtct  2040
gagtgggcgg caaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
a                                                                  2161

SEQ ID NO: 173         moltype = DNA  length = 46
FEATURE                Location/Qualifiers
source                 1..46
                       mol_type = other DNA
                       organism = synthetic construct
SEQUENCE: 173
agaaataaga gagaaaagaa gagtaagaag aaatataaga gccacc                 46

SEQ ID NO: 174         moltype = RNA  length = 69
FEATURE                Location/Qualifiers
source                 1..69
                       mol_type = other RNA
                       organism = synthetic construct
SEQUENCE: 174
agactcctcc ccatcctctc cctctgtccc tctgtccctc tgaccctgca ctgtcccagc  60
accgccacc                                                          69

SEQ ID NO: 175         moltype = DNA  length = 102
FEATURE                Location/Qualifiers
source                 1..102
                       mol_type = other DNA
                       organism = synthetic construct
SEQUENCE: 175
agcattctgt ggtctgatca tcctgtggtt tcgtcgccgc catcctcgtc gcgacacgct  60
gttttcggtt ctcggcccga cgagccatcg ccatcctaca gc                     102

SEQ ID NO: 176         moltype = DNA  length = 102
FEATURE                Location/Qualifiers
source                 1..102
                       mol_type = other DNA
                       organism = synthetic construct
SEQUENCE: 176
agcactcgcg ctgccatcac tcttccgccg tcttcgccgc catcctcggc gcgactcgct  60
tctttcggtt ctaccaggta gagtccgccg ccatcctcca cc                     102

SEQ ID NO: 177         moltype = DNA  length = 102
FEATURE                Location/Qualifiers
source                 1..102
                       mol_type = other DNA
                       organism = synthetic construct
SEQUENCE: 177
agcttgtctc gctccgggga acgctcggaa actcccggcc gccgccaccc gcgtctgttc  60
tgttacacaa gggaagaaaa gccgctgccg cactccgagt gt                     102

SEQ ID NO: 178         moltype = DNA  length = 110
```

```
FEATURE                Location/Qualifiers
source                 1..110
                       mol_type = other DNA
                       organism = synthetic construct
SEQUENCE: 178
gctggagcct cggtggccat gcttcttgcc ccttgggcct ccccccagcc cctcctcccc  60
ttcctgcacc cgtacccccg tggtctttga ataaagtctg agtgggcggc             110

SEQ ID NO: 179         moltype = DNA  length = 132
FEATURE                Location/Qualifiers
source                 1..132
                       mol_type = other DNA
                       organism = synthetic construct
SEQUENCE: 179
gctcgctttc ttgctgtcca atttctatta aaggttcctt tgttccctaa gtccaactac  60
taaactgggg gatattatga agggccttga gcatctggat tctgcctaat aaaaaacatt  120
tattttcatt gc                                                      132

SEQ ID NO: 180         moltype = DNA  length = 88
FEATURE                Location/Qualifiers
source                 1..88
                       mol_type = other DNA
                       organism = synthetic construct
SEQUENCE: 180
ttctggactt ctggacttct ggacttctgg acttctggac ttctggactt ctggacttct  60
ggacttctgg acttctggac ttctggac                                     88

SEQ ID NO: 181         moltype = DNA  length = 115
FEATURE                Location/Qualifiers
source                 1..115
                       mol_type = other DNA
                       organism = synthetic construct
SEQUENCE: 181
cctcgccccg gacctgccct cccgccaggt gcacccacct gcaataaatg cagcgaagcc  60
gggacctcgc cccggacctg ccctcccgcc aggtgcaccc acctgcaata aatgc       115

SEQ ID NO: 182         moltype = AA  length = 6
FEATURE                Location/Qualifiers
source                 1..6
                       mol_type = protein
                       organism = synthetic construct
SEQUENCE: 182
SESTDT                                                             6

SEQ ID NO: 183         moltype = AA  length = 6
FEATURE                Location/Qualifiers
source                 1..6
                       mol_type = protein
                       organism = synthetic construct
SEQUENCE: 183
AEAADA                                                             6

SEQ ID NO: 184         moltype = AA  length = 4
FEATURE                Location/Qualifiers
source                 1..4
                       mol_type = protein
                       organism = synthetic construct
SEQUENCE: 184
AYRV                                                               4

SEQ ID NO: 185         moltype = AA  length = 4
FEATURE                Location/Qualifiers
source                 1..4
                       mol_type = protein
                       organism = synthetic construct
SEQUENCE: 185
YAGL                                                               4

SEQ ID NO: 186         moltype = AA  length = 11
FEATURE                Location/Qualifiers
source                 1..11
                       mol_type = protein
                       organism = synthetic construct
SEQUENCE: 186
YRVDKSPYNQ S                                                       11

SEQ ID NO: 187         moltype = AA  length = 19
FEATURE                Location/Qualifiers
source                 1..19
```

-continued

```
                         mol_type = protein
                         organism = synthetic construct
SEQUENCE: 187
YRVDKSPYNQ SMYYAGLPV                                                19

SEQ ID NO: 188           moltype = AA  length = 4
FEATURE                  Location/Qualifiers
source                   1..4
                         mol_type = protein
                         organism = synthetic construct
SEQUENCE: 188
SSTT                                                                4

SEQ ID NO: 189           moltype = AA  length = 12
FEATURE                  Location/Qualifiers
source                   1..12
                         mol_type = protein
                         organism = synthetic construct
SEQUENCE: 189
AYRVYAGLSS TT                                                       12

SEQ ID NO: 190           moltype = AA  length = 8
FEATURE                  Location/Qualifiers
source                   1..8
                         mol_type = protein
                         organism = synthetic construct
SEQUENCE: 190
YAGLSSTT                                                            8

SEQ ID NO: 191           moltype = AA  length = 8
FEATURE                  Location/Qualifiers
source                   1..8
                         mol_type = protein
                         organism = synthetic construct
SEQUENCE: 191
AYRVYAGL                                                            8
```

What is claimed is:

1. An immunogenic composition, comprising a ribonucleic acid (RNA) of a varicella-zoster virus (VZV) encoding a variant of the wild-type VZV gE glycoprotein;

wherein the sequence of the wild-type VZV gE glycoprotein is SEQ ID NO: 3;

wherein the variant of the VZV gE glycoprotein is the variant selected from: YK-VZV-020, YK-VZV-030, YK-VZV-031, YK-VZV-009, YK-VZV-010, YK-VZV-011, YK-VZV-012, YK-VZV-013 and YK-VZV-014,

| Name | Sequence truncation | Site mutation | Sequence deletion |
|---|---|---|---|
| YK-VZV-020 | gE (1 to 573) | Y569K | No sequence deletion |
| YK-VZV-030 | gE (1 to 587) | A568D; Y569K; R570E; V571K; Y582A | No sequence deletion |
| YK-VZV-031 | gE (1 to 587) | A568D; Y569K; R570E; V571K; Y582G | No sequence deletion |
| YK-VZV-009 | No sequence truncation | Y569K; Y582A | No sequence deletion |
| YK-VZV-010 | No sequence truncation | Y569K; Y582A; S593A; S595A; T596A; T598A | No sequence deletion |
| YK-VZV-011 | No sequence truncation | A568D; Y569K; R570E; V571K | No sequence deletion |
| YK-VZV-012 | No sequence truncation | A568D; Y569K; R570E; V571K; S593A; S595A; T596A; T598A | No sequence deletion |
| YK-VZV-013 | No sequence truncation | A568D; Y569K; R570E; V571K; Y582A | No sequence deletion |
| YK-VZV-014 | No sequence truncation | A568D; Y569K; R570E; V571K; Y582A; S593A; S595A; T596A; T598A. | No sequence deletion |

2. The composition according to claim 1, wherein the amino acid sequence of the variant of the VZV gE glycoprotein is as shown in SEQ ID NO: 27, 31, 35, 39, 43, 47, 71, 111, or 115.

3. The composition according to claim 1, wherein the RNA of the VZV has an open reading frame (ORF) encoding a variant of the VZV gE glycoprotein, the sequence of the open reading frame is as shown in SEQ ID NO: 26, 30, 34, 38, 42, 46, 70, 110 or 114.

4. The composition according to claim 1, wherein the RNA of the VZV further comprises a 5' untranslated region (UTR).

5. The composition according to claim 4, wherein the sequence of the 5' UTR is as shown in SEQ ID NO: 173, 174, 175, 176, or 177.

6. The composition according to claim 1, wherein the RNA of the VZV further comprises a 3' untranslated region (UTR).

7. The composition according to claim 6, wherein the sequence of the 3' UTR is as shown in SEQ ID NO: 178, 179, 180, or 181.

8. The composition according to claim 1, wherein the RNA of the VZV further comprises a poly(A) tail.

9. The composition according to claim 8, wherein the poly(A) tail has a length of 50 to 150 nucleotides.

10. The composition according to claim 1, wherein the RNA of the VZV further comprises a 5' terminal cap.

11. The composition according to claim 10, wherein the 5' terminal cap is 7 mG (5') ppp (5') NlmpNp.

12. The composition according to claim 3, wherein the sequence of the open reading frame is codon-optimized.

13. The composition according to claim 12, wherein the sequence of the open reading frame comprises at least one base modification.

14. The composition according to claim 13, wherein the base modification is selected from one or more of the following: pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyluridine.

15. The composition according to claim 14, wherein the base modification is replacement of uracil by pseudouridine, or N1-methylpseudouridine.

16. The composition according to claim 13, wherein the base modification is 1 to 100% base modification.

17. The composition according to claim 16, wherein the base modification is 100% base modification.

18. The composition according to claim 1, wherein the sequence of the RNA of the VZV is as shown in SEQ ID NO: 28, 32, 36, 40, 44, 48, 72, 112, or 116.

19. The composition according to claim 1, wherein the RNA of the VZV is mRNA.

20. The composition according to claim 1, wherein the sequence of the RNA encoding the VZV gE glycoprotein corresponding to a DNA sequence shown in SEQ ID NO: 25, 29, 33, 37, 41, 45, 69, 109, or 113.

21. A method for preparing the composition according to claim 1, comprising:

providing a template that can transcribe the RNA of the VZV;

transcribing the RNA using the template under conditions suitable for transcription.

22. The method according to claim 21, further comprising a purification step selected from: lithium chloride precipitation, affinity chromatography, ultrafiltration exchange, and cellulose chromatography.

23. The composition according to claim 1, wherein the composition is a vaccine, and further comprises a pharmaceutically acceptable carrier.

24. The composition according to claim 23, wherein the carrier comprises a lipid mixture.

25. The composition according to claim 24, wherein the lipid mixture is a lipid nanoparticle (LNP).

26. The composition according to claim 23, wherein the vaccine is an mRNA vaccine.

27. The composition according to claim 26, wherein the lipid nanoparticle (LNP) comprises a cationic lipid, a neutral lipid, a structural lipid, and a polymer-conjugated lipid.

28. The composition according to claim 27, wherein the cationic lipid is selected from: YK-009, YK-305, ALC0315, SM102 and DLIN-MC3-DMA:

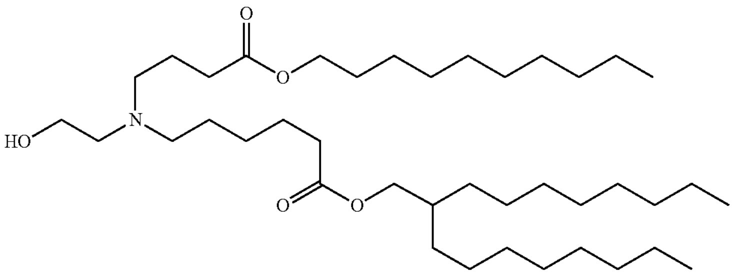

YK-009

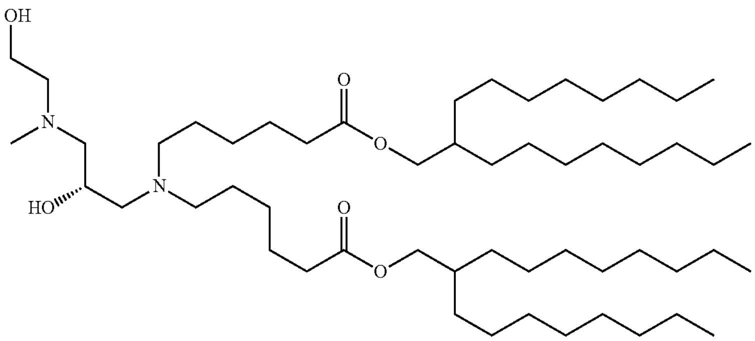

YK-305

-continued

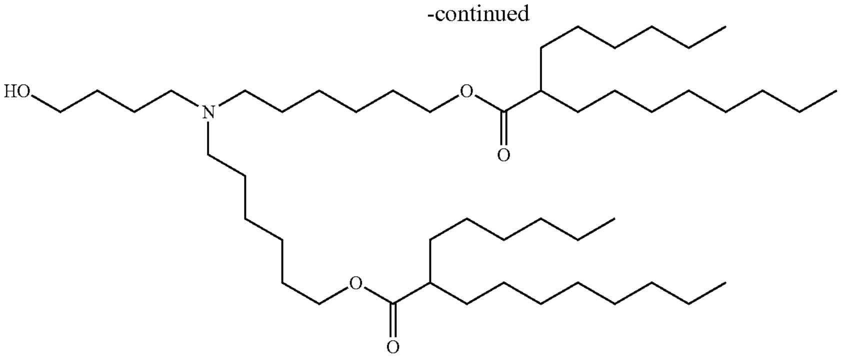

ALC0315

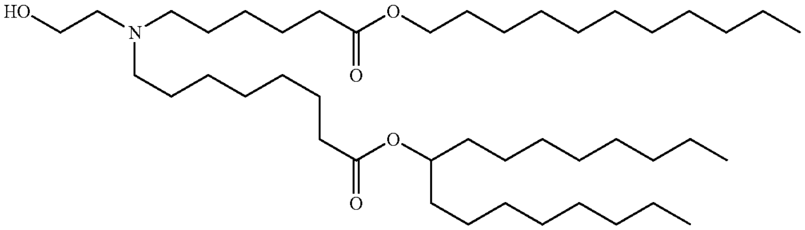

SM102

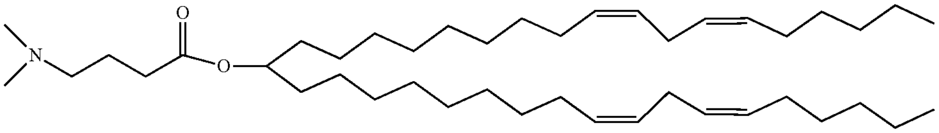

DLIN-MC3 .

29. The composition according to claim 27, wherein the molar ratio of the cationic lipid to the neutral lipid is (1 to 10):1.

30. The composition according to claim 27, wherein the molar ratio of the cationic lipid to the structural lipid is (1 to 5):1.

31. The composition according to claim 27, wherein the molar ratio of the cationic lipid, the neutral lipid, the structural lipid, and the polymer-conjugated lipid is (25 to 75):(5 to 25):(15 to 65):(0.5 to 10).

32. The composition according to claim 31, wherein the molar ratio of the cationic lipid, the neutral lipid, the structural lipid, and the polymer-conjugated lipid is (35 to 49):(7.5 to 15):(35 to 55):(1 to 5).

33. The composition according to claim 32, wherein the molar ratio of the cationic lipid, the neutral lipid, the structural lipid, and the polymer-conjugated lipid is 49:10:43.5:1.5.

34. The composition according to claim 27, wherein the neutral lipid is selected from phosphatidylcholine, phosphatidylethanolamine, sphingomyelin, ceramide, derivatives thereof, and any combination thereof.

35. The composition according to claim 27, wherein the neutral lipid is selected from: 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearoyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), and mixtures thereof.

36. The composition according to claim 27, wherein the neutral lipid is DOPE, or DSPC.

37. The composition according to claim 27, wherein the structural lipid is selected from: sterol, cholesterol, non-sterol, sitosterol, ergosterol, campesterol, stigmasterol, brassinosterol, tomatine, ursolic acid, α-tocopherol, corticosteroid, and any combination thereof.

38. The composition according to claim 37, wherein the structural lipid comprises cholesterol.

39. The composition of claim 38, wherein the structural lipid is cholesterol.

40. The composition according to claim 27, wherein the polymer-conjugated lipid is selected from: PEG-modified phosphatidylethanolamine, PEG-modified phosphatidic acid, PEG-modified ceramide, PEG-modified dialkylamine, PEG-modified diacylglycerol, PEG-modified dialkylglycerol, and any combination thereof.

41. The composition according to claim 40, wherein the polymer-conjugated lipid is selected from: distearoyl phosphatidylethanolamine polyethylene glycol 2000 (DSPE-PEG2000), dimyristoylglycero-3-methoxypolyethylene glycol 2000 (DMG-PEG2000), methoxypolyethylene glycol ditetradecylacetamide (ALC-0159), and any combination thereof.

42. The composition according to claim 23, wherein the effective dose for the RNA of the VZV is 25 μg to 200 μg.

43. The composition according to claim 42, wherein the effective dose for the RNA of the VZV is 50 μg to 100 μg.

44. The composition according to claim 23, wherein the vaccine is an injection.

45. The composition according to claim 44, wherein the vaccine is a liquid preparation or a lyophilized preparation.

46. A method for preparing the composition according to claim 23, comprising: mixing the RNA of the VZV with the pharmaceutically acceptable carrier.

47. The method according to claim 46, wherein the method comprises encapsulating at least a portion of the RNA in lipid nanoparticles.

48. A use of the composition according to claim 1 in the preparation of a medicament for inducing a protective immune response against VZV in a subject.

49. The use according to claim 48, wherein the protective immune response comprises the production of a neutralizing antibody.

* * * * *